(12) United States Patent
Fortunak et al.

(10) Patent No.: US 6,492,515 B2
(45) Date of Patent: Dec. 10, 2002

(54) 4,4-DISUBSTITUTED-1, 4-DIHYDRO-2H-3, 1-BENZOXAZIN-2-ONES USEFUL AS HIV REVERSE TRANSCRIPTASE INHIBITORS AND INTERMEDIATES AND PROCESSES FOR MAKING THE SAME

(75) Inventors: Joseph Marian Fortunak, Newark; Mona Patel, Wilmington, both of DE (US)

(73) Assignee: Bristol-Myers Squibb Pharma Company, Princeton, NJ (US)

( * ) Notice: Subject to any disclaimer, the term of this patent is extended or adjusted under 35 U.S.C. 154(b) by 0 days.

(21) Appl. No.: 09/919,065

(22) Filed: Jul. 31, 2001

(65) Prior Publication Data

US 2002/0040138 A1 Apr. 4, 2002

Related U.S. Application Data

(62) Division of application No. 09/627,213, filed on Jul. 27, 2000, now Pat. No. 6,303,780, which is a division of application No. 09/176,491, filed on Oct. 21, 1998, now Pat. No. 6,140,499, which is a division of application No. 08/942,031, filed on Oct. 1, 1997, now Pat. No. 5,874,430.
(60) Provisional application No. 60/045,138, filed on Apr. 30, 1997, and provisional application No. 60/027,137, filed on Oct. 2, 1996.

(51) Int. Cl.[7] .................... C07D 237/20; C07D 239/42; C07D 241/20; C07C 215/68
(52) U.S. Cl. ...................... 544/224; 544/322; 544/336; 546/309; 546/311; 546/312; 552/104; 560/29; 564/442
(58) Field of Search ................................ 544/224, 322, 544/336; 546/309, 311, 312; 552/104; 564/442; 560/29

(56) References Cited

U.S. PATENT DOCUMENTS

| | | | |
|---|---|---|---|
| 4,518,597 A | 5/1985 | Narr et al. ..................... 544/54 |
| 5,250,548 A | * 10/1993 | Winn et al. .................. 514/340 |
| 5,519,021 A | 5/1996 | Young et al. ............ 514/230.5 |
| 5,932,726 A | 8/1999 | Pierce et al. ................... 544/90 |

FOREIGN PATENT DOCUMENTS

| | | |
|---|---|---|
| GB | 1135899 | 7/1967 |
| GB | 2080296 | 2/1982 |
| WO | 9637457 | 11/1996 |

OTHER PUBLICATIONS

Tordeux et al, *J. Chem. Soc. Perkin Trans.* 1990 1, 1951–1957, "Reactions of Trifluoromethyl Bromide and Related Halides: Part 9. Comparison between Additions to Carbonyl Compounds, Enamines, and Sulphur Dioxide in the Presence of zinc".

Kotun et al, *J. Org. Chem.* 1992, 57, 1124–1131, "Fluorinated Tertiary Alcohols and Alkoxides from Nucleophilic Trifluoromethylation of Carbonyl Compounds".

Prakash et al, J. Am. Chem. Soc. 1989, 111 (1), 393–395, "Fluoride–Induced Trifluoromethylation of Carbonyl Compounds with Trifluoromethyltrimethylsilane (TMS–$CF_3$ ). A Trifluoromethide Equivalent".

Kitasume et al, *J. Org. Chem.* 1988, 53, 2349–2350, "A Remarkably Simple Perfluoroalkylation in the Presence of an Electron Mediator".

Krishnamurti et al, *J. Org. Chem.* 1991, 56, 984–989, "Preparation of Trifluoromethyl and Other Perfluoroalkyl Compounds with (Perfluoralkyl) trimethylsilanes".

Mack et al, *J. Heterocyclic Chem.* 1987, 24, 1733–1739, "The Preparation of Quinolines and Related Fused–Ring Heterocycles from the Dianions of Benzoylacetone, Certain Cyclic Ketone Oximes, or Certain Substituted Hydrazones".

Coppola et al,*J. Org. Chem.* 1976, 41 (5), 825–831, "Chemistry of 2H–3, 1–Benzoxazine–2, 4 (1H) –dione (Isatoic Anhydride). 2. Reactions with Thiopseudoreas and Carbanions".

Takimoto et al, *Fukuoka Univ. Sci, Reports* 1985, 15 (1), 37–38, "Reactions of Isatoic Anhydride with Various Nucleophiles in the Presence of 4–Pyrrolidinopyridine".

Kadin et al, *Synthesis Jul. 1977*, 500–501, "A Convenient Synthesis of 2–Amino–4–hydroxyquinolines".

Staiger et al, *J. Org. Chem.* 1959, 24, 1214–1219, "Isatoic Anhydride. IV, Reactions with Various Nucleophiles".

\* cited by examiner

*Primary Examiner*—Richard L. Raymond
(74) *Attorney, Agent, or Firm*—Mary K. VanAtten

(57) ABSTRACT

The present invention relates to benzoxazinones of formula I:

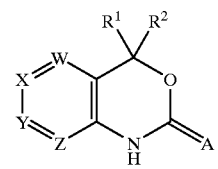

or stereoisomeric forms or mixtures, or pharmaceutically acceptable salt forms thereof, which are useful as inhibitors of HIV reverse transcriptase, and to pharmaceutical compositions and diagnostic kits comprising the same, methods of using the same for treating viral infection or as an assay standard or reagent, and intermediates and processes for making the same.

4 Claims, No Drawings

4,4-DISUBSTITUTED-1, 4-DIHYDRO-2H-3, 1-BENZOXAZIN-2-ONES USEFUL AS HIV REVERSE TRANSCRIPTASE INHIBITORS AND INTERMEDIATES AND PROCESSES FOR MAKING THE SAME

This application is a division of application Ser. No. 09/627,213, filed Jul. 27, 2000, now U.S. Pat. No. 6,303,780 which is a division of application Ser. No. 09/176,491, filed Oct. 21, 1998, now U.S. Pat. No. 6,140,499, which is a division of application Ser. No. 08/942,031, filed Oct. 1, 1997, now U.S. Pat. No. 5,874,430, which claims the benefit of U.S. Provisional Application No. 60/045,138, filed Apr. 30, 1997 and U.S. Provisional Application No. 60/027,137, filed Oct. 2, 1996.

FIELD OF THE INVENTION

This invention relates generally to 4,4-disubstituted-1,4-dihydro-2H-3,1-benzoxazin-2-ones which are useful as inhibitors of HIV reverse transcriptase, pharmaceutical compositions and diagnostic kits comprising the same, methods of using the same for treating viral infection or as assay standards or reagents, and intermediates and processes for making the same.

BACKGROUND OF THE INVENTION

Two distinct retroviruses, human immunodeficiency virus (HIV) type-1 (HIV-1) or type-2 (HIV-2), have been etiologically linked to the immunosuppressive disease, acquired immunodeficiency syndrome (AIDS). HIV seropositive individuals are initially asymptomatic but typically develop AIDS related complex (ARC) followed by AIDS. Affected individuals exhibit severe immunosuppression which predisposes them to debilitating and ultimately fatal opportunistic infections.

The disease AIDS is the end result of an HIV-1 or HIV-2 virus following its own complex life cycle. The virion life cycle begins with the virion attaching itself to the host human T-4 lymphocyte immune cell through the bonding of a glycoprotein on the surface of the virion's protective coat with the CD4 glycoprotein on the lymphocyte cell. Once attached, the virion sheds its glycoprotein coat, penetrates into the membrane of the host cell, and uncoats its RNA. The virion enzyme, reverse transcriptase, directs the process of transcribing the RNA into single-stranded DNA. The viral RNA is degraded and a second DNA strand is created. The now double-stranded DNA is integrated into the human cell's genes and those genes are used for virus reproduction.

At this point, RNA polymerase transcribes the integrated DNA into viral RNA. The viral RNA is translated into the precursor gag-pol fusion polyprotein. The polyprotein is then cleaved by the HIV protease enzyme to yield the mature viral proteins. Thus, HIV protease is responsible for regulating a cascade of cleavage events that lead to the virus particle's maturing into a virus that is capable of full infectivity.

The typical human immune system response, killing the invading virion, is taxed because the virus infects and kills the immune system's T cells. In addition, viral reverse transcriptase, the enzyme used in making a new virion particle, is not very specific, and causes transcription mistakes that result in continually changed glycoproteins on the surface of the viral protective coat. This lack of specificity decreases the immune system's effectiveness because antibodies specifically produced against one glycoprotein may be useless against another, hence reducing the number of antibodies available to fight the virus. The virus continues to reproduce while the immune response system continues to weaken. Eventually, the HIV largely holds free reign over the body's immune system, allowing opportunistic infections to set in and without the administration of antiviral agents, immunomodulators, or both, death may result.

There are at least three critical points in the virus's life cycle which have been identified as possible targets for antiviral drugs: (1) the initial attachment of the virion to the T-4 lymphocyte or macrophage site, (2) the transcription of viral RNA to viral DNA (reverse transcriptase, RT), and (3) the processing of gag-pol protein by HIV protease.

Inhibition of the virus at the second critical point, the viral RNA to viral DNA transcription process, has provided a number of the current therapies used in treading AIDS. This transcription must occur for the virion to reproduce because the virion's genes are encoded in RNA and the host cell reads only DNA. By introducing drugs that block the reverse transcriptase from completing the formation of viral DNA, HIV-1 replication can be stopped.

A number of compounds that interfere with viral replication have been developed to treat AIDS. For example, nucleoside analogs, such as 3'-azido-3'-deoxythymidine (AZT), 2',3'-dideoxycytidine (ddC), 2',3'-dideoxythymidinene (d4T), 2',3'-dideoxyinosine (ddI), and 2',3'-dideoxy-3'-thia-cytidine (3TC) have been shown to be relatively effective in halting HIV replication at the reverse transcriptase (RT) stage.

Non-nucleoside HIV reverse transcriptase inhibitors have also been discovered. As an example, it has been found that certain benzoxazinones are useful in the inhibition of HIV reverse transcriptase, the prevention or treatment of infection by HIV and the treatment of AIDS. U.S. Pat. No. 5,519,021, the contents of which are hereby incorporated herein by reference, describe reverse transcriptase inhibitors which are benzoxazinones of the formula:

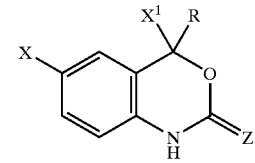

wherein X is a halogen, Z may be O. However, benzoxazinones of this type are specifically excluded from the present invention.

In U.S. Pat. No. 5,519,021 one compound in particular, (−) 6-chloro-4-cyclopropylethynyl-4-trifluoromethyl-1,4-dihydro-2H-3,1-benzoxazin-2-one (NNRTI), shown below,

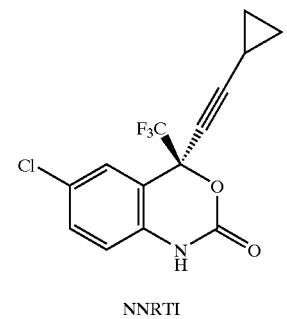

NNRTI has been found to be a potent and specific inhibitor of HIV-1 reverse transcriptase worthy of further study. NNRTI is described in Step D of Example 6 of the disclosure. Rat, monkey, and human microsomes treated with NNRTI, during investigation of the cytochrome P450 metabolism of NNRTI, produced a metabolite which was discovered to also be a potent inhibitor of HIV reverse transcriptase. This metabolite, its stereoisomer, stereoisomeric mixtures, and derivatives thereof are an embodiment of the present invention.

Even with the current success of reverse transcriptase inhibitors, it has been found that HIV patients can become resistant to a single inhibitor. Thus, it is desirable to develop additional inhibitors to further combat HIV infection.

SUMMARY OF THE INVENTION

Accordingly, one object of the present invention is to provide novel reverse transcriptase inhibitors.

It is another object of the present invention to provide a novel method for treating HIV infection which comprises administering to a host in need of such treatment a therapeutically effective amount of at least one of the compounds of the present invention or a pharmaceutically acceptable salt or prodrug form thereof.

It is another object of the present invention to provide a novel method for treating HIV infection which comprises administering to a host in need thereof a therapeutically effective combination of (a) one of the compounds of the present invention and (b) one or more compounds selected form the group consisting of HIV reverse transcriptase inhibitors and HIV protease inhibitors.

It is another object of the present invention to provide pharmaceutical compositions with reverse transcriptase inhibiting activity comprising a pharmaceutically acceptable carrier and a therapeutically effective amount of at least one of the compounds of the present invention or a pharmaceutically acceptable salt or prodrug form thereof.

It is another object of the present invention to provide a method of inhibiting HIV present in a body fluid sample which comprises treating the body fluid sample with an effective amount of a compound of the present invention.

It is another object of the present invention to provide a kit or container containing at least one of the compounds of the present invention in an amount effective for use as a standard or reagent in a test or assay for determining the ability of a potential pharmaceutical to inhibit HIV reverse transcriptase, HIV growth, or both.

These and other objects, which will become apparent during the following detailed description, have been achieved by the inventors' discovery that compounds of formula (I):

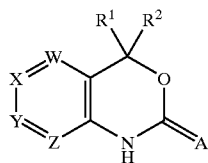

wherein A, W, X, Y, Z, $R^1$ and $R^2$ are defined below, stereoisomeric forms, mixtures of stereoisomeric forms, or pharmaceutically acceptable salt forms thereof, are effective reverse transcriptase inhibitors.

DETAILED DESCRIPTION OF PREFERRED EMBODIMENTS

[1] Thus, in a first embodiment, the present invention provides a novel compound of formula I:

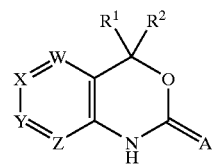

or a stereoisomer or pharmaceutically acceptable salt form thereof, wherein:

A is O or S;

W is N or $CR^3$;

X is N or $CR^4$;

Y is N or $CR^5$;

Z is N or $CR^6$;

provided that if two of W, X, Y, and Z are N, then the remaining are other than N;

also, provided that if X is $CR^4$ and $R^4$ is F, Cl, Br, or I, then:
(a) at least one of W, Y, and Z is other than CH;
(b) $R^2$ is —$OCHR^7R^8$ or —$NHCHR^7R^8$;
(c) if $R^2$ is C≡C—$R^8$, then $R^8$ is $C_{3-7}$ cycloalkyl substituted with 1 $R^9$; or
(d) any combination of (a), (b), and (c);

$R^1$ is selected from $CF_3$, $CF_2H$, $C_2F_5$, $C_{1-4}$ alkyl, $C_{3-5}$ cycloalkyl, $C_{2-4}$ alkenyl, and $C_{2-4}$ alkynyl;

$R^2$ is selected from —$QCHR^7R^8$, —$QCHR^7C≡C—R^8$, —$QCHR^7C=C—R^8$, —$Q(CH_2)_pCHR^7R^8$, —C≡C—$R^8$, —CH=$CR^7R^8$, —$(CH_2)_pCHR^7R^8$, —$CHR^7C≡C—R^8$, —$CHR^7CH=CHR^8$, and CH=$CHCHR^7R^8$;

provided that when $R^1$ is $C_{1-4}$ alkyl, then $R^2$ is —C≡C—$R^8$;

$R^3$ is selected from H, F, Cl, Br, I, $C_{1-3}$ alkoxy, and $C_{1-3}$ alkyl;

$R^4$ is selected from H, F, Cl, Br, I, $C_{1-3}$ alkyl substituted with 0–3 $R^{11}$, $C_{2-3}$ alkenyl, $C_{2-3}$ alkynyl, $C_{1-3}$ alkoxy, $OCF_3$, —CN, $NO_2$, CHO, $C(O)CH_3$, $C(O)CF_3$, $C(O)NH_2$, $C(O)NHCH_3$, $NR^7R^{7a}$, $NR^7C(O)OR^{7a}$, $C(O)OR^7$, $S(O)_pR^7$, $SO_2NHR^7$, $NR^7SO_2R^{7b}$, phenyl substituted with 0–2 $R^{10}$, and 5–6 membered aromatic heterocycle system containing from 1–4 heteroatoms selected from the group consisting of N, O, and S substituted with 0–2 $R^{10}$;

alternatively, $R^3$ and $R^4$ together form —$OCH_2O$—;

$R^5$ is selected from H, F, Cl, Br, and I;

alternatively, $R^4$ and $R^5$ together form —$OCH_2O$— or a fused benzo ring;

$R^6$ is selected from H, OH, $C_{1-3}$ alkoxy, —CN, F, Cl, Br, I, $NO_2$, $CF_3$, CHO, $C_{1-3}$ alkyl, and $C(O)NH_2$;

$R^7$ is selected from H and $C_{1-3}$ alkyl;

$R^{7a}$ is selected from H and $C_{1-3}$ alkyl;

$R^{7b}$ is $C_{1-3}$ alkyl;

$R^8$ is selected from H, $C_{1-6}$ alkyl substituted with 0–3 $R^{11}$, CH(—$OCH_2CH_2O$—), $C_{2-6}$ alkenyl, $C_{3-7}$ cycloalkyl substituted with 0–2 $R^9$, phenyl substituted with 0–2 $R^{10}$, and 5–6 membered aromatic heterocycle system containing from 1–4 heteroatoms selected from the group consisting of N, O, and S substituted with 0–2 $R^{10}$;

$R^9$ is selected from D, OH, $C_{1-3}$ alkoxy, $C_{1-3}$ alkyl, and F;

$R^{10}$ is selected from OH, $C_{1-3}$ alkyl, $C_{1-3}$ alkoxy, F, Cl, Br, I, CN, $NR^7R^{7a}$, and $C(O)CH_3$;

$R^{11}$ is selected from $OR^7$, CN, F, Cl, Br, I, $NO_2$, $NR^7R^{7a}$, CHO, $C(O)CH_3$, $C(O)NH_2$;

Q is selected from O, S and NH; and, p is selected from 0, 1, and 2.

[2] In a preferred embodiment, the present invention provides a novel compound of formula I, wherein:

$R^1$ is selected from $CF_3$, $CF_2H$, $C_2F_5$, $C_{1-3}$ alkyl, $C_{3-5}$ cycloalkyl; and, $R^8$ is selected from H, $C_{1-6}$ alkyl substituted with 0–3 $R^{11}$, CH(—OCH$_2$CH$_2$O—), $C_{2-6}$ alkenyl, $C_{3-5}$ cycloalkyl substituted with 0–1 $R^9$, phenyl substituted with 0–1 $R^{10}$, and 5–6 membered aromatic heterocycle system containing from 1–4 heteroatoms selected from the group consisting of N, O, and S substituted with 0–1 $R^{10}$.

[3] In a more preferred embodiment, the present invention provides a novel compound of formula I, wherein:

$R^1$ is selected from $CF_3$, $CF_2H$, $C_2F_5$, $C_2H_5$, isopropyl, cyclopropyl;

$R^3$ is selected from H, F, Cl, Br, I, $OCH_3$, $CH_3$;

$R^4$ is selected from H, F, Cl, Br, I, $C_{1-3}$ alkyl substituted with 0–3 $R^{11}$, $C_{2-3}$ alkenyl, $C_{2-3}$ alkynyl, $C_{1-3}$ alkoxy, $OCF_3$, —CN, $NO_2$, CHO, $C(O)CH_3$, $C(O)CF_3$, $C(O)NH_2$, $C(O)NHCH_3$, $NR^7R^{7a}$, $NR^7C(O)OR^{7a}$, $C(O)OR^7$, $S(O)_pR^7$, $SO_2NHR^7$, $NR^7SO_2R^{7b}$, phenyl, and 5–6 membered aromatic heterocycle system containing from 1–4 heteroatoms selected from the group consisting of N, O, and S;

alternatively, $R^3$ and $R^4$ together form —$OCH_2O$—;

$R^5$ is selected from H, F;

$R^6$ is selected from H, OH, $OCH_3$, —CN, F, $CF_3$, $CH_3$, and $C(O)NH_2$;

$R^7$ is selected from H and $CH_3$;

$R^{7a}$ is selected from H and $CH_3$;

$R^{7b}$ is $CH_3$;

$R^8$ is selected from H, $C_{1-4}$ alkyl substituted with 0–3 $R^{11}$, CH(—OCH$_2$CH$_2$O—), $C_{2-4}$ alkenyl, $C_{3-5}$ cycloalkyl substituted with 0–1 $R^9$, phenyl substituted with 0–1 $R^{10}$, and 5–6 membered aromatic heterocycle system containing from 1–4 heteroatoms selected from the group consisting of N, O, and S substituted with 0–1 $R^{10}$;

$R^9$ is selected from D, OH, $OCH_3$, $OH_3$, and F;

$R^{10}$ is selected from OH, $CH_3$, $OCH_3$, F, Cl, Br, I, CN, $NR^7R^{7a}$, and $C(O)CH_3$; and, p is selected from 1 and 2.

[4] In an even more preferred embodiment, the present invention provides a novel compound of formula I, wherein:

A is O;

$R^1$ is selected from $CF_3$, $CF_2H$, $C_2F_5$;

$R^2$ is selected from —$OCHR^7R^8$, —$OCH_2C\equiv C-R^8$, —$OCH_2C=C-R^8$, —$OCH_2CHR^7R^8$, —$C\equiv C-R^8$, —$CH=CR^7R^8$, —$CH_2CHR^7R^8$, —$CH_2C\equiv C-R^8$, $CHR^7CH=CHR^8$, and $CH=CHCHR^7R^8$;

$R^3$ is selected from H, F, Cl, Br, I;

$R^4$ is selected from H, F, Cl, Br, I, $C_{1-3}$ alkyl substituted with 0–3 $R^{11}$, $CH=CH_2$, $C\equiv CH$, $OCH_3$, $OCF_3$, —CN, $NO_2$, CHO, $C(O)CH_3$, $C(O)CF_3$, $C(O)NH_2$, $C(O)NHCH_3$, $NR^7R^{7a}$, $C(O)OR^7$, $NR^7SO_2R^{7b}$, and 5–6 membered aromatic heterocycle system containing from 1–4 heteroatoms selected from the group consisting of N, O, and S;

alternatively, $R^3$ and $R^4$ together form —$OCH_2O$—; and, $R^{11}$ is selected from OH, $OCH_3$, CN, F, Cl, $NR^7R^{7a}$, $C(O)CH_3$, and $C(O)NH_2$.

[5] In a further preferred embodiment, the compound of the present invention is selected from:

(+/−)-6-Chloro-4-(cyclopropylethynyl)-8-hydroxy-4-(trifluoromethyl)-1,4-dihydro-2H-3,1-benzoxazin-2-one;

(−)-6-Chloro-4-(cyclopropylethynyl)-8-hydroxy-4-(trifluoromethyl)-1,4-dihydro-2H-3,1-benzoxazin-2-one;

(+/−)-6-Chloro-4-(cyclopropylethynyl)-8-fluoro-4-(trifluoromethyl)-1,4-dihydro-2H-3,1-benzoxazin-2-one;

(+/−)-4-Clopropylethynyl-4-isopropyl-6-methyl-1,4-dihydro-2H-3,1-benzoxazin-2-one;

(+/−)-4-Isopropylethynyl-4-trifluoromethyl-6-methyl-1,4-dihydro-2H-3,1-benzoxazin-2-one;

(+/−)-6-Acetyl-4-cyclopropylethynyl-4-trifluoromethyl-1,4-dihydro-2H-3,1-benzoxazin-2-one;

(+/−)-5,6-Difluoro-4-(3-methyl)-1-buten-1-yl-4-trifluoromethyl-1,4-dihydro-2H-3,1-benzoxazin-2-one;

(+/−)-4-Isopropylethynyl-4-trifluoromethyl-5,6-difluoro-1,4-dihydro-2H-3,1-benzoxazin-2-one;

(+/−)-4-Cyclopropylethynyl-6-chloro-4-trifluoromethyl-7-aza-1,4-dihydro-2H-3,1-benzoxazin-2-one;

(+/−)-6-Chloro-4-(2-methoxyethoxy)-4-(trifluoromethyl)-1,4-dihydro-2H-3,1-benzoxazin-2-one;

(+/−)-6-Chloro-4-propylamino-4-(trifluoromethyl)-1,4-dihydro-2H-3,1-benzoxazin-2-one;

(+/−)-6-Chloro-4-(2-(furan-2-yl)ethynyl)-4-(trifluoromethyl)-1,4-dihydro-2H-3,1-benzoxazin-2-one;

(+/−)-4-(1-Butynyl)-6-methoxy-4-trifluoromethyl-1,4-dihydro-2H-3,1-benzoxazin-2-one;

(+/−)-4-(1'-Hydroxy)-cyclopropylethynyl-4-trifluoromethyl-6-chloro-1,4-dihydro-2H-3,1-benzoxazin-2-one;

(+/−)-4-Isopropylethynyl-4-trifluoromethyl-5-fluoro-1,4-dihydro-2H-3,1-benzoxazin-2-one;

(+/−)-6-Chloro-4-(1-deuterocycloprop-1-ylethynyl)-4-(trifluoromethyl)-1,4-dihydro-2H-3,1-benzoxazin-2-one; and, (+/−)-4-Isopropylethynyl-4-trifluoromethyl-5-fluoro-1,4-dihydro-2H-3,1-benzoxazin-2-one.

[6] In a second embodiment, the present invention provides a novel compound of formula II:

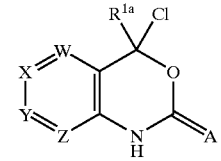

II or a salt or stereoisomer thereof, wherein:

A is O or S;

W is N or $CR^3$;

X is N or $CR^4$;

Y is N or $CR^5$;

Z is N or $CR^6$;

provided that if two of W, X, Y, and Z are N, then the remaining are other than N;

$R^{1a}$ is selected from $CF_3$, $CF_2H$, $C_2F_5$, $C_{1-4}$ alkyl, $C_{3-5}$ cycloalkyl, $C_{2-4}$ alkenyl, and $C_{2-4}$ alkynyl;

$R^3$ is selected from H, F, Cl, Br, I, $C_{1-3}$ alkoxy, and $C_{1-3}$ alkyl;

$R^4$ is selected from H, F, Cl, Br, I, $C_{1-3}$ alkyl substituted with 0–3 $R^{11}$, $C_{2-3}$ alkenyl, $C_{2-3}$ alkynyl, $C_{1-3}$ alkoxy, $OCF_3$, —CN, $NO_2$, CHO, $C(O)CH_3$, $C(O)CF_3$, $C(O)NH_2$, $C(O)NHCH_3$, $NR^7R^{7a}$, $NR^7C(O)OR^{7a}$, $C(O)OR^7$, $S(O)_pR^7$, $SO_2NHR^7$, $NR^7SO_2R^{7b}$, phenyl substituted with 0–2 $R^{10}$, and 5–6 membered aromatic heterocycle system containing from 1–4 heteroatoms selected from the group consisting of N, O, and S substituted with 0–2 $R^{10}$;

alternatively, $R^3$ and $R^4$ together form —$OCH_2O$—;

$R^5$ is selected from H, F, Cl, Br, and I;

alternatively, $R^4$ and $R^5$ together form —$OCH_2O$— or a fused benzo ring;

$R^6$ is selected from H, OH, $C_{1-3}$ alkoxy, —CN, F, Cl, Br, I, $NO_2$, $CF_3$, CHO, $C_{1-3}$ alkyl, and $C(O)NH_2$;

$R^7$ is selected from H and $C_{1-3}$ alkyl;

$R^{7a}$ is selected from H and $C_{1-3}$ alkyl;

$R^{7b}$ is $C_{1-3}$ alkyl;

$R^{10}$ is selected from OH, $C_{1-3}$ alkyl, $C_{1-3}$ alkoxy, F, Cl, Br, I, CN, $NR^7R^{7a}$, and $C(O)CH_3$;

$R^{11}$ is selected from $OR^7$, CN, F, Cl, Br, I, $NO_2$, $NR^7R^{7a}$, CHO, $C(O)CH_3$, $C(O)NH_2$;

p is selected from 0, 1, and 2.

[7] In a another preferred embodiment, the present invention provides a novel compound of formula II, wherein:

A is O; and, $R^{1a}$ is selected from $CF_3$, $CF_2H$, $C_2F_5$, $C_{1-3}$ alkyl, $C_{3-5}$ cycloalkyl.

[8] In a more preferred embodiment, the present invention provides a novel compound of formula II, wherein:

$R^{1a}$ is selected from $CF_3$, $CF_2H$, $C_2F_5$, $C_2H_5$, isopropyl, cyclopropyl;

$R^3$ is selected from H, F, Cl, Br, I, $OCH_3$, $CH_3$;

$R^4$ is selected from H, F, Cl, Br, I, $C_{1-3}$ alkyl substituted with 0–3 $R^{11}$, $C_{2-3}$ alkenyl, $C_{2-3}$ alkynyl, $C_{1-3}$ alkoxy, $OCF_3$, —CN, $NO_2$, CHO, $C(O)CH_3$, $C(O)CF_3$, $C(O)NH_2$, $C(O)NHCH_3$, $NR^7R^{7a}$, $NR^7C(O)OR^{7a}$, $C(O)OR^7$, $S(O)_pR^7$, $SO_2NHR^7$, $NR^7SO_2R^{7b}$, phenyl, and 5–6 membered aromatic heterocycle system containing from 1–4 heteroatoms selected from the group consisting of N, O, and S;

alternatively, $R^3$ and $R^4$ together form —$OCH_2O$—;

$R^5$ is selected from H, F;

$R^6$ is selected from H, OH, $OCH_3$, —CN, F, $CF_3$, $CH_3$, and $C(O)NH_2$;

$R^7$ is selected from H and $CH_3$;

$R^{7a}$ is selected from H and $CH_3$;

$R^{7b}$ is $CH_3$;

$R^{10}$ is selected from OH, $CH_3$, $OCH_3$, F, Cl, Br, I, CN, $NR^7R^{7a}$, and $C(O)CH_3$; and, p is selected from 1 and 2.

[9] In an even more preferred embodiment, the present invention provides a novel compound of formula II, wherein:

$R^{1a}$ is selected from $CF_3$, $CF_2H$, $C_2F_5$;

$R^3$ is selected from H, F, Cl, Br, I;

$R^4$ is selected from H, F, Cl, Br, I, $C_{1-3}$ alkyl substituted with 0–3 $R^{11}$, $CH=CH_2$, $C\equiv CH$, $OCH_3$, $OCF_3$, —CN, $NO_2$, CHO, $C(O)CH_3$, $C(O)CF_3$, $C(O)NH_2$, $C(O)NHCH_3$, $NR^7R^{7a}$, $C(O)OR^7$, $NR^7SO_2R^{7b}$, and 5–6 membered aromatic heterocycle system containing from 1–4 heteroatoms selected from the group consisting of N, O, and S;

alternatively, $R^3$ and $R^4$ together form —$OCH_2O$—; and, $R^{11}$ is selected from OH, $OCH_3$, CN, F, Cl, $NR^7R^{7a}$, $C(O)CH_3$, and $C(O)NH_2$.

[10] In a third embodiment, the present invention provides a novel process for making a compound of formula II:

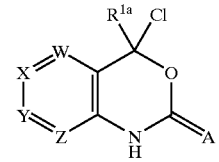

II or a salt or stereoisomer thereof, comprising:

(a) contacting a compound of formula III:

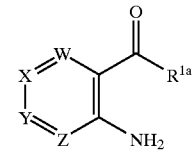

III or a suitable salt form thereof, with a carbonyl or thiocarbonyl delivering agent in the presence of a suitable solvent, wherein:

A is O or S;

W is N or $CR^3$;

X is N or $CR^4$;

Y is N or $CR^5$;

Z is N or $CR^6$;

provided that if two of W, X, Y, and Z are N, then the remaining are other than N;

$R^{1a}$ is selected from $CF_3$, $CF_2H$, $C_2F_5$, $C_{1-4}$ alkyl, $C_{3-5}$ cycloalkyl, $C_{2-4}$ alkenyl, and $C_{2-4}$ alkynyl;

$R^3$ is selected from H, F, Cl, Br, I, $C_{1-3}$ alkoxy, and $C_{1-3}$ alkyl;

$R^4$ is selected from H, F, Cl, Br, I, $C_{1-3}$ alkyl substituted with 0–3 $R^{11}$, $C_{2-3}$ alkenyl, $C_{2-3}$ alkynyl, $C_{1-3}$ alkoxy, $OCF_3$, —CN, $NO_2$, CHO, $C(O)CH_3$, $C(O)CF_3$, $C(O)NH_2$, $C(O)NHCH_3$, $NR^7R^{7a}$, $NR^7C(O)OR^{7a}$, $C(O)OR^7$, $S(O)_pR^7$, $SO_2NHR^7$, $NR^7SO_2R^{7b}$, phenyl substituted with 0–2 $R^{10}$, and 5–6 membered aromatic heterocycle system containing from 1–4 heteroatoms selected from the group consisting of N, O, and S substituted with 0–2 $R^{10}$;

alternatively, $R^3$ and $R^4$ together form —$OCH_2$—;

$R^5$ is selected from H, F, Cl, Br, and I;

alternatively, $R^4$ and $R^5$ together form —$OCH_2O$— or a fused benzo ring;

$R^6$ is selected from H, OH, $C_{1-3}$ alkoxy, —CN, F, Cl, Br, I, $NO_2$, $CF_3$, CHO, $C_{1-3}$ alkyl, and $C(O)NH_2$;

$R^7$ is selected from H and $C_{1-3}$ alkyl;

$R^{7a}$ is selected from H and $C_{1-3}$ alkyl;

$R^{7b}$ is $C_{1-3}$ alkyl;

$R^{10}$ is selected from OH, $C_{1-3}$ alkyl, $C_{1-3}$ alkoxy, F, Cl, Br, I, CN, $NR^7R^{7a}$, and $C(O) CH_3$;

$R^{11}$ is selected from $OR^7$, CN, F, Cl, Br, I, $NO_2$, $NR^7R^{7a}$, CHO, $C(O)CH_3$, $C(O)NH_2$;

Q is selected from O, S and NH; and, p is selected from 0, 1, and 2.

[11] In another preferred embodiment, in formulae II and III,

A is O;

$R^{1a}$ is selected from $CF_3$, $CF_2H$, $C_2F_5$;

$R^3$ is selected from H, F, Cl, Br, I;

$R^4$ is selected from H, F, Cl, Br, I, $C_{1-3}$ alkyl substituted with 0–3 $R^{11}$, $CH=CH_2$, $C\equiv CH$, $OCH_3$, $OCF_3$, —CN, $NO_2$, CHO, $C(O)CH_3$, $C(O)CF_3$, $C(O)NH_2$, $C(O)NHCH_3$, $NR^7R^{7a}$, $C(O)OR^7$, $NR^7SO_2R^{7b}$, and 5–6 membered aromatic heterocycle system containing from 1–4 heteroatoms selected from the group consisting of N, O, and S;

alternatively, $R^3$ and $R^4$ together form —$OCH_2O$—; and, $R^5$ is selected from H, F;

$R^6$ is selected from H, OH, $OCH_3$, —CN, F, $CF_3$, $CH_3$, and $C(O)NH_2$;

$R^7$ is selected from H and $CH_3$;

$R^{7a}$ is selected from H and $CH_3$;

$R^{7b}$ is $CH_3$;

$R^{10}$ is selected from OH, $CH_3$, $OCH_3$, F, Cl, Br, I, CN, $NR^7R^{7a}$, and $C(O)CH_3$;

$R^{11}$ is selected from OH, $OCH_3$, CN, F, Cl, $NR^7R^{7a}$, $C(O)CH_3$, and $C(O)NH_2$; and, p is selected from 1 and 2.

[12] In another more preferred embodiment, the carbonyl delivering agent is selected from phosgene, carbonyldiimidazole, chloromethylcarbonate, chloroethylcarbonate, dimethylcarbonate, diethylcarbonate, and di-t-butylcarbonate.

[13] In another even more preferred embodiment, the carbonyl delivering agent is phosgene and the solvent is toluene.

[14] In another more preferred embodiment, in step (a) a base is present and is selected from trimethylamine, triethylamine, and N,N-disopropylethylamine.

[15] In a fourth embodiment, the present invention provides of process for making a compound of formula Ia:

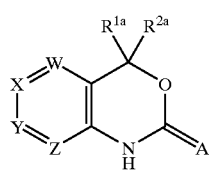

Ia or a stereoisomer or pharmaceutically acceptable salt form thereof, comprising:

(a) contacting a nucleophile, $R^{2b}$, with a compound of formula II:

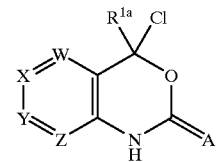

II or stereoisomer thereof in a suitable solvent, wherein:

$R^{2b}$ is selected from $R^8R^7CH$—OH, $R^8R^7CH$—OM, $R^8R^7CHNH_2$, $R^8R^7CHNH$—M, $R^8$—$C\equiv C$—M, $R^7R^8C=CH$—M, $R^8R^7CH(CH_2)_p$—M, $R^8CH=CHC(H)(R^7)$—M, $R^8R^7CHCH=CH$—M;

M is selected from Na, Li, Mg, Zn, Cu, Pd, Pt, Sn, Al, and B;

A is O or S;

W is N or $CR^3$;

X is N or $CR^4$;

Y is N or $CR^5$;

Z is N or $CR^6$;

provided that if two of W, X, Y, and Z are N, then the remaining are other than N;

$R^{1a}$ is selected from $CF_3$, $CH_2H$, $C_2F_5$, $C_{1-4}$ alkyl $C_{3-5}$ cycloalkyl, $C_{2-4}$ alkenyl, and $C_{2-4}$ alkynyl;

$R^{2a}$ is selected from —$QCHR^7R^8$, —$QCHR^7C\equiv C$—$R^8$, —$QCHR^7C=C$—$R^8$, —$Q(CH_2)_pCHR^7R^8$, —$C\equiv C$—$R^8$, —$CH=CR^7R^8$, —$(CH_2)_pCHR^7R^8$, —$CHR^7C\equiv C$—$R^8$, —$CHR^7CH=CHR^8$, and $CH=CHCHR^7R^8$;

$R^3$ is selected from H, F, Cl, Br, I, $C_{1-3}$ alkoxy, and $C_{1-3}$ alkyl;

$R^4$ is selected from H, F, Cl, Br, I, $C_{1-3}$ alkyl substituted with 0–3 $R^{11}$, $C_{2-3}$ alkenyl, $C_{2-3}$ alkynyl, $C_{1-3}$ alkoxy, $OCF_3$, —CN, $NO_2$, CHO, $C(O)CH_3$, $C(O)CF_3$, $C(O)NH_2$, $C(O)NHCH_3$, $NR^7R^{7a}$, $NR^7C(O)OR^{7a}$, $C(O)OR^7$, $S(O)_pR^7$, $SO_2NHR^7$, $NR^7SO_2R^{7b}$, phenyl substituted with 0–2 $R^{10}$, and 5–6 membered aromatic heterocycle system containing from 1–4 heteroatoms selected from the group consisting of N, O, and S substituted with 0–2 $R^{10}$;

alternatively, $R^3$ and $R^4$ together form —$OCH_2O$—;

$R^5$ is selected from H, F, Cl, Br, and I;

alternatively, $R^4$ and $R^5$ together form —$OCH_2O$— or a fused benzo ring;

$R^6$ is selected from H, OH, $C_{1-3}$ alkoxy, —CN, F, Cl, Br, I, $NO_2$, $CF_3$, CHO, $C_{1-3}$ alkyl, and $C(O)NH_2$;

$R^7$ is selected from H and $C_{1-3}$ alkyl;

$R^{7a}$ is selected from H and $C_{1-3}$ alkyl;

$R^{7b}$ is $C_{1-3}$ alkyl;

$R^8$ is selected from H, $C_{1-6}$ alkyl substituted with 0–3 $R^{11}$, $CH(-OCH_2CH_2O-)$, $C_{2-6}$ alkenyl, $C_{3-7}$ cycloalkyl substituted with 0–2 $R^9$, phenyl substituted with 0–2 $R^{10}$, and 5–6 membered aromatic heterocycle system containing from 1–4 heteroatoms selected from the group consisting of N, O, and S substituted with 0–2 $R^{10}$;

$R^9$ is selected from D, OH, $C_{1-3}$ alkoxy, $C_{1-3}$ alkyl, and F;

$R^{10}$ is selected from OH, $C_{1-3}$ alkyl, $C_{1-3}$ alkoxy, F, Cl, Br, I, CN, $NR^7R^{7a}$, and $C(O)CH_3$;

$R^{11}$ is selected from $OR^7$, CN, F, Cl, Br, I, $NO_2$, $NR^7R^{7a}$, CHO, $C(O)CH_3$, $C(O)NH_2$;

Q is selected from O, S and NH; and, p is selected from 0, 1, and 2.

[16] In another preferred embodiment, in formulae Ia and II,

A is O;

$R^{1a}$ is selected from $CF_3$, $CF_2H$, $C_2F_5$;

$R^{2a}$ is selected from $—OCHR^7R^8$, $—OCH_2C{\equiv}C—R^8$, $—OCH_2CH{=}C—R^8$, $—OCH_2CHR^7R^8$, $—C{\equiv}C—R^8$, $—CH{=}CR^7R^8$, $—CH_2CHR^7R^8$, $—CH_2C{\equiv}C—R^8$, $CHR^7CH{=}CHR^8$, and $CH{=}CHCHR^7R^8$;

$R^3$ is selected from H, F, Cl, Br, I;

$R^4$ is selected from H, F, Cl, Br, I, $C_{1-3}$ alkyl substituted with 0–3 $R^{11}$, $CH{=}CH_2$, $C{\equiv}CH$, $OCH_3$, $OCF_3$, —CN, $NO_2$, CHO, $C(O)CH_3$, $C(O)CF_3$, $C(O)NH_2$, $C(O)NHCH_3$, $NR^7R^{7a}$, $C(O)OR^7$, $NR^7SO_2R^{7b}$, and 5–6 membered aromatic heterocycle system containing from 1–4 heteroatoms selected from the group consisting of N, O, and S;

alternatively, $R^3$ and $R^4$ together form $—OCH_2O—$; and, $R^5$ is selected from H, F;

$R^6$ is selected from H, OH, $OCH_3$, —CN, F, $CF_3$, $CH_3$, and $C(O)NH_2$;

$R^7$ is selected from H and $CH_3$;

$R^{7a}$ is selected from H and $CH_3$;

$R^{7b}$ is $CH_3$;

$R^8$ is selected from H, $C_{1-4}$ alkyl substituted with 0–3 $R^{11}$, $CH(—OCH_2CH_2O—)$, $C_{2-4}$ alkenyl, $C_{3-5}$ cycloalkyl substituted with 0–1 $R^9$, phenyl substituted with 0–1 $R^{10}$, and 5–6 membered aromatic heterocycle system containing from 1–4 heteroatoms selected from the group consisting of N, O, and S substituted with 0–1 $R^{10}$;

$R^9$ is selected from D, OH, $OCH_3$, $CH_3$, and F;

$R^{10}$ is selected from OH, $CH_3$, $OCH_3$, F, Cl, Br, I, CN, $NR^7R^{7a}$, and $C(O)CH_3$;

$R^{11}$ is selected from OH, $OCH_3$, CN, F, Cl, $NR^7R^{7a}$, $C(O)CH_3$, and $C(O)NH_2$; and, p is selected from 1 and 2.

[17] In another more preferred embodiment, in step (a), the compound of formula II is added to a solution containing the nucleophile.

[18] In another more preferred embodiment, in step (a), $R^{2b}$ is $R^8—C{\equiv}C—M$; and M is selected from Li, Mg, and Zn.

[19] In another even more preferred embodiment, in step (a), $R^8—C{\equiv}C—M$ is formed in situ by addition of a strong base to a solution containing $R^8—C{\equiv}C—H$.

[20] In another further preferred embodiment, in step (a), the strong base is selected from n-butyl lithium, s-butyl lithium, t-butyl lithium, phenyl lithium, and methyl lithium.

[21] In another further preferred embodiment, the compound of formula Ia is:

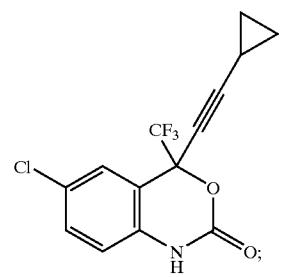

the compound of formula Ia is:

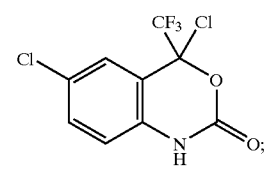

the nucleophile $R^{2b}$ is lithium cyclopropylacetylide; and, the solvent is THF.

[22] In a fifth embodiment, the present invention provides a novel method of making a compound of formula IIIb:

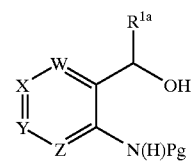

IIIb or stereoisomer or salt form thereof, comprising:

(a) contacting a compound of formula IIIa:

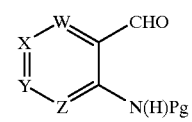

IIIa with $R^{1a}$-TMS and an anion, wherein:

the anion is a fluoride or oxyanion and is selected from tetrabutylammonium fluoride, sodium fluoride, potassium fluoride, lithium fluoride, cesium fluoride, potassium tert-butoxide, sodium methoxide, sodium ethoxide and sodium trimethylsilanolate;

Pg is an amine protecting group;

W is N or $CR^3$;

X is N or $CR^4$;

Y is N or $CR^5$;

Z is N or $CR^6$;

provided that if two of W, X, Y, and Z are N, then the remaining are other than N;

$R^{1a}$ is selected from $CF_3$, $CF_3CF_2$, and $CF_3CF_2CF_2$;

$R^3$ is selected from H, F, Cl, Br, I, $C_{1-3}$ alkoxy, and $C_{1-3}$ alkyl;

$R^4$ is selected from H, F, Cl, Br, I, $C_{1-3}$ alkyl substituted with 0–3 $R^{11}$, $C_{2-3}$ alkenyl, $C_{2-3}$ alkynyl, $C_{1-3}$ alkoxy, $OCF_3$, —CN, $NO_2$, CHO, $C(O)CH_3$, $C(O)CF_3$, $C(O)NH_2$, $C(O)NHCH_3$, $NR^7R^{7a}$, $NR^7C(O)OR^{7a}$, $C(O)OR^7$, $S(O)_pR^7$, $SO_2NHR^7$, $NR^7SO_2R^{7b}$, phenyl substituted with 0–2 $R^{10}$, and 5–6 membered aromatic heterocycle system containing from 1–4 heteroatoms selected from the group consisting of N, O, and S substituted with 0–2 $R^{10}$;

alternatively, $R^3$ and $R^4$ together form —$OCH_2O$—;

$R^5$ is selected from H, F, Cl, Br, and I;

alternatively, $R^4$ and $R^5$ together form —$OCH_2O$— or a fused benzo ring;

$R^6$ is selected from H, OH, $C_{1-3}$ alkoxy, —CN, F, Cl, Br, I, $NO_2$, $CF_3$, CHO, $C_{1-3}$ alkyl, and $C(O)NH_2$;

$R^7$ is selected from H and $C_{1-3}$ alkyl;

$R^{7a}$ is selected from H and $C_{1-3}$ alkyl;

$R^{7b}$ is $C_{1-3}$ alkyl;

$R^{10}$ is selected from OH, $C_{1-3}$ alkyl, $C_{1-3}$ alkoxy, F, Cl, Br, I, CN, $NR^7R^{7a}$, and $C(O)CH_3$;

$R^{11}$ is selected from $OR^7$, CN, F, Cl, Br, I, $NO_2$, $NR^7R^{7a}$, CHO, $C(O)CH_3$, $C(O)NH_2$;

p is selected from 0, 1, and 2.

[23] In another preferred embodiment, in formulae IIIa and IIIb, the $R^{1a}$-TMS is trifluoromethyl trimethylsilane;

the anion is tetrabutylammonium fluoride;

Pg is trityl;

$R^{1a}$ is $CF_3$;

$R^3$ is selected from H, F, Cl, Br, I;

$R^4$ is selected from H, F, Cl, Br, I, $C_{1-3}$ alkyl substituted with 0–3 $R^{11}$, $CH=CH_2$, $C\equiv CH$, $OCH_3$, $OCF_3$, —CN, $NO_2$, CHO, $C(O)CH_3$, $C(O)CF_3$, $C(O)NH_2$, $C(O)NHCH_3$, $NR^7R^{7a}$, $C(O)OR^7$, $NR^7SO_2R^{7b}$, and 5–6 membered aromatic heterocycle system containing from 1–4 heteroatoms selected from the group consisting of N, O, and S;

alternatively, $R^3$ and $R^4$ together form —$OCH_2O$—; and, $R^5$ is selected from H, F;

$R^6$ is selected from H, OH, $OCH_3$, —CN, F, $CF_3$, $CH_3$, and $C(O)NH_2$;

$R^7$ is selected from H and $CH_3$;

$R^{7a}$ is selected from H and $CH_3$;

$R^{7b}$ is $CH_3$;

$R^{10}$ is selected from OH, $CH_3$, $OCH_3$, F, Cl, Br, I, CN, $NR^7R^{7a}$, and $C(O)CH_3$;

$R^{11}$ is selected from OH, $OCH_3$, CN, F, Cl, $NR^7R^{7a}$, $C(O)CH_3$, and $C(O)NH_2$; and, p is selected from 1 and 2.

[24] In another more preferred embodiment, the process further comprises:

(b) contacting a compound of formula IIIb with an oxidizing agent to form compound of formula IIIc:

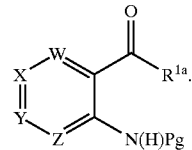

IIIc

[25] In another even more preferred embodiment, the oxidizing agent is $MnO_2$.

In a fifth embodiment, the present invention provides a novel pharmaceutical composition comprising a pharmaceutically acceptable carrier and a therapeutically effective amount of a compound of formula I or pharmaceutically acceptable salt form thereof.

In a sixth embodiment, the present invention provides a novel method for treating HIV infection which comprises administering to a host in need of such treatment a therapeutically effective amount of a compound of formula I or pharmaceutically acceptable salt form thereof.

In a seventh embodiment, the present invention provides a novel method of treating HIV infection which comprises administering, in combination, to a host in need thereof a therapeutically effective amount of:

(a) a compound of formula I; and, (b) at least one compound selected from the group consisting of HIV reverse transcriptase inhibitors and HIV protease inhibitors.

In another preferred embodiment, the reverse transcriptase inhibitor is a nucleoside reverse transcriptase inhibitor.

In another more preferred embodiment, the nucleoside reverse transcriptase inhibitor is selected from AZT, 3TC, rescriptor, ddI, ddC, and d4T and the protease inhibitor is selected from saquinavir, ritonavir, indinavir, VX-478, nelfinavir, KNI-272, CGP-61755, and U-103017.

In an even more preferred embodiment, the nucleoside reverse transcriptase inhibitor is selected from AZT, rescriptor, and 3TC and the protease inhibitor is selected from saquinavir, ritonavir, indinavir, and nelfinavir.

In a still further preferred ebodiment, the nucleoside reverse transcriptase inhibitor is AZT.

In another still further preferred embodiment, the protease inhibitor is indinavir.

In a eighth embodiment, the present invention provides a pharmaceutical kit useful for the treatment of HIV infection, which comprises a therapeutically effective amount of:

(a) a compound of formula I; and, (b) at least one compound selected from the group consisting of HIV reverse transcriptase inhibitors and HIV protease inhibitors, in one or more sterile containers.

In a ninth embodiment, the present invention provides a novel method of inhibiting HIV present in a body fluid sample which comprises treating the body fluid sample with an effective amount of a compound of formula I.

In a tenth embodiment, the present invention to provides a novel a kit or container comprising a compound of formula (I) in an amount effective for use as a standard or reagent in a test or assay for determining the ability of a potential pharmaceutical to inhibit HIV reverse transcriptase, HIV growth, or both.

Definitions

As used herein, the following terms and expressions have the indicated meanings. It will be appreciated that the compounds of the present invention contain an asymmetrically substituted carbon atom, and may be isolated in optically active or racemic forms. It is well known in the art how to prepare optically active forms, such as by resolution of racemic forms or by synthesis, from optically active starting materials. All chiral, diastereomeric, racemic forms and all geometric isomeric forms of a structure are intended, unless the specific stereochemistry or isomer form is specifically indicated.

The processes of the present invention are contemplated to be practiced on at least a multigram scale, kilogram scale, multikilogram scale, or industrial scale. Multigram scale, as used herein, is preferably the scale wherein at least one starting material is present in 10 grams or more, more preferably at least 50 grams or more, even more preferably at least 100 grams or more. Multikilogram scale, as used herein, is intended to mean the scale wherein more than one kilogram of at least one starting material is used. Industrial scale as used herein is intended to mean a scale which is other than a laboratory scale and which is sufficient to supply product sufficient for either clinical tests or distribution to consumers.

The reactions of the synthetic methods claimed herein may be, as noted herein, carried out in the presence of a suitable base, said suitable base being any of a variety of bases, the presence of which in the reaction facilitates the synthesis of the desired product. Suitable bases may be selected by one of skill in the art of organic synthesis. Suitable bases include, but are not intended to be limited to, inorganic bases such as alkali metal, alkali earth metal, thallium, and ammonium hydroxides, alkoxides, phosphates, and carbonates, such as sodium hydroxide, potassium hydroxide, sodium carbonate, potassium carbonate, cesium carbonate, thallium hydroxide, thallium carbonate, tetra-n-butylammonium carbonate, and ammonium hydroxide. Suitable bases also include organic bases, including but not limited to aromatic and aliphatic amines, such as pyridine; trialkyl amines such as triethylamine, N,N-diisopropylethylamine, N,N-diethylcyclohexylamine, N,N-dimethylcyclohexylamine, N,N,N'-triethylenediamine, N,N-dimethyloctylamine; 1,5-diazabicyclo[4.3.0]non-5-ene (DBN); 1,4-diazabicyclo[2.2.2]octane (DABCO); 1,8-diazabicyclo[5.4.0]undec-7-ene (DBU); tetramethylethylenediamine (TMEDA); and substituted pyridines such as N,N-dimethylaminopyridine (DMAP), 4-pyrrolidinopyridine, 4-piperidinopyridine.

Suitable halogenated solvents include: carbon tetrachloride, bromodichloromethane, dibromochloromethane, bromoform, chloroform, bromochloromethane, dibromomethane, butyl chloride, dichloromethane, tetrachloroethylene, trichloroethylene, 1,1,1-trichloroethane, 1,1,2-trichloroethane, 1,1-dichloroethane, 2-chloropropane, hexafluorobenzene, 1,2,4-trichlorobenzene, o-dichlorobenzene, chlorobenzene, or fluorobenzene.

Suitable ether solvents include, but are not intended to be limited to, dimethoxymethane, tetrahydrofuran, 1,3-dioxane, 1,4-dioxane, furan, diethyl ether, ethylene glycol dimethyl ether, ethylene glycol diethyl ether, diethylene glycol dimethyl ether, diethylene glycol diethyl ether, triethylene glycol dimethyl ether, or t-butyl methyl ether.

Suitable protic solvents may include, by way of example and without limitation, water, methanol, ethanol, 2-nitroethanol, 2-fluoroethanol, 2,2,2-trifluoroethanol, ethylene glycol, 1-propanol, 2-propanol, 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, anisole, benzyl alcohol, phenol, or glycerol.

Suitable aprotic solvents may include, by way of example and without limitation, tetrahydrofuran (THF), dimethylformamide (DMF), dimethylacetamide (DMAC), 1,3-dimethyl-3,4,5,6-tetrahydro-2(1H)-pyrimidinone (DMPU), 1,3-dimethyl-2-imidazolidinone (DMI), N-methylpyrrolidinone (NMP), formamide, N-methylacetamide, N-methylformamide, acetonitrile, dimethyl sulfoxide, propionitrile, ethyl formate, methyl acetate, hexachloroacetone, acetone, ethyl methyl ketone, ethyl acetate, sulfolane, N,N-dimethylpropionamide, tetramethylurea, nitromethane, nitrobenzene, or hexamethylphosphoramide.

Suitable hydrocarbon solvents include, but are not intended to be limited to, benzene, cyclohexane, pentane, hexane, toluene, cycloheptane, methylcyclohexane, heptane, ethylbenzene, m-, o-, or p-xylene, octane, indane, nonane, or naphthalene.

As used herein, the term "amine protecting group" (or "N-protected") refers to any group known in the art of organic synthesis for the protection of amine groups. As used herein, the term "amine protecting group reagent" refers to any reagent known in the art of organic synthesis for the protection of amine groups which may be reacted with an amine to provide an amine protected with an amine protecting group. Such amine protecting groups include those listed in Greene and Wuts, "Protective Groups in Organic Synthesis" John Wiley & Sons, New York (1991) and "The Peptides: Analysis, Synthesis, Biology, Vol. 3, Academic Press, New York (1981), the disclosure of which is hereby incorporated by reference. Examples of amine protecting groups include, but are not limited to, the following: 1) acyl types such as formyl, trifluoroacetyl, phthalyl, and p-toluenesulfonyl; 2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); 3) aliphatic carbamate types such as tert-butyloxycarbonyl (Boc), ethoxycarbonyl, diisopropylmethoxycarbonyl, and allyloxycarbonyl; 4) cyclic alkyl carbamate types such as cyclopentyloxycarbonyl and adamantyloxycarbonyl; 5) alkyl types such as triphenylmethyl (trityl) and benzyl; 6) trialkylsilane such as trimethylsilane; and 7) thiol containing types such as phenylthiocarbonyl and dithiasuccinoyl.

Amine protecting groups may include, but are not limited to the following: 2,7-di-t-butyl-[9-(10,10-dioxo-10,10,10, 10-tetrahydrothio-xanthyl)]methyloxycarbonyl; 2-trimethylsilylethyloxycarbonyl; 2-phenylethyloxycarbonyl; 1,1-dimethyl-2,2-dibromoethyloxycarbonyl; 1-methyl-1-(4-biphenylyl) ethyloxycarbonyl; benzyloxycarbonyl; p-nitrobenzyloxycarbonyl; 2-(p-toluenesulfonyl) ethyloxycarbonyl; m-chloro-p-acyloxybenzyloxycarbonyl; 5-benzyisoxazolylmethyloxycarbonyl; p-(dihydroxyboryl) benzyloxycarbonyl; m-nitrophenyloxycarbonyl; o-nitrobenzyloxycarbonyl; 3,5-dimethoxybenzyloxycarbonyl; 3,4-dimethoxy-6-nitrobenzyloxycarbonyl; N'-p-toluenesulfonylaminocarbonyl; t-amyloxycarbonyl; p-decyloxybenzyloxycarbonyl; diisopropylmethyloxycarbonyl; 2,2-dimethoxycarbonylvinyloxycarbonyl; di(2-pyridyl)methyloxycarbonyl; 2-furanylmethyloxycarbonyl; phthalimide; dithiasuccinimide; 2,5-dimethylpyrrole; benzyl; 5-dibenzylsuberyl; triphenylmethyl; benzylidene; diphenylmethylene; or methanesulfonamide.

As used herein, "alkyl" is intended to include both branched and straight-chain saturated aliphatic hydrocarbon groups having the specified number of carbon atoms. Examples of alkyl include, but are not limited to, methyl, ethyl, n-propyl, i-propyl, n-butyl, s-butyl, t-butyl, n-pentyl, and s-pentyl. "Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, and pentachloroethyl. "Alkoxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. "Cycloalkyl" is intended to include saturated ring groups, such as cyclopropyl, cyclobutyl, or cyclopentyl. "Alkenyl" is intended to include hydrocarbon chains of either a straight or branched configuration and one or more unsaturated carbon-carbon bonds which may occur in any stable point along the chain, such as ethenyl, propenyl and the like. "Alkynyl" is intended to include hydrocarbon chains of either a straight or branched configuration and one or more triple carbon-carbon bonds which may occur in any stable point along the chain, such as ethynyl, propynyl and the like.

"Halo" or "halogen" as used herein refers to fluoro, chloro, bromo and iodo. "Counterion" is used to represent a small, negatively charged species such as chloride, bromide, hydroxide, acetate, sulfate and the like.

As used herein, "aryl" or "aromatic residue" is intended to mean an aromatic moiety containing the specified number of carbon atoms, such as phenyl or naphthyl. As used herein, "carbocycle" or "carbocyclic residue" is intended to mean any stable 3- to 7-membered monocyclic or bicyclic which may be saturated, partially unsaturated, or aromatic. Examples of such carbocyles include, but are not limited to, cyclopropyl, cyclopentyl, cyclohexyl, phenyl, biphenyl, naphthyl, indanyl, adamantyl, or tetrahydronaphthyl (tetralin).

As used herein, the term "heterocycle" or "heterocyclic system" is intended to mean a stable 5- to 6-membered monocyclic heterocyclic ring which is saturated partially unsaturated or unsaturated (aromatic), and which consists of carbon atoms and from 1 to 3 heteroatoms independently selected from the group consisting of N, O and S. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic system" is intended to mean a stable 5- to 6-membered monocyclic heterocyclic aromatic ring which consists of carbon atoms and from 1 to 3 heterotams independently selected from the group consisting of N, O and S. It is preferred that the total number of S and O atoms in the aromatic heterocycle is not more than 1.

Examples of heterocycles include, but are not limited to, 2-pyrrolidonyl, 2H-pyrrolyl, 4-piperidonyl, 6H-1,2,5-thiadiazinyl, 2H,6H-1,5,2-dithiazinyl, furanyl, furazanyl, imidazolidinyl, imidazolinyl, imidazolyl, isoxazolyl, morpholinyl, oxadiazolyl, 1,2,3-oxadiazolyl, 1,2,4-oxadiazolyl, 1,2,5-oxadiazolyl, 1,3,4-oxadiazolyl, oxazolidinyl., oxazolyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridinyl, pyridyl, pyrimidinyl, pyrrolidinyl, pyrrolinyl, pyrrolyl, tetrahydrofuranyl, 6H-1,2,5-thiadiazinyl, 1,2,3-thiadiazolyl, 1,2,4-thiadiazolyl, 1,2,5-thiadiazolyl, 1,3,4-thiadiazolyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, and 1,3,4-triazolyl. Preferred heterocycles include, but are not limited to, pyridinyl, furanyl, thienyl, pyrrolyl, pyrazolyl, imidazolyl, and oxazolidinyl. Also included are fused ring and spiro compounds containing, for example, the above heterocycles.

As used herein, "HIV reverse transcriptase inhibitor" is intended to refer to both nucleoside and non-nucleoside inhibitors of HIV reverse transcriptase (RT). Examples of nucleoside RT inhibitors include, but are not limited to, AZT, ddC, ddI, d4T, and 3TC. Examples of non-nucleoside RT inhibitors include, but are not limited to, rescriptor (delavirdine, Pharmacia and Upjohn), viviradine (Pharmacia and Upjohn U90152S), TIBO derivatives, BI-RG-587, nevirapine, L-697,661, LY 73497, and Ro 18,893 (Roche).

As used herein, "HIV protease inhibitor" is intended to refer to compounds which inhibit HIV protease. Examples include, but are not limited, saquinavir (Roche, Ro31-8959), ritonavir (Abbott, ABT-538), indinavir (Merck, MK-639), VX-478 (Vertex/Glaxo Wellcome), nelfinavir (Agouron, AG-1343), KNI-272 (Japan Energy), CGP-61755 (Ciba-Geigy), and U-103017 (Pharmacia and Upjohn). Additional examples include the cyclic protease inhibitors disclosed in WO93/07128, WO 94/19329, WO 94/22840, and PCT Application Number US96/03426.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

"Prodrugs" are intended to include any covalently bonded carriers which release the active parent drug according to formula (I) or other formulas or compounds of the present invention in vivo when such prodrug is administered to a mammalian subject. Prodrugs of a compound of the present invention, for example formula (I), are prepared by modifying functional groups present in the compound in such a way that the modifications are cleaved, either in routine manipulation or in vivo, to the parent compound. Prodrugs include compounds of the present invention wherein the hydroxy or amino group is bonded to any group that, when the prodrug is administered to a mammalian subject, cleaves to form a free hydroxyl or free amino, respectively. Examples of prodrugs include, but are not limited to, acetate, formate and benzoate derivatives of alcohol and amine functional groups in the compounds of the present invention, and the like. "Stable compound" and "stable structure" are meant to indicate a compound that is sufficiently robust to survive isolation to a useful degree of purity from a reaction mixture, and formulation into an efficacious therapeutic agent. Only stable compounds are contemplated by the present invention.

"Substituted" is intended to indicate that one or more hydrogens on the atom indicated in the expression using "substituted" is replaced with a selection from the indicated group(s), provided that the indicated atom's normal valency is not exceeded, and that the substitution results in a stable compound. When a substituent is keto (i.e., =O) group, then 2 hydrogens on the atom are replaced.

"Therapeutically effective amount" is intended to include an amount of a compound of the present invention or an amount of the combination of compounds claimed effective to inhibit HIV infection or treat the symptoms of HIV infection in a host. The combination of compounds is preferably a synergistic combination. Synergy, as described for example by Chou and Talalay, Adv. Enzyme Regul. 22:27–55 (1984), occurs when the effect (in this case, inhibition of HIV replication) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased antiviral effect, or some other beneficial effect of the combination compared with the individual components.

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Each of the references cited below are hereby incorporated herein by reference.

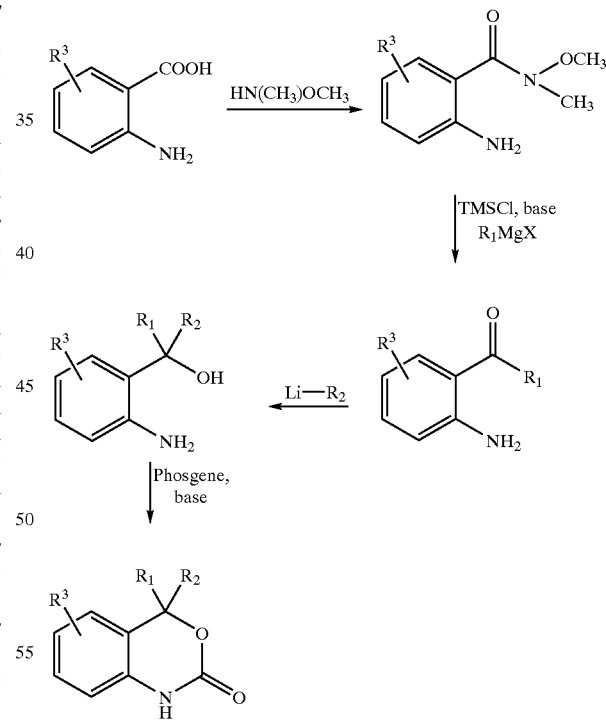

Scheme 1 illustrates a method of making 4,4-disubstituted-1,4-dihydro-2H-3,1-benzoxazin-2-ones starting from an appropriately substituted 2-aminobenzoic acid. The acid is converted to its N-methoxy-N-methyl amide derivative which can then be displaced to obtain the $R^1$-substituted ketone. Subsequent addition of another metallic species provides the alcohol which is readily cyclized with phosgene or an equivalent thereof.

SCHEME 2

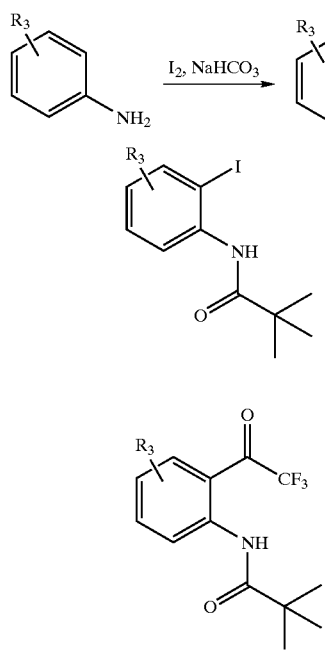

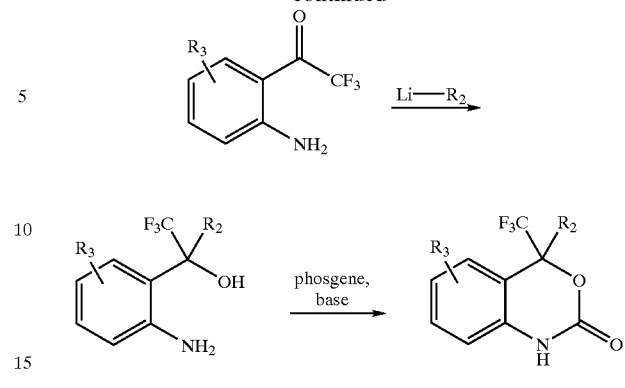

Scheme 2 describes a means of obtaining 4-trifluoromethyl-1,4-dihydro-2H-3,1-benzoxazin-2-ones starting from an appropriately substituted aniline. After iodination, the trifluoromethyl group can be introduced using a strong base and ethyl trifluoroacetate. The second 4-substituent can then be added through anion attack on the ketone or using other means well known to those of skill in the art. Cyclization can be then be completed as in Scheme 1.

SCHEME 3

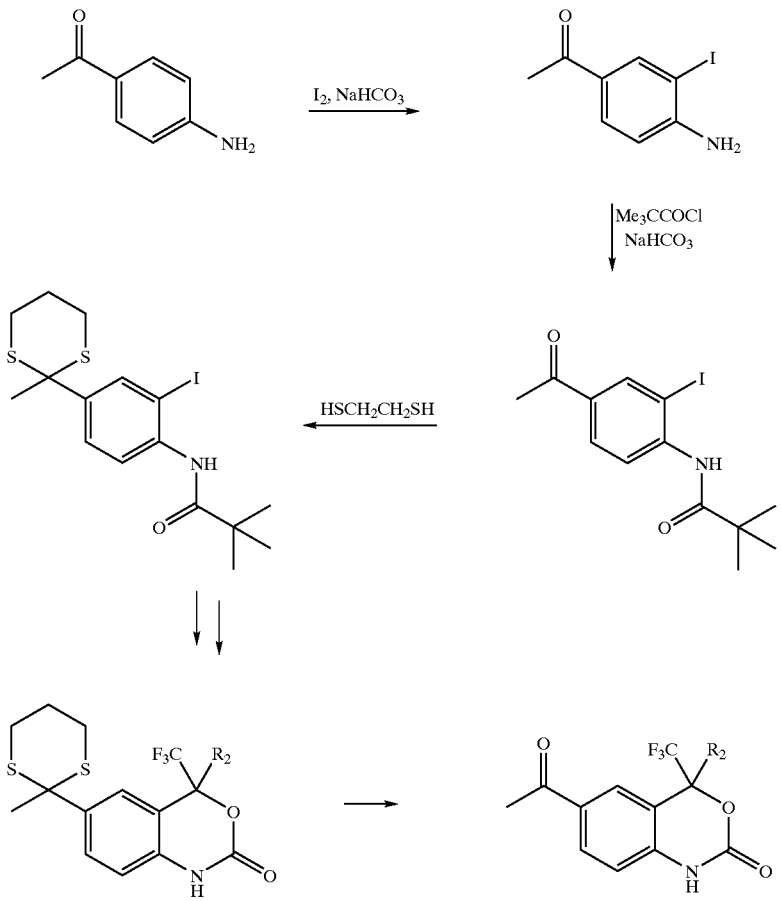

Because certain benzo-substituents are incompatible with the methods of Schemes 1 and 2, it may be necessary to protect these groups before forming the benzoxazinone. In Scheme 3 there is shown a means of obtaining carbonyl-substituted 4,4-disubstituted-1,4-dihydro-2H-3,1-benzoxazin-2-ones. After iodination of an acetyl-aniline, the acetyl group is protected by means well known to those of skill in the art, such as using 1,3-propanedithiol. The same procedures as in Scheme 2 are used to arrive at the cyclized product. Deprotection of the ketone can then be achieved using $HgCl_2$ and HgO or other means well known to those of skill in the art.

SCHEME 4

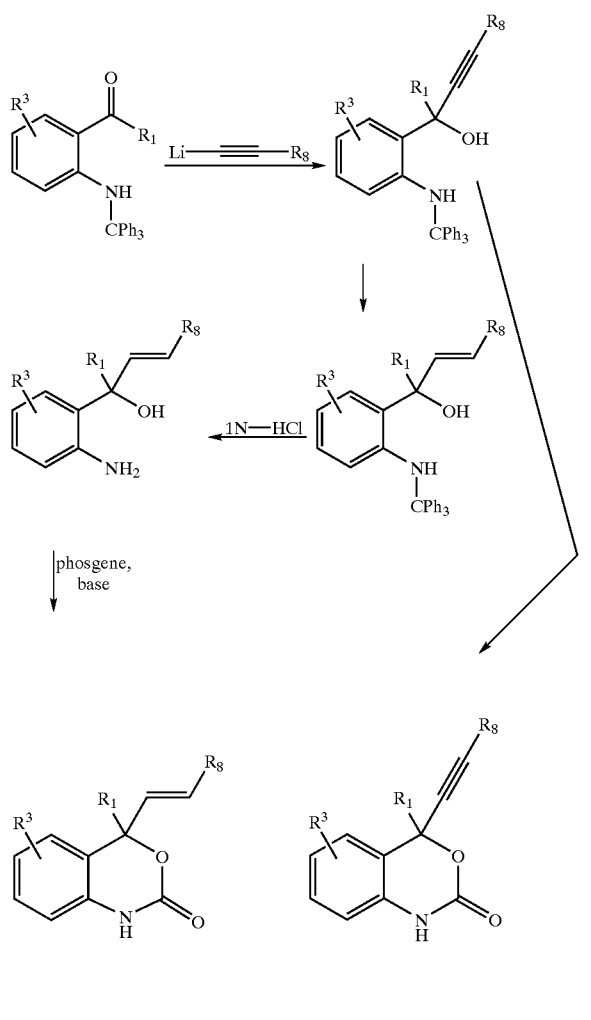

A method for forming 4,4-disubstituted-1,4-dihydro-2H-3,1-benzoxazin-2-ones, wherein $R^2$ is a vinyl or alkynyl group, is described in Scheme 4. Starting from an appropriately substituted ketone which can be obtained using the procedure of Scheme 1 or 2, an acetylide is added. The product can be deprotected and cyclized to obtain the alkynyl-substituted material. Alternatively, the vinyl compounds can be obtained by reduction of the alkyne with a reducing agent, such as $LiAlH_4$, deprotection by standard means, and cyclization.

SCHEME 5

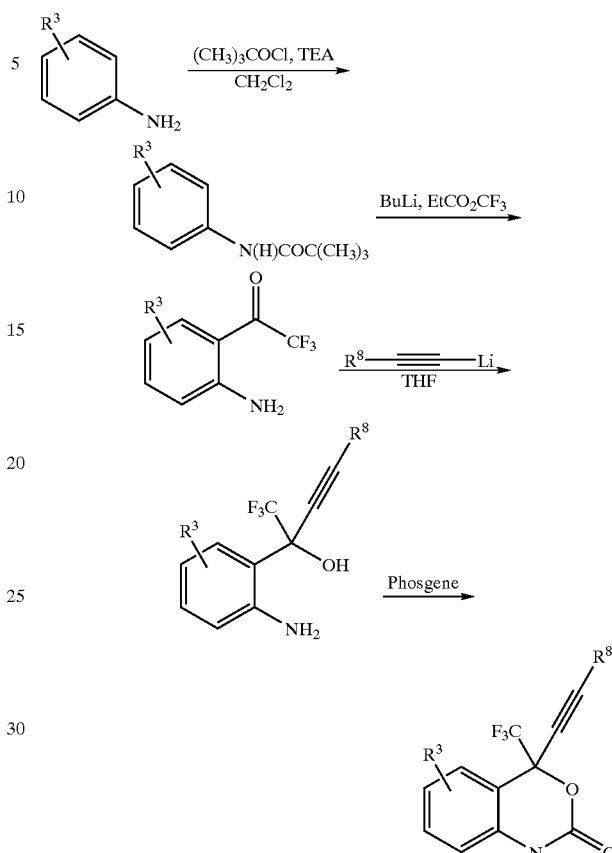

Scheme 5 describes an alternate route to 4,4-disubstituted-1,4-dihydro-2H-3,1-benzoxazin-2-ones from anilines, wherein the aniline is protected, ester addition is accomplished using a strong base and the amine protecting group is removed. The $R^2$ group can then be added, e.g. via an acetylide, followed by cyclization.

SCHEME 6

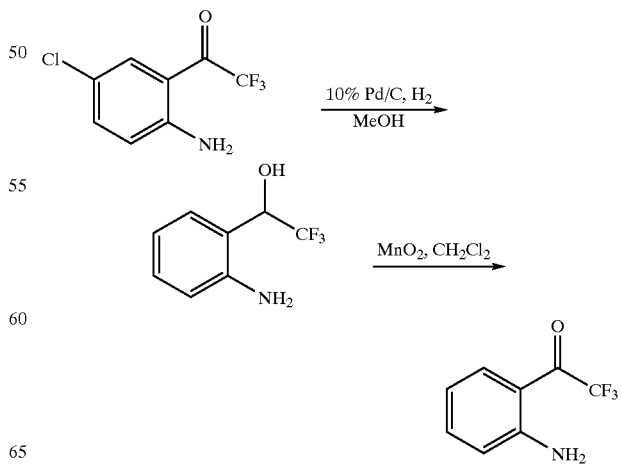

An intermediate useful in the preparation of the presently claimed compounds is 2-trifluoroacetylaniline. The starting 4-chloro-2-trifluoroacetylaniline can be made as shown in Scheme 2. Reduction and reoxidation removes the chloro group leaving the desired intermediate.

SCHEME 7A

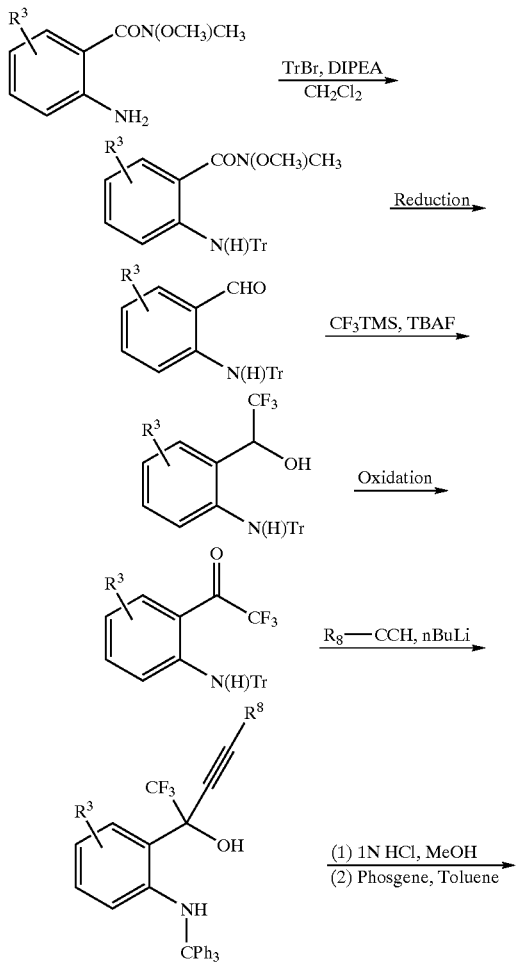

SCHEME 7B

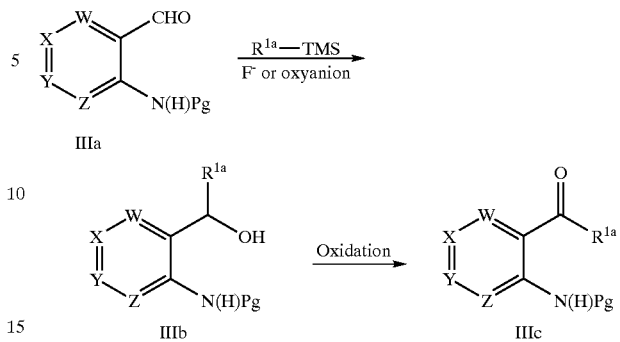

Scheme 7B illustrates specific steps of Scheme 7A. Intermediate IIIb ($R^{1a}$ is selected from $CF_3$, $CF_3CF_2$, and $CF_3CF_2CF_2$) is useful for making some of the presently claimed compounds. Pg is an amine protecting group as defined previously, preferably trityl (triphenylmethyl). The protected or unprotected aminobenzaldehyde, preferably protected, is treated with a perfluoroalkyl trimethylsilane, preferably trifluoromethyl trimethylsilane, followed by fluoride anion, preferably tetrabutylammonium fluoride. In the same fashion, $CF_3CF_2TMS$, $CF_3CF_2CF_2TMS$ can also be used to prepare the appropriately substituted ketones. Other sources of fluoride anion such as sodium fluoride, potassium fluoride, lithium fluoride, cesium fluoride as well as oxyanionic species such as potassium tert-butoxide, sodium methoxide, sodium ethoxide and sodium trimethylsilanolate can also be used. Aprotic solvents such as DMF and THF can be used, preferably THF. The amount of perfluoralkyl trimethylsilane used can be from about 1 to about 3 equivalents with an equivalent amount of fluoride anion or oxyanionic species. The reaction can be typically carried out at temperatures between about −20° C. to about 50° C., preferably about −10 to about 10° C., more preferably about 0° C.

Conversion of IIIb to IIIc can be achieved by using an oxidizing agent well known to one of skill in the art such as $MnO_2$, PDC, PCC, $K_2Cr_2O_7$, $CrO_3$, $KMnO_4$, $BaMnO_4$, $Pb(OAc)_4$, and $RuO_4$. A preferred oxidant is $MnO_2$. Such conversion can be performed in an aprotic solvent like THF, DMF, dichloromethane dichloroethane, or tetrachloroethane, preferably dichloromethane.

SCHEME 8

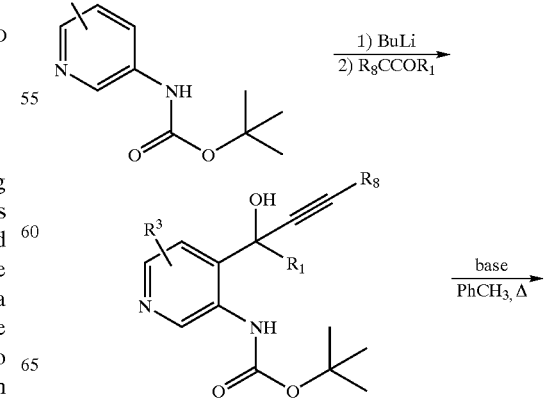

Scheme 7A describes a novel method of making 2-trifluoroacetylanilines as well as how these compounds can be further modified to make the presently claimed compounds. The protected aldehyde can be made from the N-methoxy-N-methyl amide of Scheme 1, by addition of a protecting group, preferably trityl, and reduction of the amide to the aldehyde. Other protecting groups known to those of skill in the art can be used in place of the shown trityl group.

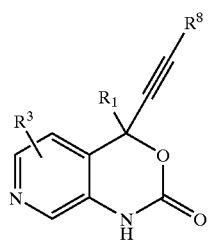

Scheme 8 illustrates a method of forming aza-4,4-disubstituted-1,4-dihydro-2H-3,1-benzoxazin-2-ones from an appropriately substituted amino-pyridine. Carbonyl addition to the pyridine can be accomplished using a strong base and an appropriate ketone. Addition of base can afford the cyclized product.

SCHEME 9

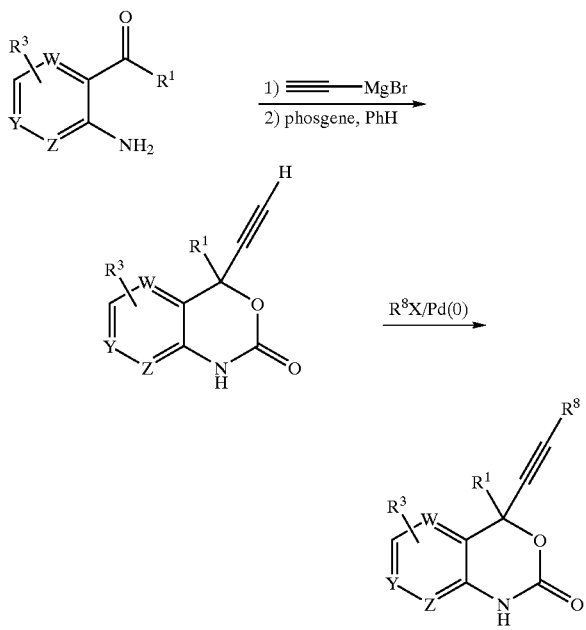

An additional means of making 4-alkynyl-1,4-dihydro-2H-3,1-benzoxazin-2-ones is shown in Scheme 9. The alkyne group is added to the keto-aniline via a Grignard type addition, followed by cyclization. The alkyne group of the product can then be modified to obtain the desired compound.

SCHEME 10

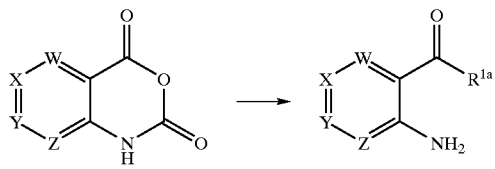

In addition to the methods of obtaining keto-anilines described in Schemes 1 and 2, nucleophilic opening of isatoic anhydrides can also be used as shown in Scheme 10. This reaction is accomplished by using an anionic nucleophile of the group $R^{1a}$. See Mack et al, *J. Heterocyclic Chem.* 1987, 24, 1733–1739; Coppola et al, *J. Org. Chem.* 1976, 41(6), 825–831; Takimoto et al, *Fukuoka Univ. Sci. Reports* 1985, 15(1), 37–38; Kadin et al, *Synthesis* 1977, 500–501; Staiger et al, *J. Org. Chem.* 1959, 24, 1214–1219.

It is preferred that the stoichiometry of the isatoic anhydride reagent to nucleophile is about 1.0 to 2.1 molar equivalents. The use of 1.0 eq. or more (e.g., 1.1, 1.2, 1.3, 1.4, 1.5, 1.6, 1.7, 1.8, 1.9, or 2.0) of anion (or anion precursor) is preferred to force the conversion and improve the isolated yield. Preferably, the temperature used is from −20 to +35° C., with temperatures below 0° C. being more preferred and −20° C. being even more preferred. Reactions are run to about completion with time dependent upon inter alia nucleophile, solvent, and temperature. Preferably this nucleophilic addition is run in THF, but any aprotic solvent would be suitable. Reaction with the active nucleophilic anion is the only criterion for exclusion of a solvent.

SCHEME 11

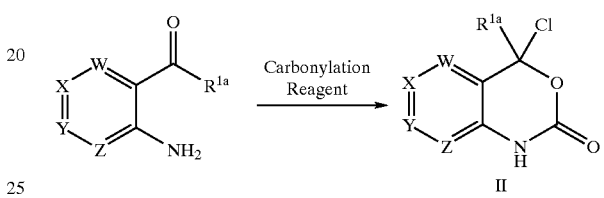

An intermediate in this novel process is the chlorobenzoxazinone (II) which can be synthesized from the corresponding keto-aniline as shown in Scheme 11. The preparation of compounds of formula II works well with either the free base of the keto-aniline or its hydrochloride hydrate, though the free base is preferred due to its inherent reactivity. The carbonylation or thiocarbonylation reagent is selected from the group: phosgene ($COCl_2$), thiophosgene ($CSCl_2$), carbonyldiimidazole (CDI), chloromethylcarbonate, chloroethylcarbonate, dimethylcarbonate, diethylcarbonate, and di-t-butylcarbonate. Preferably, phosgene is used as the carbonylation reagent.

About 1, 2, 3, 4, or 5 equivalents of carbonylation or thiocarbonylation reagent are used, preferably from about 1 to about 2.5, even more preferably from about 1 to 2, and still further preferably about 1, 1.1, 1.2, 1.3, 1.4, or 1.5 equivalents. With volatile reagents like phosgene more than one equivalent can help the conversion and yield of the reaction but is not necessary to effect transformation.

Solvents such as toluene may be used. Additional non-reactive solvents, such as ethers (e.g., dimethyl ether and diethyl ether), hydrocarbons (e.g., hexane and cyclohexane) or other aromatic solvents (e.g., benzene, anisole, or quinoline) can also be used. Solvents with boiling points around that of toluene or higher are preferred. Use of such solvents allows heat to be applied to the reaction to promote the cyclization. When the preferred carbonylation reagent, phosgene is use, heat helps drive off the HCl generated and promote the closure reaction. When toluene is used, it is preferred to run the reaction near toluene's boiling point. However, one of ordinary skill in the art would recognize that too high of a temperature may decompose the product. In addition, too low of a temperature may cause an undesirably slow reaction. Reaction progress may be determined by the decoloration of the reaction mixture (indicating consumption of starting material) and confirmation of completeness by proton NMR. The reaction may be catalyzed by the addition of an acid scavenger such as an amine base (e.g., triethylamine or Hunigs base) or an inorganic base (e.g., sodium carbonate or potassium).

SCHEME 12

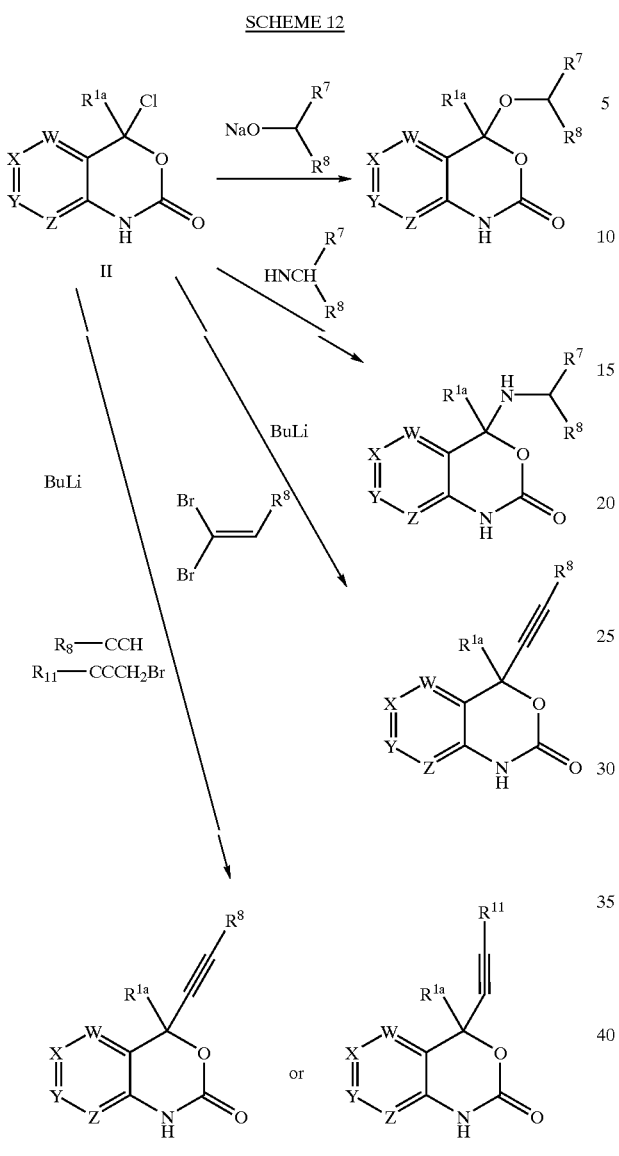

Scheme 12 describes routes to a variety of R²-substituted compounds of formula Ia by reacting a nucleophile (R$^{2b}$) with a compound of formula II (preferably R$^{1a}$ is CF$_3$). This displacement reaction is quite versatile and a large range of nucleophiles can be used. Preferably the nucleophile is an amine (e.g., R$^8$R$^7$CHNH) or a metallic species selected from R$^8$R$^7$CH—OM, R$^8$R$^7$CH—SM, R$^8$R$^7$CHNH—M, R$^8$—C≡C—M, R$^7$R$^8$C═CH—M, R$^8$R$^7$CH(CH$_2$)$_p$—M, R$^8$CH═CHC(H)(R$^7$)—M, and R$^8$R$^7$CHCH═CH—M. In addition, R$^8$R$^7$CH—OH and its thiol analog, R$^8$R$^7$CH—SH, can be used without formation of their corresponding anions. The metallic moiety, M, is selected from the group Na, Li, Zn, Mg, Cu, Pd, Pt, Sn, Al, and B, preferably Li, Mg, or Zn.

If an metallic nucleophile is used, it may be made in situ by methods known to those of skill in the art or formed by methods known to those of skill in the art and then added to a solution. In either case, it is preferred that the compound of formula II is added to a solution containing the nucleophile.

Preferably, the nucleophile is an acetylide (i.e., R$^8$—C≡C—M) with Li, Mg, or Zn as the counterion. Acetylides are well known in the art. Preferably, R$^8$—C≡C—M is formed in situ by addition of a strong base to a solution containing R$^8$—C≡C—H. Strong bases are well known to those of skill in the art and include, but are not limited to n-butyl lithium, s-butyl lithium, t-butyl lithium, phenyl lithium, and methyl lithium. Preferably, the strong base is n-butyl lithium. The acetylide may also be made in situ by addition of a strong base to a dihalo-olefin (e.g., Br$_2$C═CHR$^8$).

In the nucleophilic addition reactions the stochiometery is preferably about one equivalent of benzoxazinone to about 1.0 to 2.5 equivalents of nucleophile (e.g., 1.0, 1.1, 1.2, 1.3, 1.4, 1.5, 1.6, 1.7, 1.8, 1.9, 2.0, 2.1, 2.2, 2.3, 2.4, or 2.5). More preferable about 1.8 to 2.4 equivalents are used. Even more preferably, 2.1 equivalents of nucleophile are used. It is noted that less than one equivalent may be used, but care must be taken as N—H deprotonation reaction may compete with nucleophilic addition. It is preferable to run the additions from −40 to 0° C., more preferably about −20° C. The solvent used is preferably THF, but any aprotic solvent, such as dimethyl ether, diethyl ether, benzene, or toluene, should be suitable. Non-reaction with the nucleophile, specifically the nucleophilic anion, is the only criterion for exclusion of a solvent.

An additional example of the utility of the final nucleophilic addition step of the present invention is shown in Scheme 13.

SCHEME 13

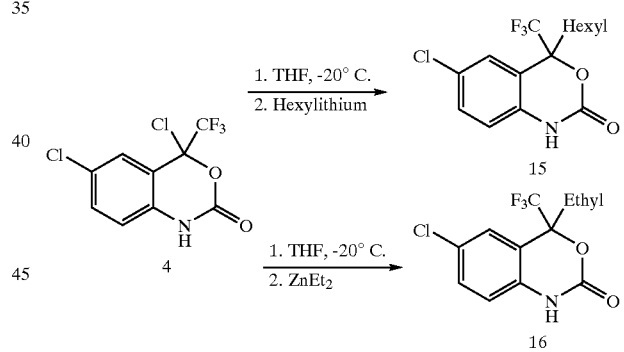

A preferred example of the present process is shown in Scheme 14.

SCHEME 14

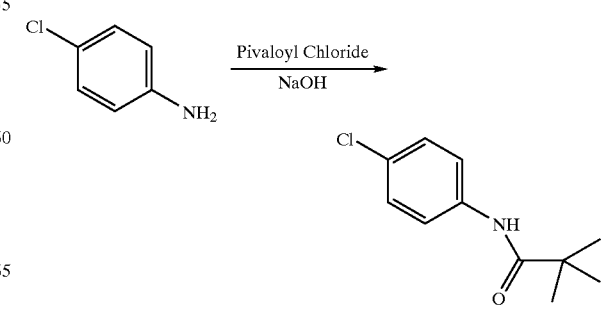

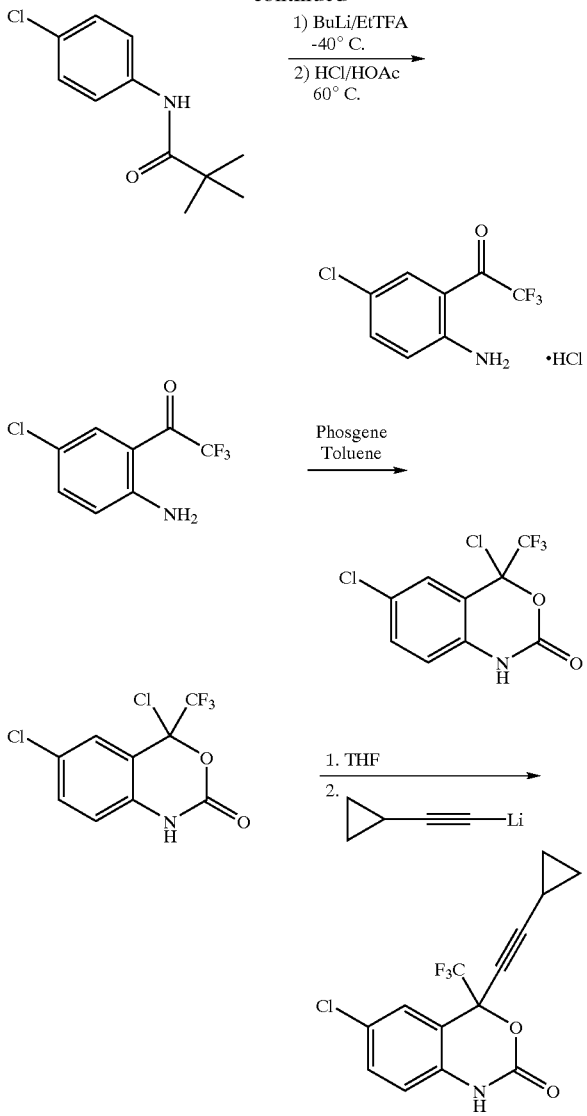

In Scheme 14, the preferred temperature of the carbonylation reaction is from about 104 to about 110° C. and the preferred temperature of the acetylide addition is about −20° C.

One enantiomer of a compound of Formula I may display superior activity compared with the other. Thus, both of the following stereochemistries are considered to be a part of the present invention.

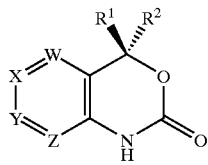

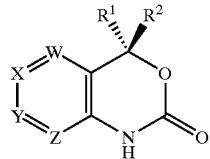

When required, separation of the racemic material can be achieved by HPLC using a chiral column or by a resolution using a resolving agent such as camphonic chloride as in Steven D. Young, et al, *Antimicrobial Agents and Chemotheraphy*, 1995, 2602–2605. A chiral compound of Formula I may also be directly synthesized using a chiral catalyst or a chiral ligand, e.g. Andrew S. Thompson, et al, *Tet. lett.* 1995,36, 8937–8940.

Another method of forming a compound wherein Z is C(OH) involves incubating NNRTI, or a derivative thereof, in microsomes obtained from male rats, male rhesus monkeys or humans, preferably male rats. In addition, it is preferable to orally dose the male rats with NNRTI prior to collection of their livers and microsomal isolation. This procedure will be described in the following Example section.

Other features of the invention will become apparent in the course of the following descriptions of exemplary embodiments which are given for illustration of the invention and are not intended to be limiting thereof.

EXAMPLES

Abbreviations used in the Examples are defined as follows: "°C." for degrees Celsius, "d" for doublet, "dd" for doublet of doublets, "eq" for equivalent or equivalents, "g" for gram or grams, "mg" for milligram or milligrams, "mL" for milliliter or milliliters, "H" for hydrogen or hydrogens, "hr" for hour or hours, "m" for multiplet, "M" for molar, "min" for minute or minutes, "MHz" for megahertz, "MS" for mass spectroscopy, "nmr" or "NMR" for nuclear magnetic resonance spectroscopy, "t" for triplet, "TLC" for thin layer chromatography, "EDAC" for 1-(3-dimethylaminopropyl)-3-ethylcarbodiimide hydrochloride, "DIPEA" for diisopropylethylamine, "TBAF" for tetrabutylammonium fluoride, "LAH" for lithium aluminium hydride, and "TEA" for triethylamine.

Example 1

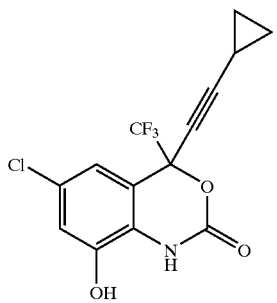

Preparation of (+/−)-6-Chloro-4-(cyclopropylethynyl)-8-hydroxy-4-(trifluoromethyl)-1,4-dihydro-2H-3,1-benzoxazin-2-one Part A: Preparation of 4'-Chloro-2'-methoxy-2,2-dimethylpropionanilide A stirred solution of 22.6 g (100 mmol) of stannous chloride dihydrate in 40 mL of absolute ethanol was heated to reflux and treated with 3.75 g (20 mmol) of 5-chloro-2-nitroanisole in 20 mL of 1:1 ethanol-tetrahydrofuran over 3 min. Stirring at reflux for an additional 10 minutes gave a clear solution which was then cooled to 0° C. The mixture was treated with aqueous $Na_2CO_3$ until a pH of 8–9 was reached. The colloidal suspension was extracted twice with ethyl acetate, and the combined organic extracts were washed with saturated $NaHCO_3$ then brine. The solution was dried ($MgSO_4$) and concentrated under reduced pressure. The crude oil was dissolved in 40 mL of $CH_2Cl_2$ and cooled to 0° C. The solution was treated with 4.2 mL (30 mmol) of triethylamine followed by 2.8 mL (23 mmol) of pivaloyl chloride. After stirring 2 h at 0° C. the mixture was quenched with 0.5 N HCl, and the phases were separated. The aqueous phase was extracted with 100 mL of 1:1 ether-hexanes, and the combined organic extracts were washed sequentially with 0.1 N HCl, dilute $K_2CO_3$, water, and brine. The solution was dried ($MgSO_4$) and concentrated under reduced pressure to give 4.68 g (97%) of 4'-chloro-2'-methoxy-2,2-dimethylpropionanilide as an tan solid, mp 66–69° C. $^1$H NMR (300 MHz, $CDCl_3$) δ8.36(d, 1H, J=8.8 Hz); 8.03(br. s, 1H); 6.94(dd, 1H, J=8.8, 2 2 Hz); 6.86(d, 1H, J=2.2 Hz); 3.90(s, 3H); 1.32(s, 9H). High resolution mass spec: calculated for $C_{12}H_{17}NO_2Cl(M+H)^+$: 242.0948, found: 242.0943. Analysis calculated for $C_{12}H_{16}NO_2Cl$: C, 59.63; H, 6.67; N, 5.79; Cl, 14.67. Found: C, 59.73; H, 6.67; N, 5.57; Cl, 14.42.

Part B: Preparation of 2'-Amino-5'-chloro-3'-methoxy-2,2,2-trifluoroacetophenone To a stirred, cooled (−20° C.) solution of 12.1 g (50 mmol) of 4'-chloro-2'-methoxy-2,2-dimethylpropionanilide in 150 mL of THF was added 87 mL (115 mmol) of 1.3 M s-BuLi in cyclohexane over 15 min. The dark solution was warmed to 0° C. and stirred for 1.2 h. The solution was re-cooled to −20° C. and treated with 14.3 mL (120 mmol) of ethyl trifluoroacetate over 5 min. The reaction was warmed to 0° C., stirred 15 min., and quenched with saturated aqueous $NaHCO_3$. The mixture was extracted with hexanes and then with ether, and the combined organic extracts were washed sequentially with 0.5 N HCl, water, and brine. The solution was dried ($MgSO_4$) and concentrated under reduced pressure to give a dark oil. The crude amide was dissolved in 20 mL of 1,2-dimethoxyethane and treated with 100 mL of 6 N aqueous HCl. The mixture was stirred at reflux for 2 h, cooled to 0° C., and brought to pH 9 with $K_2CO_3$. The mixture was extracted twice with ether, and the combined organic extracts were washed with brine, dried ($MgSO_4$), and concentrated under reduced pressure to give an oily solid. This crude product was recrystallized from hexanes and a minimal ammount of ethyl acetate to give 7.75 g (61%) of 2'-amino-5'-chloro-3'-methoxy-2,2,2-trifluoroacetophenone as yellow needles, mp 124.5–125.5° C. $^1$H NMR (300 MHz, $CDCl_3$) δ7.32–7.35(m, 1H); 6.87(br. s, 2H); 6.84(d, 1H, J=1.8 Hz); 3.92(s, 3H). High resolution mass spec: calculated for $C_9H_8NO_2ClF_3(M+H)^+$: 254.0196, found: 254.0194. Analysis calculated for $C_9H_7NO_2ClF_3$: C, 42.62; H, 2.78; N, 5.52; Cl, 13.98. Found: C, 42.52; H, 3.04; N, 5.40; Cl, 13.74.

Part C: Preparation of 2'-Amino-5'-chloro-3'-hydroxy-2,2,2-trifluoroacetophenone To a stirred, cooled (0° C.) solution of 31.2 g (123 mmol) of 2'-amino-5'-chloro-3'-methoxy-2,2,2-trifluoroacetophenone in 150 mL of $CH_2Cl_2$ was added 550 mL (550 mmol) of 1 M $BBr_3$ in $CH_2Cl_2$ over 20 min. The dark solution was stirred 17 h at ambient temperature, re-cooled to 0° C., and fitted with a pressure-equalizing dropping addition funnel and a Claisen adapter connected by rubber tubing to a large water scrubber. The reaction was carefully quenched by dropwise addition of aqueous $Na_2CO_3$ until a pH of 7–8 was reached. The phases were separated, and the aqueous phase was extracted with 1 liter of 1:1 ether-hexanes. The combined organic phases were washed with water then brine, dried ($MgSO_4$), and concentrated under reduced pressure to afford 30.1 g (100%) of 2'-amino-5'-chloro-3'-hydroxy-2,2,2-trifluoroacetophenone as a chalky brown solid, mp 120–122° C. $^1$H NMR (300 MHz, $CDCl_3$) δ7.33–7.36(m, 1H); 6.88(d, 1H, J=1.8 Hz); 6.75(br. s, 2H); 5.78(br. s, 1H). High resolution mass spec: calculated for $C_8H_6NO_2ClF_3(M+H)^+$: 240.0039, found: 240.0029.

Part D: Preparation of 2'-Amino-5'-chloro-3'-(t-butyldimethylsilyloxy)-2,2,2-trifluoroacetophenone To a stirred, cooled (0° C.) solution of 29.3 g (122 mmol) of 2'-amino-5'-chloro-3'-hydroxy-2,2,2-trifluoroacetophenone in 280 mL of DMF was added 23.8 g (350 mmol) of imidazole followed by 66 g (250 nmol) of t-butyldimethylsilyl trifluoromethanesulfonate over 10 min. The reaction was stirred 5 h at 0° C. and diluted with 800 mL of 1:1 ether-hexanes. The solution was washed twice with water and once with brine, dried ($MgSO_4$) and concentrated under reduced pressure to give a dark oil. The crude product was rapidly passed through an 800 g plug of silica gel (elution with hexanes followed by 6:1 hexanes-ether) to afford, after evaporation of solvent, 42.5 g (98%) of 2'-amino-5'-chloro-3'-(t-butyldimethylsilyloxy)-2,2,2-trifluoroacetophenone as a yellow oil. The product solidified after extended evacuation at 0.01 torr to give a yellow solid, mp 45–46.5° C. $^1$H NMR (300 MHz, CDCl3) δ7.34–7.36(m, 1H); 6.85(d, 1H, J=2.2 Hz); 6.7–6.8(br. s, 2H); 1.03(s, 9H); 0.30(s, 6H). High resolution mass spec: calculated for $C_{14}H_{20}NO_2ClF_3Si(M+H)^+$: 354.0904, found: 354.0900. Analysis calculated for $C_{14}H_{19}NO_2ClF_3Si$: C, 47.52; H, 5.41; N, 3.97; Cl, 10.02. Found: C, 47.71; H, 5.36; N, 3.87; Cl, 10.02.

Part E: Preparation of (+/−)-2-(2-Amino-5-chloro-3-(t-butyldimethylsilyloxy)phenyl)-4-cyclopropyl-1,1,1-trifluoro-3-butyn-2-ol To a stirred, cooled (0° C.) solution of 31.8 mL (300 mmol) of 5-chloro-1-pentyne in 250 mL of THF was added 252 mL (630 mmol) of 2.5 M n-BuLi in hexanes over 20 min. Over the course of the addition the internal temperature had warmed to ambient temperature, and the mixture was stirred at this temperature for 40 min. The reaction was cooled to −20° C. and treated with a solution of 32.7 g (97.4 mmol) of 2'-amino-5'-chloro-3'-(t-butyldimethylsilyloxy)-2,2,2-trifluoroacetophenone in 50 mL of THF over 10 min. The dark solution was stirred an additional 30 min. and the cold bath was removed. The reaction was stirred 5 min and poured into 800 mL of 0° C. 1 N citric acid with rapid stirring. The mixture was extracted twice with ether, and the combined organic extracts were washed with water then brine, dried ($MgSO_4$), and concentrated under reduced pressure. Chromatography on silica gel (elution with hexanes then 3:1 hexanes-ether) afforded 28.8 g (70%) of (+/−)-2-(2-amino-5-chloro-3-(t-butyldimethylsilyloxy)phenyl)-4-cyclopropyl-1,1,1-trifluoro-3-butyn-2-ol as an off-white solid, mp 125–126° C. $^1$H NMR (300 MHz, $CDCl_3$) δ7.22(d, 1H, J=2.2 Hz); 6.76(d, 1H, J=2.2 Hz) ; 4.86(br. s, 1H); 4.39(br. s, 2H); 1.32–1.43(m, 1H); 1.02(s, 9H); 0.79–0.92

(m, 4H); 0.27(s, 3H); 0.26(s, 3H). High resolution mass spec: calculated for $C_{19}H_{26}NO_2ClF_3Si(M+H)^+$: 420.1373, found: 420.1363.

Part F: Preparation of (+/−)-6-Chloro-4-(cyclopropylethynyl)-8-hydroxy-4-(trifluoromethyl)-1,4-dihydro-2H-3,1-benzoxazin-2-one To a stirred, cooled (−25° C.) solution of 28.8 g(68.6 mmol) (+/−)-2-(2-amino-5-chloro-3-(t-butyldimethylsilyloxy)phenyl)-4-cyclopropyl-1,1,1-trifluoro-3-butyn-2-ol in 600 mL of toluene was added 36 mL (206 mmol) of N,N-diisopropylethylamine followed by 38.9 mL (75 mmol) of a 1.93 M solution of phosgene in toluene over 20 min. The solution was stirred an additional 20 min. at −25° C. after which time it was warmed to −5° C. and quenched with water. The mixture was washed with 100 mL of 1 N aqueous HCl then brine, dried (MgSO_4), and concentrated under reduced pressure to afford a tan solid. The crude product was dissolved in 200 mL of THF, cooled to 0° C., and treated with 40 mL of 1 M tetra-(n-butyl) ammonium fluoride in THF over 5 min. The solution was diluted with 200 mL of ether and washed sequentially with 1 M aqueous citric acid, water, and brine. The solution was dried (MgSO_4), concentrated under reduced pressure, and chromatographed on silica gel. Elution with 1:3 ether-hexanes then 1:1 ether-hexanes afforded, after concentration under reduced pressure, 21.4 g (94%) of (+/−)-6-chloro-4-(cyclopropylethynyl)-8-hydroxy-4-(trifluoromethyl)-1,4-dihydro-2H-3,1-benzoxazin-2-one as an off-white solid. $^1$H NMR (300 MHz, CDCl_3) δ8.46(br s, 1H); 7.01–7.07(m, 2H); 1.33–1.43(m, 1H); 0.81–0.97(m, 4H). High resolution mass spec: calculated for $C_{14}H_{10}NO_3ClF_3(M+H)^+$: 332.0301, found: 332.0283.

Example 2

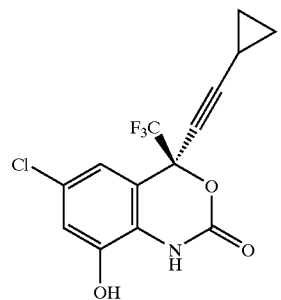

Preparation of (−)-6-Chloro-4-(cyclopropylethynyl)-8-hydroxy-4-(trifluoromethyl)-1,4-dihydro-2H-3,1-benzoxazin-2-one Chromatography of 22 g of racemic 6-chloro-4-(cyclopropylethynyl)-8-hydroxy-4-(trifluoromethyl)-1,4-dihydro-2H-3,1-benzoxazin-2-one (I) on a Chiralpak AD-7.5 cm I.D.×30 gm column using 20% methanol-80% carbon dioxide as the mobile phase at a flow rate of 120 mL/min. gave two fractions. The faster-eluting fraction was concentrated and recrystallized from hexanes and a minimal amount of ethyl acetate to afford 5 g of the title compound as a white solid, mp 170–172° C. $^1$H NMR (300 MHz, CDCl_3) δ8.46(br s, 1H); 7.01–7.07(m, 2H); 1.33–1.43(m, 1H); 0.81–0.97(m, 4H). [α]Na_d (25° C.)−=32°, c=0.28. Analysis calculated for $C_{14}H_9NO_3ClF_3$: C, 50.70; H. 2.75; N, 4.22; Cl, 10.69. Found: C, 50.74; H, 2.86; N, 4.26; Cl, 10.77.

Example 3

Preparation of (−) 6-Chloro-4-(cyclopropylethynyl)-8-hydroxy-4-(trifluoromethyl)-1,4-dihydro-2H-3,1-benzoxazin-2-one by Rat Hepatic Microsomal Fractions Incubation of (−) 6-Chloro-4-cyclopropylethynyl-4-trifluoromethyl-1,4-dihydro-2H-3,1-benzoxazin-2-one (NNRTI) with hepatic microsomes from rats previously treated with NNRTI and cofactors required to support cytochromes P450 oxidative metabolism resulted in the formation of one major metabolite separable from NNRTI by reverse phase high performance liquid chromatography (HPLC). Incubations were conducted for 2 hours at 37° C. in a physiological buffer. After precipitating the protein with acetonitrile, the supernatants were dried under nitrogen and reconstituted in a mixture of 55:45 (v/v) acetonitrile:0.01% aqueous formic acid (pH 3.5) and injected onto the HPLC system. The column effluent was monitored at 247 nm. The single peak observed to elute at approximately 4 minutes was collected and combined from multiple injections. Final purification was accomplished using the same HPLC system and a linear gradient developed over 15 minutes starting with solvent A (50:50 (v/v) methanol:0.01% aqueous formic acid, pH 3.5) and increasing the proportion of solvent B (80:20 v/v methanol:0.01% aqueous formic acid pH 3.5), then holding solvent B constant for 5 minutes before re-equilibration with solvent A. The single, sharp peak eluting at approximately 16.5 minutes was collected and dried under vacuum.

The purified metabolite described above was dissolved in 0.2 mL of methanol-d4 and placed in a 3 mm NMR tube. The proton NMR spectrum was acquired using a 30 degree pulse, a 4 second acquisition time and a 2 second relaxation delay during which the residual water signal was suppressed by selective irradiation. The spectrum was referenced to solvent at 3.30 ppm.

Example 4

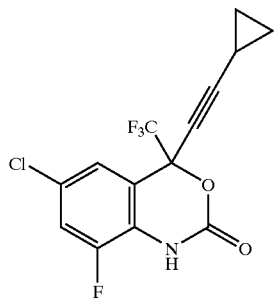

Preparation of (+/−)-6-Chloro-4-(cyclopropylethynyl)-8-fluoro-4-(trifluoromethyl)-1,4-dihydro-2H-3,1-benzoxazin-2-one Part A: Preparation of 4'-Chloro-2'-fluoro-2,2-dimethylpropionanilide To a stirred, cooled (0° C.) solution of 3.64 g (25.0 mmol) of 4-chloro-2-fluoroaniline and 4.2 mL (30 mmol) of triethylamine in 50 mL of THF was added 4.18 mL (26 mmol) of pivaloyl chloride. After stirring for 10 min. at 0° C. the mixture was warmed to ambient temperature and poured into 0.5N HCl. The mixture was extracted with 100 mL of ether, and the organic extract was washed sequentially with NaHCO$_3$ and brine. The solution was dried (MgSO$_4$), concentrated under reduced pressure, and chromatographed on silica gel (elution with 3:1 hexanes-ether) to give, after removal of solvent, 5.2 g (92%) of 4'-chloro-2'-fluoro-2,2-dimethylpropionanilide as a pale pink solid (IX), mp 70.5–71° C. $^1$H NMR (300 MHz, CDCl$_3$) δ8.36(t, 1H, J=8.4 Hz); 7.57(br. s, 1H); 7.10–7.17(m, 2H); 1.30(s, 9H). $^{19}$F NMR (282 MHz, CDCl$_3$) δ–129.8. High resolution mass spec: calculated for C$_{11}$H$_{14}$NOClF(M+H)$^+$: 230.0748, found: 230.0760.

Part B: Preparation of 2'-(Trimethylacetamido)-5'-chloro-3'-fluoro-2,2,2-trifluoroacetophenone To a stirred, cooled (–50° C.) solution of 0.92 g (4.0 mmol) of 4'-chloro-2'-fluoro-2,2-dimethylpropionanilide in 10 mL of THF was added 2.5 mL (4.2 mmol) of 1.7 M t-BuLi in pentane over 5 min. The solution was stirred for 5 min. and treated with 1.0 mL (8.4 mmol) of ethyl trifluoroacetate over 2 min. The reaction was warmed to ambient temperature, stirred 15 min., and quenched with 1N aqueous citric acid. The mixture was extracted with ether, and the organic extract was washed sequentially with water then brine. The solution was dried(MgSO$_4$) and concentrated under reduced pressure to give an oil. The crude amide was chromatographed on silica gel (elution with 3:1 hexanes-ether followed by 1:1 hexanes-ether) to give 570 mg (43%) of 2'-(trimethylacetamido)-5'-chloro-3'-fluoro-2,2,2-trifluoroacetophenone as an off-white solid. $^1$H NMR(300 MHz, CDCl$_3$) δ8.68(s, 1H); 7.45–7.47(m, 1H); 7.08(dd, 1H, J=9.5, 2.6 Hz); 1.3(s, 9H). High resolution mass spec: calculated for C$_{13}$H$_{13}$NO$_2$ClF$_4$(M+H)$^+$: 326.0571, found: 326.0579.

Part C: Preparation of 2'-Amino-5'-chloro-3'-fluoro-2,2,2-trifluoroacetophenone

A stirred solution of 0.35 g (1.07 mmol) of 2'-(trimethylacetamido)-5'-chloro-3'-fluoro-2,2,2-trifluoroacetophenone in 3 mL of 1,2-dimethoxyethane and treated with 24 mL of 6N aq. HCl. The mixture was stirred at reflux for 2 h, cooled to RT, and brought to pH 9 with K$_2$CO$_3$. The mixture was extracted twice with ether and the combined organic extracts were washed with brine, dried (MgSO$_4$), and concentrated under reduced pressure to give 240 mg (92%) of 2'-amino-5'-chloro-3'-fluoro-2,2,2-trifluoroacetophenone as an oily orange solid. $^1$H NMR (300 MHz, CDCl$_3$) δ7.54(m, 1H); 7.25(dd, 1H, J=10.6, 2.2 Hz); 6.40–6.60(br. s, 2H). High resolution mass spec: calculated for C$_8$H$_4$NOClF$_4$(M$^+$): 240.9918, found: 240.9914. $^{19}$F NMR (282 MHz, CDCl$_3$) δ–132.7(s, 1F), –70.6(s, 3F).

Part D: Preparation of (+/–)-2-Amino-5-chloro-3-fluoro-α-(cyclopropylethynyl)-α-(trifluoromethyl)benzyl alcohol To a stirred, cooled (0° C.) solution of 2.0 mL (7.0 mmol) of 3.5 M cyclopropylacetylene in toluene was added 2 mL of THF followed by 2.8 mL (7.0 mmol) of 2.5 M n-BuLi in hexanes over 2 min. The solution was stirred 5 min. at 0° C., warmed to RT, and stirred a further 20 min. The reaction was cooled to 0° C. and treated with a solution of 300 mg (1.24 mmol) of 2'-amino-5'-chloro-3'-fluoro-2,2,2-trifluoroacetophenone in 3 mL of THF over 2 min. The solution was stirred an additional 10 min. and the cold bath was removed. The reaction was stirred 5 min and poured into 0.5 N citric acid. The mixture was extracted with ether, and the organic extract was washed with water then brine, dried (MgSO$_4$), and concentrated under reduced pressure. Chromatography on silica gel (elution with hexanes then 3:1 hexanes-ether) afforded 185 mg (49%) of (+/–)-2-amino-5-chloro-3-fluoro-α-(cyclopropylethynyl)-α-(trifluoromethyl)benzyl alcohol as an off-white solid, mp 131–135° C. $^1$H NMR (300 MHz, CDCl$_3$) δ7.34–7.36(m, 1H); 7.04(dd, 1H, J=10.4, 2.4 Hz); 4.58(br. s, 2H); 3.82(br. s, 1H); 1.35–1.44 (m, 1H); 0.80–0.99(m, 4H). $^{19}$F NMR (282 MHz, CDCl$_3$) δ–131.5(s, 1F), –80.5(s, 3F). High resolution mass spec: calculated for C$_{13}$H$_{11}$NOClF$_4$(M+H)$^+$: 308.0470, found: 308.0465.

Part E: Preparation of (+/–)-6-Chloro-4-(cyclopropylethynyl)-8-fluoro-4-(trifluoromethyl)-1,4-dihydro-2H-3,1-benzoxazin-2-one To a stirred, cooled (–25° C.) solution of 144 mg (0.47 mmol) of (+/–)-2-amino-5-chloro-3-fluoro-α-(cyclopropylethynyl)-α-(trifluoromethyl)benzyl alcohol in 6 mL of toluene was added 0.28 mL (2.0 mmol) of triethylamine followed by 0.62 mL(1.2 mmol) of a 1.93 M solution of phosgene in toluene over 3 min. The solution was stirred an additional 30 min. at –25° C. after which time it was warmed to ambient temperatue and quenched with 0.5 N aq. citric acid. The mixture was extracted once with ether and once with ethyl acetate, and the combined organic extracts were washed sequentially with sat'd aq. NaHCO$_3$, water, and brine. The solution was dried (MgSO$_4$), and concentrated under reduced pressure to afford a tan solid. The crude product was chromatographed on silica gel(elution with 3:1 hexanes-ether) to afford, after concentration, 90 mg (58%) of (+/–)-6-chloro-4-(cyclopropylethynyl)-8-fluoro-4-(trifluoromethyl)-1,4-dihydro-2H-3,1-benzoxazin-2-one as an off-white solid. $^1$H NMR (300 MHz, CDCl$_3$) δ7.65(br s, 1H); 7.32–7.34(m, 1H); 7.22(d, 1H, J=2.2 Hz); 1.36–1.43 (m, 1H); 0.82–0.98(m, 4H). $^{19}$F NMR (282 MHz, CDCl$_3$) δ–132.5(s, 1F), –81.1(s, 3F). High resolution mass spec: calculated for C$_{14}$H$_9$NO$_2$ClF$_4$(M+H)$^+$: 334.0258, found: 334.0244.

Example 5

Preparation of (+/–)-4-Cyclopropylethynyl-4-isopropyl-6-methyl-1,4-dihydro-2H-3,1-benzoxazin-2-one Part A: Preparation of 2-Amino-5-methylbenzoyl N-methoxy-methylamide To a solution of 2-amino-5-methylbenzoic acid (7.6 g, 50.3 mmol) and N,O-dimethylhydroxylamine hydrochloride (12.5 g, 60.4 mmol) in acetonitrile (80 mL) were added triethylamine (15.8 mL, 60.4 mmol) and 1-(3-dimethylaminopropyl)-3-ethylcarbodiimide hydrochloride (10.3 g, 55.3 mmol) and the mixture was stirred at room temperature for 5 hours. At the end of the stirring, methylene chloride (200 mL) was added and washed with water and brine. The organic layer was dried over anhydrous sodium sulfate and evaporated in vacuo to give a yellow syrupy residue. It was purified by column chromatography on silica gel with elution by 15:85 ethyl acetate-hexane to give pure 2-amino-5-methylbenzoyl N-methoxy-methylamide.

Part B: Preparation of 2-Amino-5-methylphenylisopropylketone

To a solution of 2-amino-5-methylbenzoyl N-methoxy-methylamide (472.6 mg, 2.4 mmol) in dry THF (3 mL) at –20° C. were added diisopropylethylamine (0.84 mL, 4.8 mmol) and chlorotrimethylsilane (0.61 mL, 4.8 mmol) dropwise and the mixture was stirred for 1 hour at −20~5° C. It was then cooled to −20° C. again and was added 2M-isopropyl magnesium chloride in THF (4.8 mL, 9.6 mmol) dropwise. The mixture was stirred for 1.5 hours at −20~10° C. After cooling to 0° C. was added saturated ammonium chloride and extracted with EtOAc. The organic layer was washed with 1N-HCl, water, saturated sodium bicarbonate and water, and dried over anhydrous sodium sulfate. It was evaporated in vacuo to give an oily residue. Column chromatography on silica gel with elution by 1:9 ethyl acetate-hexane affored pure 2-amino-5-methylphenylisopropylketone (201 mg) as an oil.

Part C: Preparation of 2-Amino-5-methyl-α-cyclopropylethynyl-α-isopropyl-benzyl alcohol To a solution of cyclopropylacetylene (105 mg, 1.59 mmol) in THF (3 mL) at −20° C. was added 1.6M-nBuLi in hexane (0.96 mL, 1.54 mmol) dropwise and the mixture was stirred at the same temperature for 0.5 hours. Then a solution of 2-amino-5-methylphenylisopropylketone (94.5 mg, 0.53 mmol) in THF (3 mL) was added and the mixtire was stirred for 5 hours at −20 ~20° C. The reaction was quenched with saturated $NH_4Cl$ and the product was extraxted with ethyl acetate. After washing with brine, the extract was dried over anhydrous sodium sulfate and evaporated to give the crude amino-alcohol as an oil.

Part D: Preparation of 4-Cyclopropylethynyl-4-isopropyl-6-methyl-1,4-dihydro-2H-3,1-benzoxazin-2-one To a solution of the crude amino-alcohol (0.53 mmol) in dry toluene (5 mL) at −20° C. were added diisopropylethylamine (0.29 mL, 1.89 mmol) and 0.31 mL of 20% solution of phosgene in toluene dropwise and the mixture was stirred for 1 hour at −20~0° C. After addition of water (5 mL) it was extracted with ethyl acetate and the organic layer was washed with brine. It was dried over $Na_2SO_4$ and evaporated in vacuo to give an oily residue. Column chromatography on silica gel (2:8 EtOAc-hexane) provided pure titled compound (38 mg).

Example 6

Preparation of (+/−)-4-Isopropylethynyl-4-trifluoromethyl-6-methyl-1,4-dihydro-2H-3,1-benzoxazin-2-one Part A: Preparation of 2-Iodo-4-methylaniline To a stirred solution of p-toluidine (5 g, 46.7 mmol) in methylene chloride (25 mL) was added a solution of sodium bicarbonate (4.7 g, 56 mmol) in water (75 mL). Then was added iodine (11.26 g, 44.33 mmol) in small portions and the mixture was stirred for 16 hours at room temperature. The reaction was quenched with saturated $NaHSO_3$ and the product was extracted with methylene chloride. The methylene chloride layer was washed with brine, dried over $Na_2SO_4$, and evaporated in vacuo to give a crude 2-iodo-4-methylaniline.

Part B: Preparation of Trimethylacetyl 2-iodo-4-methylanilide

To a stirred mixture of 2-iodo-4-methylaniline (46.7 mmol) in chloroform (50 mL) and 50 mL of saturated sodium carbonate was added trimethylacetyl chloride dropwise over a period of 15 minutes and the mixture was stirred vigorously for 45 minutes at room temperature. The product was extracted with chloroform, washed with water and dried over $Na_2SO_4$. Evaporation of the solvent in vacuo affored the pivaloyl amide as a solid. It was recrystallized from ethyl acetate and hexane.

Part C: Preparation of Trimethylacetyl 4-methyl-2-trifluoroacetylanilide

To a stirred solution of trimethylacetyl 2-iodo-4-methylanilide (10.7 g, 33.75 mmol) in 50 mL of dry THF at −78° C. was added 1.6M-nBuLi in hexane (48.5 mL, 77.6 mmol) dropwise and the mixture was stirred for an hour at the same temperature. Then ethyl trifluoroacetate (9.6 mL, 81 mmol) was added dropwise and the mixture was stirred for 0.5 hours at −78° C. At the end of the stirring saturated $NH_4Cl$ solution was added and the mixture was warmed up to room temperature. The product was extracted with ethyl acetate, washed with water and brine, and dried over $Na_2SO_4$. The solution was concentrated and the residue was column chromatographed on silica gel (1:9 EtOAc-hexane) to give the desired trimethylacetyl 4-methyl-2-trifluoroacetylanilide (1.29 g, 13% yield) and trimethylacetyl 4-methylanilide (major product).

Part D: Preparation of 4-Methyl-2-trifluoroacetylaniline

To a solution of trimethylacetyl 4-methyl-2-trifluoroacetylanilide (1.29 g) in 10 mL of dimethoxyethane was added 6N-HCl (5 mL) and the mixture was refluxed for 2.5 hours with stirring. After cooling it was poured over ice and was made basic with saturated $NaHCO_3$. The product was extracted with ethyl acetate, washed with brine, and dried over $Na_2SO_4$. Evaporation of the solvent provided the aniline as a yellow solid in near quantitative yield.

Part E: Preparation of 2-Amino-5-methyl-α-isopropylethynyl-α-trifluoromethyl-benzyl alcohol To stirred solution of 3-methyl-1-butyne (0.26 mL, 2.59 mmol) in 5 mL of dry THF at −20° C. was added 1.6M-nBuLi in hexane (1.4 mL, 2.24 mmol) dropwise and the mixture was warmed up to 0° C. over a period of 1 hour with stirring. It was the cooled back to −20° C. and was added dropwise a solution of 4-methyl-2-trifluoroacetylaniline (150 mg, 0.74 mmol) in 2 mL of THF. After stirring for an hour at −20~0° C. was added saturated $NH_4Cl$ (~5 mL), and the product was extracted with ethyl acetate, washed with brine and dried over $Na_2SO_4$. The solvents were evaporated off to give crude amino-alcohol as a yellow solid residue.

Part F: Preparation of 4-Isopropylethynyl-4-trifluoromethyl-6-methyl-1,4-dihydro-2H-3,1-benzoxazin-2-one To a solution of the crude amino-alcohol (0.74 mmol) in dry toluene (7.5 mL) at −20° C. were added diisopropylethylamine (0.39 mL, 2.22 mmol) and 0.42 mL of 20% solution of phosgene in toluene dropwise and the mixture was stirred for 1 hour at −20~0° C. After addition of water (5 mL) it was extracted with ethyl acetate and the organic layer was washed with brine. It was dried over $Na_2SO_4$ and evaporated in vacuo to give an oily residue. Column chromatography on silica gel (2:8 EtOAc-hexane) and recrystallization (EtOAc and hexane) provided pure titled compound (61 mg, 28% yield for 2 steps) as white crystals, mp 198–199° C.

Example 7

Preparation of (+/−)-6-Acetyl-4-cyclopropylethynyl-4-trifluoromethyl-1,4-dihydro-2H-3,1-benzoxazin-2-one Part A: Preparation of 4-Amino-3-iodo-acetophenone To a solution of 4-aminoacetophenone (5 g, 37 mmol) in 15 mL of $CH_2Cl_2$ and 75 mL of water was added sodium bicarbonate (3.73 g, 44.4 mmol) followed by iodine (8.92 g, 35.1 mmol), and the mixture was stirred for 5 hours at room temperature. The reaction was quenched by portionwise addition of sodium bisulfite until the iodine color disappeared. The product was extracted with $CH_2Cl_2$, washed with water, dried over $Na_2SO_4$. Evaporation of the solvent gave crude 4-amino-3-iodo-acetophenone as solid (7.92 g).

Part B: Preparation of Trimethylacetyl 2-iodo-4-acetylanilide

To a stirred mixture of 4-amino-3-iodo-acetophenone (7.92 g, 30.3 mmol) in chloroform (50 mL) and 50 mL of saturated sodium carbonate was added trimethylacetyl chloride (7.8 mL, 63.7 mmol) dropwise over a period of 15 minutes and the mixture was stirred vigorously for 16 hours at room temperature. The product was extracted with chloroform, washed with water and dried over $Na_2SO_4$. Evaporation of the solvent in vacuo affored the pivaloyl amide as a brown oil. It was column chromatographed (silica gel, 1:9 EtOAc-hexane) to afford pure trimethylacetyl 2-iodo-4-acetylanilide (5.83 g) as white crystals.

Part C: Preparation of Trimethylacetyl 2-iodo-4-(2-methyl-1,3-dithian-2-yl)anilide To a stirred solution of trimethylacetyl 2-iodo-4-acetylanilide (2.9 g, 8.45 mmol) and 1,3-propanedithiol in 25 mL of THF at 0° C. was added borontrifluorate etherate (0.63 mL, 5.1 mmol) and the mixture was stirred for 16 hours at room temperature. Then was added second portion of borontrifluorate etherate (0.63 mL, 5.1 mmol) and it was continued to stir for 44 hours. The reaction mixture was poured into water and extracted with ethyl acetate. The extract was washed with water saturated $NaHCO_3$ and brine, dried over $MgSO_4$ and evaporated to a clear oil. It was column chromatographed (silica gel, 5:95 EtOAc-hexane) to give pure thioaketal as a foamy solid (2.85 g).

Part D: Preparation of Trimethylacetyl 4-(2-methyl-1,3-dithian-2-yl)-2-trifluoroacetylanilide To a stirred solution of trimethylacetyl 2-iodo-4-(2-methyl-1,3-dithian-2-yl)anilide (2.29 g, 5.26 mmol) in 20 mL of dry THF at -78° C. was added 1.6M-nBuLi in hexane (6.7 mL, 10.7 mmol) dropwise and the mixture was stirred for 45 minutes at the same temperature. Then ethyl trifluoroacetate (12.6 mL, 105.2 mmol) was added dropwise and the mixture was gradually warmed up to room temperature over a period of 3 hours. At the end of the stirring saturated $NH_4Cl$ solution was added, and the product was extracted with ethyl acetate, washed with water and brine, and dried over $Na_2SO_4$. The solution was concentrated and the residue was column chromatographed on silica gel (1:9 EtOAc-hexane) to give the desired trimethylacetyl 4-(2-methyl-1,3-dithian-2-yl)-2-trifluoroacetylanilide (0.63 g) and trimethylacetyl 4-(2-methyl-1,3-dithian-2-yl)anilide (1.33 g).

Part E: Preparation of 4-(2-Methyl-1,3-dithian-2-yl)-2-trifluoroacetylaniline To a solution of trimethylacetyl 4-(2-methyl-1,3-dithian-2-yl)-2-trifluoroacetylanilide (0.63 g) in 10 mL of methanol was added 6N-HCl (2 mL) and the mixture was refluxed for 4 hours with stirring. After cooling it was poured over ice and was made basic with saturated $NaHCO_3$. The product was extracted with ethyl acetate, washed with brine, and dried over $Na_2SO_4$. Evaporation of the solvent provided the desired 4-(2-methyl-1,3-dithian-2-yl)-2-trifluoroacetylaniline as a bright yellow solid.

Part F: Preparation of 2-Amino-5-(2-methyl-1,3-dithian-2-yl)-α-cyclopropylethynyl-α-trifluoromethyl-benzyl alcohol To stirred solution of cyclopropylacetylene (122 mg, 1.9 mmol) in 5 mL of dry THF at -20° C. was added 1.6M-nBuLi in hexane (0.99 mL, 1.59 mmol) dropwise and the mixture was warmed up to 0° C. over a period of 45 minutes with stirring. It was the cooled back to —20° C. and was added dropwise a solution of 4-methyl-2-trifluoroacetylaniline (150 mg, 0.74 mmol) in 2 mL of THF. After stirring for 1.5 hours at -20~0° C. was added saturated $NH_4Cl$ (~5 mL), and the product was extracted with ethyl acetate, washed with brine and dried over $Na_2SO_4$. The solvents were evaporated off to give crude amino-alcohol as a bright yellow solid residue.

Part G: Preparation of 4-Cyclopropylethynyl-4-trifluoromethyl-6-(2-methyl-1,3-dithian-2-yl)-1,4-dihydro-2H-3,1-benzoxazin-2-one To a solution of the crude amino-alcohol (0.53 mmol) in dry toluene (5 mL) at -20° C. were added diisopropylethylamine (0.28 mL, 1.59 mmol) and 0.3 mL of 20% solution of phosgene in toluene dropwise and the mixture was stirred for 1.5 hours at -20~0° C. and for 5 minutes at room temperature. After addition of water (5 mL) it was extracted with ethyl acetate and the organic layer was washed with brine. It was dried over $Na_2SO_4$ and evaporated in vacuo to give an oily residue. It was purified by preparative TLC on a silica gel plate (3:7 EtOAc-hexane) to give pure titled compound (77 mg).

Part H: Preparation of 6-Acetyl-4-cyclopropylethynyl-4-trifluoromethyl-1,4-dihydro-2H-3,1-benzoxazin-2-one To a stirred solution of 4-cyclopropylethynyl-4-trifluoromethyl-6-(2-methyl-1,3-dithian-2-yl)-1,4-dihydro-2H-3,1-benzoxazin-2-one (64 mg, 0.154 mmol) in 5 mL of methanol and 0.5 mL of water were added mercuric chloride (92 mg, 0.339 mmol) and mercuric oxide (50 mg, 0.23 mmol), and the mixture was refluxed for 2 hours. After cooling it was filtered through Celite and rinsed with EtOAc. The filtrate was washed with water and brine, dried over $MgSO_4$, and evaporated to give an oily residue. Column chromatography (silica gel, 2:8 EtOAc-hexane) afforded pure 6-6cetyl-4-cyclopropylethynyl-4-trifluoromethyl-1,4-dihydro-2H-3,1-benzoxazin-2-one.

Example 8

Preparation of (+/−)-5,6-Difluoro-4-(3-methyl)-1-buten-1-yl-4-trifluoromethyl-1,4-dihydro-2H-3,1-benzoxazin-2-one

Part A: Preparation of 2,3-Difluoro-6-triphenylmethylamino-α-1-(3-methyl)-1-butynyl-α-trifluoromethyl-benzyl alcohol To a solution of 3-methyl-1-butyne (0.73 g, 10.7 mmol) in dry THF (5 mL) at -20° C. was added 1.6M-nBuLi in hexane dropwise and the mixture was stirred for 15 minutes at the same temperature. Then a solution of 2,3-diflupro-6-triphenylmethylamino-α,α,α-trifluoroacetophenone (1 g, 2.14 mmol) in 5 mL of THF was added dropwise at -20° C. After stirring for 10 minutes, the cooling bath was removed and it was allowed to warm up to room temperature. The mixture was stirred for 45 minutes and was poured into saturated $NH_4Cl$. The product was extracted with ether, washed with saturated NaHCO$_3$ and brine and dried over MgSO$_4$. Evaporation of solvent gave an oily residue, which was crystallized from methanol, ether and hexane mixture to provide pure product (0.432 g, 37.6%).

Part B: Preparation of 2,3-Difluoro-6-triphenylmethylamino-α-1-(3-methyl)-1-butenyl-α-trifluoromethyl-benzyl alcohol To a solution of 2,3-difluoro-6-triphenylmethylamino-α-1-(3-methyl)-1-butynyl-α-trifluoromethyl-benzyl alcohol (0.431 g, 0.8 mmol) in 5 mL of dry THF was added 1M-lithium aluminumhydride in THF (2.41 mL, 2.41 mmol) at room temperature and the mixture was stirred for 1 hour. The reaction was quenched with several drops of saturated NH$_4$Cl and was added about 20 mL of ether. After stirring for 10 minutes it was washed with saturated NaHCO3 and dried over MgSO4. Evaporation of the solvent gave the desired transolefinic compound in near quantitative yield.

Part C: Preparation of 6-Amino-2,3-Difluoro-α-1-(3-methyl)-1-butenyl-α-trifluoromethyl-benzyl alcohol A solution of the crude product of step 2 (0.8 mmol) and 1.33 mL of c-HCl in methanol (5 mL) was stirred for 1 hour at room temperature and basified with saturated NaHCO3. It was extracted with ether and washed with brine. After drying over MgSO4, the solvent was evaporated off to give an oily residue. It was crystallized from hexane to give pure 6-amino-2,3-Difluoro-α-1-(3-methyl)-1-butenyl-α-trifluoromethyl-benzyl alcohol (0.184 g, 78%).

Part D: Preparation of 5,6-Difluoro-4-(3-methyl)-1-buten-1yl-4-trifluoromethyl-1,4-dihydro-2H-3,1-benzoxazin-2-one To a solution of the crude amino-alcohol (0.13 g, 0.44 mmol) in dry toluene (5 mL) at 0° C. were added diisopropylethylamine (0.23 mL, 1.32 mmol) and 0.24 mL of 2M-phosgene in toluene (0.48 mmol) dropwise and the mixture was stirred for 5 minutes at 0° C. and for 30 minutes at room temperature. After addition of saturated NH$_4$Cl (5 mL) it was extracted with ether and the organic layer was washed with brine. It was dried over MgSO$_4$ and evaporated in vacuo to give an oily residue. It was purified by column chromatography on Silica gel (1:9 ether-hexane) to give pure titled compound (0.051 g, 36%).

Example 9

Preparation of (+/−)-4-Isopropylethynyl-4-trifluoromethyl-5,6-difluoro-1,4-dihydro-2H-3,1-benzoxazin-2-one

Part A: Preparation of N-trimethylacetyl-3,4-difluoroanilide

To a solution of 3,4-difluoroaniline (19 mL, 191 mmol) in methylene chloride (500 mL) at 0° C. was added triethylamine (32 mL, 230 mmol) followed dropwise with trimethylacetyl chloride (24 mL, 191 mmol) and the resulting reaction mixture was allowed to stir at room temperature for 3 h. The reaction mixture was poured onto 3N HCl and extracted with methylene chloride (3×100 mL) and the combined organic extracts were dried over anhydrous NaSO$_4$ and concentrated in vacuo. The residue was taken up in hexanes (300 mL) and filtered through a sintered glass funnel. The solids are washed thoroughly with hexanes (500 mL) and dried under vacuum to give 37.36 g of the pivaloyl amide as a solid (40.68 g theoretical, 92% yield).

Part B: Preparation of N-Trimethylacetyl 5,6-difluoro-2-trifluoroacetylanilide To a solution of N-trimethylacetyl-3,4-difluoroanilide (4.0 g, 14.6 mmol) in THF (60 mL) at −78° C. was added dropwise 1.6M nBuLi in hexane (22 mL, 35 mmol) and the resulting reaction mixture was allowed to stir at −78° C. for 1 h. The Ethyl trifluoroacetate (4 mL, 33.6 mmol) is added to the reaction mixture and the resulting solution was allowed to stir with warming to room temperature (ice bath removed after the addition of reagent) for 0.5 h. The reaction mixture was poured onto saturated NH$_4$Cl and extracted with ether (3×50 mL). The combined ether extracts were dried over anhydrous MgSO$_4$ and concentrated in vacuo to give an orange oil. This product was used in the next step of the synthetic sequence without further purification.

Part C: Preparation of 5,6-Difluoro-2-trifluoroacetylaniline

To a solution of the orange oil in DME (15 mL) was added 6N HCl (75 mL) and the resulting mixture was allowed to reflux for 2 h. The reaction mixture was cooled, made basic with solid Na$_2$CO$_3$ and extracted with ether (3×50 mL). The combined ether extracts were dried over anhydrous MgSO$_4$ and concentrated in vacuo. Chromatography (SiO$_2$, 20% EtOAc-hexanes eluant) provided 2110 mg of 5,6-Difluoro-2-trifluoroacetylaniline as a yellow solid (3285 mg theoretical, 64% yield).

Part D: Preparation of 2-Amino-5,6-difluoro-α-isopropylethynyl-α-trifluoromethyl-benzyl alcohol To a solution of 3-methyl-1-butyne (0.36 mL, 3.56 mmol) in THF (6 mL) at 0° C. was added 1.6M nBuLi in hexane (2.2 mL, 3.56 mmol) and the resulting reaction mixture was allowed to stir at 0° C. for 0.5 h. A solution of 5,6-Difluoro-2-trifluoroacetylaniline (200 mg, 0.89 mmol) in THF (6 mL) was added to the reaction mixture and the resulting reaction mixture was allowed to stir with warming to room temperature (ice bath removed after addition of reagent) for 0.5 h. The reaction mixture was poured onto saturated NH$_4$Cl and extracted with ether (3×50 mL). The combined ether extracts were dried over anhydrous MgSO$_4$ and concentrated in vacuo to give an orange oil. This product was used in the next step of the synthetic sequence without further purification.

Part E: Preparation of 4-Isopropylethynyl-4-trifluoromethyl-5,6-difluoro-1,4-dihydro-2H-3,1-benzoxazin-2-one To a solution of amino-alcohol (crude product, 1.21 mmol) in toluene (4 mL) at 0° C. was added N,N-diisopropylethylamine (0.54 mL, 3.12 mmol) followed by a solution of 1.93M phosgene in toluene (0.6 mL, 1.16 mmol) and the resulting solution was allowed to stir at 0° C. for 0.1 h. The reaction mixture was poured onto water and extracted with ether (3×50 mL). The combined ether extracts were dried over anhydrous MgSO$_4$ and concentrated in vacuo. Chromatography (SiO$_2$, 20% EtOAc-hexanes eluant) provided 45 mg of the title compound (284 mg theoretical, 16% yield).

Example 10

Preparation of 2-Trifluoroacetylaniline

Part A: Preparation of 2-Amino-α-trifluoromethyl-benzyl alcohol

To a solution of amino ketone (155 mg, 0.7 mmol) in methanol (2 mL) at room temperature was added Pd(OH)$_2$ (20 mg) and hydrogenated (H₂/balloon) for 2 h. The reaction mixture was filtered through Celite and concentrated in vacuo. The solids were triturated with ether (20 mL) and dried in vacuo to give 117 mg of 2-Amino-α-trifluoromethyl-benzyl alcohol as a pale yellow solid. (134 mg theoretical, 87% yield).

Part B: Preparation of 2-Trifluoroacetylaniline

To a slurry of amino alcohol (520 mg, 2.72 mmol) in methylene chloride (5 mL) at room temperature was added MnO₂ (10×wt, 5 g) and the resulting reaction mixture was allowed to stir at room temperature for 0.75 h. The reaction mixture was filtered through Celite and concentrated in vacuo to give an orange oil which is used without further purification due to instability of compound.

Example 11

Preparation of 3-Fluoro-2-trifluoroacetyl-triphenylmethylaniline

Part A: Preparation of 2-Amino-6-fluorobenzoyl N-methoxy-methylamide

To a solution of 2-amino-6-fluorobenzoic acid (5 g, 32.26 mmol) in AcCN (100 mL) at room temperature was added N,O-dimethylhydroxylamine hydrochloride (3.8 g, 38.71 mmol), EDAC (7.4 g, 38.71 mmol) followed by triethylamine (5.38 mL, 38.71 mmol) and the resulting reaction mixture was allowed to stir at room temperature for 6 h. The reaction mixture was poured onto saturated NaHCO₃ and extracted with EtOAc (3×100 mL). The combined EtOAc extracts were dried over anhydrous NaSO₄ and concentrated in vacuo. Chromatography (SiO₂, 25% EtOAc-hexanes eluant) provided 4.29 g of the desired compound (5.87 g theoretical, 73% yield).

Part B: Preparation of 2-Triphenylmethylamino-6-fluorobenzoyl N-methoxy-methylamide To a solution of 2-amino-6-fluorobenzoyl N-methoxy-methylamide (300 mg, 2.14 mmol) in methylene chloride (10 mL) at room temperature was added N,N'-diisopropylamine (1.2 mL, 6.4 mmol) followed by triphenylmethyl bromide (830 mg, 2.57 mmol) and the resulting reaction mixture is allowed to stir at room temperature for 0.5 h. The reaction mixture was poured onto water and extracted with methylene chloride (3×50 mL) and the combined organic extracts were dried over anhydrous NaSO₄ and concentrated in vacuo. Chromatography (SiO₂, 10% EtOAc-hexanes) provided 832 mg of the desired compound (942 mg theoretical, 88% yield).

Part C: Preparation of 2-Triphenylmethylamino-6-fluorobenzaldehyde

To a solution of 2-triphenylmethylamino-6-fluorobenzoyl N-methoxy-methylamide (300 mg, 0.68 mmol) in THF (4 mL) at −78° C. was added lithium aluminum hydride (30 mg, 0.82 mmol) and the resulting reaction mixture was allowed to stir with warming to room temperature (dry ice bath removed after addition of reagent) for 1 h. The reaction mixture was quenched with 20% KHSO₄ and extracted with EtOAc (3×100 mL) and the combined EtOAc extracts were dried over anhydrous NaSO₄ and concentrated in vacuo. Chromatography (SiO₂, 5% EtOAc-hexanes) provided 182 mg of the title compound (260 mg theoretical, 70% yield).

Part D: Preparation of 2-Amino-6-fluoro-α-trifluoromethyl-benzyl alcohol

To a solution of 2-triphenylmethylamino-6-fluorobenzaldehyde (100 mg, 0.24 mmol) in THF (2 mL) at 0° C. was added trifluoromethyltrimethylsilane (0.06 mL, 0.36 mmol) followed by a solution of tetrabutylammonium fluoride in THF (1M, 0.36 mL, 0.36 mmol) and the resulting reaction mixture was allowed to stir with warming to room temperature (ice bath removed after the addition of reagents) for 0.5 h. The reaction mixture was poured onto water and extracted with EtOAc (3×50 mL) and the combined EtOAc extracts were dried over anhydrous NaSO₄ and concentrated in vacuo. Chromatography (SiO₂, 10% EtOAc-hexanes) provided 88 mg of the title compound (108 mg theoretical, 82% yield).

Part E: Preparation of 3-Fluoro-2-trifluoroacetyl-triphenylmethylaniline

To a solution of 2-amino-6-fluoro-α-trifluoromethyl-benzyl alcohol (88 mg, 0.2 mmol) in methylene chloride (6 mL) at room temperature was added manganese(IV)oxide (900 mg, 10×wt) and the resulting reaction mixture was allowed to stir at room temperature for 5 h. The reaction mixture is filtered through Celite and concentrated in vacuo. Chromatography (SiO₂, 5% EtOAc-hexanes) provided 52 mg of the title compound (90 mg theoretical, 58% yield).

Example 12

Preparation of (+/−)-4-Cyclopropylethynyl-6-chloro-4-trifluoromethyl-7-aza-1,4-dihydro-2H-3,1-benzoxazin-2-one Part A: Preparation of 5-(t-Butoxycarbonylamino)-2-chloropyridine.

To a stirred solution of 2.83 g(22.0 mmol) of 5-amino-2-chloropyridine in 20 mL of anhydrous THF was added 44.0 mL(44.0 mmol) of a 1.0M solution of NaHMDS in toluene over 5 min. The dark solution was stirred 15 min. and 4.36 g(20 mmol) of di-t-butyldicarbonate in 5 mL of THF was introduced over 2 min. The thick mixture was stirred an additional 1 h and poured into 0.5N aq. HCl. The solution was extracted with ethyl acetate, and the organic extract was washed with saturated aq. NaHCO₃, water, and brine. The solution was dried (MgSO₄), concentrated under reduced pressure, and chromatographed on silica gel (gradient elution with 3:1 hexanes-ether then ether) to give, after evaporation of solvents, 3.81 g(83%) of 5-(t-butoxycarbonylamino)-2-chloropyridine as a white solid, mp 122–123° C. $^1$H NMR(300 MHz, CDCl₃) δ8.23(d, 1H, J=2 Hz); 7.98(br. d, 1H, J=8 Hz); 7.25(d, 1H, J=8 Hz); 6.58(s, 1H); 1.52(s, 9H).

Part B: Preparation of 2-(5-(t-Butoxycarbonylamino)-2-chloropyrid-4-yl)-4-cyclopropyl-1,1,1-trifluoro-3-butyn-2-ol To a stirred, cooled (−50° C.) solution of 643 mg(2.8 nmol) of 5-(t-butoxycarbonylamino)-2-chloropyridine in 8 mL of anhydrous THF was added 4.7 mL(7.0 mmol) of t-BuLi in pentane over 3 min. The solution was stirred an additional 35 min. at −50° C. after which time 1 mL(large excess) of 4-cyclopropyl-1,1,1-trifluoro-3-butyn-2-one. The solution was stirred an additional 20 min., warming to ambient temperature. The reaction was poured into 10% aq. citric acid, and the mixture was extracted with 1:1 ether-ethyl acetate. The organic extract was washed with saturated aq. NaHCO₃, then brine, dried (MgSO₄), and concentrated under reduced pressure. Chromatography on silica gel (gradient elution with 6:1 then 3:1 hexanes-ethyl acetate) afforded, after removal of solvent, 620 mg(56%) of 2-(5-(t- butoxycarbonylamino)-2-chloropyrid-4-yl)-4-cyclopropyl-1,1,1-trifluoro-3-butyn-2-ol as an amorphous solid. Mass spec.($NH_3$—CI): 391(($M+H)^+$, 100%); 291(($M+H-t-Boc)^+$, 49%). $^1$H NMR(300 MHz, $CDCl_3$) δ9.08(br. s, 1H); 8.19(br. s, 1H); 7.59(s, 1H); 1.50(s, 9H); 1.37–1.43(m, 1H); 0.81–0.97(m, 4H).

Part C: Preparation of 4-Cyclopropylethynyl-6-chloro-4-trifluoromethyl-7-aza-1,4-dihydro-2H-3,1-benzoxazin-2-one To a stirred solution of 230 mg(0.59 mmol) of 2-(5-(t-butoxycarbonylamino)-2-chloropyrid-4-yl)-4-cyclopropyl-1,1,1-trifluoro-3-butyn-2-ol in 6 mL of anhydrous toluene was added 0.92 mL of a 2.5M solution of n-BuLi in hexanes. The solution was brought to reflux and stirred 10 min. after which time an additional 0.10 mL of n-BuLi was added. The solution was stirred an additional 20 min. at reflux and cooled to ambient temperature. The reaction was poured into 10% aq. citric acid and extracted with ether. The organic extract was washed with brine, dried($MgSO_4$), and concentrated under reduced pressure. Chromatography on silica gel(elution with 3:1 hexanes-ethyl acetate) afforded 25 mg (13%) of 4-cyclopropylethynyl-6-chloro-4-trifluoromethyl-7-aza-1,4-dihydro-2H-3,1-benzoxazin-2-one as an amorphous solid. Mass spec.($NH_3$—CI): 334(($M+NH_4)^+$, 100%); 317(($M+H)^+$, 100%); 273(($M+H—CO_2)^+$, 21%). $^1$H NMR (300 MHz, $CDCl_3$) δ9.62(br. s, 1H); 8.17(s, 1H); 7.44(s, 1H); 1.36–1.44(m, 1H); 0.82–0.99(m, 4H).

Example 13

Preparation of (+/−)-6-Chloro-4-(2-methoxyethoxy)-4-(trifluoromethyl)-1,4-dihydro-2H-3,1-benzoxazin-2-one Part A: Preparation of 4-Chloro-6-methoxy-4-trifluoromethyl-1,4-dihydro-2H-3,1-benzoxazin-2-one To a stirred, gently refluxing solution of 7.0 g(31.9 mmol) of 2-amino-5-methoxy-(1',1',1'-trifluoro)acetophenone in 27 mL of anhydrous toluene was added 24.8 mL(47.9 mmol) of a 1.93M solution of phosgene in toluene over 2 min. (Note: A dry ice-acetone cold finger is used to condense phosgene during this reaction.). The solution is warmed at reflux for 2 h, cooled, and charged with 15 mL of hexanes. Upon stirring overnight at ambient temperature a precipitate formed which was filtered, washed with hexanes, and briefly air-dried to give 5.06 g(60%) of 4-chloro-6-methoxy-4-trifluoromethyl-1,4-dihydro-2H-3,1-benzoxazin-2-one as an off-white solid mp 112–114° C. $^1$H NMR(300 MHz, $CDCl_3$) δ9.05(br. s, 1H); 7.07(br. s, 1H); 7.02(dd, 1H, J=8, 2 Hz); 6.90(d, 1H, J=8 Hz); 3.83(s, 3H).

Part B: Preparation of 6-Chloro-4-(2-methoxyethoxy)-4-(trifluoromethyl)-1,4-dihydro-2H-3,1-benzoxazin-2-one To a solution of 0.15 mL of 2-methoxyethanol in 5 mL of anhydrous THF at ambient temperature was added 20 mg of 100% sodium hydride. After 20 min, 100 mg of 4,6-dichloro-4-(trifluoromethyl)benzoxazinone was added, and the resulting solution was stirred at ambient temperature for 30 min. The reaction mixture was poured onto aqueous ammonium chloride and was extracted with ethyl acetate. The organic extracts were washed with brine, dried and evaporated. The crude product was purified by preparative TLC on silica gel (elution with ethyl acetate/hexanes 1:1) to afford a material which was crystallized from ethyl acetate-hexanes to afford 81 mg (71%) of the title compound.

Example 14

Preparation of (+/−)-6-Chloro-4-propylamino-4-(trifluoromethyl)-1,4-dihydro-2H-3,1-benzoxazin-2-one To a solution of 230 mg of 4,6-dichloro-4-(trifluoromethyl)benzoxazinone in 20 mL of dry ether was added 0.250 mL of n-propylamine. After stirring 30 min at ambient temperature, the solution was partitioned between ether and water, and the organic layer was washed with brine, dried, and evaporated. The crude product was purified by column chromatography on silica gel (elution with ethyl acetate-hexanes 1:3) to afford after crystallization from hexanes 24 mg (9.7%) of the title compound.

Example 15

Preparation of (+/−)-6-Chloro-4-[2-(furan-2-yl)ethynyl]-4-(trifluoromethyl)-1,4-dihydro-2H-3,1-benzoxazin-2-one To a solution of 5.9 g (25 mmoles) of 1,1-dibromo-2-(furan-2-yl)ethylene in 124 mL of anhydrous THF at −20° was added dropwise 31.0 mL of 1.6 M n-butyllithium in hexanes (50 mmoles). This solution was allowed to warm to ambient temperature over a period of 30 min, after which time it was cooled to −50°. 4,6-Dichloro-4-(trifluoromethyl)-2H-3,1-benzoxazin-2-one (2.65 g, 9.27 mmoles) was added in one portion, and the resulting solution was allowed to warm to −35° over 40 min. The reaction was quenched by the addition of aqueous ammonium chloride, and this mixture was poured onto water and extracted twice with ethyl acetate. The combined extracts were washed with brine, dried over sodium sulfate, and evaporated. The crude product was purified by column chromatography on silica gel (elution with 15% and 30% ethyl acetate in hexanes) affording 3.5 g of a solid which was recrystallized from ethyl acetate/hexanes to afford 3.03 g (95.7%) of the title compound.

Example 16

Preparation of (+/−)-4-(1-Butynyl)-6-methoxy-4-trifluoromethyl-1,4-dihydro-2H-3,1-benzoxazin-2-one To a stirred, cooled(−78° C.) solution of 0.5 g(excess) of 1-butyne in 3 mL of anhydrous THF was added 1.6 mL(4.0 mmol) of a 2.5M solution of n-BuLi in hexanes over 3 min. The solution was stirred 5 min. and charged with 266 mg(1.00 mmol) of 4-chloro-6-methoxy-4-trifluoromethyl-1,4-dihydro-2H-3,1-benzoxazin-2-one as a single portion. The solution was warmed to −10° C. over 20 min., whereupon it was quenched with 20% aqueous citric acid. The mixture was extracted with ether, and the organic extract was washed with saturated aq. $NaHCO_3$ then brine. The solution was concentrated under reduced pressure, and the crude product was recrystallized from ethyl acetate-hexanes to afford 144 mg(48%) of 4-(1-butynyl)-6-methoxy-4-trifluoromethyl-1,4-dihydro-2H-3,1-benzoxazin-2-one as a white solid, mp 161–162° C. $^1$H NMR(300 MHz, $CDCl_3$) δ8.81(br. s, 1H); 7.07(d, 1H, J=2 Hz); 6.94(dd, 1H, J=9, 2 Hz); 6.81(d, 1H, J=8 Hz); 3.82(s, 3H); 2.34(q, 2H, J=7 Hz); 1.22(t, 3H, J=7 Hz).

Example 17

Preparation of (+/−)-4-(1'-hydroxy)-cyclopropylethynyl-4-trifluoromethyl-6-chloro-1,4-dihydro-2H-3,1-benzoxazin-2-one

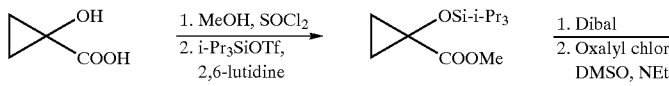

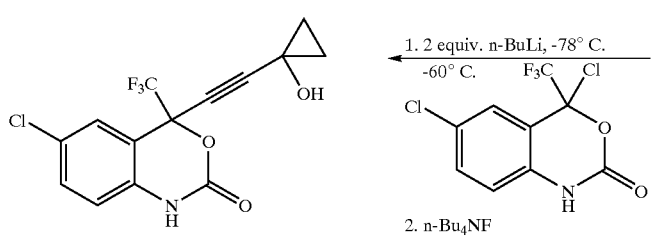

Part A: Preparation of Methyl 1-hydroxy-1-cyclopropanecarboxylate

1-Hydroxy-1-cyclopropanecarboxylic acid (587 mg, 5.75 mmol) was dissolved in methanol (20 mL) under nitrogen. Thionyl chloride (4 drops) were added and the reaction was stirred overnight at room temperature. Triethylamine was then added until the reaction was alkaline as judged by moistened pH paper. The solvent was then removed on the rotary evaporator.

Part B: Preparation of Methyl 1-triisopropylsilylhydroxy-1-cyclopropanecarboxylate The residue was then dissolved in dry methylene chloride (20 mL) under a nitrogen atmosphere. Dry 2,6-lutidine (distilled from calcium hydride, 1.0 mL, 8.62 mmol) was added and the reaction cooled to 0° C. Triisopropylsilyl trifluoromethanesulfonate (2.3 mL, 8.62 mmol) was then added dropwise and stirring continued for 1 hour. The reaction was then poured into 1 N HCl and extracted with hexanes. The organic layer was washed successively with water and brine, then dried with magnesium sulfate, filtered and evaporated. The crude material was purified by flash chromatography (silica) using 19:1 hexanes/ethyl acetate. This provided the silyl methyl ester in 87% yield for two steps (1.35 g).

Part C: Preparation of 1-Triisopropylsilylhydroxy-1-cyclopropanemethanol

The silyl methyl ester (1.05 g, 3.86 mmol) was dissolved in hexane (12 mL) under nitrogen. The reaction was cooled in a dry ice/acetone bath and a solution of diisobutylaluminum hydride (1.5 M in toluene, 6.4 mL, 9.64 mmol) was introduced dropwise. Stirring was continued for 2 hours when the reaction was quenched by the addition of methanol (12 mL). The reaction was warmed to room temperature and poured into a saturated aqueous solution of sodium potassium tartrate. The clarified solution was extracted with ether and the organic layer washed with water and brine. After drying over magnesium sulfate, the product was isolated by filtration and evaporation (894.4 mg, 95%). This material was of sufficient purity for direct use in the next step.

Part D: Preparation of 1-Triisopropylsilylhydroxy-1-cyclopropanecarboxaldehyde A 100 mL flask was flame-dried and sealed under nitrogen. The flask was charged with dry methylene chloride (11 mL) and oxalyl chloride (0.44 mL, 5.07 mmol). The solution was cooled in a dry ice/acetone bath and dimethylsulfoxide was introduced (0.73 mL, 10.3 mmol). After stirring for 5 minutes, the starting material (1.065 g, 4.36 mmol) was added as a solution in methylene cholride (5.0 mL) After stirring for 20 minutes, triethylamine (3.1 mL, 22.4 mmol) was added and the reaction was allowed to warm to room temperature. The reaction was then poured into 1 N HCl and extracted with ether. The organic layer was washed twice with water and once with brine. Drying with magnesium sulfate, filtration and evaporation then provided the crude product. This material was of sufficient purity for use in the next step.

Part E: Preparation of 1-Triisopropylsilylhydroxy-1-(2',2'-dibromoethene)cyclopropane A 500 mL flask was charged with carbon tetrabromide (2.89 g, 8.72 mmol) dissolved in dry methylene chloride (87 mL). The solution was cooled to −20° C. when triphenylphosphine (recrystallized from hexanes, 2.28 g, 8.72 mmol) was added and stirring continued for 45 minutes. The reaction was then cooled to −60° C. where the crude aldehyde (maximum of 4.36 mmol) dissolved in dry methylene chloride (40 mL) containing triethylamine (0.61 mL, 4.26 mmol) was added. Stiirring was continued overnight with warming to room temperature. The reaction was then diluted with hexanes (1 l) and filtered through a pad of magnesium sulfate. Evaporation and purification by flash column chromatography (silica, hexanes) gave the desired dibromoolefin (35%, 607.1 mg).

Part F: Preparation of (+/−)-4-(1'-Triisopropylsilylhydroxy)-cyclopropylethynyl-4-trifluoromethyl-6-chloro-1,4-dihydro-2H-3,1-benzoxazin-2-one A 50 mL two-necked flasked was flame-dried in vacuo and sealed under nitrogen. The dibromoolefin was dissolved in dry tetrahydrofuran (8.0 mL) and transferred to the reaction flask. The reaction was cooled to −78° C. and a solution of n-butyllithium (2.5 M in hexanes, 1.2 mL, 2.96 mmol) was added dropwise. Stirring was continued for 20 minutes when a solution of the chlorobenzoxazinone (212 mg, 0.74 mmol) in dry tetrahydrofuran (2.0 mL) was added. The reaction was warmed to −60° C. and stirring continued for 30 minutes. The reaction was then poured into a saturated aqueous solution of ammonium chloride and extracted with ethyl acetate. The organic phase was washed with water and brine and then dried over magnesium sulfate. The crude product was isolated by filtration and evaporation. Flash chromatography (silica, 4:1 hexanes/ethyl acetate) gave the partially purified product (235 mg). A subsequent chromatography under similar conditions gave the desired material (35%, 118 mg) with suitable purity for the next step.

Part G: Preparation of 4-(1'-Hydroxy)-cyclopropylethynyl-4-trifluoromethyl-6-chloro-1,4-dihydro-2H-3,1-benzoxazin-2-one The starting material (53.0 mg, 0.117 mmol) was dissolved in dry tetrahydrofuran (2.0 mL) under nitrogen. A solution of tetra-n-butylammonium fluoride (1M in tetrahydrofuran, 0.12 mL, 0.12 mmol) was added and stirring continued for 15 minutes. The reaction was then diluted with 1:1 hexanes/ethyl acetate and washed twice with water and once with brine. Drying with magnesium sulfate, filtration, and evaporation gave the crude product. The compound was purified by flash chromatography (silica, 4:1 hexanes/ethyl acetate to 2:1 hexanes/ethyl acetate). The desired product was isolated in 74% yield (28.7 mg). m.p. 192–194° C. HRMS: calculated for $C_{14}H_{10}ClF_3NO_3$, M+H): 332.0301; found 332.0296.

Example 18

Preparation of (+/−)-4-isopropylethynyl-4-trifluoromethyl-5-fluoro-1,4-dihydro-2H-3,1-benzoxazin-2-one Part A: Preparation of 2-Triphenylmethylamino-5-fluoro-α-isopropylethynyl-α-trifluoromethyl-benzyl alcohol To a solution of 3-methyl-1-butyne (0.16 mL, 1.51 mmol) in THF (2 mL) at 0° C. was added 1.6M nBuLi in hexane (0.84 mL, 1.34 mmol) and the resulting reaction mixture was allowed to stir at 0° C. for 0.5 h. A solution of 5-fluoro-2-trifluoroacetyl-triphenylmethylaniline (300 mg, 0.67 mmol) in THF (2 mL) was added to the reaction mixture and the resulting reaction mixture was allowed to stir at 0° C. for 0.5 h. The reaction mixture was poured onto saturated $NH_4Cl$ and extracted with ether (3×50 mL). The combined ether extracts were dried over anhydrous $MgSO_4$ and concentrated in vacuo to give an orange oil. This product was used in the next step of the synthetic sequence without further purification.

Part B: Preparation of 2-Amino-5-fluoro-α-isopropylethynyl-α-trifluoromethyl-benzyl alcohol To a solution of the benzyl alcohol (crude product, approx. 0.67 mmol) in methanol (5 mL) at room temperature was added concentrated hydrochloric acid (0.1 mL) and the resulting reaction mixture was allowed to stir at room temperature for 0.25 h. The reaction mixture was quenched with saturated $NaHCO_3$ and extracted with ether (3×50 mL). The combined ether extracts were dried over anhydrous $MgSO_4$ and concentrated in vacuo. Chromatography ($SiO_2$, 15% EtOAc-hexanes eluant) provided 103 mg of the title compound (184 mg theoretical, 56% yield over two steps).

Part C: Preparation of 4-Isopropylethynyl-4-trifluoromethyl-5-fluoro-1,4-dihydro-2H-3,1-benzoxazin-2-one To a solution of amino-alcohol (103 mg 0.37 mmol) in toluene (3 mL) at 0° C. was added N,N-diisopropylethylamine (0.23 mL, 1.30 mmol) followed by a solution of 1.93M phosgene in toluene (0.25 mL, 0.48 mmol) and the resulting solution was allowed to stir at 0° C. for 0.1 h. The reaction mixture was poured onto water and extracted with ether (3×50 mL). The combined ether extracts were dried over anhydrous $MgSO_4$ and concentrated in vacuo. Chromatography ($SiO_2$, 20% EtOAc-hexanes eluant) provided 89 mg of the title compound (111 mg theoretical, 80% yield).

Example 19

Preparation of 4-Chloro-2-cyclopropylacetylaniline

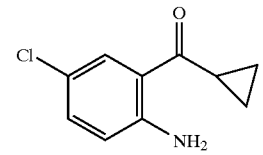

Cyclopropyllithium was prepared by the procedure of Dakkouri (*Chem. Ber.* 1979, 112,3523.). To a 3 neck 100 ml flask equipped with a magnetic stir bar, a thermocouple probe, a West condenser and a nitrogen line was charged 1.0 g (0.14 mol.) of freshly cleaned Li ribbon and 20 ml anhydrous ether. The mixture was cooled to 0° C. and 5.6 ml of cyclopropylbromide (70 mmol) in 10 ml of anhydrous ether was added dropwise. The bromide solution was added over 45 min. due to the exothermic nature of the metalation reaction. After the addition was complete the lithium reagent was aged for 30 min. then cooled to −65° C. A solution of 5.53 g (28 mmol.) of 5-chloroisatoic anhydride in 80 ml THF was prepared in a dry 3 neck flask and cooled to −40° C. The cyclopropyllithium solution was transferred via canula into the anhydride solution over 30 min. The resulting milky solution was aged for 1 h at −40° C. during which time the solution became clear with a pale green color. The anion solution was quenched by addition of 1 M citric acid solution and then warmed to ambient temperature. The phases were separated and the organic layer washed with water and concentrated to provide a tacky yellow solid which was chromatographed on silica gel with ethyl acetate/hexanes (3:1) to provide 3.56 g of the title compound in 65% yield. Crystallization from heptane provides the title compound as a pale yellow solid: m.p. 73.7° C.; $^1H$ NMR (300 MHz, $CDCl_3$) δ7.96 (d, J=1.5 Hz, 1 H), 7.22 (dd, J=2.3, 8.7 Hz, 1H), 6.59 (d, J=8.7 Hz, 1H), 6.13 (brs, 2H), 2.56 (m, 1 H),. 1.18 (m, 2 H), 1.00 (m, 2 H); $^{13}C$ NMR (75 MHz, $CDCl_3$) δ201.06, 148.23, 133.83, 130.41, 121.70, 119.69, 118.56, 17.37, 11.08; IR (cm$^{-1}$) 3315, 3012, 1628, 1582, 1533, 1481, 1464, 1414, 1389, 1343, 1313, 1217, 1183, 1158, 1082, 1053, 1032, 985, 893, 868, 813.

Example 20

Preparation of 4-Chloro-2-((cyclopropylenthynyl)acetyl)aniline

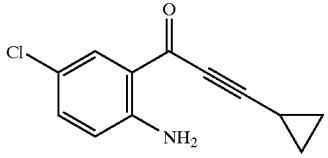

To a 3 neck 100 ml flask equipped with a magnetic stir bar, a thermocouple probe, a solid addition funnel and a nitrogen line was charged 3.7 g (56.0 mmol.) of cyclopropylacetylene and 30 ml of anhydrous THF. The solution was cooled to −60° C. and 30 ml (53.1 mmol.) of 1.8 M hexyllithium in hexanes was added dropwise while maintaining the internal temperature below −20° C. The solution was aged at −40° C. for 30 min. and then 5 g (25.3 mmol.) of 5-chloroisatoic anhydride was added as a solid in small portions. The resulting solution was aged for 2 h at −40° C. during which time the solution became clear with a pale yellow color. The anion solution was quenched by addition of 1 M citric acid solution and then warmed to ambient temperature. The phases were separated and the organic layer washed with water and concentrated to provide a an orange solid. The product was triturated with heptanes to provides 9 as a tan solid: $^1$H NMR (300 MHz, CDCl$_3$) δ8.43 (m, 1 H), 8.02 (m, 1H), 7.36 (m, 1H), 1.48 (m, 1 H), 0.99 (m, 2 H), 0.87 (m, 2 H); IR (cm$^{-1}$) 2978, 2221, 1641, 1579, 1502, 1434, 1410, 1370, 1299, 1055, 906, 829, 731.

Example 21

Preparation of (S)-6-Chloro-4-(chloro)-4-(trifluoromethyl)-1,4-dihydro-2H-3,1-benzoxazin-2-one

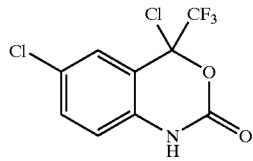

To a 3 neck flask equipped with a magnetic stirrer, a thermocouple probe and a dry ice condenser was charged 25 g (0.11 mol.) of trifluoroketone 3 and 150 ml of anhydrous toluene. This yellow solution was then heated to gentle reflux and a solution (87 ml, 0.17 mol.) of phosgene (1.93 M) in toluene was added subsurface. The solution was heated to reflux (temperature range at 104 to 110° C.) for 3 h after which time the yellow color had dissipated and the starting ketone was not detected by $^1$H NMR. The solution was cooled to ambient temperature and then concentrated to provide a heterogeneous solution. The product was triturated with heptane (100 ml) and filtered to provide 29.24 g (92%) of the desired chlorobenzoxazinone as a white solid. m.p. 140.8° C.; $^1$H NMR (300 MHz) δ9.26 (b, 1H), 7.57 (s, 1H), 7.45 (dd, J=1.9, 8.3 Hz, 1H), 6.94 (d, J=8.7 Hz, 1H) ; $^{13}$C NMR (75 MHz) δ146.32, 132.88, 132.42, 130.27, 125.80, 122.83, 119.06, 116.79, 115.85, 0.013; $^{19}$F NMR (282 MHz) δ−79.5; IR (cm$^{-1}$) 3191, 1764, 1601, 1498, 1403, 1335, 1316, 1252, 1199, 1073, 991, 901, 874, 826, 683.

Example 22

Preparation of (+/−)-6-Chloro-4-(cyclopropylethynyl)-4-(trifluoromethyl)-1,4-dihydro-2H-3,1-benzoxazin-2-one

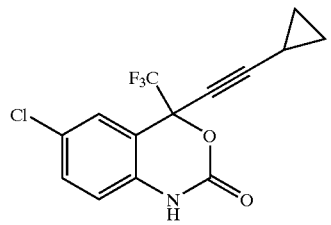

To a 50 ml 3 neck flask equipped with a magnetic stir bar, a thermocouple probe and nitrogen inlet was charged 10 ml anhydrous THF and 2.2 eq cyclopropylacetylene (0.23 g, 3.4 mmol.). The solution was cooled to −50° C. and 2.0 eq. of n-hexyllithium in hexanes (1.8 M, 1.8 ml, 3.26 mmol.) was added dropwise via syringe. The internal temperature was maintained below −30° C. during the organolithium charge. The solution was aged for 30 minutes and then a solution of 0.44 g (1.55 mmol.) of the chlorobenzoxazinone in 5 ml THF was added dropwise. The reaction solution was maintained below −20° C. during the addition. The mixture was aged at −20° C. for 4 h after which time all of the starting material had been consumed by TLC. The mixture was then quenched while cold with saturated ammonium chloride solution and the layers separated. The organic solution was dried over sodium sulfate, concentrated to provide a light yellow solid. The product was then triturated with heptanes to provide 0.47 g (95%) of racemic title product as a white solid. HPLC: 99.8 area %; m.p. 183–6° C.; $^1$H NMR (400 MHz, DMSO-d$_6$) δ11.05 (s, 1H), 7.54 (dd, J=2.5, 7 Hz, 1H), 7.43 (d, J=2.5 Hz, 1H), 6.99 (d, J=7 Hz, 1H), 1.58 (m, 1H), 0.92 (m, 2H), 0.77 (m, 2H); $^{13}$C NMR (100 MHz, DMSO-d$_6$) δ146.23, 134.71, 132.04, 126.93, 126.57, 122.24, 116.83, 114.08, 95.63, 77.62, 65.85, 8.48, 8.44, −1.32; $^{19}$F NMR (282 MHz, DMSO-d$_6$) δ−81.1; IR (cm$^{-1}$) 3316, 3094, 2250, 1752, 1602, 1498, 1196, 1186. HRMS calcd. for C$_{14}$H$_{10}$F$_3$ClNO$_2$ (M+H) 316.0352, found 316.0338. Anal. Calcd. for C$_{14}$H$_9$F$_3$ClNO$_2$: C, 53.27; H, 2.87; N, 4.45; Cl 11.23; F, 18.05. Found: C, 53.15; H, 2.73; N, 4.37; Cl, 11.10; F, 17.84.

Example 23

Preparation of (S)-6-Chloro-4-(1-pyridylethynyl)-4-(trifluoromethyl)-1,4-dihydro-2H-3,1-benzoxazin-2-one

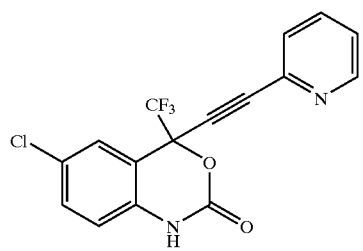

To a 50 ml 3 neck flask equipped with a magnetic stir bar, thermocouple and nitrogen inlet was charged 20 ml anhydrous THF and 2.2 eq pyridylethyne (1.1 g, 10.2 mmol.).

The solution was cooled to −50° C. and 2.0 eq. of n-hexyllithium in hexanes (1.8 M, 4.0 ml, 10.0 mmol.) was added dropwise via syringe. The internal temperature was maintained below −30° C. during the organolithium charge. The solution was aged for 30 minutes and then a solution of 1.5 g (5.2 mmol.) of the chlorobenzoxazinone from Example 21 in 15 ml THF was added dropwise. The reaction solution was maintained above −20° C. during the addition. The mixture was aged at −20° C. for 2 h at which time all of the starting material had been consumed by TLC. The mixture was then quenched while cold with saturated ammonium chloride solution and the layers separated. The organic solution was dried over sodium sulfate, concentrated to provide a brown solid. The product was purified by flash chromatography (hexanes/ethyl acetate; 3:1) and then triturated with heptanes to provide 1.06 g (57%) of the title compound as a white solid. HPLC: 99.8 area %; m.p. 185.8° C.; $^1$H NMR (300 MHz) δ9.62 (s, 1H), 8.68 (d, J=4.2 Hz, 1 H), 7.76 (dd, J=7.6, 9.5 Hz, 1H), 7.61 (d, J=5.7 Hz, 2H), 7.40 (m, 2 H), 6.91 (d, J=8.7 Hz, 1H; $^{13}$C NMR (75 MHz) δ150.38, 148.20, 140.32, 136.57, 133.43, 132.06, 129.34, 128.30, 127.60, 124.65, 123.94, 120.13, 116.37, 114.01, 88.72, 78.75,; $^{19}$F NMR (282 MHz) δ−81.4; IR (cm$^{-1}$)3245, 3157, 3069, 2946, 2876, 2252, 1757, 1603, 1581, 1498, 1467, 1428, 1401, 1305, 1256, 1243, 1186, 1142, 1401, 1304, 1256+, 1243, 1186, 1142, 1103, 1072, 1037, 997, 971, 940, 866, 822, 780, 740. MS FIA/PCI (M+H) 353 m/z.

Example 24

Preparation of (+/−)-6-Chloro-4-(1-deuterocycloprop-1-ylethynyl)-4-(trifluoromethyl)-1,4-dihydro-2H-3,1-benzoxazin-2-one

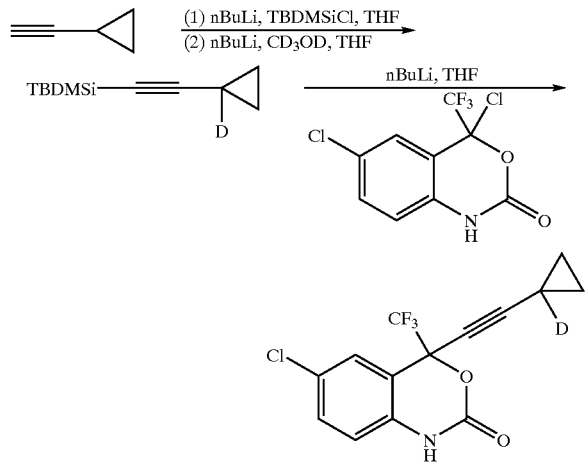

Part A: Preparation of 1-(t-Butyldimethylsilyl)-2-cyclopropylacetylene

To a stirred, cooled (0° C.) solution of 188 mL (658 mmol) of a 3.5 M solution of cyclopropylacetylene in toluene was added 200 mL of THF. The solution was re-cooled to 0° C. and treated with 264 mL (660 mmol) of a 2.5 M solution of n-BuLi in hexanes over 15 min. The solution was stirred an additional 40 min. at 0° C. and treated with 100 g(663 mmol) of t-butyldimethylsilyl chloride in 60 mL of THF over 10 min. After stirring 90 min. at 0° C. the reaction was quenched with saturated aq. NH$_4$Cl and poured into 500 mL of water. The mixture was extracted with 500 mL of ether, and the organic extract was washed three times with water and once with brine. Concentration under reduced pressure followed by distillation afforded 49 g(42%) of 1-(t-butyldimethylsilyl)-2-cyclopropylacetylene as a colorless oil (b.p. 39–42° C. at 0.5 torr). $^1$H NMR (CDCl$_3$, 300 MHz) δ1.17–1.24(m, 1H); 0.95(s, 9H); 0.61–0.75(m, 4H); 0.00(s, 6H).

Part B: Preparation of 1-Deutero-1-ethynylcyclpropane

To a stirred, cooled(−30° C.) solution of 130 g(720 mmol) of 1-(t-butyldimethylsilyl)-2-cyclopropylacetylene in 400 mL of THF was added 403 mL(1.01 mol) of a 2.5 M solution of n-BuLi in hexanes over 15 min. The solution was stirred 1.5 h at −20° C. and then treated with 49 mL(1.2 mol) of CD$_3$OD over 10 min. After stirring 10 min. at −10° C. the reaction was quenched with 10 mL of D$_2$O, followed 15 min later with 1 L of 20% aq. citric acid. The mixture was extracted with 1 L of ether, and the organic extract was washed sequentially with water, sat'd aq. NaHCO$_3$, and brine. The solution was dried(MgSO$_4$), concentrated under reduced pressure, and re-dissolved in 300 mL of THF. This solution was treated with 780 mL(350 mmol) of a 1 M solution of (n-Bu)$_4$NF in THF and stirred 6 h at ambient temperature. The solution was cooled to 0° C., washed with 1 L of water, and the aqueous phase was extracted with 150 mL of p-xylene. The organic extract was washed with 500 mL of water, and the combined aqueous phases were extracted with 70 mL of p-xylene. The two organic phases were combined, and washed 5 times with water and once with brine, dried(MgSO$_4$), and distilled. The fraction which boiled up to 105° C. at ambient pressure was collected to give 88 g of a solution having a deuterocyclopropylacetylene concentration of c. 43%. The remainder is primarily THF with some xylene and some 1-butene.

Part C: Preparation of (+/−) 6-Chloro-4-(1-deuterocycloprop-1-ylethynyl)-4-trifluoromethyl-1,4-dihydro-2H-3,1-benzoxazin-2-one To a stirred, cooled(−60° C.) solution of 12.6 g of a 60% solution of 1-deutero-1-ethynylcyclopropane in 65 mL of anhydrous THB was added 41 mL(102 mmol) of a 2.5M solution co n-BuLi in hexanes over 20 min. The solution was stirred 30 min. and charged with 9.7 g(33.9 mmol) of 4,6-dichloro-4-trifluoromethyl-1,4-dihydro-2H-3,1-benzoxazin-2-one in 10 mL of THF over 2 min. The solution was warmed to −30° C. over 1 h, whereupon it was quenched with 20% aqueous citric acid. The mixture was extracted with ether, and the organic extract was washed with saturated aq. NaHCO$_3$ then brine. The solution was concentrated under reduced pressure, and the crude product was chromatographed on silica gel(elution with 2:1 hexanes-ether) to afford 5.8 g(54%) of (+/−) 6-chloro-4-(1-deuterocycloprop-1-ylethynyl)-4-trifluoromethyl-1,4-dihydro-2H-3,1-benzoxazin-2-one as a white solid, mp 180–181° C. $^1$H NMR(300 MHz, CDCl$_3$) δ9.32(br. s, 1H); 7.50(m, 1H); 7.37(dd, 1H, J=8, 1 Hz); 6.95(d, 1H, J=8 Hz); 0.82–0.96(m, 4H). Chiral chromatographic resolution provides (−) 6-Chloro-4-(1-deuterocycloprop-1-ylethynyl)-4-trifluoromethyl-1,4-dihydro-2H-3,1-benzoxazin-2-one as a white solid, mp 133–134° C.

Example 25

Preparation of 4-Isopropylethynyl-4-trifluoromethyl-5-fluoro-1,4-dihydro-2H-3,1-benzoxazin-2-one Part A: Preparation of 2-Amino-6-fluoro-α-trifluoromethyl-benzyl alcohol To a solution of 2-triphenylmethylamino-6-fluorobenzaldehyde (100 mg, 0.24 mmol) in THF (2 mL) at 0° C. was added trifluoromethyltrimethylsilane (0.06 mL, 0.36 mmol) followed by a solution of tetrabutylammonium fluoride in THF (1M, 0.36 mL, 0.36 mmol) and the resulting reaction mixture was allowed to stir with warming to room temperature (ice bath removed after the addition of reagents) for 0.5 h. The reaction mixture was poured onto water and extracted with EtOAc (3×50 mL) and the combined EtOAc extracts were dried over anhydrous $NaSO_4$ and concentrated in vacuo. Chromatography ($SiO_2$, 10% EtOAc-hexanes) provided 88 mg of the title compound (108 mg theoretical, 82% yield).

Part B: Preparation of 3-Fluoro-2-trifluoroacetyl-triphenylmethylaniline

To a solution of 2-amino-6-fluoro-α-trifluoromethyl-benzyl alcohol (88 mg, 0.2 mmol) in methylene chloride (6 mL) at room temperature was added manganese(IV)oxide (900 mg, 10×wt) and the resulting reaction mixture was allowed to stir at room temperature for 5 h. The reaction mixture is filtered through Celite and concentrated in vacuo. Chromatography ($SiO_2$, 5% EtOAc-hexanes) provided 52 mg of the title compound (90 mg theoretical, 58% yield).

Part C: Preparation of 2-Triphenylmethylamino-6-fluoro-α-isopropylethynyl-α-trifluoromethyl-benzyl alcohol To a solution of 3-methyl-1-butyne (0.15 mL, 1.51 mmol) in THF (2 mL) at 0° C. was added 1.6M nBuLi in hexane (0.84 mL, 1.34 mmol) and the resulting reaction mixture was allowed to stir at 0° C. for 0.5 h. A solution of 6-fluoro-2-trifluoroacetylaniline (300 mg, 0.67 mmol) in THF (2 mL) was added to the reaction mixture and the resulting reaction mixture was allowed to stir with warming to room temperature (ice bath removed after addition of reagent) for 0.5 h. The reaction mixture was poured onto saturated $NH_4Cl$ and extracted with ether (3×50 mL)). The combined ether extracts were dried over anhydrous $MgSO_4$ and concentrated in vacuo to give an orange oil This product was used in the next step of the synthetic sequence without further purification.

Part D: Preparation of 4-Isopropylethynyl-4-trifluoromethyl-5-fluoro-1,4-dihydro-2H-3,1-benzoxazin-2-one To a solution of the crude trityl protected amino-alcohol (crude product, 0.67 mmol) in methanol (5 mL) at room temperature was added concentrated HCl (0.1 mL) and the resulting reaction mixture is allowed to stir at room temperature for 0.25 h. The reaction mixture is concentrated in vacuo and the residue is taken up in ether (10 mL) and washed with saturated $NaHCO_3$. The ether extracts were dried over anhydrous $MgSO_4$ and concentrated in vacuo. Chromatography ($SiO_2$, 15% EtOAc-hexanes) provided 103 mg of the deprotected amino-alcohol (184 mg theoretical, 56% yield).

To a solution of amino-alcohol (103 mg, 0.37 mmol) in toluene (3 mL) at 0° C. was added N,N-diisopropylethylamine (0.23 mL, 1.3 mmol) followed by a solution of 1.93M phosgene in toluene (0.25 mL, 0.48 mmol) and the resulting solution was allowed to stir at 0° C. for 1 h. The reaction mixture was poured onto water and extracted with ether (3×50 mL). The combined ether extracts were dried over anhydrous $MgSO_4$ and concentrated in vacuo. Chromatography ($SiO_2$, 20% EtOAc-hexanes eluant) provided 89 mg of the title compound (111 mg theoretical, 80% yield).

TABLE 1

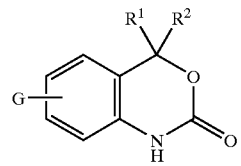

| Ex. # | G | $R^1$ | $R^2$ | m.p. (° C.) | Mass Spec |
|---|---|---|---|---|---|
| 1 | 6-Cl, 8-OH | $CF_3$ | C≡C-cycPr | | 332.0301 |
| 2 (−) | 6-Cl, 8-OH | $CF_3$ | C≡C-cycPr | 170–172 | |
| 3 (−) | 6-Cl, 8-OH | $CF_3$ | C≡C-cycPr | | |
| 4 | 6-Cl, 8-F | $CF_3$ | C≡C-cycPr | 169–171 | 334.0244 |
| 5 | 6-$CH_3$ | iPr | C—C-cycPr | 138–138.5 | 270.1494 |
| 6 | 6-$CH_3$ | $CF_3$ | C≡C-iPr | 198–199 | 298.1047 |
| 7 | 6-$COCH_3$ | $CF_3$ | C≡C-cycPr | 197–200 | |
| 8 | 5,6-diF | $CF_3$ | 3-methyl-1-buten-1-yl | | |
| 9 | 5,6-diF | $CF_3$ | C≡C-iPr | | 319.0616 |
| 12 | 6-Cl, 7-aza | $CF_3$ | C≡C-cycPr | | 317.0322 |
| 13 | 6-Cl | $CF_3$ | methoxyethoxy | | |
| 14 | 6-Cl | $CF_3$ | n-propylamino | | |
| 15 | 6-Cl | $CF_3$ | furan-2-yl—≡— | | |
| 16 | 6-OMe | $CF_3$ | C≡C—Et | 161–162 | 300.0841 |
| 17 | 6-Cl | $CF_3$ | ≡—(1'-OH-cycPr) | | 332.0296 |
| 18 | 5-F | $CF_3$ | ≡-iPr | | |
| 22 | 6-Cl | $CF_3$ | ≡-cycPr | | 316.0352 |
| 23 | 6-Cl | $CF_3$ | ≡—2-pyridyl | | 353 (M + H) |
| 24 | 6-Cl | $CF_3$ | ≡—(1-detero-cycloprop-1-yl) | 133–134 | |
| 25 | 5-F | $CF_3$ | ≡-iPr | | |
| 26 | 6-Cl, 8-OMe | $CF_3$ | C≡C-cycPr | | 346.0477 |
| 27 | 6-Cl, 7-OH | $CF_3$ | C≡C-cycPr | | 332.0286 |

TABLE 1-continued

| Ex. # | G | R¹ | R² | m.p. (° C.) | Mass Spec |
|---|---|---|---|---|---|
| 28 | 6-Cl, 8-F | $CF_3$ | C≡C—Et | 191–192 | 339.0525 (M + $NH_4^+$) |
| 29 | 6-Cl, 8-F | $CF_3$ | $CH_2CH_2CH(CH_3)_2$ | 160–162 | 340 ($MH^+$) |
| 30 | 5,6-diF | $CF_3$ | C≡C-cycPr | | 318.0550 ($MH^+$) |
| 31 | 5,6-diF | $CF_3$ | C≡C-iPr | amorphous | |
| 32 | 5,6-diF | $CF_3$ | C≡C-nPr | | 320.0691 |
| 33 | 5,6-diF | $CF_3$ | C≡C—Et | | 306.0550 ($MH^+$) |
| 34 | 5,6-diF | $CF_3$ | C≡C—Me | 217 | |
| 35 | 5,6-diF | $CF_3$ | $CH_2CH_2CH_2CH_2CH_3$ | | 324.1008 |
| 36 | 5,6-diF | $CF_3$ | $CH_2CH_2CH(CH_3)_2$ | | 324.1003 |
| 37 | 5,6-diF | $CF_3$ | $CH_2CH_2CH_2CH_3$ | | 310.0878 |
| 38 | 5,6-OCH$_2$O— | $CF_3$ | C≡C-cycPr | 223–225 | 326.0639 |
| 39 | 5,6-OCH$_2$O— | $CF_3$ | C≡C-iPr | 240 | 328.0797 |
| 40 | 5,6-OCH$_2$O— | $CF_3$ | C≡C-nPr | 208–210 | |
| 41 | 5,6-OCH$_2$O— | $CF_3$ | C≡C—Et | 230–232 | |
| 42 | 5,6-OCH$_2$O— | $CF_3$ | $CH_2C≡C—CH_2CH_3$ | 215–217 | 328.0800 |
| 43 | 5,6-OCH$_2$O— | $CF_3$ | $CH_2C≡C—CH_3$ | 207–208 | 314.0640 |
| 44 | 5,6-OCH$_2$O— | $CF_3$ | $CH_2CH_2CH(CH_3)_2$ | 199–200 | |
| 45 | 6-OMe | $CF_3$ | C≡C-cycPr | 155–157 | 312.0835 |
| 46 | 6-OMe | $CF_3$ | C≡C-cycPr | 143–144 | 312.0843 |
| 47 | 6-OMe | $CF_3$ | C≡C-cycPr | 142–144 | 312.0836 |
| 48 | 6-OMe | $CF_3$ | C≡C-iPr | 158–159 | 314.0998 |
| 49 | 6-OMe | $CF_3$ | C≡C-nPr | 148–150 | 314.1007 |
| 50 | 6-OMe | $CF_3$ | C≡C—Me | 177–180 | 286.0691 |
| 51 | 6-OMe | $CF_3$ | $CH_2C≡C—CH_2CH_3$ | 119–122 | 314.0989 |
| 52 | 6-OMe | $CF_3$ | $CH_2CH_2CH(CH_3)_2$ | | 318 ($MH^+$) |
| 53 | 6-OMe | $CF_3$ | $CH_2CH_2CH_2CH_3$ | | 304.1167 |
| 54 | 6-OMe | $CF_3$ | $CH_2CH_2—Ph$ | | 352.1153 |
| 55 | 6-OMe, 8-F | $CF_3$ | C≡C-cycPr | 188–189 | 330.0738 |
| 56 | 6-NMe$_2$ | $CF_3$ | C≡C-cycPr | | 325.1173 |
| 57 | 6-NMe$_2$ | $CF_3$ | C≡C-iPr | | 327.1322 |
| 58 | 6-NMe$_2$ | $CF_3$ | $CH_2CH_2CH_2CH_3$ | | 331.1641 |
| 59 | 6-NMe$_2$ | $CF_3$ | $CH_2CH_2CH(CH_3)_2$ | | 331.1637 |
| 60 | 6-COCH$_3$ | $CF_3$ | C≡C—Et | 180–183 | |
| 61 | 6-CH$_3$ | $CF_3$ | C≡C-cycPr | 189 | 296.0905 |
| 62 | 6-CH$_3$ | $CF_3$ | C≡C—Et | 222 | 284.0882 |
| 63 | 6,8-diCl | $CF_3$ | C≡C-cycPr | 152–153 | 348.9870 |
| 64 | 6,8-diCl | $CF_3$ | $CH_2CH_2—Ph$ | | 389.0188 (M+) |
| 65 | 5,6,8-triF | $CF_3$ | C≡C-cycPr | amorphous | |
| 66 | 5,6,8-triF | $CF_3$ | C≡C-iPr | amorphous | |
| 67 | 5,6,8-triF | $CF_3$ | C≡C-nPr | amorphous | |
| 68 | 5,6,8-triF | $CF_3$ | C≡C—Et | amorphous | |
| 69 | 5,8-diF | $CF_3$ | C≡C-cycPr | | 335.0834 (M + $NH_4^+$) |
| 70 | 5,8-diF | $CF_3$ | C≡C-iPr | | 320.0710 ($MH^+$) |
| 71 | 5,8-diF | $CF_3$ | C≡C-nPr | | 337.0970 (M + $NH_4^+$) |
| 72 | 5,8-diF | $CF_3$ | C≡C—Et | | 323.8817 (M + $NH_4^+$) |
| 73 | 6-iPr | $CF_3$ | C≡C-cycPr | | 324.1203 |
| 74 | 6-iPr | $CF_3$ | C≡C-iPr | | 326.1361 |
| 75 | 6-iPr | $CF_3$ | C≡C—Ph | | 360.1204 |
| 76 | 6-iPr | $CF_3$ | $CH_2CH_2CH_2CH_2CH_3$ | | 330.1672 |
| 77 | 6-iPr | $CF_3$ | $CH_2CH_2-iPr$ | | 330.1673 |
| 78 | 6-iPr | $CF_3$ | $CH_2CH_2—Ph$ | | 364.1517 |
| 79 | 6-OCF$_3$ | $CF_3$ | C≡C-cycPr | | 366.0561 |
| 80 | 6-OCF$_3$ | $CF_3$ | C≡C-iPr | | 368.0712 |
| 81 | 6-OCF$_3$ | $CF_3$ | C≡C—Ph | | 401.0475 |
| 82 | 6-OCF$_3$ | $CF_3$ | $CH_2CH_2CH_2CH_2CH_3$ | | 372.1018 |
| 83 | 6-OCF$_3$ | $CF_3$ | $CH_2CH_2-iPr$ | | 372.1039 |
| 84 | 6-OCF$_3$ | $CF_3$ | $CH_2CH_2—Ph$ | | 405.0795 |
| 85 | H | $CF_3$ | $CH_2CH_2—Ph$ | | 282.0735 |

TABLE 1-continued

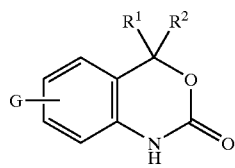

| Ex. # | G | R¹ | R² | m.p. (° C.) | Mass Spec |
|---|---|---|---|---|---|
| 86 | H | $CF_3$ | C≡C-iPr | | 284.0894 |
| 87 | H | $CF_3$ | C≡C—Ph | | 318.0748 |
| 88 | H | $CF_3$ | $CH_2CH_2CH_2CH_2CH_3$ | | 288.1201 |
| 89 | H | $CF_3$ | $CH_2CH_2$-iPr | 121–122 | |
| 90 | H | $CF_3$ | $CH_2CH_2$—Ph | | 322.1055 |
| 91 | 6-Ph | $CF_3$ | C≡C-cycPr | 185–186 | 358.1055 |
| 92 | 6-Ph | $CF_3$ | C≡C-iPr | 179–180 | 360.1211 |
| 93 | 6-Ph | $CF_3$ | C≡C-nPr | 143–144 | 360.1211 |
| 94 | 6-Ph | $CF_3$ | C≡C-iBu | 163–164 | 374.1352 |
| 95 | 6-Ph | $CF_3$ | C≡C—Et | 195 | 346.1055 |
| 96 | 6-Ph | $CF_3$ | $CH_2CH_2$-iPr | 147–148 | 364.1524 |
| 97 | 6-OMe | iPr | C≡C-cycPr | | 286.1428 |
| 98 | 6-OMe | iPr | C≡C-iPr | | 288.1583 |
| 99 | 6-$CH_3$ | cycPr | C≡C-iPr | 133–134 | 270.1498 |
| 100 | 6-$CH_3$ | iPr | C≡C-iPr | 133–134 | 272.1648 |
| 101 | 6-$CH_3$ | Et | C≡C-iPr | 138–139 | 258.1505 |
| 102 | 6-$CH_3$ | Et | C≡C—Et | 138.5–139 | 244.1333 |
| 103 | 6,7-diCl | cycPr | C≡C-iPr | | |
| 104 | 6,7-diCl | iPr | C≡C-iPr | amorphous | |
| 105 | 7-Cl | cycPr | C≡C-cycPr | | 288.0783 |
| 106 | 7-Cl | cycPr | C≡C-iPr | | 290.0941 |
| 107 | 7-Cl | cycPr | C≡C-iBu | 117–118 | 304.1110 |
| 108 | 7-Cl | iPr | C≡C-cycPr | | 290.0940 |
| 109 | 7-Cl | iPr | C≡C-iPr | | 292.1103 |
| 110 | 6-Cl, 8-aza | $CF_3$ | C≡C-cycPr | | 317.0317 |
| 111 | 6-Cl, 8-aza | $CF_3$ | C≡C-iPr | | 319 ($MH^+$) |
| 112 | 6-Cl, 8-aza | $CF_3$ | $CH_2CH_2$—Ph | 214–215 | 357.0625 |
| 113 | 6-$OCH_3$, 7-aza | $CF_3$ | C≡C-cycPr | 181–182 | 313.0800 |
| 114 | 6-aza | $CF_3$ | C≡C-cycPr | | |

*Unless otherwise noted, stereochemistry is (+/−).

TABLE 2

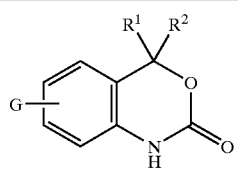

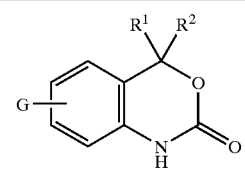

| Ex. # | G | R¹ | R² |
|---|---|---|---|
| 201 | 6-Cl, 8-F | $CF_3$ | C≡C—iPr |
| 202 | 6-Cl, 8-F | $CF_3$ | C≡C—nPr |
| 203 | 6-Cl, 8-F | $CF_3$ | C≡C—Bu |
| 204 | 6-Cl, 8-F | $CF_3$ | C≡C—iBu |
| 205 | 6-Cl, 8-F | $CF_3$ | C≡C—tBu |
| 206 | 6-Cl, 8-F | $CF_3$ | C≡C—Me |
| 207 | 6-Cl, 8-F | $CF_3$ | C≡C—Ph |
| 208 | 6-Cl, 8-F | $CF_3$ | C≡C—(2-Cl)Ph |
| 209 | 6-Cl, 8-F | $CF_3$ | C≡C—(3-Cl)Ph |
| 210 | 6-Cl, 8-F | $CF_3$ | C≡C—(2-F)Ph |
| 211 | 6-Cl, 8-F | $CF_3$ | C≡C—(3-F)Ph |
| 212 | 6-Cl, 8-F | $CF_3$ | C≡C—(2-OH)Ph |
| 213 | 6-Cl, 8-F | $CF_3$ | C≡C—(3-OH)Ph |
| 214 | 6-Cl, 8-F | $CF_3$ | C≡C—(2-OMe)Ph |
| 215 | 6-Cl, 8-F | $CF_3$ | C≡C—(3-OMe)Ph |
| 216 | 6-Cl, 8-F | $CF_3$ | C≡C—(2-CN)Ph |
| 217 | 6-Cl, 8-F | $CF_3$ | C≡C—(3-CN)Ph |
| 218 | 6-Cl, 8-F | $CF_3$ | C≡C—(2-$NH_2$)Ph |
| 219 | 6-Cl, 8-F | $CF_3$ | C≡C—(3-$NH_2$)Ph |
| 220 | 6-Cl, 8-F | $CF_3$ | C≡C—(2-$NMe_2$)Ph |
| 221 | 6-Cl, 8-F | $CF_3$ | C≡C—(3-$NMe_2$)Ph |
| 222 | 6-Cl, 8-F | $CF_3$ | C≡C-2-Pyridyl |
| 223 | 6-Cl, 8-F | $CF_3$ | C≡C-3-Pyridyl |
| 224 | 6-Cl, 8-F | $CF_3$ | C≡C-4-Pyridyl |
| 225 | 6-Cl, 8-F | $CF_3$ | C≡C-2-furanyl |
| 226 | 6-Cl, 8-F | $CF_3$ | C≡C-3-furanyl |
| 227 | 6-Cl, 8-F | $CF_3$ | C≡C-2-thienyl |
| 228 | 6-Cl, 8-F | $CF_3$ | C≡C-3-thienyl |
| 229 | 6-Cl, 8-F | $CF_3$ | CH=CH—cycPr |
| 230 | 6-Cl, 8-F | $CF_3$ | CH=CH—iPr |
| 231 | 6-Cl, 8-F | $CF_3$ | CH=CH—nPr |
| 232 | 6-Cl, 8-F | $CF_3$ | CH=CH—Bu |
| 233 | 6-Cl, 8-F | $CF_3$ | CH=CH—iBu |
| 234 | 6-Cl, 8-F | $CF_3$ | CH=CH—tBu |
| 235 | 6-Cl, 8-F | $CF_3$ | CH=CH—Et |
| 236 | 6-Cl, 8-F | $CF_3$ | CH=CH—Me |
| 237 | 6-Cl, 8-F | $CF_3$ | CH=CH—Ph |
| 238 | 6-Cl, 8-F | $CF_3$ | CH=CH-2-Pyridyl |
| 239 | 6-Cl, 8-F | $CF_3$ | CH=CH-3-Pyridyl |
| 240 | 6-Cl, 8-F | $CF_3$ | CH=CH-4-Pyridyl |

TABLE 2-continued

| Ex. # | G | R¹ | R² |
|---|---|---|---|
| 241 | 6-Cl, 8-F | $CF_3$ | CH=CH-2-furanyl |
| 242 | 6-Cl, 8-F | $CF_3$ | CH=CH-3-furanyl |
| 243 | 6-Cl, 8-F | $CF_3$ | CH=CH-2-thienyl |
| 244 | 6-Cl, 8-F | $CF_3$ | CH=CH-3-thienyl |
| 245 | 6-Cl, 8-F | $CF_3$ | $CH_2CH_2CH_2CH_2CH_3$ |
| 246 | 6-Cl, 8-F | $CF_3$ | $CH_2CH_2CH_2CH_3$ |
| 247 | 6-Cl, 8-F | $CF_3$ | $CH_2CH_2$—cycPr |
| 248 | 6-Cl, 8-F | $CF_3$ | $CH_2CH_2$—tBu |
| 249 | 6-Cl, 8-F | $CF_3$ | $CH_2CH_2$—Ph |
| 250 | 6-Cl, 8-F | $CF_3$ | $CH_2CH_2$-2-Pyridyl |
| 251 | 6-Cl, 8-F | $CF_3$ | $CH_2CH_2$-3-Pyridyl |
| 252 | 6-Cl, 8-F | $CF_3$ | $CH_2CH_2$-4-Pyridyl |
| 253 | 6-Cl, 8-F | $CF_3$ | $CH_2CH_2$-2-furanyl |
| 254 | 6-Cl, 8-F | $CF_3$ | $CH_2CH_2$-3-furanyl |
| 255 | 6-Cl, 8-F | $CF_3$ | $CH_2CH_2$-2-thienyl |
| 256 | 6-Cl, 8-F | $CF_3$ | $CH_2CH_2$-3-thienyl |
| 257 | 5,6-diF | $CF_3$ | C≡C—Bu |
| 258 | 5,6-diF | $CF_3$ | C≡C—iBu |
| 259 | 5,6-diF | $CF_3$ | C≡C—tBu |
| 260 | 5,6-diF | $CF_3$ | C≡CCH$_2$CH$_2$OH |
| 261 | 5,6-diF | $CF_3$ | C≡C—CH(OH)Me |
| 262 | 5,6-diF | $CF_3$ | C≡C—Ph |
| 263 | 5,6-diF | $CF_3$ | C≡C—(2-Cl)Ph |
| 264 | 5,6-diF | $CF_3$ | C≡C—(3-Cl)Ph |
| 265 | 5,6-diF | $CF_3$ | C≡C—(4-Cl)Ph |
| 266 | 5,6-diF | $CF_3$ | C≡C—(2-F)Ph |
| 267 | 5,6-diF | $CF_3$ | C≡C—(3-F)Ph |
| 268 | 5,6-diF | $CF_3$ | C≡C—(4-F)Ph |
| 269 | 5,6-diF | $CF_3$ | C≡C—(2-OH)Ph |
| 270 | 5,6-diF | $CF_3$ | C≡C—(3-OH)Ph |
| 271 | 5,6-diF | $CF_3$ | C≡C—(4-OH)Ph |
| 272 | 5,6-diF | $CF_3$ | C≡C—(2-OMe)Ph |
| 273 | 5,6-diF | $CF_3$ | C≡C—(3-OMe)Ph |
| 274 | 5,6-diF | $CF_3$ | C≡C—(4-OMe)Ph |
| 275 | 5,6-diF | $CF_3$ | C≡C—(2-CN)Ph |
| 276 | 5,6-diF | $CF_3$ | C≡C—(3-CN)Ph |
| 277 | 5,6-diF | $CF_3$ | C≡C—(4-CN)Ph |
| 278 | 5,6-diF | $CF_3$ | C≡C—(2-NO$_2$)Ph |
| 279 | 5,6-diF | $CF_3$ | C≡C—(3-NO$_2$)Ph |
| 280 | 5,6-diF | $CF_3$ | C≡C—(4-NO$_2$)Ph |
| 281 | 5,6-diF | $CF_3$ | C≡C—(2-NH$_2$)Ph |
| 282 | 5,6-diF | $CF_3$ | C≡C—(3-NH$_2$)Ph |
| 283 | 5,6-diF | $CF_3$ | C≡C—(4-NH$_2$)Ph |
| 284 | 5,6-diF | $CF_3$ | C≡C—(2-NMe$_2$)Ph |
| 285 | 5,6-diF | $CF_3$ | C≡C—(3-NMe$_2$)Ph |
| 286 | 5,6-diF | $CF_3$ | C≡C—(4-NMe$_2$)Ph |
| 287 | 5,6-diF | $CF_3$ | C≡C-2-Pyridyl |
| 288 | 5,6-diF | $CF_3$ | C≡C-3-Pyridyl |
| 289 | 5,6-diF | $CF_3$ | C≡C-4-Pyridyl |
| 290 | 5,6-diF | $CF_3$ | C≡C-2-furanyl |
| 291 | 5,6-diF | $CF_3$ | C≡C-3-furanyl |
| 292 | 5,6-diF | $CF_3$ | C≡C-2-thienyl |
| 293 | 5,6-diF | $CF_3$ | C≡C-3-thienyl |
| 294 | 5,6-diF | $CF_3$ | C≡C-2-oxazolyl |
| 295 | 5,6-diF | $CF_3$ | C≡C-2-thiazolyl |
| 296 | 5,6-diF | $CF_3$ | C≡C-4-isoxazolyl |
| 297 | 5,6-diF | $CF_3$ | C≡C-2-imidazolyl |
| 298 | 5,6-diF | $CF_3$ | CH$_2$C≡C—CH$_3$ |
| 299 | 5,6-diF | $CF_3$ | CH$_2$C≡C—CH$_2$CH$_3$ |
| 300 | 5,6-diF | $CF_3$ | CH=CH—cycPr |
| 301 | 5,6-diF | $CF_3$ | CH=CH—iPr |
| 302 | 5,6-diF | $CF_3$ | CH=CH—nPr |
| 303 | 5,6-diF | $CF_3$ | CH=CH—Bu |
| 304 | 5,6-diF | $CF_3$ | CH=CH—iBu |
| 305 | 5,6-diF | $CF_3$ | CH=CH—tBu |
| 306 | 5,6-diF | $CF_3$ | CH=CH—Et |
| 307 | 5,6-diF | $CF_3$ | CH=CH—Me |
| 308 | 5,6-diF | $CF_3$ | CH=CH—Ph |
| 309 | 5,6-diF | $CF_3$ | CH=CH-2-Pyridyl |
| 310 | 5,6-diF | $CF_3$ | CH=CH-3-Pyridyl |
| 311 | 5,6-diF | $CF_3$ | CH=CH-4-Pyridyl |
| 312 | 5,6-diF | $CF_3$ | CH=CH-2-furanyl |
| 313 | 5,6-diF | $CF_3$ | CH=CH-3-furanyl |
| 314 | 5,6-diF | $CF_3$ | CH=CH-2-thienyl |
| 315 | 5,6-diF | $CF_3$ | CH=CH-3-thienyl |
| 316 | 5,6-diF | $CF_3$ | $CH_2CH_2CH_3$ |
| 317 | 5,6-diF | $CF_3$ | $CH_2CH_2$—cycPr |
| 318 | 5,6-diF | $CF_3$ | $CH_2CH_2$—tBu |
| 319 | 5,6-diF | $CF_3$ | $CH_2CH_2CH_2CH_2OH$ |
| 320 | 5,6-diF | $CF_3$ | $CH_2CH_2$—CH(OH)Me |
| 321 | 5,6-diF | $CF_3$ | $CH_2CH_2Ph$ |
| 322 | 5,6-diF | $CF_3$ | $CH_2CH_2$—(2-Cl)Ph |
| 323 | 5,6-diF | $CF_3$ | $CH_2CH_2$—(3-Cl)Ph |
| 324 | 5,6-diF | $CF_3$ | $CH_2CH_2$—(4-Cl)Ph |
| 325 | 5,6-diF | $CF_3$ | $CH_2CH_2$—(2-F)Ph |
| 326 | 5,6-diF | $CF_3$ | $CH_2CH_2$—(3-F)Ph |
| 327 | 5,6-diF | $CF_3$ | $CH_2CH_2$—(4-F)Ph |
| 328 | 5,6-diF | $CF_3$ | $CH_2CH_2$—(2-OH)Ph |
| 329 | 5,6-diF | $CF_3$ | $CH_2CH_2$—(3-OH)Ph |
| 330 | 5,6-diF | $CF_3$ | $CH_2CH_2$—(4-OH)Ph |
| 331 | 5,6-diF | $CF_3$ | $CH_2CH_2$—(2-OMe)Ph |
| 332 | 5,6-diF | $CF_3$ | $CH_2CH_2$—(3-OMe)Ph |
| 333 | 5,6-diF | $CF_3$ | $CH_2CH_2$—(4-OMe)Ph |
| 334 | 5,6-diF | $CF_3$ | $CH_2CH_2$—(2-CN)Ph |
| 335 | 5,6-diF | $CF_3$ | $CH_2CH_2$—(3-CN)Ph |
| 336 | 5,6-diF | $CF_3$ | $CH_2CH_2$—(4-CN)Ph |
| 337 | 5,6-diF | $CF_3$ | $CH_2CH_2$—(2-NO$_2$)Ph |
| 338 | 5,6-diF | $CF_3$ | $CH_2CH_2$—(3-NO$_2$)Ph |
| 339 | 5,6-diF | $CF_3$ | $CH_2CH_2$—(4-NO$_2$)Ph |
| 340 | 5,6-diF | $CF_3$ | $CH_2CH_2$—(2-NH$_2$)Ph |
| 341 | 5,6-diF | $CF_3$ | $CH_2CH_2$—(3-NH$_2$)Ph |
| 342 | 5,6-diF | $CF_3$ | $CH_2CH_2$—(4-NH$_2$)Ph |
| 343 | 5,6-diF | $CF_3$ | $CH_2CH_2$—(2-NMe$_2$)Ph |
| 344 | 5,6-diF | $CF_3$ | $CH_2CH_2$—(3-NMe$_2$)Ph |
| 345 | 5,6-diF | $CF_3$ | $CH_2CH_2$—(4-NMe$_2$)Ph |
| 346 | 5,6-diF | $CF_3$ | $CH_2CH_2$-2-Pyridyl |
| 347 | 5,6-diF | $CF_3$ | $CH_2CH_2$-3-Pyridyl |
| 348 | 5,6-diF | $CF_3$ | $CH_2CH_2$-4-Pyridyl |
| 349 | 5,6-diF | $CF_3$ | $CH_2CH_2$-2-furanyl |
| 350 | 5,6-diF | $CF_3$ | $CH_2CH_2$-3-furanyl |
| 351 | 5,6-diF | $CF_3$ | $CH_2CH_2$-2-thienyl |
| 352 | 5,6-diF | $CF_3$ | $CH_2CH_2$-3-thienyl |
| 353 | 5,6-diF | $CF_3$ | $CH_2CH_2$-2-oxazolyl |
| 354 | 5,6-diF | $CF_3$ | $CH_2CH_2$-2-thiazolyl |
| 355 | 5,6-diF | $CF_3$ | $CH_2CH_2$-4-isoxazolyl |
| 356 | 5,6-diF | $CF_3$ | $CH_2CH_2$-2-imidazolyl |
| 357 | 5,6-diCl | $CF_3$ | C≡C—cycPr |
| 358 | 5,6-diCl | $CF_3$ | C≡C—iPr |
| 359 | 5,6-diCl | $CF_3$ | C≡C—nPr |
| 360 | 5,6-diCl | $CF_3$ | C≡C—Bu |
| 361 | 5,6-diCl | $CF_3$ | C≡C—iBu |
| 362 | 5,6-diCl | $CF_3$ | C≡C—tBu |
| 363 | 5,6-diCl | $CF_3$ | C≡C—Et |
| 364 | 5,6-diCl | $CF_3$ | C≡C—Me |
| 365 | 5,6-diCl | $CF_3$ | C≡CCH$_2$CH$_2$OH |
| 366 | 5,6-diCl | $CF_3$ | C≡C—CH(OH)Me |
| 367 | 5,6-diCl | $CF_3$ | C≡C—Ph |
| 368 | 5,6-diCl | $CF_3$ | C≡C—(2-Cl)Ph |
| 369 | 5,6-diCl | $CF_3$ | C≡C—(3-Cl)Ph |
| 370 | 5,6-diCl | $CF_3$ | C≡C—(4-Cl)Ph |
| 371 | 5,6-diCl | $CF_3$ | C≡C—(2-F)Ph |
| 372 | 5,6-diCl | $CF_3$ | C≡C—(3-F)Ph |
| 373 | 5,6-diCl | $CF_3$ | C≡C—(4-F)Ph |
| 374 | 5,6-diCl | $CF_3$ | C≡C—(2-OH)Ph |
| 375 | 5,6-diCl | $CF_3$ | C≡C—(3-OH)Ph |
| 376 | 5,6-diCl | $CF_3$ | C≡C—(4-OH)Ph |

TABLE 2-continued

| Ex. # | G | R¹ | R² |
|---|---|---|---|
| 377 | 5,6-diCl | $CF_3$ | C≡C—(2-OMe)Ph |
| 378 | 5,6-diCl | $CF_3$ | C≡C—(3-OMe)Ph |
| 379 | 5,6-diCl | $CF_3$ | C≡C—(4-OMe)Ph |
| 380 | 5,6-diCl | $CF_3$ | C≡C—(2-CN)Ph |
| 381 | 5,6-diCl | $CF_3$ | C≡C—(3-CN)Ph |
| 382 | 5,6-diCl | $CF_3$ | C≡C—(4-CN)Ph |
| 383 | 5,6-diCl | $CF_3$ | C≡C—(2-$NO_2$)Ph |
| 384 | 5,6-diCl | $CF_3$ | C≡C—(3-$NO_2$)Ph |
| 385 | 5,6-diCl | $CF_3$ | C≡C—(4-$NO_2$)Ph |
| 386 | 5,6-diCl | $CF_3$ | C≡C—(2-$NH_2$)Ph |
| 387 | 5,6-diCl | $CF_3$ | C≡C—(3-$NH_2$)Ph |
| 388 | 5,6-diCl | $CF_3$ | C≡C—(4-$NH_2$)Ph |
| 389 | 5,6-diCl | $CF_3$ | C≡C—(2-$NMe_2$)Ph |
| 390 | 5,6-diCl | $CF_3$ | C≡C—(3-$NMe_2$)Ph |
| 391 | 5,6-diCl | $CF_3$ | C≡C—(4-$NMe_2$)Ph |
| 392 | 5,6-diCl | $CF_3$ | C≡C-2-Pyridyl |
| 393 | 5,6-diCl | $CF_3$ | C≡C-3-Pyridyl |
| 394 | 5,6-diCl | $CF_3$ | C≡C-4-Pyridyl |
| 395 | 5,6-diCl | $CF_3$ | C≡C-2-furanyl |
| 396 | 5,6-diCl | $CF_3$ | C≡C-3-furanyl |
| 397 | 5,6-diCl | $CF_3$ | C≡C-2-thienyl |
| 398 | 5,6-diCl | $CF_3$ | C≡C-3-thienyl |
| 399 | 5,6-diCl | $CF_3$ | CH=CH—cycPr |
| 400 | 5,6-diCl | $CF_3$ | CH=CH—iPr |
| 401 | 5,6-diCl | $CF_3$ | CH=CH—nPr |
| 402 | 5,6-diCl | $CF_3$ | CH=CH—Bu |
| 403 | 5,6-diCl | $CF_3$ | CH=CH—iBu |
| 404 | 5,6-diCl | $CF_3$ | CH=CH—tBu |
| 405 | 5,6-diCl | $CF_3$ | CH=CH—Et |
| 406 | 5,6-diCl | $CF_3$ | CH=CH—Me |
| 407 | 5,6-diCl | $CF_3$ | CH=CH—Ph |
| 408 | 5,6-diCl | $CF_3$ | CH=CH-2-Pyridyl |
| 409 | 5,6-diCl | $CF_3$ | CH=CH-3-Pyridyl |
| 410 | 5,6-diCl | $CF_3$ | CH=CH-4-Pyridyl |
| 411 | 5,6-diCl | $CF_3$ | CH=CH-2-furanyl |
| 412 | 5,6-diCl | $CF_3$ | CH=CH-3-furanyl |
| 413 | 5,6-diCl | $CF_3$ | CH=CH-2-thienyl |
| 414 | 5,6-diCl | $CF_3$ | CH=CH-3-thienyl |
| 415 | 5,6-diCl | $CF_3$ | $CH_2CH_2CH_2CH_2CH_3$ |
| 416 | 5,6-diCl | $CF_3$ | $CH_2CH_2CH(CH_3)_2$ |
| 417 | 5,6-diCl | $CF_3$ | $CH_2CH_2CH_2CH_3$ |
| 418 | 5,6-diCl | $CF_3$ | $CH_2CH_2$—cycPr |
| 419 | 5,6-diCl | $CF_3$ | $CH_2CH_2$—tBu |
| 420 | 5,6-diCl | $CF_3$ | $CH_2CH_2CH_2CH_2OH$ |
| 421 | 5,6-diCl | $CF_3$ | $CH_2CH_2$—CH(OH)Me |
| 422 | 5,6-diCl | $CF_3$ | $CH_2CH_2$—Ph |
| 423 | 5,6-diCl | $CF_3$ | $CH_2CH_2$-2-Pyridyl |
| 424 | 5,6-diCl | $CF_3$ | $CH_2CH_2$-3-Pyridyl |
| 425 | 5,6-diCl | $CF_3$ | $CH_2CH_2$-4-Pyridyl |
| 426 | 5,6-diCl | $CF_3$ | $CH_2CH_2$-2-furanyl |
| 427 | 5,6-diCl | $CF_3$ | $CH_2CH_2$-3-furanyl |
| 428 | 5,6-diCl | $CF_3$ | $CH_2CH_2$-2-thienyl |
| 429 | 5,6-diCl | $CF_3$ | $CH_2CH_2$-3-thienyl |
| 430 | 5-Cl, 6-F | $CF_3$ | C≡C—cycPr |
| 431 | 5-Cl, 6-F | $CF_3$ | C≡C—iPr |
| 432 | 5-Cl, 6-F | $CF_3$ | C≡C—nPr |
| 433 | 5-Cl, 6-F | $CF_3$ | C≡C—Bu |
| 434 | 5-Cl, 6-F | $CF_3$ | C≡C—iBu |
| 435 | 5-Cl, 6-F | $CF_3$ | C≡C—tBu |
| 436 | 5-Cl, 6-F | $CF_3$ | C≡C—Et |
| 437 | 5-Cl, 6-F | $CF_3$ | C≡C—Me |
| 438 | 5-Cl, 6-F | $CF_3$ | C≡C$CH_2CH_2$OH |
| 439 | 5-Cl, 6-F | $CF_3$ | C≡C—CH(OH)Me |
| 440 | 5-Cl, 6-F | $CF_3$ | C≡C—Ph |
| 441 | 5-Cl, 6-F | $CF_3$ | C≡C—(2-Cl)Ph |
| 442 | 5-Cl, 6-F | $CF_3$ | C≡C—(3-Cl)Ph |
| 443 | 5-Cl, 6-F | $CF_3$ | C≡C—(4-Cl)Ph |
| 444 | 5-Cl, 6-F | $CF_3$ | C≡C—(2-F)Ph |
| 445 | 5-Cl, 6-F | $CF_3$ | C≡C—(3-F)Ph |
| 446 | 5-Cl, 6-F | $CF_3$ | C≡C—(4-F)Ph |
| 447 | 5-Cl, 6-F | $CF_3$ | C≡C—(2-OH)Ph |
| 448 | 5-Cl, 6-F | $CF_3$ | C≡C—(3-OH)Ph |
| 449 | 5-Cl, 6-F | $CF_3$ | C≡C—(4-OH)Ph |
| 450 | 5-Cl, 6-F | $CF_3$ | C≡C—(2-OMe)Ph |
| 451 | 5-Cl, 6-F | $CF_3$ | C≡C—(3-OMe)Ph |
| 452 | 5-Cl, 6-F | $CF_3$ | C≡C—(4-OMe)Ph |
| 453 | 5-Cl, 6-F | $CF_3$ | C≡C—(2-CN)Ph |
| 454 | 5-Cl, 6-F | $CF_3$ | C≡C—(3-CN)Ph |
| 455 | 5-Cl, 6-F | $CF_3$ | C≡C—(4-CN)Ph |
| 456 | 5-Cl, 6-F | $CF_3$ | C≡C—(2-$NO_2$)Ph |
| 457 | 5-Cl, 6-F | $CF_3$ | C≡C—(3-$NO_2$)Ph |
| 458 | 5-Cl, 6-F | $CF_3$ | C≡C—(4-$NO_2$)Ph |
| 459 | 5-Cl, 6-F | $CF_3$ | C≡C—(2-$NH_2$)Ph |
| 460 | 5-Cl, 6-F | $CF_3$ | C≡C—(3-$NH_2$)Ph |
| 461 | 5-Cl, 6-F | $CF_3$ | C≡C—(4-$NH_2$)Ph |
| 462 | 5-Cl, 6-F | $CF_3$ | C≡C—(2-$NMe_2$)Ph |
| 463 | 5-Cl, 6-F | $CF_3$ | C≡C—(3-$NMe_2$)Ph |
| 464 | 5-Cl, 6-F | $CF_3$ | C≡C—(4-$NMe_2$)Ph |
| 465 | 5-Cl, 6-F | $CF_3$ | C≡C-2-Pyridyl |
| 466 | 5-Cl, 6-F | $CF_3$ | C≡C-3-Pyridyl |
| 467 | 5-Cl, 6-F | $CF_3$ | C≡C-4-Pyridyl |
| 468 | 5-Cl, 6-F | $CF_3$ | C≡C-2-furanyl |
| 469 | 5-Cl, 6-F | $CF_3$ | C≡C-3-furanyl |
| 470 | 5-Cl, 6-F | $CF_3$ | C≡C-2-thienyl |
| 471 | 5-Cl, 6-F | $CF_3$ | C≡C-3-thienyl |
| 472 | 5-Cl, 6-F | $CF_3$ | CH=CH—cycPr |
| 473 | 5-Cl, 6-F | $CF_3$ | CH=CH—iPr |
| 474 | 5-Cl, 6-F | $CF_3$ | CH=CH—nPr |
| 475 | 5-Cl, 6-F | $CF_3$ | CH=CH—Bu |
| 476 | 5-Cl, 6-F | $CF_3$ | CH=CH—iBu |
| 477 | 5-Cl, 6-F | $CF_3$ | CH=CH—tBu |
| 478 | 5-Cl, 6-F | $CF_3$ | CH=CH—Et |
| 479 | 5-Cl, 6-F | $CF_3$ | CH=CH—Me |
| 480 | 5-Cl, 6-F | $CF_3$ | CH=CH—Ph |
| 481 | 5-Cl, 6-F | $CF_3$ | CH=CH-2-Pyridyl |
| 482 | 5-Cl, 6-F | $CF_3$ | CH=CH-3-Pyridyl |
| 483 | 5-Cl, 6-F | $CF_3$ | CH=CH-4-Pyridyl |
| 484 | 5-Cl, 6-F | $CF_3$ | CH=CH-2-furanyl |
| 485 | 5-Cl, 6-F | $CF_3$ | CH=CH-3-furanyl |
| 486 | 5-Cl, 6-F | $CF_3$ | CH=CH-2-thienyl |
| 487 | 5-Cl, 6-F | $CF_3$ | CH=CH-3-thienyl |
| 488 | 5-Cl, 6-F | $CF_3$ | $CH_2CH_2CH_2CH_2CH_3$ |
| 489 | 5-Cl, 6-F | $CF_3$ | $CH_2CH_2CH(CH_3)_2$ |
| 490 | 5-Cl, 6-F | $CF_3$ | $CH_2CH_2CH_2CH_3$ |
| 491 | 5-Cl, 6-F | $CF_3$ | $CH_2CH_2$—cycPr |
| 492 | 5-Cl, 6-F | $CF_3$ | $CH_2CH_2$—tBu |
| 493 | 5-Cl, 6-F | $CF_3$ | $CH_2CH_2CH_2CH_2CH$ |
| 494 | 5-Cl, 6-F | $CF_3$ | $CH_2CH_2$—CH(OH)Me |
| 495 | 5-Cl, 6-F | $CF_3$ | $CH_2CH_2$—Ph |
| 496 | 5-Cl, 6-F | $CF_3$ | $CH_2CH_2$-2-Pyridyl |
| 497 | 5-Cl, 6-F | $CF_3$ | $CH_2CH_2$-3-Pyridyl |
| 498 | 5-Cl, 6-F | $CF_3$ | $CH_2CH_2$-4-Pyridyl |
| 499 | 5-Cl, 6-F | $CF_3$ | $CH_2CH_2$-2-furanyl |
| 500 | 5-Cl, 6-F | $CF_3$ | $CH_2CH_2$-3-furanyl |
| 501 | 5-Cl, 6-F | $CF_3$ | $CH_2CH_2$-2-thienyl |
| 502 | 5-Cl, 6-F | $CF_3$ | $CH_2CH_2$-3-thienyl |
| 503 | 5,6-O$CH_2$O— | $CF_3$ | C≡C—Bu |
| 504 | 5,6-O$CH_2$O— | $CF_3$ | C≡C—iBu |
| 505 | 5,6-O$CH_2$O— | $CF_3$ | C≡C—tBu |
| 506 | 5,6-O$CH_2$O— | $CF_3$ | C≡C—Me |
| 507 | 5,6-O$CH_2$O— | $CF_3$ | C≡C$CH_2CH_2$OH |
| 508 | 5,6-O$CH_2$O— | $CF_3$ | C≡C—CH(OH)Me |
| 509 | 5,6-O$CH_2$O— | $CF_3$ | C≡C—Ph |
| 510 | 5,6-O$CH_2$O— | $CF_3$ | C≡C—(2-Cl)Ph |
| 511 | 5,6-O$CH_2$O— | $CF_3$ | C≡C—(3-Cl)Ph |
| 512 | 5,6-O$CH_2$O— | $CF_3$ | C≡C—(4-Cl)Ph |

TABLE 2-continued

| Ex. # | G | R¹ | R² |
|---|---|---|---|
| 513 | 5,6-OCH₂O— | CF₃ | C≡C—(2-F)Ph |
| 514 | 5,6-OCH₂O— | CF₃ | C≡C—(3-F)Ph |
| 515 | 5,6-OCH₂O— | CF₃ | C≡C—(4-F)Ph |
| 516 | 5,6-OCH₂O— | CF₃ | C≡C—(2-OH)Ph |
| 517 | 5,6-OCH₂O— | CF₃ | C≡C—(3-OH)Ph |
| 518 | 5,6-OCH₂O— | CF₃ | C≡C—(4-OH)Ph |
| 519 | 5,6-OCH₂O— | CF₃ | C≡C—(2-OMe)Ph |
| 520 | 5,6-OCH₂O— | CF₃ | C≡C—(3-OMe)Ph |
| 521 | 5,6-OCH₂O— | CF₃ | C≡C—(4-OMe)Ph |
| 522 | 5,6-OCH₂O— | CF₃ | C≡C—(2-CN)Ph |
| 523 | 5,6-OCH₂O— | CF₃ | C≡C—(3-CN)Ph |
| 524 | 5,6-OCH₂O— | CF₃ | C≡C—(4-CN)Ph |
| 525 | 5,6-OCH₂O— | CF₃ | C≡C—(2-NO₂)Ph |
| 526 | 5,6-OCH₂O— | CF₃ | C≡C—(3-NO₂)Ph |
| 527 | 5,6-OCH₂O— | CF₃ | C≡C—(4-NO₂)Ph |
| 528 | 5,6-OCH₂O— | CF₃ | C≡C—(2-NH₂)Ph |
| 529 | 5,6-OCH₂O— | CF₃ | C≡C—(3-NH₂)Ph |
| 530 | 5,6-OCH₂O— | CF₃ | C≡C—(4-NH₂)Ph |
| 531 | 5,6-OCH₂O— | CF₃ | C≡C—(2-NMe₂)Ph |
| 532 | 5,6-OCH₂O— | CF₃ | C≡C—(3-NMe₂)Ph |
| 533 | 5,6-OCH₂O— | CF₃ | C≡C—(4-NMe₂)Ph |
| 534 | 5,6-OCH₂O— | CF₃ | C≡C-2-Pyridyl |
| 535 | 5,6-OCH₂O— | CF₃ | C≡C-3-Pyridyl |
| 536 | 5,6-OCH₂O— | CF₃ | C≡C-4-Pyridyl |
| 537 | 5,6-OCH₂O— | CF₃ | C≡C-2-furanyl |
| 538 | 5,6-OCH₂O— | CF₃ | C≡C-3-furanyl |
| 539 | 5,6-OCH₂O— | CF₃ | C≡C-2-thienyl |
| 540 | 5,6-OCH₂O— | CF₃ | C≡C-3-thienyl |
| 541 | 5,6-OCH₂O— | CF₃ | CH=CH—cycPr |
| 542 | 5,6-OCH₂O— | CF₃ | CH=CH—iPr |
| 543 | 5,6-OCH₂O— | CF₃ | CH=CH—nPr |
| 544 | 5,6-OCH₂O— | CF₃ | CH=CH—Bu |
| 545 | 5,6-OCH₂O— | CF₃ | CH=CH—iBu |
| 546 | 5,6-OCH₂O— | CF₃ | CH=CH—tBu |
| 547 | 5,6-OCH₂O— | CF₃ | CH=CH—Et |
| 548 | 5,6-OCH₂O— | CF₃ | CH=CH—Me |
| 549 | 5,6-OCH₂O— | CF₃ | CH=CH—Ph |
| 550 | 5,6-OCH₂O— | CF₃ | CH=CH-2-Pyridyl |
| 551 | 5,6-OCH₂O— | CF₃ | CH=CH-3-Pyridyl |
| 552 | 5,6-OCH₂O— | CF₃ | CH=CH-4-Pyridyl |
| 553 | 5,6-OCH₂O— | CF₃ | CH=CH-2-furanyl |
| 554 | 5,6-OCH₂O— | CF₃ | CH=CH-3-furanyl |
| 555 | 5,6-OCH₂O— | CF₃ | CH=CH-2-thienyl |
| 556 | 5,6-OCH₂O— | CF₃ | CH=CH-3-thienyl |
| 557 | 5,6-OCH₂O— | CF₃ | CH₂CH₂CH₂CH₃ |
| 558 | 5,6-OCH₂O— | CF₃ | CH₂CH₂CH₂CH₃ |
| 559 | 5,6-OCH₂O— | CF₃ | CH₂CH₂—cycPr |
| 560 | 5,6-OCH₂O— | CF₃ | CH₂CH₂—tBu |
| 561 | 5,6-OCH₂O— | CF₃ | CH₂CH₂CH₂CH₂OH |
| 562 | 5,6-OCH₂O— | CF₃ | CH₂CH₂—CH(OH)Me |
| 563 | 5,6-OCH₂O— | CF₃ | CH₂CH₂—Ph |
| 564 | 5,6-OCH₂O— | CF₃ | CH₂CH₂-2-Pyridyl |
| 565 | 5,6-OCH₂O— | CF₃ | CH₂CH₂-3-Pyridyl |
| 566 | 5,6-OCH₂O— | CF₃ | CH₂CH₂-4-Pyridyl |
| 567 | 5,6-OCH₂O— | CF₃ | CH₂CH₂-2-furanyl |
| 568 | 5,6-OCH₂O— | CF₃ | CH₂CH₂-3-furanyl |
| 569 | 5,6-OCH₂O— | CF₃ | CH₂CH₂-2-thienyl |
| 570 | 5,6-OCH₂O— | CF₃ | CH₂CH₂-3-thienyl |
| 571 | 5-F | CF₃ | C≡C-cycPr |
| 572 | 5-F | CF₃ | C≡C—iPr |
| 573 | 5-F | CF₃ | C≡C—nPr |
| 574 | 5-F | CF₃ | C≡C—Bu |
| 575 | 5-F | CF₃ | C≡C—iBu |
| 576 | 5-F | CF₃ | C≡C—tBu |
| 577 | 5-F | CF₃ | C≡C—Et |
| 578 | 5-F | CF₃ | C≡C—Me |
| 579 | 5-F | CF₃ | C≡CCH₂CH₂OH |
| 580 | 5-F | CF₃ | C≡C—CH(OH)Me |
| 581 | 5-F | CF₃ | C≡C—Ph |
| 582 | 5-F | CF₃ | C≡C—(2-Cl)Ph |
| 583 | 5-F | CF₃ | C≡C—(3-Cl)Ph |
| 584 | 5-F | CF₃ | C≡C—(4-Cl)Ph |
| 585 | 5-F | CF₃ | C≡C—(2-F)Ph |
| 586 | 5-F | CF₃ | C≡C—(3-F)Ph |
| 587 | 5-F | CF₃ | C≡C—(4-F)Ph |
| 588 | 5-F | CF₃ | C≡C—(2-OH)Ph |
| 589 | 5-F | CF₃ | C≡C—(3-OH)Ph |
| 590 | 5-F | CF₃ | C≡C—(4-OH)Ph |
| 591 | 5-F | CF₃ | C≡C—(2-OMe)Ph |
| 592 | 5-F | CF₃ | C≡C—(3-OMe)Ph |
| 593 | 5-F | CF₃ | C≡C—(4-OMe)Ph |
| 594 | 5-F | CF₃ | C≡C—(2-CN)Ph |
| 595 | 5-F | CF₃ | C≡C—(3-CN)Ph |
| 596 | 5-F | CF₃ | C≡C—(4-CN)Ph |
| 597 | 5-F | CF₃ | C≡C—(2-NO₂)Ph |
| 598 | 5-F | CF₃ | C≡C—(3-NO₂)Ph |
| 599 | 5-F | CF₃ | C≡C—(4-NO₂)Ph |
| 600 | 5-F | CF₃ | C≡C—(2-NH₂)Ph |
| 601 | 5-F | CF₃ | C≡C—(3-NH₂)Ph |
| 602 | 5-F | CF₃ | C≡C—(4-NH₂)Ph |
| 603 | 5-F | CF₃ | C≡C—(2-NMe₂)Ph |
| 604 | 5-F | CF₃ | C≡C—(3-NMe₂)Ph |
| 605 | 5-F | CF₃ | C≡C—(4-NMe₂)Ph |
| 606 | 5-F | CF₃ | C≡C-2-Pyridyl |
| 607 | 5-F | CF₃ | C≡C-3-Pyridyl |
| 608 | 5-F | CF₃ | C≡C-4-Pyridyl |
| 609 | 5-F | CF₃ | C≡C-2-furanyl |
| 610 | 5-F | CF₃ | C≡C-3-furanyl |
| 611 | 5-F | CF₃ | C≡C-2-thienyl |
| 612 | 5-F | CF₃ | C≡C-3-thienyl |
| 613 | 5-F | CF₃ | CH=CH—cycPr |
| 614 | 5-F | CF₃ | CH=CH—iPr |
| 615 | 5-F | CF₃ | CH=CH—nPr |
| 616 | 5-F | CF₃ | CH=CH—Bu |
| 617 | 5-F | CF₃ | CH=CH—iBu |
| 618 | 5-F | CF₃ | CH=CH—tBu |
| 619 | 5-F | CF₃ | CH=CH—Et |
| 620 | 5-F | CF₃ | CH=CH—Me |
| 621 | 5-F | CF₃ | CH=CH—Ph |
| 622 | 5-F | CF₃ | CH=CH-2-Pyridyl |
| 623 | 5-F | CF₃ | CH=CH-3-Pyridyl |
| 624 | 5-F | CF₃ | CH=CH-4-Pyridyl |
| 625 | 5-F | CF₃ | CH=CH-2-furanyl |
| 626 | 5-F | CF₃ | CH=CH-3-furanyl |
| 627 | 5-F | CF₃ | CH=CH-2-thienyl |
| 628 | 5-F | CF₃ | CH=CH-3-thienyl |
| 629 | 5-F | CF₃ | CH₂CH₂CH₂CH₃ |
| 630 | 5-F | CF₃ | CH₂CH₂CH(CH₃)₂ |
| 631 | 5-F | CF₃ | CH₂CH₂CH₂CH₃ |
| 632 | 5-F | CF₃ | CH₂CH₂—cycPr |
| 633 | 5-F | CF₃ | CH₂CH₂—tBu |
| 634 | 5-F | CF₃ | CH₂CH₂CH₂CH₂OH |
| 635 | 5-F | CF₃ | CH₂CH₂—CH(OH)Me |
| 636 | 5-F | CF₃ | CH₂CH₂—Ph |
| 637 | 5-F | CF₃ | CH₂CH₂-2-Pyridyl |
| 638 | 5-F | CF₃ | CH₂CH₂-3-Pyridyl |
| 639 | 5-F | CF₃ | CH₂CH₂-4-Pyridyl |
| 640 | 5-F | CF₃ | CH₂CH₂-2-furanyl |
| 641 | 5-F | CF₃ | CH₂CH₂-3-furanyl |
| 642 | 5-F | CF₃ | CH₂CH₂-2-thienyl |
| 643 | 5-F | CF₃ | CH₂CH₂-3-thienyl |
| 644 | 5-Cl | CF₃ | C≡C—cycPr |
| 645 | 5-Cl | CF₃ | C≡C-iPr |
| 646 | 5-Cl | CF₃ | C≡C—nPr |
| 647 | 5-Cl | CF₃ | C≡C—Bu |
| 648 | 5-Cl | CF₃ | C≡C—iBu |

TABLE 2-continued

![Structure with R1, R2 on carbon connected to O, benzene ring with G substituent, fused to ring with NH-C(=O)-O]

| Ex. # | G | R¹ | R² |
|---|---|---|---|
| 649 | 5-Cl | CF₃ | C≡C—tBu |
| 650 | 5-Cl | CF₃ | C≡C-Et |
| 651 | 5-Cl | CF₃ | C≡C—Me |
| 652 | 5-Cl | CF₃ | C≡CCH₂CH₂OH |
| 653 | 5-Cl | CF₃ | C≡C—CH(OH)Me |
| 654 | 5-Cl | CF₃ | C≡C—Ph |
| 655 | 5-Cl | CF₃ | C≡C—(2-Cl)Ph |
| 656 | 5-Cl | CF₃ | C≡C—(3-Cl)Ph |
| 657 | 5-Cl | CF₃ | C≡C—(4-Cl)Ph |
| 658 | 5-Cl | CF₃ | C≡C—(2-F)Ph |
| 659 | 5-Cl | CF₃ | C≡C—(3-F)Ph |
| 660 | 5-Cl | CF₃ | C≡C—(4-F)Ph |
| 661 | 5-Cl | CF₃ | C≡C—(2-OH)Ph |
| 662 | 5-Cl | CF₃ | C≡C—(3-OH)Ph |
| 663 | 5-Cl | CF₃ | C≡C—(4-OH)Ph |
| 664 | 5-Cl | CF₃ | C≡C—(2-OMe)Ph |
| 665 | 5-Cl | CF₃ | C≡C—(3-OMe)Ph |
| 666 | 5-Cl | CF₃ | C≡C—(4-OMe)Ph |
| 667 | 5-Cl | CF₃ | C≡C—(2-CN)Ph |
| 668 | 5-Cl | CF₃ | C≡C—(3-CN)Ph |
| 669 | 5-Cl | CF₃ | C≡C—(4-CN)Ph |
| 670 | 5-Cl | CF₃ | C≡C—(2-NO₂)Ph |
| 671 | 5-Cl | CF₃ | C≡C—(3-NO₂)Ph |
| 672 | 5-Cl | CF₃ | C≡C—(4-NO₂)Ph |
| 673 | 5-Cl | CF₃ | C≡C—(2-NH₂)Ph |
| 674 | 5-Cl | CF₃ | C≡C—(3-NH₂)Ph |
| 675 | 5-Cl | CF₃ | C≡C—(4-NH₂)Ph |
| 676 | 5-Cl | CF₃ | C≡C—(2-NMe₂)Ph |
| 677 | 5-Cl | CF₃ | C≡C—(3-NMe₂)Ph |
| 678 | 5-Cl | CF₃ | C≡C—(4-NMe₂)Ph |
| 679 | 5-Cl | CF₃ | C≡C-2-Pyridyl |
| 680 | 5-Cl | CF₃ | C≡C-3-Pyridyl |
| 681 | 5-Cl | CF₃ | C≡C-4-Pyridyl |
| 682 | 5-Cl | CF₃ | C≡C-2-furanyl |
| 683 | 5-Cl | CF₃ | C≡C-3-furanyl |
| 684 | 5-Cl | CF₃ | C≡C-2-thienyl |
| 685 | 5-Cl | CF₃ | C≡C-3-thienyl |
| 686 | 5-Cl | CF₃ | CH=CH-cycPr |
| 687 | 5-Cl | CF₃ | CH=CH-iPr |
| 688 | 5-Cl | CF₃ | CH=CH—nPr |
| 689 | 5-Cl | CF₃ | CH=CH—Bu |
| 690 | 5-Cl | CF₃ | CH=CH—iBu |
| 691 | 5-Cl | CF₃ | CH=CH—tBu |
| 692 | 5-Cl | CF₃ | CH=CH—Et |
| 693 | 5-Cl | CF₃ | CH=CH—Me |
| 694 | 5-Cl | CF₃ | CH=CH—Ph |
| 695 | 5-Cl | CF₃ | CH=CH-2-Pyridyl |
| 696 | 5-Cl | CF₃ | CH=CH-3-Pyridyl |
| 697 | 5-Cl | CF₃ | CH=CH-4-Pyridyl |
| 698 | 5-Cl | CF₃ | CH=CH-2-furanyl |
| 699 | 5-Cl | CF₃ | CH=CH-3-furanyl |
| 700 | 5-Cl | CF₃ | CH=CH-2-thienyl |
| 701 | 5-Cl | CF₃ | CH=CH-3-thienyl |
| 702 | 5-Cl | CF₃ | CH₂CH₂CH₂CH₂CH₃ |
| 703 | 5-Cl | CF₃ | CH₂CH₂CH(CH₃)₂ |
| 704 | 5-Cl | CF₃ | CH₂CH₂CH₂CH₃ |
| 705 | 5-Cl | CF₃ | CH₂CH₂-cycPr |
| 706 | 5-Cl | CF₃ | CH₂CH₂-tBu |
| 707 | 5-Cl | CF₃ | CH₂CH₂CH₂CH₂OH |
| 708 | 5-Cl | CF₃ | CH₂CH₂—CH(OH)Me |
| 709 | 5-Cl | CF₃ | CH₂CH₂—Ph |
| 710 | 5-Cl | CF₃ | CH₂CH₂-2-Pyridyl |
| 711 | 5-Cl | CF₃ | CH₂CH₂-3-Pyridyl |
| 712 | 5-Cl | CF₃ | CH₂CH₂-4-Pyridyl |
| 713 | 5-Cl | CF₃ | CH₂CH₂-2-furanyl |
| 714 | 5-Cl | CF₃ | CH₂CH₂-3-furanyl |
| 715 | 5-Cl | CF₃ | CH₂CH₂-2-thienyl |
| 716 | 5-Cl | CF₃ | CH₂CH₂-3-thienyl |
| 717 | 6-OMe | CF₃ | C≡C—Bu |
| 718 | 6-OMe | CF₃ | C≡C—iBu |
| 719 | 6-OMe | CF₃ | C≡C—tBu |
| 720 | 6-OMe | CF₃ | C≡CCH₂CH₂OH |
| 721 | 6-OMe | CF₃ | C≡C—CH(OH)Me |
| 722 | 6-OMe | CF₃ | C≡C—Ph |
| 723 | 6-OMe | CF₃ | C≡C—(2-Cl)Ph |
| 724 | 6-OMe | CF₃ | C≡C—(3-Cl)Ph |
| 725 | 6-OMe | CF₃ | C≡C—(4-Cl)Ph |
| 726 | 6-OMe | CF₃ | C≡C—(2-F)Ph |
| 727 | 6-OMe | CF₃ | C≡C—(3-F)Ph |
| 728 | 6-OMe | CF₃ | C≡C—(4-F)Ph |
| 729 | 6-OMe | CF₃ | C≡C—(2-OH)Ph |
| 730 | 6-OMe | CF₃ | C≡C—(3-OH)Ph |
| 731 | 6-OMe | CF₃ | C≡C—(4-OH)Ph |
| 732 | 6-OMe | CF₃ | C≡C—(2-OMe)Ph |
| 733 | 6-OMe | CF₃ | C≡C—(3-OMe)Ph |
| 734 | 6-OMe | CF₃ | C≡C—(4-OMe)Ph |
| 735 | 6-OMe | CF₃ | C≡C—(2-CN)Ph |
| 736 | 6-OMe | CF₃ | C≡C—(3-CN)Ph |
| 737 | 6-OMe | CF₃ | C≡C—(4-CN)Ph |
| 738 | 6-OMe | CF₃ | C≡C—(2-NO₂)Ph |
| 739 | 6-OMe | CF₃ | C≡C—(3-NO₂)Ph |
| 740 | 6-OMe | CF₃ | C≡C—(4-NO₂)Ph |
| 741 | 6-OMe | CF₃ | C≡C—(2-NH₂)Ph |
| 742 | 6-OMe | CF₃ | C≡C—(3-NH₂)Ph |
| 743 | 6-OMe | CF₃ | C≡C—(4-NH₂)Ph |
| 744 | 6-OMe | CF₃ | C≡C—(2-NMe₂)Ph |
| 745 | 6-OMe | CF₃ | C≡C—(3-NMe₂)Ph |
| 746 | 6-OMe | CF₃ | C≡C—(4-NMe₂)Ph |
| 747 | 6-OMe | CF₃ | C≡C-2-Pyridyl |
| 748 | 6-OMe | CF₃ | C≡C-3-Pyridyl |
| 749 | 6-OMe | CF₃ | C≡C-4-Pyridyl |
| 750 | 6-OMe | CF₃ | C≡C-2-furanyl |
| 751 | 6-OMe | CF₃ | C≡C-3-furanyl |
| 752 | 6-OMe | CF₃ | C≡C-2-thienyl |
| 753 | 6-OMe | CF₃ | C≡C-3-thienyl |
| 754 | 6-OMe | CF₃ | C≡C-2-oxazolyl |
| 755 | 6-OMe | CF₃ | C≡C-2-thiazolyl |
| 756 | 6-OMe | CF₃ | C≡C-4-isoxazolyl |
| 757 | 6-OMe | CF₃ | C≡C-2-imidazolyl |
| 758 | 6-OMe | CF₃ | CH₂C≡C—CH₃ |
| 759 | 6-OMe | CF₃ | CH=CH-cycPr |
| 760 | 6-OMe | CF₃ | CH=CH-iPr |
| 761 | 6-OMe | CF₃ | CH=CH—nPr |
| 762 | 6-OMe | CF₃ | CH=CH—Bu |
| 763 | 6-OMe | CF₃ | CH=CH—iBu |
| 764 | 6-OMe | CF₃ | CH=CH—tBu |
| 765 | 6-OMe | CF₃ | CH=CH—Et |
| 766 | 6-OMe | CF₃ | CH=CH—Me |
| 767 | 6-OMe | CF₃ | CH=CH—Ph |
| 768 | 6-OMe | CF₃ | CH=CH-2-Pyridyl |
| 769 | 6-OMe | CF₃ | CH=CH-3-Pyridyl |
| 770 | 6-OMe | CF₃ | CH=CH-4-Pyridyl |
| 771 | 6-OMe | CF₃ | CH=CH-2-furanyl |
| 772 | 6-OMe | CF₃ | CH=CH-3-furanyl |
| 773 | 6-OMe | CF₃ | CH=CH-2-thienyl |
| 774 | 6-OMe | CF₃ | CH=CH-3-thienyl |
| 775 | 6-OMe | CF₃ | CH₂CH₂CH₂CH₂CH₃ |
| 776 | 6-OMe | CF₃ | CH₂CH₂CH₃ |
| 777 | 6-OMe | CF₃ | CH₂CH₂-cycPr |
| 778 | 6-OMe | CF₃ | CH₂CH₂-tBu |
| 779 | 6-OMe | CF₃ | CH₂CH₂CH₂CH₂OH |
| 780 | 6-OMe | CF₃ | CH₂CH₂—CH(OH)Me |
| 781 | 6-OMe | CF₃ | CH₂CH₂—(2-Cl)Ph |
| 782 | 6-OMe | CF₃ | CH₂CH₂—(3-Cl)Ph |
| 783 | 6-OMe | CF₃ | CH₂CH₂—(4-Cl)Ph |
| 784 | 6-OMe | CF₃ | CH₂CH₂—(2-F)Ph |

TABLE 2-continued

| Ex. # | G | R¹ | R² |
|---|---|---|---|
| 785 | 6-OMe | CF₃ | CH₂CH₂—(3-F)Ph |
| 786 | 6-OMe | CF₃ | CH₂CH₂—(4-F)Ph |
| 787 | 6-OMe | CF₃ | CH₂CH₂—(2-OH)Ph |
| 788 | 6-OMe | CF₃ | CH₂CH₂—(3-OH)Ph |
| 789 | 6-OMe | CF₃ | CH₂CH₂—(4-OH)Ph |
| 790 | 6-OMe | CF₃ | CH₂CH₂—(2-OMe)Ph |
| 791 | 6-OMe | CF₃ | CH₂CH₂—(3-OMe)Ph |
| 792 | 6-OMe | CF₃ | CH₂CH₂—(4-OMe)Ph |
| 793 | 6-OMe | CF₃ | CH₂CH₂—(2-CN)Ph |
| 794 | 6-OMe | CF₃ | CH₂CH₂—(3-CN)Ph |
| 795 | 6-OMe | CF₃ | CH₂CH₂—(4-CN)Ph |
| 796 | 6-OMe | CF₃ | CH₂CH₂—(2-NO₂)Ph |
| 797 | 6-OMe | CF₃ | CH₂CH₂—(3-NO₂)Ph |
| 798 | 6-OMe | CF₃ | CH₂CH₂—(4-NO₂)Ph |
| 799 | 6-OMe | CF₃ | CH₂CH₂—(2-NH₂)Ph |
| 800 | 6-OMe | CF₃ | CH₂CH₂—(3-NH₂)Ph |
| 801 | 6-OMe | CF₃ | CH₂CH₂—(4-NH₂)Ph |
| 802 | 6-OMe | CF₃ | CH₂CH₂—(2-NMe₂)Ph |
| 803 | 6-OMe | CF₃ | CH₂CH₂—(3-NMe₂)Ph |
| 804 | 6-OMe | CF₃ | CH₂CH₂—(4-NMe₂)Ph |
| 805 | 6-OMe | CF₃ | CH₂CH₂-2-Pyridyl |
| 806 | 6-OMe | CF₃ | CH₂CH₂-3-Pyridyl |
| 807 | 6-OMe | CF₃ | CH₂CH₂-4-Pyridyl |
| 808 | 6-OMe | CF₃ | CH₂CH₂-2-furanyl |
| 809 | 6-OMe | CF₃ | CH₂CH₂-3-furanyl |
| 810 | 6-OMe | CF₃ | CH₂CH₂-2-thienyl |
| 811 | 6-OMe | CF₃ | CH₂CH₂-3-thienyl |
| 812 | 6-OMe | CF₃ | CH₂CH₂-2-oxazolyl |
| 813 | 6-OMe | CF₃ | CH₂CH₂-2-thiazolyl |
| 814 | 6-OMe | CF₃ | CH₂CH₂-4-isoxazolyl |
| 815 | 6-OMe | CF₃ | CH₂CH₂-2-imidazolyl |
| 816 | 6-OMe, 8-F | CF₃ | C≡C-iPr |
| 817 | 6-OMe, 8-F | CF₃ | C≡C-nPr |
| 818 | 6-OMe, 8-F | CF₃ | C≡C-Et |
| 819 | 6-OMe, 8-F | CF₃ | C≡C—Me |
| 820 | 6-OMe, 8-F | CF₃ | C≡C—Ph |
| 821 | 6-OMe, 8-F | CF₃ | C≡C-2-Pyridyl |
| 822 | 6-OMe, 8-F | CF₃ | C≡C-3-Pyridyl |
| 823 | 6-OMe, 8-F | CF₃ | C≡C-4-Pyridyl |
| 824 | 6-OMe, 8-F | CF₃ | C≡C-2-furanyl |
| 825 | 6-OMe, 8-F | CF₃ | C≡C-3-furanyl |
| 826 | 6-OMe, 8-F | CF₃ | C≡C-2-thienyl |
| 827 | 6-OMe, 8-F | CF₃ | C≡C-3-thienyl |
| 828 | 6-OMe, 8-F | CF₃ | CH=CH-cycPr |
| 829 | 6-OMe, 8-F | CF₃ | CH=CH-iPr |
| 830 | 6-OMe, 8-F | CF₃ | CH=CH-nPr |
| 831 | 6-OMe, 8-F | CF₃ | CH=CH—Et |
| 832 | 6-OMe, 8-F | CF₃ | CH=CH—Me |
| 833 | 6-OMe, 8-F | CF₃ | CH=CH—Ph |
| 834 | 6-OMe, 8-F | CF₃ | CH=CH-2-Pyridyl |
| 835 | 6-OMe, 8-F | CF₃ | CH=CH-3-Pyridyl |
| 836 | 6-OMe, 8-F | CF₃ | CH=CH-4-Pyridyl |
| 837 | 6-OMe, 8-F | CF₃ | CH=CH-2-furanyl |
| 838 | 6-OMe, 8-F | CF₃ | CH=CH-3-furanyl |
| 839 | 6-OMe, 8-F | CF₃ | CH=CH-2-thienyl |
| 840 | 6-OMe, 8-F | CF₃ | CH=CH-3-thienyl |
| 841 | 6-OMe, 8-F | CF₃ | CH₂CH₂CH₂CH₂CH₃ |
| 842 | 6-OMe, 8-F | CF₃ | CH₂CH₂CH(CH₃)₂ |
| 843 | 6-OMe, 8-F | CF₃ | CH₂CH₂CH₂CH₃ |
| 844 | 6-OMe, 8-F | CF₃ | CH₂CH₂-cycPr |
| 845 | 6-OMe, 8-F | CF₃ | CH₂CH₂—Ph |
| 846 | 6-OMe, 8-F | CF₃ | CH₂CH₂-2-Pyridyl |
| 847 | 6-OMe, 8-F | CF₃ | CH₂CH₂-3-Pyridyl |
| 848 | 6-OMe, 8-F | CF₃ | CH₂CH₂-4-Pyridyl |
| 849 | 6-OMe, 8-F | CF₃ | CH₂CH₂-2-furanyl |
| 850 | 6-OMe, 8-F | CF₃ | CH₂CH₂-3-furanyl |
| 851 | 6-OMe, 8-F | CF₃ | CH₂CH₂-2-thienyl |
| 852 | 6-OMe, 8-F | CF₃ | CH₂CH₂-3-thienyl |
| 853 | 5-F, 6-OMe | CF₃ | C≡C-cycPr |
| 854 | 5-F, 6-OMe | CF₃ | C≡C-iPr |
| 855 | 5-F, 6-OMe | CF₃ | C≡C-nPr |
| 856 | 5-F, 6-OMe | CF₃ | C≡C—Bu |
| 857 | 5-F, 6-OMe | CF₃ | C≡C-iBu |
| 858 | 5-F, 6-OMe | CF₃ | C≡C-tBu |
| 859 | 5-F, 6-OMe | CF₃ | C≡C-Et |
| 860 | 5-F, 6-OMe | CF₃ | C≡C—Me |
| 861 | 5-F, 6-OMe | CF₃ | C≡C—Ph |
| 862 | 5-F, 6-OMe | CF₃ | C≡C—(2-Cl)Ph |
| 863 | 5-F, 6-OMe | CF₃ | C≡C—(3-Cl)Ph |
| 864 | 5-F, 6-OMe | CF₃ | C≡C—(2-F)Ph |
| 865 | 5-F, 6-OMe | CF₃ | C≡C—(3-F)Ph |
| 866 | 5-F, 6-OMe | CF₃ | C≡C—(2-OH)Ph |
| 867 | 5-F, 6-OMe | CF₃ | C≡C—(3-OH)Ph |
| 868 | 5-F, 6-OMe | CF₃ | C≡C—(2-OMe)Ph |
| 869 | 5-F, 6-OMe | CF₃ | C≡C—(3-OMe)Ph |
| 870 | 5-F, 6-OMe | CF₃ | C≡C—(2-CN)Ph |
| 871 | 5-F, 6-OMe | CF₃ | C≡C—(3-CN)Ph |
| 872 | 5-F, 6-OMe | CF₃ | C≡C—(2-NH₂)Ph |
| 873 | 5-F, 6-OMe | CF₃ | C≡C—(3-NH₂)Ph |
| 874 | 5-F, 6-OMe | CF₃ | C≡C—(2-NMe₂)Ph |
| 875 | 5-F, 6-OMe | CF₃ | C≡C—(3-NMe₂)Ph |
| 876 | 5-F, 6-OMe | CF₃ | C≡C-2-Pyridyl |
| 877 | 5-F, 6-OMe | CF₃ | C≡C-3-Pyridyl |
| 878 | 5-F, 6-OMe | CF₃ | C≡C-4-Pyridyl |
| 879 | 5-F, 6-OMe | CF₃ | C≡C-2-furanyl |
| 880 | 5-F, 6-OMe | CF₃ | C≡C-3-furanyl |
| 881 | 5-F, 6-OMe | CF₃ | C≡C-2-thienyl |
| 882 | 5-F, 6-OMe | CF₃ | C≡C-3-thienyl |
| 883 | 5-F, 6-OMe | CF₃ | CH=CH-cycPr |
| 884 | 5-F, 6-OMe | CF₃ | CH=CH-iPr |
| 885 | 5-F, 6-OMe | CF₃ | CH=CH-nPr |
| 886 | 5-F, 6-OMe | CF₃ | CH=CH—Bu |
| 887 | 5-F, 6-OMe | CF₃ | CH=CH-iBu |
| 888 | 5-F, 6-OMe | CF₃ | CH=CH-tBu |
| 889 | 5-F, 6-OMe | CF₃ | CH=CH—Et |
| 890 | 5-F, 6-OMe | CF₃ | CH=CH—Me |
| 891 | 5-F, 6-OMe | CF₃ | CH=CH—Ph |
| 892 | 5-F, 6-OMe | CF₃ | CH=CH-2-Pyridyl |
| 893 | 5-F, 6-OMe | CF₃ | CH=CH-3-Pyridyl |
| 894 | 5-F, 6-OMe | CF₃ | CH=CH-4-Pyridyl |
| 895 | 5-F, 6-OMe | CF₃ | CH=CH-2-furanyl |
| 896 | 5-F, 6-OMe | CF₃ | CH=CH-3-furanyl |
| 897 | 5-F, 6-OMe | CF₃ | CH=CH-2-thienyl |
| 898 | 5-F, 6-OMe | CF₃ | CH=CH-3-thienyl |
| 899 | 5-F, 6-OMe | CF₃ | CH₂CH₂CH₂CH₂CH₃ |
| 900 | 5-F, 6-OMe | CF₃ | CH₂CH₂CH(CH₃)₂ |
| 901 | 5-F, 6-OMe | CF₃ | CH₂CH₂CH₂CH₃ |
| 902 | 5-F, 6-OMe | CF₃ | CH₂CH₂-cycPr |
| 903 | 5-F, 6-OMe | CF₃ | CH₂CH₂-tBu |
| 904 | 5-F, 6-OMe | CF₃ | CH₂CH₂—Ph |
| 905 | 5-F, 6-OMe | CF₃ | CH₂CH₂-2-Pyridyl |
| 906 | 5-F, 6-OMe | CF₃ | CH₂CH₂-3-Pyridyl |
| 907 | 5-F, 6-OMe | CF₃ | CH₂CH₂-4-Pyridyl |
| 908 | 5-F, 6-OMe | CF₃ | CH₂CH₂-2-furanyl |
| 909 | 5-F, 6-OMe | CF₃ | CH₂CH₂-3-furanyl |
| 910 | 5-F, 6-OMe | CF₃ | CH₂CH₂-2-thienyl |
| 911 | 5-F, 6-OMe | CF₃ | CH₂CH₂-3-thienyl |
| 912 | 6-NMe₂ | CF₃ | C≡C-nPr |
| 913 | 6-NMe₂ | CF₃ | C≡C—Bu |
| 914 | 6-NMe₂ | CF₃ | C≡C-iBu |
| 915 | 6-NMe₂ | CF₃ | C≡C-tBu |
| 916 | 6-NMe₂ | CF₃ | C≡C-Et |
| 917 | 6-NMe₂ | CF₃ | C≡C—Me |
| 918 | 6-NMe₂ | CF₃ | C≡C—Ph |
| 919 | 6-NMe₂ | CF₃ | C≡C—(2-Cl)Ph |
| 920 | 6-NMe₂ | CF₃ | C≡C—(3-Cl)Ph |

TABLE 2-continued

Structure: 4H-3,1-benzoxazin-2(1H)-one with G substituent on benzene ring, R¹ and R² at position 4.

| Ex. # | G | R¹ | R² |
|---|---|---|---|
| 921 | 6-NMe₂ | CF₃ | C≡C—(2-F)Ph |
| 922 | 6-NMe₂ | CF₃ | C≡C—(3-F)Ph |
| 923 | 6-NMe₂ | CF₃ | C≡C—(2-OH)Ph |
| 924 | 6-NMe₂ | CF₃ | C≡C—(3-OH)Ph |
| 925 | 6-NMe₂ | CF₃ | C≡C—(2-OMe)Ph |
| 926 | 6-NMe₂ | CF₃ | C≡C—(3-OMe)Ph |
| 927 | 6-NMe₂ | CF₃ | C≡C—(2-CN)Ph |
| 928 | 6-NMe₂ | CF₃ | C≡C—(3-CN)Ph |
| 929 | 6-NMe₂ | CF₃ | C≡C—(2-NH₂)Ph |
| 930 | 6-NMe₂ | CF₃ | C≡C—(3-NH₂)Ph |
| 931 | 6-NMe₂ | CF₃ | C≡C—(2-NMe₂)Ph |
| 932 | 6-NMe₂ | CF₃ | C≡C—(3-NMe₂)Ph |
| 933 | 6-NMe₂ | CF₃ | C≡C-2-Pyridyl |
| 934 | 6-NMe₂ | CF₃ | C≡C-3-Pyridyl |
| 935 | 6-NMe₂ | CF₃ | C≡C-4-Pyridyl |
| 936 | 6-NMe₂ | CF₃ | C≡C-2-furanyl |
| 937 | 6-NMe₂ | CF₃ | C≡C-3-furanyl |
| 938 | 6-NMe₂ | CF₃ | C≡C-2-thienyl |
| 939 | 6-NMe₂ | CF₃ | C≡C-3-thienyl |
| 940 | 6-NMe₂ | CF₃ | CH=CH-cycPr |
| 941 | 6-NMe₂ | CF₃ | CH=CH-iPr |
| 942 | 6-NMe₂ | CF₃ | CH=CH-nPr |
| 943 | 6-NMe₂ | CF₃ | CH=CH—Bu |
| 944 | 6-NMe₂ | CF₃ | CH=CH—iBu |
| 945 | 6-NMe₂ | CF₃ | CH=CH-tBu |
| 946 | 6-NMe₂ | CF₃ | CH=CH—Et |
| 947 | 6-NMe₂ | CF₃ | CH=CH—Me |
| 948 | 6-NMe₂ | CF₃ | CH=CH—Ph |
| 949 | 6-NMe₂ | CF₃ | CH=CH-2-Pyridyl |
| 950 | 6-NMe₂ | CF₃ | CH=CH-3-Pyridyl |
| 951 | 6-NMe₂ | CF₃ | CH=CH-4-Pyridyl |
| 952 | 6-NMe₂ | CF₃ | CH=CH-2-furanyl |
| 953 | 6-NMe₂ | CF₃ | CH=CH-3-furanyl |
| 954 | 6-NMe₂ | CF₃ | CH=CH-2-thienyl |
| 955 | 6-NMe₂ | CF₃ | CH=CH-3-thienyl |
| 956 | 6-NMe₂ | CF₃ | CH₂CH₂CH₂CH₃ |
| 957 | 6-NMe₂ | CF₃ | CH₂CH₂-cycPr |
| 958 | 6-NMe₂ | CF₃ | CH₂CH₂-tBu |
| 959 | 6-NMe₂ | CF₃ | CH₂CH₂—Ph |
| 960 | 6-NMe₂ | CF₃ | CH₂CH₂-2-Pyridyl |
| 961 | 6-NMe₂ | CF₃ | CH₂CH₂-3-Pyridyl |
| 962 | 6-NMe₂ | CF₃ | CH₂CH₂-4-Pyridyl |
| 963 | 6-NMe₂ | CF₃ | CH₂CH₂-2-furanyl |
| 964 | 6-NMe₂ | CF₃ | CH₂CH₂-3-furanyl |
| 965 | 6-NMe₂ | CF₃ | CH₂CH₂-2-thienyl |
| 966 | 6-NMe₂ | CF₃ | CH₂CH₂-3-thienyl |
| 967 | 6-COCH₃ | CF₃ | C≡C-iPr |
| 968 | 6-COCH₃ | CF₃ | C≡C-nPr |
| 969 | 6-COCH₃ | CF₃ | C≡C—Bu |
| 970 | 6-COCH₃ | CF₃ | C≡C-iBu |
| 971 | 6-COCH₃ | CF₃ | C≡C-tBu |
| 972 | 6-COCH₃ | CF₃ | C≡C—Me |
| 973 | 6-COCH₃ | CF₃ | C≡C—Ph |
| 974 | 6-COCH₃ | CF₃ | C≡C—(2-Cl)Ph |
| 975 | 6-COCH₃ | CF₃ | C≡C—(3-Cl)Ph |
| 976 | 6-COCH₃ | CF₃ | C≡C—(2-F)Ph |
| 977 | 6-COCH₃ | CF₃ | C≡C—(3-F)Ph |
| 978 | 6-COCH₃ | CF₃ | C≡C—(2-OH)Ph |
| 979 | 6-COCH₃ | CF₃ | C≡C—(3-OH)Ph |
| 980 | 6-COCH₃ | CF₃ | C≡C—(2-OMe)Ph |
| 981 | 6-COCH₃ | CF₃ | C≡C—(3-OMe)Ph |
| 982 | 6-COCH₃ | CF₃ | C≡C—(2-CN)Ph |
| 983 | 6-COCH₃ | CF₃ | C≡C—(3-CN)Ph |
| 984 | 6-COCH₃ | CF₃ | C≡C—(2-NH₂)Ph |
| 985 | 6-COCH₃ | CF₃ | C≡C—(3-NH₂)Ph |
| 986 | 6-COCH₃ | CF₃ | C≡C—(2-NMe₂)Ph |
| 987 | 6-COCH₃ | CF₃ | C≡C—(3-NMe₂)Ph |
| 988 | 6-COCH₃ | CF₃ | C≡C-2-Pyridyl |
| 989 | 6-COCH₃ | CF₃ | C≡C-3-Pyridyl |
| 990 | 6-COCH₃ | CF₃ | C≡C-4-Pyridyl |
| 991 | 6-COCH₃ | CF₃ | C≡C-2-furanyl |
| 992 | 6-COCH₃ | CF₃ | C≡C-3-furanyl |
| 993 | 6-COCH₃ | CF₃ | C≡C-2-thienyl |
| 994 | 6-COCH₃ | CF₃ | C≡C-3-thienyl |
| 995 | 6-COCH₃ | CF₃ | CH=CH-cycPr |
| 996 | 6-COCH₃ | CF₃ | CH=CH-iPr |
| 997 | 6-COCH₃ | CF₃ | CH=CH-nPr |
| 998 | 6-COCH₃ | CF₃ | CH=CH—Bu |
| 999 | 6-COCH₃ | CF₃ | CH=CH-iBu |
| 1000 | 6-COCH₃ | CF₃ | CH=CH-tBu |
| 1001 | 6-COCH₃ | CF₃ | CH=CH—Et |
| 1002 | 6-COCH₃ | CF₃ | CH=CH—Me |
| 1003 | 6-COCH₃ | CF₃ | CH=CH—Ph |
| 1004 | 6-COCH₃ | CF₃ | CH=CH-2-Pyridyl |
| 1005 | 6-COCH₃ | CF₃ | CH=CH-3-Pyridyl |
| 1006 | 6-COCH₃ | CF₃ | CH=CH-4-Pyridyl |
| 1007 | 6-COCH₃ | CF₃ | CH=CH-2-furanyl |
| 1008 | 6-COCH₃ | CF₃ | CH=CH-3-furanyl |
| 1009 | 6-COCH₃ | CF₃ | CH=CH-2-thienyl |
| 1010 | 6-COCH₃ | CF₃ | CH=CH-3-thienyl |
| 1011 | 6-COCH₃ | CF₃ | CH₂CH₂CH₂CH₂CH₃ |
| 1012 | 6-COCH₃ | CF₃ | CH₂CH₂CH(CH₃)₂ |
| 1013 | 6-COCH₃ | CF₃ | CH₂CH₂CH₂CH₃ |
| 1014 | 6-COCH₃ | CF₃ | CH₂CH₂-cycPr |
| 1015 | 6-COCH₃ | CF₃ | CH₂CH₂-tBu |
| 1016 | 6-COCH₃ | CF₃ | CH₂CH₂—Ph |
| 1017 | 6-COCH₃ | CF₃ | CH₂CH₂-2-Pyridyl |
| 1018 | 6-COCH₃ | CF₃ | CH₂CH₂-3-Pyridyl |
| 1019 | 6-COCH₃ | CF₃ | CH₂CH₂-4-Pyridyl |
| 1020 | 6-COCH₃ | CF₃ | CH₂CH₂-2-furanyl |
| 1021 | 6-COCH₃ | CF₃ | CH₂CH₂-3-furanyl |
| 1022 | 6-COCH₃ | CF₃ | CH₂CH₂-2-thienyl |
| 1023 | 6-COCH₃ | CF₃ | CH₂CH₂-3-thienyl |
| 1024 | 6-CH₃ | CF₃ | C≡C-nPr |
| 1025 | 6-CH₃ | CF₃ | C≡C—Bu |
| 1026 | 6-CH₃ | CF₃ | C≡C-iBu |
| 1027 | 6-CH₃ | CF₃ | C≡C-tBu |
| 1028 | 6-CH₃ | CF₃ | C≡C—Me |
| 1029 | 6-CH₃ | CF₃ | C≡C—Ph |
| 1030 | 6-CH₃ | CF₃ | C≡C—(2-Cl)Ph |
| 1031 | 6-CH₃ | CF₃ | C≡C—(3-Cl)Ph |
| 1032 | 6-CH₃ | CF₃ | C≡C—(2-F)Ph |
| 1033 | 6-CH₃ | CF₃ | C≡C—(3-F)Ph |
| 1034 | 6-CH₃ | CF₃ | C≡C—(2-OH)Ph |
| 1035 | 6-CH₃ | CF₃ | C≡C—(3-OH)Ph |
| 1036 | 6-CH₃ | CF₃ | C≡C—(2-OMe)Ph |
| 1037 | 6-CH₃ | CF₃ | C≡C—(3-OMe)Ph |
| 1038 | 6-CH₃ | CF₃ | C≡C—(2-CN)Ph |
| 1039 | 6-CH₃ | CF₃ | C≡C—(3-CN)Ph |
| 1040 | 6-CH₃ | CF₃ | C≡C—(2-NH₂)Ph |
| 1041 | 6-CH₃ | CF₃ | C≡C—(3-NH₂)Ph |
| 1042 | 6-CH₃ | CF₃ | C≡C—(2-NMe₂)Ph |
| 1043 | 6-CH₃ | CF₃ | C≡C—(3-NMe₂)Ph |
| 1044 | 6-CH₃ | CF₃ | C≡C-2-Pyridyl |
| 1045 | 6-CH₃ | CF₃ | C≡C-3-Pyridyl |
| 1046 | 6-CH₃ | CF₃ | C≡C-4-Pyridyl |
| 1047 | 6-CH₃ | CF₃ | C≡C-2-furanyl |
| 1048 | 6-CH₃ | CF₃ | C≡C-3-furanyl |
| 1049 | 6-CH₃ | CF₃ | C≡C-2-thienyl |
| 1050 | 6-CH₃ | CF₃ | C≡C-3-thienyl |
| 1051 | 6-CH₃ | CF₃ | CH=CH-cycPr |
| 1052 | 6-CH₃ | CF₃ | CH=CH-iPr |
| 1053 | 6-CH₃ | CF₃ | CH=CH-nPr |
| 1054 | 6-CH₃ | CF₃ | CH=CH—Bu |
| 1055 | 6-CH₃ | CF₃ | CH=CH-iBu |
| 1056 | 6-CH₃ | CF₃ | CH=CH-tBu |

TABLE 2-continued

| Ex. # | G | R¹ | R² |
|---|---|---|---|
| 1057 | 6-CH₃ | CF₃ | CH=CH—Et |
| 1058 | 6-CH₃ | CF₃ | CH=CH—Me |
| 1059 | 6-CH₃ | CF₃ | CH=CH—Ph |
| 1060 | 6-CH₃ | CF₃ | CH=CH-2-Pyridyl |
| 1061 | 6-CH₃ | CF₃ | CH=CH-3-Pyridyl |
| 1062 | 6-CH₃ | CF₃ | CH=CH-4-Pyridyl |
| 1063 | 6-CH₃ | CF₃ | CH=CH-2-furanyl |
| 1064 | 6-CH₃ | CF₃ | CH=CH-3-furanyl |
| 1065 | 6-CH₃ | CF₃ | CH=CH-2-thienyl |
| 1066 | 6-CH₃ | CF₃ | CH=CH-3-thienyl |
| 1067 | 6-CH₃ | CF₃ | CH₂CH₂CH₂CH₂CH₃ |
| 1068 | 6-CH₃ | CF₃ | CH₂CH₂CH(CH₃)₂ |
| 1069 | 6-CH₃ | CF₃ | CH₂CH₂CH₂CH₃ |
| 1070 | 6-CH₃ | CF₃ | CH₂CH₂-cycPr |
| 1071 | 6-CH₃ | CF₃ | CH₂CH₂-tBu |
| 1072 | 6-CH₃ | CF₃ | CH₂CH₂—Ph |
| 1073 | 6-CH₃ | CF₃ | CH₂CH₂-2-Pyridyl |
| 1074 | 6-CH₃ | CF₃ | CH₂CH₂-3-Pyridyl |
| 1075 | 6-CH₃ | CF₃ | CH₂CH₂-4-Pyridyl |
| 1076 | 6-CH₃ | CF₃ | CH₂CH₂-2-furanyl |
| 1077 | 6-CH₃ | CF₃ | CH₂CH₂-3-furanyl |
| 1078 | 6-CH₃ | CF₃ | CH₂CH₂-2-thienyl |
| 1079 | 6-CH₃ | CF₃ | CH₂CH₂-3-thienyl |
| 1080 | 6,8-diCl | CF₃ | C≡C-iPr |
| 1081 | 6,8-diCl | CF₃ | C≡C-nPr |
| 1082 | 6,8-diCl | CF₃ | C≡C—Et |
| 1083 | 6,8-diCl | CF₃ | C≡C—Me |
| 1084 | 6,8-diCl | CF₃ | C≡C—Ph |
| 1085 | 6,8-diCl | CF₃ | C≡C-2-Pyridyl |
| 1086 | 6,8-diCl | CF₃ | C≡C-3-Pyridyl |
| 1087 | 6,8-diCl | CF₃ | C≡C-4-Pyridyl |
| 1088 | 6,8-diCl | CF₃ | C≡C-2-furanyl |
| 1089 | 6,8-diCl | CF₃ | C≡C-3-furanyl |
| 1090 | 6,8-diCl | CF₃ | C≡C-2-thienyl |
| 1091 | 6,8-diCl | CF₃ | C≡C-3-thienyl |
| 1092 | 6,8-diCl | CF₃ | CH=CH-cycPr |
| 1093 | 6,8-diCl | CF₃ | CH=CH-iPr |
| 1094 | 6,8-diCl | CF₃ | CH=CH-nPr |
| 1095 | 6,8-diCl | CF₃ | CH=CH—Et |
| 1096 | 6,8-diCl | CF₃ | CH=CH—Me |
| 1097 | 6,8-diCl | CF₃ | CH=CH—Ph |
| 1098 | 6,8-diCl | CF₃ | CH=CH-2-Pyridyl |
| 1099 | 6,8-diCl | CF₃ | CH=CH-3-Pyridyl |
| 1100 | 6,8-diCl | CF₃ | CH=CH-4-Pyridyl |
| 1101 | 6,8-diCl | CF₃ | CH=CH-2-furanyl |
| 1102 | 6,8-diCl | CF₃ | CH=CH-3-furanyl |
| 1103 | 6,8-diCl | CF₃ | CH=CH-2-thienyl |
| 1104 | 6,8-diCl | CF₃ | CH=CH-3-thienyl |
| 1105 | 6,8-diCl | CF₃ | CH₂CH₂CH₂CH₂CH₃ |
| 1106 | 6,8-diCl | CF₃ | CH₂CH₂CH(CH₃)₂ |
| 1107 | 6,8-diCl | CF₃ | CH₂CH₂CH₂CH₃ |
| 1108 | 6,8-diCl | CF₃ | CH₂CH₂-cycPr |
| 1109 | 6,8-diCl | CF₃ | CH₂CH₂-2-Pyridyl |
| 1110 | 6,8-diCl | CF₃ | CH₂CH₂-3-Pyridyl |
| 1111 | 6,8-diCl | CF₃ | CH₂CH₂-4-Pyridyl |
| 1112 | 6,8-diCl | CF₃ | CH₂CH₂-2-furanyl |
| 1113 | 6,8-diCl | CF₃ | CH₂CH₂-3-furanyl |
| 1114 | 6,8-diCl | CF₃ | CH₂CH₂-2-thienyl |
| 1115 | 6,8-diCl | CF₃ | CH₂CH₂-3-thienyl |
| 1116 | 5,6,8-triF | CF₃ | C≡C—Me |
| 1117 | 5,6,8-triF | CF₃ | C≡C—Ph |
| 1118 | 5,6,8-triF | CF₃ | C≡C-2-Pyridyl |
| 1119 | 5,6,8-triF | CF₃ | C≡C-3-Pyridyl |
| 1120 | 5,6,8-triF | CF₃ | C≡C-4-Pyridyl |
| 1121 | 5,6,8-triF | CF₃ | C≡C-2-furanyl |
| 1122 | 5,6,8-triF | CF₃ | C≡C-3-furanyl |
| 1123 | 5,6,8-triF | CF₃ | C≡C-2-thienyl |
| 1124 | 5,6,8-triF | CF₃ | C≡C-3-thienyl |
| 1125 | 5,6,8-triF | CF₃ | CH=CH-cycPr |
| 1126 | 5,6,8-triF | CF₃ | CH=CH-iPr |
| 1127 | 5,6,8-triF | CF₃ | CH=CH-nPr |
| 1128 | 5,6,8-triF | CF₃ | CH=CH—Et |
| 1129 | 5,6,8-triF | CF₃ | CH=CH—Me |
| 1130 | 5,6,8-triF | CF₃ | CH=CH—Ph |
| 1131 | 5,6,8-triF | CF₃ | CH=CH-2-Pyridyl |
| 1132 | 5,6,8-triF | CF₃ | CH=CH-3-Pyridyl |
| 1133 | 5,6,8-triF | CF₃ | CH=CH-4-Pyridyl |
| 1134 | 5,6,8-triF | CF₃ | CH=CH-2-furanyl |
| 1135 | 5,6,8-triF | CF₃ | CH=CH-3-furanyl |
| 1136 | 5,6,8-triF | CF₃ | CH=CH-2-thienyl |
| 1137 | 5,6,8-triF | CF₃ | CH=CH-3-thienyl |
| 1138 | 5,6,8-triF | CF₃ | CH₂CH₂CH₂CH₂CH₃ |
| 1139 | 5,6,8-triF | CF₃ | CH₂CH₂CH(CH₃)₂ |
| 1140 | 5,6,8-triF | CF₃ | CH₂CH₂CH₂CH₃ |
| 1141 | 5,6,8-triF | CF₃ | CH₂CH₂-cycPr |
| 1142 | 5,6,8-triF | CF₃ | CH₂CH₂—Ph |
| 1143 | 5,6,8-triF | CF₃ | CH₂CH₂-2-Pyridyl |
| 1144 | 5,6,8-triF | CF₃ | CH₂CH₂-3-Pyridyl |
| 1145 | 5,6,8-triF | CF₃ | CH₂CH₂-4-Pyridyl |
| 1146 | 5,6,8-triF | CF₃ | CH₂CH₂-2-furanyl |
| 1147 | 5,6,8-triF | CF₃ | CH₂CH₂-3-furanyl |
| 1148 | 5,6,8-triF | CF₃ | CH₂CH₂-2-thienyl |
| 1149 | 5,6,8-triF | CF₃ | CH₂CH₂-3-thienyl |
| 1150 | 5,8-diF | CF₃ | C≡C—Me |
| 1151 | 5,8-diF | CF₃ | C≡C—Ph |
| 1152 | 5,8-diF | CF₃ | C≡C-2-Pyridyl |
| 1153 | 5,8-diF | CF₃ | C≡C-3-Pyridyl |
| 1154 | 5,8-diF | CF₃ | C≡C-4-Pyridyl |
| 1155 | 5,8-diF | CF₃ | C≡C-2-furanyl |
| 1156 | 5,8-diF | CF₃ | C≡C-3-furanyl |
| 1157 | 5,8-diF | CF₃ | C≡C-2-thienyl |
| 1158 | 5,8-diF | CF₃ | C≡C-3-thienyl |
| 1159 | 5,8-diF | CF₃ | CH=CH-cycPr |
| 1160 | 5,8-diF | CF₃ | CH=CH-iPr |
| 1161 | 5,8-diF | CF₃ | CH=CH-nPr |
| 1162 | 5,8-diF | CF₃ | CH=CH—Et |
| 1163 | 5,8-diF | CF₃ | CH=CH—Me |
| 1164 | 5,8-diF | CF₃ | CH=CH—Ph |
| 1165 | 5,8-diF | CF₃ | CH=CH-2-Pyridyl |
| 1166 | 5,8-diF | CF₃ | CH=CH-3-Pyridyl |
| 1167 | 5,8-diF | CF₃ | CH=CH-4-Pyridyl |
| 1168 | 5,8-diF | CF₃ | CH=CH-2-furanyl |
| 1169 | 5,8-diF | CF₃ | CH=CH-3-furanyl |
| 1170 | 5,8-diF | CF₃ | CH=CH-2-thienyl |
| 1171 | 5,8-diF | CF₃ | CH=CH-3-thienyl |
| 1172 | 5,8-diF | CF₃ | CH₂CH₂CH₂CH₂CH₃ |
| 1173 | 5,8-diF | CF₃ | CH₂CH₂CH(CH₃)₂ |
| 1174 | 5,8-diF | CF₃ | CH₂CH₂CH₂CH₃ |
| 1175 | 5,8-diF | CF₃ | CH₂CH₂-cycPr |
| 1176 | 5,8-diF | CF₃ | CH₂CH₂—Ph |
| 1177 | 5,8-diF | CF₃ | CH₂CH₂-2-Pyridyl |
| 1178 | 5,8-diF | CF₃ | CH₂CH₂-3-Pyridyl |
| 1179 | 5,8-diF | CF₃ | CH₂CH₂-4-Pyridyl |
| 1180 | 5,8-diF | CF₃ | CH₂CH₂-2-furanyl |
| 1181 | 5,8-diF | CF₃ | CH₂CH₂-3-furanyl |
| 1182 | 5,8-diF | CF₃ | CH₂CH₂-2-thienyl |
| 1183 | 5,8-diF | CF₃ | CH₂CH₂-3-thienyl |
| 1184 | 6-iPr | CF₃ | C≡C-nPr |
| 1185 | 6-iPr | CF₃ | C≡C-Et |
| 1186 | 6-iPr | CF₃ | C≡C—Me |
| 1187 | 6-iPr | CF₃ | C≡C-3-Pyridyl |
| 1188 | 6-iPr | CF₃ | C≡C-2-furanyl |
| 1189 | 6-iPr | CF₃ | C≡C-3-furanyl |
| 1190 | 6-iPr | CF₃ | C≡C-2-thienyl |
| 1191 | 6-iPr | CF₃ | C≡C-3-thienyl |
| 1192 | 6-iPr | CF₃ | CH=CH-cycPr |

TABLE 2-continued

| Ex. # | G | R¹ | R² |
|---|---|---|---|
| 1193 | 6-iPr | CF₃ | CH=CH-iPr |
| 1194 | 6-iPr | CF₃ | CH=CH-nPr |
| 1195 | 6-iPr | CF₃ | CH=CH—Et |
| 1196 | 6-iPr | CF₃ | CH=CH—Me |
| 1197 | 6-iPr | CF₃ | CH=CH—Ph |
| 1198 | 6-iPr | CF₃ | CH=CH-2-furanyl |
| 1199 | 6-iPr | CF₃ | CH=CH-3-furanyl |
| 1200 | 6-iPr | CF₃ | CH=CH-2-thienyl |
| 1201 | 6-iPr | CF₃ | CH=CH-3-thienyl |
| 1202 | 6-iPr | CF₃ | CH₂CH₂CH₂CH₃ |
| 1203 | 6-iPr | CF₃ | CH₂CH₂-cycPr |
| 1204 | 6-OCF₃ | CF₃ | C≡C—nPr |
| 1205 | 6-OCF₃ | CF₃ | C≡C—Et |
| 1206 | 6-OCF₃ | CF₃ | C≡C—Me |
| 1207 | 6-OCF₃ | CF₃ | C≡C-3-Pyridyl |
| 1208 | 6-OCF₃ | CF₃ | C≡C-2-furanyl |
| 1209 | 6-OCF₃ | CF₃ | C≡C-3-furanyl |
| 1210 | 6-OCF₃ | CF₃ | C≡C-2-thienyl |
| 1211 | 6-OCF₃ | CF₃ | C≡C-3-thienyl |
| 1212 | 6-OCF₃ | CF₃ | CH=CH-cycPr |
| 1213 | 6-OCF₃ | CF₃ | CH=CH-iPr |
| 1214 | 6-OCF₃ | CF₃ | CH=CH-nPr |
| 1215 | 6-OCF₃ | CF₃ | CH=CH—Et |
| 1216 | 6-OCF₃ | CF₃ | CH=CH—Me |
| 1217 | 6-OCF₃ | CF₃ | CH=CH—Ph |
| 1218 | 6-OCF₃ | CF₃ | CH=CH-3-Pyridyl |
| 1219 | 6-OCF₃ | CF₃ | CH=CH-2-furanyl |
| 1220 | 6-OCF₃ | CF₃ | CH=CH-3-furanyl |
| 1221 | 6-OCF₃ | CF₃ | CH=CH-2-thienyl |
| 1222 | 6-OCF₃ | CF₃ | CH=CH-3-thienyl |
| 1223 | 6-OCF₃ | CF₃ | CH₂CH₂CH₂CH₃ |
| 1224 | 6-OCF₃ | CF₃ | CH₂CH₂-cycPr |
| 1225 | 6-(pyrazol-5-yl) | CF₃ | C≡C-cycPr |
| 1226 | 6-(pyrazol-5-yl) | CF₃ | C≡C-iPr |
| 1227 | 6-(pyrazol-5-yl) | CF₃ | C≡C-nPr |
| 1228 | 6-(pyrazol-5-yl) | CF₃ | C≡C-Et |
| 1229 | 6-(pyrazol-5-yl) | CF₃ | C≡C—Me |
| 1230 | 6-(pyrazol-5-yl) | CF₃ | C≡C—Ph |
| 1231 | 6-(pyrazol-5-yl) | CF₃ | C≡C-3-Pyridyl |
| 1232 | 6-(pyrazol-5-yl) | CF₃ | C≡C-2-furanyl |
| 1233 | 6-(pyrazol-5-yl) | CF₃ | C≡C-3-furanyl |
| 1234 | 6-(pyrazol-5-yl) | CF₃ | C≡C-2-thienyl |
| 1235 | 6-(pyrazol-5-yl) | CF₃ | C≡C-3-thienyl |
| 1236 | 6-(pyrazol-5-yl) | CF₃ | CH=CH-cycPr |
| 1237 | 6-(pyrazol-5-yl) | CF₃ | CH=CH-iPr |
| 1238 | 6-(pyrazol-5-yl) | CF₃ | CH=CH-nPr |
| 1239 | 6-(pyrazol-5-yl) | CF₃ | CH=CH—Et |
| 1240 | 6-(pyrazol-5-yl) | CF₃ | CH=CH—Me |
| 1241 | 6-(pyrazol-5-yl) | CF₃ | CH=CH—Ph |
| 1242 | 6-(pyrazol-5-yl) | CF₃ | CH=CH-3-Pyridyl |
| 1243 | 6-(pyrazol-5-yl) | CF₃ | CH=CH-2-furanyl |
| 1244 | 6-(pyrazol-5-yl) | CF₃ | CH=CH-3-furanyl |
| 1245 | 6-(pyrazol-5-yl) | CF₃ | CH=CH-2-thienyl |
| 1246 | 6-(pyrazol-5-yl) | CF₃ | CH=CH-3-thienyl |
| 1247 | 6-(pyrazol-5-yl) | CF₃ | Pentyl |
| 1248 | 6-(pyrazol-5-yl) | CF₃ | CH₂CH₂-iPr |
| 1249 | 6-(pyrazol-5-yl) | CF₃ | CH₂CH₂CH₂CH₃ |
| 1250 | 6-(pyrazol-5-yl) | CF₃ | CH₂CH₂-cycPr |
| 1251 | H | CF₃ | C≡C-nPr |
| 1252 | H | CF₃ | C≡C-Et |
| 1253 | H | CF₃ | C≡C—Me |
| 1254 | H | CF₃ | C≡C-3-Pyridyl |
| 1255 | H | CF₃ | C≡C-2-furanyl |
| 1256 | H | CF₃ | C≡C-3-furanyl |
| 1257 | H | CF₃ | C≡C-2-thienyl |
| 1258 | H | CF₃ | C≡C-3-thienyl |
| 1259 | H | CF₃ | CH=CH-cycPr |
| 1260 | H | CF₃ | CH=CH-iPr |
| 1261 | H | CF₃ | CH=CH-nPr |
| 1262 | H | CF₃ | CH=CH—Et |
| 1263 | H | CF₃ | CH=CH—Me |
| 1264 | H | CF₃ | CH=CH—Ph |
| 1265 | H | CF₃ | CH=CH-3-Pyridyl |
| 1266 | H | CF₃ | CH=CH-2-furanyl |
| 1267 | H | CF₃ | CH=CH-3-furanyl |
| 1268 | H | CF₃ | CH=CH-2-thienyl |
| 1269 | H | CF₃ | CH=CH-3-thienyl |
| 1270 | H | CF₃ | CH₂CH₂CH₂CH₃ |
| 1271 | H | CF₃ | CH₂CH₂-cycPr |
| 1272 | 6-Ph | CF₃ | C≡C—Me |
| 1273 | 6-Ph | CF₃ | C≡C—Ph |
| 1274 | 6-Ph | CF₃ | C≡C-3-Pyridyl |
| 1275 | 6-Ph | CF₃ | C≡C-2-furanyl |
| 1276 | 6-Ph | CF₃ | C≡C-3-furanyl |
| 1277 | 6-Ph | CF₃ | C≡C-2-thienyl |
| 1278 | 6-Ph | CF₃ | C≡C-3-thienyl |
| 1279 | 6-Ph | CF₃ | CH=CH-cycPr |
| 1280 | 6-Ph | CF₃ | CH=CH-iPr |
| 1281 | 6-Ph | CF₃ | CH=CH-nPr |
| 1282 | 6-Ph | CF₃ | CH=CH—Et |
| 1283 | 6-Ph | CF₃ | CH=CH—Me |
| 1284 | 6-Ph | CF₃ | CH=CH—Ph |
| 1285 | 6-Ph | CF₃ | CH=CH-3-Pyridyl |
| 1286 | 6-Ph | CF₃ | CH=CH-2-furanyl |
| 1287 | 6-Ph | CF₃ | CH=CH-3-furanyl |
| 1288 | 6-Ph | CF₃ | CH=CH-2-thienyl |
| 1289 | 6-Ph | CF₃ | CH=CH-3-thienyl |
| 1290 | 6-Ph | CF₃ | Pentyl |
| 1291 | 6-Ph | CF₃ | CH₂CH₂CH₂CH₃ |
| 1292 | 6-Ph | CF₃ | CH₂CH₂-cycPr |
| 1293 | 6-CN | CF₃ | C≡C-cycPr |
| 1294 | 6-CN | CF₃ | C≡C-iPr |
| 1295 | 6-CN | CF₃ | C≡C-nPr |
| 1296 | 6-CN | CF₃ | C≡C-Et |
| 1297 | 6-CN | CF₃ | C≡C-3-Pyridyl |
| 1298 | 6-CN | CF₃ | C≡C-2-furanyl |
| 1299 | 6-CN | CF₃ | C≡C-3-furanyl |
| 1300 | 6-CN | CF₃ | C≡C-2-thienyl |
| 1301 | 6-CN | CF₃ | C≡C-3-thienyl |
| 1302 | 6-CN | CF₃ | CH=CH-cycPr |
| 1303 | 6-CN | CF₃ | CH=CH-iPr |
| 1304 | 6-CN | CF₃ | CH=CH-nPr |
| 1305 | 6-CN | CF₃ | CH=CH—Et |
| 1306 | 6-CN | CF₃ | CH=CH-3-Pyridyl |
| 1307 | 6-CN | CF₃ | CH=CH-2-furanyl |
| 1308 | 6-CN | CF₃ | CH=CH-3-furanyl |
| 1309 | 6-CN | CF₃ | CH=CH-2-thienyl |
| 1310 | 6-CN | CF₃ | CH=CH-3-thienyl |
| 1311 | 6-NO₂ | CF₃ | C≡C-cycPr |
| 1312 | 6-NO₂ | CF₃ | C≡C-iPr |
| 1313 | 6-NO₂ | CF₃ | C≡C-nPr |
| 1314 | 6-NO₂ | CF₃ | C≡C-Et |
| 1315 | 6-NO₂ | CF₃ | C≡C-3-Pyridyl |
| 1316 | 6-NO₂ | CF₃ | C≡C-2-furanyl |
| 1317 | 6-NO₂ | CF₃ | C≡C-3-furanyl |
| 1318 | 6-NO₂ | CF₃ | C≡C-2-thienyl |
| 1319 | 6-NO₂ | CF₃ | C≡C-3-thienyl |
| 1320 | 6-NHMe | CF₃ | C≡C-cycPr |
| 1321 | 6-NHMe | CF₃ | C≡C-iPr |
| 1322 | 6-NHMe | CF₃ | C≡C-nPr |
| 1323 | 6-NHMe | CF₃ | C≡C-Et |
| 1324 | 6-NHMe | CF₃ | C≡C-3-Pyridyl |
| 1325 | 6-NHMe | CF₃ | C≡C-2-furanyl |
| 1326 | 6-NHMe | CF₃ | C≡C-3-furanyl |
| 1327 | 6-NHMe | CF₃ | C≡C-2-thienyl |
| 1328 | 6-NHMe | CF₃ | C≡C-3-thienyl |

TABLE 2-continued

| Ex. # | G | R¹ | R² |
|---|---|---|---|
| 1329 | 6-NHMe | $CF_3$ | CH=CH-cycPr |
| 1330 | 6-NHMe | $CF_3$ | CH=CH-iPr |
| 1331 | 6-NHMe | $CF_3$ | CH=CH-nPr |
| 1332 | 6-NHMe | $CF_3$ | CH=CH—Et |
| 1333 | 6-NHMe | $CF_3$ | CH=CH-3-Pyridyl |
| 1334 | 6-NHMe | $CF_3$ | CH=CH-2-furanyl |
| 1335 | 6-NHMe | $CF_3$ | CH=CH-3-furanyl |
| 1336 | 6-NHMe | $CF_3$ | CH=CH-2-thienyl |
| 1337 | 6-NHMe | $CF_3$ | CH=CH-3-thienyl |
| 1338 | 6,7-OCH₂O— | $CF_3$ | C≡C-cycPr |
| 1339 | 6,7-OCH₂O— | $CF_3$ | C≡C-iPr |
| 1340 | 6,7-OCH₂O— | $CF_3$ | C≡C-nPr |
| 1341 | 6,7-OCH₂O— | $CF_3$ | C≡C-Et |
| 1342 | 6,7-OCH₂O— | $CF_3$ | C≡C-3-Pyridyl |
| 1343 | 6,7-OCH₂O— | $CF_3$ | C≡C-2-furanyl |
| 1344 | 6,7-OCH₂O— | $CF_3$ | C≡C-3-furanyl |
| 1345 | 6,7-OCH₂O— | $CF_3$ | C≡C-2-thienyl |
| 1346 | 6,7-OCH₂O— | $CF_3$ | C≡C-3-thienyl |
| 1347 | 6,7-diCl | $CF_3$ | C≡C-cycPr |
| 1348 | 6,7-diCl | $CF_3$ | C≡C-iPr |
| 1349 | 6,7-diCl | $CF_3$ | C≡C-nPr |
| 1350 | 6,7-diCl | $CF_3$ | C≡C-Et |
| 1351 | 6,7-diCl | $CF_3$ | C≡C-3-Pyridyl |
| 1352 | 6,7-diCl | $CF_3$ | C≡C-2-furanyl |
| 1353 | 6,7-diCl | $CF_3$ | C≡C-3-furanyl |
| 1354 | 6,7-diCl | $CF_3$ | C≡C-2-thienyl |
| 1355 | 6,7-diCl | $CF_3$ | C≡C-3-thienyl |
| 1356 | 7-Cl | $CF_3$ | C≡C-cycPr |
| 1357 | 7-Cl | $CF_3$ | C≡C-iPr |
| 1358 | 7-Cl | $CF_3$ | C≡C-nPr |
| 1359 | 7-Cl | $CF_3$ | C≡C-Et |
| 1360 | 7-Cl | $CF_3$ | C≡C-3-Pyridyl |
| 1361 | 7-Cl | $CF_3$ | C≡C-2-furanyl |
| 1362 | 7-Cl | $CF_3$ | C≡C-3-furanyl |
| 1363 | 7-Cl | $CF_3$ | C≡C-2-thienyl |
| 1364 | 7-Cl | $CF_3$ | C≡C-3-thienyl |

*Unless otherwise noted, stereochemistry is (+/−).

TABLE 3

| Ex. # | G | R¹ | R² |
|---|---|---|---|
| 1401 | 6-Cl, 8-F | cycPr | C≡C-cycPr |
| 1402 | 6-Cl, 8-F | cycPr | C≡C-iPr |
| 1403 | 6-Cl, 8-F | cycPr | C≡C-nPr |
| 1404 | 6-Cl, 8-F | cycPr | C≡C—Et |
| 1405 | 6-Cl, 8-F | cycPr | C≡C-3-Pyridyl |
| 1406 | 6-Cl, 8-F | cycPr | C≡C-2-furanyl |
| 1407 | 6-Cl, 8-F | cycPr | C≡C-3-furanyl |
| 1408 | 6-Cl, 8-F | cycPr | C≡C-2-thienyl |
| 1409 | 6-Cl, 8-F | cycPr | C≡C-3-thienyl |
| 1410 | 6-Cl, 8-F | iPr | C≡C-cycPr |
| 1411 | 6-Cl, 8-F | iPr | C≡C-iPr |
| 1412 | 6-Cl, 8-F | iPr | C≡C-nPr |
| 1413 | 6-Cl, 8-F | iPr | C≡C—Et |
| 1414 | 6-Cl, 8-F | iPr | C≡C-3-Pyridyl |
| 1415 | 6-Cl, 8-F | iPr | C≡C-2-furanyl |
| 1416 | 6-Cl, 8-F | iPr | C≡C-3-furanyl |
| 1417 | 6-Cl, 8-F | iPr | C≡C-2-thienyl |
| 1418 | 6-Cl, 8-F | iPr | C≡C-3-thienyl |
| 1419 | 6-Cl, 8-F | Et | C≡C-cycPr |
| 1420 | 6-Cl, 8-F | Et | C≡C-iPr |
| 1421 | 6-Cl, 8-F | Et | C≡C-nPr |
| 1422 | 6-Cl, 8-F | Et | C≡C—Et |
| 1423 | 5,6-diF | cycPr | C≡C-cycPr |
| 1424 | 5,6-diF | cycPr | C≡C-iPr |
| 1425 | 5,6-diF | cycPr | C≡C-nPr |
| 1426 | 5,6-diF | cycPr | C≡C—Et |
| 1427 | 5,6-diF | cycPr | C≡C-3-Pyridyl |
| 1428 | 5,6-diF | cycPr | C≡C-2-furanyl |
| 1429 | 5,6-diF | cycPr | C≡C-3-furanyl |
| 1430 | 5,6-diF | cycPr | C≡C-2-thienyl |
| 1431 | 5,6-diF | cycPr | C≡C-3-thienyl |
| 1432 | 5,6-diF | iPr | C≡C-cycPr |
| 1433 | 5,6-diF | iPr | C≡C-iPr |
| 1434 | 5,6-diF | iPr | C≡C-nPr |
| 1435 | 5,6-diF | iPr | C≡C—Et |
| 1436 | 5,6-diF | iPr | C≡C-3-Pyridyl |
| 1437 | 5,6-diF | iPr | C≡C-2-furanyl |
| 1438 | 5,6-diF | iPr | C≡C-3-furanyl |
| 1439 | 5,6-diF | iPr | C≡C-2-thienyl |
| 1440 | 5,6-diF | iPr | C≡C-3-thienyl |
| 1441 | 5,6-diF | Et | C≡C-cycPr |
| 1442 | 5,6-diF | Et | C≡C-iPr |
| 1443 | 5,6-diF | Et | C≡C-nPr |
| 1444 | 5,6-diF | Et | C≡C—Et |
| 1445 | 5,6-diCl | cycPr | C≡C-cycPr |
| 1446 | 5,6-diCl | cycPr | C≡C-iPr |
| 1447 | 5,6-diCl | cycPr | C≡C-nPr |
| 1448 | 5,6-diCl | cycPr | C≡C—Et |
| 1449 | 5,6-diCl | cycPr | C≡C-3-Pyridyl |
| 1450 | 5,6-diCl | cycPr | C≡C-2-furanyl |
| 1451 | 5,6-diCl | cycPr | C≡C-3-furanyl |
| 1452 | 5,6-diCl | cycPr | C≡C-2-thienyl |
| 1453 | 5,6-diCl | cycPr | C≡C-3-thienyl |
| 1454 | 5,6-diCl | iPr | C≡C-cycPr |
| 1455 | 5,6-diCl | iPr | C≡C-iPr |
| 1456 | 5,6-diCl | iPr | C≡C-nPr |
| 1457 | 5,6-diCl | iPr | C≡C—Et |
| 1458 | 5,6-diCl | iPr | C≡C-3-Pyridyl |
| 1459 | 5,6-diCl | iPr | C≡C-2-furanyl |
| 1460 | 5,6-diCl | iPr | C≡C-3-furanyl |
| 1461 | 5,6-diCl | iPr | C≡C-2-thienyl |
| 1462 | 5,6-diCl | iPr | C≡C-3-thienyl |
| 1463 | 5,6-diCl | Et | C≡C-cycPr |
| 1464 | 5,6-diCl | Et | C≡C-iPr |
| 1465 | 5,6-diCl | Et | C≡C-nPr |
| 1466 | 5,6-diCl | Et | C≡C—Et |
| 1467 | 5-Cl, 6-F | cycPr | C≡C-cycPr |
| 1468 | 5-Cl, 6-F | cycPr | C≡C-iPr |
| 1469 | 5-Cl, 6-F | cycPr | C≡C-nPr |
| 1470 | 5-Cl, 6-F | cycPr | C≡C—Et |
| 1471 | 5-Cl, 6-F | cycPr | C≡C-3-Pyridyl |
| 1472 | 5-Cl, 6-F | cycPr | C≡C-2-furanyl |
| 1473 | 5-Cl, 6-F | cycPr | C≡C-3-furanyl |
| 1474 | 5-Cl, 6-F | cycPr | C≡C-2-thienyl |
| 1475 | 5-Cl, 6-F | cycPr | C≡C-3-thienyl |
| 1476 | 5-Cl, 6-F | iPr | C≡C-cycPr |
| 1477 | 5-Cl, 6-F | iPr | C≡C-iPr |
| 1478 | 5-Cl, 6-F | iPr | C≡C-nPr |
| 1479 | 5-Cl, 6-F | iPr | C≡C—Et |
| 1480 | 5-Cl, 6-F | iPr | C≡C-3-Pyridyl |
| 1481 | 5-Cl, 6-F | iPr | C≡C-2-furanyl |
| 1482 | 5-Cl, 6-F | iPr | C≡C-3-furanyl |
| 1483 | 5-Cl, 6-F | iPr | C≡C-2-thienyl |

TABLE 3-continued

| Ex. # | G | R¹ | R² |
|---|---|---|---|
| 1484 | 5-Cl, 6-F | iPr | C≡C-3-thienyl |
| 1485 | 5-Cl, 6-F | Et | C≡C-cycPr |
| 1486 | 5-Cl, 6-F | Et | C≡C-iPr |
| 1487 | 5-Cl, 6-F | Et | C≡C-nPr |
| 1488 | 5-Cl, 6-F | Et | C≡C—Et |
| 1489 | 5,6-OCH₂O— | cycPr | C≡C-cycPr |
| 1490 | 5,6-OCH₂O— | cycPr | C≡C-iPr |
| 1491 | 5,6-OCH₂O— | cycPr | C≡C-nPr |
| 1492 | 5,6-OCH₂O— | cycPr | C≡C—Et |
| 1493 | 5,6-OCH₂O— | cycPr | C≡C-3-Pyridyl |
| 1494 | 5,6-OCH₂O— | cycPr | C≡C-2-furanyl |
| 1495 | 5,6-OCH₂O— | cycPr | C≡C-3-furanyl |
| 1496 | 5,6-OCH₂O— | cycPr | C≡C-2-thienyl |
| 1497 | 5,6-OCH₂O— | cycPr | C≡C-3-thienyl |
| 1498 | 5,6-OCH₂O— | iPr | C≡C-cycPr |
| 1499 | 5,6-OCH₂O— | iPr | C≡C-iPr |
| 1500 | 5,6-OCH₂O— | iPr | C≡C-nPr |
| 1501 | 5,6-OCH₂O— | iPr | C≡C—Et |
| 1502 | 5,6-OCH₂O— | iPr | C≡C-3-Pyridyl |
| 1503 | 5,6-OCH₂O— | iPr | C≡C-2-furanyl |
| 1504 | 5,6-OCH₂O— | iPr | C≡C-3-furanyl |
| 1505 | 5,6-OCH₂O— | iPr | C≡C-2-thienyl |
| 1506 | 5,6-OCH₂O— | iPr | C≡C-3-thienyl |
| 1507 | 5,6-OCH₂O— | Et | C≡C-cycPr |
| 1508 | 5,6-OCH₂O— | Et | C≡C-iPr |
| 1509 | 5,6-OCH₂O— | Et | C≡C-nPr |
| 1510 | 5,6-OCH₂O— | Et | C≡C—Et |
| 1511 | 5-F | cycPr | C≡C-cycPr |
| 1512 | 5-F | cycPr | C≡C-iPr |
| 1513 | 5-F | cycPr | C≡C-nPr |
| 1514 | 5-F | cycPr | C≡C—Et |
| 1515 | 5-F | cycPr | C≡C-3-Pyridyl |
| 1516 | 5-F | cycPr | C≡C-2-furanyl |
| 1517 | 5-F | cycPr | C≡C-3-furanyl |
| 1518 | 5-F | cycPr | C≡C-2-thienyl |
| 1519 | 5-F | cycPr | C≡C-3-thienyl |
| 1520 | 5-F | iPr | C≡C-cycPr |
| 1521 | 5-F | iPr | C≡C-iPr |
| 1522 | 5-F | iPr | C≡C-nPr |
| 1523 | 5-F | iPr | C≡C—Et |
| 1524 | 5-F | iPr | C≡C-3-Pyridyl |
| 1525 | 5-F | iPr | C≡C-2-furanyl |
| 1526 | 5-F | iPr | C≡C-3-furanyl |
| 1527 | 5-F | iPr | C≡C-2-thienyl |
| 1528 | 5-F | iPr | C≡C-3-thienyl |
| 1529 | 5-F | Et | C≡C-cycPr |
| 1530 | 5-F | Et | C≡C-iPr |
| 1531 | 5-F | Et | C≡C-nPr |
| 1532 | 5-F | Et | C≡C—Et |
| 1533 | 5-Cl | cycPr | C≡C-cycPr |
| 1534 | 5-Cl | cycPr | C≡C-iPr |
| 1535 | 5-Cl | cycPr | C≡C-nPr |
| 1536 | 5-Cl | cycPr | C≡C—Et |
| 1537 | 5-Cl | cycPr | C≡C-3-Pyridyl |
| 1538 | 5-Cl | cycPr | C≡C-2-furanyl |
| 1539 | 5-Cl | cycPr | C≡C-3-furanyl |
| 1540 | 5-Cl | cycPr | C≡C-2-thienyl |
| 1541 | 5-Cl | cycPr | C≡C-3-thienyl |
| 1542 | 5-Cl | iPr | C≡C-cycPr |
| 1543 | 5-Cl | iPr | C≡C-iPr |
| 1544 | 5-Cl | iPr | C≡C-nPr |
| 1545 | 5-Cl | iPr | C≡C—Et |
| 1546 | 5-Cl | iPr | C≡C-3-Pyridyl |
| 1547 | 5-Cl | iPr | C≡C-2-furanyl |
| 1548 | 5-Cl | iPr | C≡C-3-furanyl |
| 1549 | 5-Cl | iPr | C≡C-2-thienyl |
| 1550 | 5-Cl | iPr | C≡C-3-thienyl |
| 1551 | 5-Cl | Et | C≡C-cycPr |
| 1552 | 5-Cl | Et | C≡C-iPr |
| 1553 | 5-Cl | Et | C≡C-nPr |
| 1554 | 5-Cl | Et | C≡C—Et |
| 1555 | 6-OMe | cycPr | C≡C-cycPr |
| 1556 | 6-OMe | cycPr | C≡C-iPr |
| 1557 | 6-OMe | cycPr | C≡C-nPr |
| 1558 | 6-OMe | cycPr | C≡C—Et |
| 1559 | 6-OMe | cycPr | C≡C-3-Pyridyl |
| 1560 | 6-OMe | cycPr | C≡C-2-furanyl |
| 1561 | 6-OMe | cycPr | C≡C-3-furanyl |
| 1562 | 6-OMe | cycPr | C≡C-2-thienyl |
| 1563 | 6-OMe | cycPr | C≡C-3-thienyl |
| 1564 | 6-OMe | iPr | C≡C-nPr |
| 1565 | 6-OMe | iPr | C≡C—Et |
| 1566 | 6-OMe | iPr | C≡C-3-Pyridyl |
| 1567 | 6-OMe | iPr | C≡C-2-furanyl |
| 1568 | 6-OMe | iPr | C≡C-3-furanyl |
| 1569 | 6-OMe | iPr | C≡C-2-thienyl |
| 1570 | 6-OMe | iPr | C≡C-3-thienyl |
| 1571 | 6-OMe | Et | C≡C-cycPr |
| 1572 | 6-OMe | Et | C≡C-iPr |
| 1573 | 6-OMe | Et | C≡C-nPr |
| 1574 | 6-OMe | Et | C≡C—Et |
| 1575 | 5-F, 6-OMe | cycPr | C≡C-cycPr |
| 1576 | 5-F, 6-OMe | cycPr | C≡C-iPr |
| 1577 | 5-F, 6-OMe | cycPr | C≡C-nPr |
| 1578 | 5-F, 6-OMe | cycPr | C≡C—Et |
| 1579 | 5-F, 6-OMe | cycPr | C≡C-3-Pyridyl |
| 1580 | 5-F, 6-OMe | cycPr | C≡C-2-furanyl |
| 1581 | 5-F, 6-OMe | cycPr | C≡C-3-furanyl |
| 1582 | 5-F, 6-OMe | cycPr | C≡C-2-thienyl |
| 1583 | 5-F, 6-OMe | cycPr | C≡C-3-thienyl |
| 1584 | 5-F, 6-OMe | iPr | C≡C-cycPr |
| 1585 | 5-F, 6-OMe | iPr | C≡C-iPr |
| 1586 | 5-F, 6-OMe | iPr | C≡C-nPr |
| 1587 | 5-F, 6-OMe | iPr | C≡C—Et |
| 1588 | 5-F, 6-OMe | iPr | C≡C-3-Pyridyl |
| 1589 | 5-F, 6-OMe | iPr | C≡C-2-furanyl |
| 1590 | 5-F, 6-OMe | iPr | C≡C-3-furanyl |
| 1591 | 5-F, 6-OMe | iPr | C≡C-2-thienyl |
| 1592 | 5-F, 6-OMe | iPr | C≡C-3-thienyl |
| 1593 | 5-F, 6-OMe | Et | C≡C-cycPr |
| 1594 | 5-F, 6-OMe | Et | C≡C-iPr |
| 1595 | 5-F, 6-OMe | Et | C≡C-nPr |
| 1596 | 5-F, 6-OMe | Et | C≡C—Et |
| 1597 | 6-NMe₂ | cycPr | C≡C-cycPr |
| 1598 | 6-NMe₂ | cycPr | C≡C-iPr |
| 1599 | 6-NMe₂ | cycPr | C≡C-nPr |
| 1600 | 6-NMe₂ | cycPr | C≡C—Et |
| 1601 | 6-NMe₂ | cycPr | C≡C-3-Pyridyl |
| 1602 | 6-NMe₂ | cycPr | C≡C-2-furanyl |
| 1603 | 6-NMe₂ | cycPr | C≡C-3-furanyl |
| 1604 | 6-NMe₂ | cycPr | C≡C-2-thienyl |
| 1605 | 6-NMe₂ | cycPr | C≡C-3-thienyl |
| 1606 | 6-NMe₂ | iPr | C≡C-cycPr |
| 1607 | 6-NMe₂ | iPr | C≡C-iPr |
| 1608 | 6-NMe₂ | iPr | C≡C-nPr |
| 1609 | 6-NMe₂ | iPr | C≡C—Et |
| 1610 | 6-NMe₂ | iPr | C≡C-3-Pyridyl |
| 1611 | 6-NMe₂ | iPr | C≡C-2-furanyl |
| 1612 | 6-NMe₂ | iPr | C≡C-3-furanyl |
| 1613 | 6-NMe₂ | iPr | C≡C-2-thienyl |
| 1614 | 6-NMe₂ | iPr | C≡C-3-thienyl |
| 1615 | 6-NMe₂ | Et | C≡C-cycPr |
| 1616 | 6-NMe₂ | Et | C≡C-iPr |
| 1617 | 6-NMe₂ | Et | C≡C-nPr |
| 1618 | 6-NMe₂ | Et | C≡C—Et |
| 1619 | 6-COCH₃ | cycPr | C≡C-cycPr |

TABLE 3-continued

| Ex. # | G | R¹ | R² |
|---|---|---|---|
| 1620 | 6-COCH₃ | cycPr | C≡C-iPr |
| 1621 | 6-COCH₃ | cycPr | C≡C-nPr |
| 1622 | 6-COCH₃ | cycPr | C≡C—Et |
| 1623 | 6-COCH₃ | cycPr | C≡C-3-Pyridyl |
| 1624 | 6-COCH₃ | cycPr | C≡C-2-furanyl |
| 1625 | 6-COCH₃ | cycPr | C≡C-3-furanyl |
| 1626 | 6-COCH₃ | cycPr | C≡C-2-thienyl |
| 1627 | 6-COCH₃ | cycPr | C≡C-3-thienyl |
| 1628 | 6-COCH₃ | iPr | C≡C-cycPr |
| 1629 | 6-COCH₃ | iPr | C≡C-iPr |
| 1630 | 6-COCH₃ | iPr | C≡C-nPr |
| 1631 | 6-COCH₃ | iPr | C≡C—Et |
| 1632 | 6-COCH₃ | iPr | C≡C-3-Pyridyl |
| 1633 | 6-COCH₃ | iPr | C≡C-2-furanyl |
| 1634 | 6-COCH₃ | iPr | C≡C-3-furanyl |
| 1635 | 6-COCH₃ | iPr | C≡C-2-thienyl |
| 1636 | 6-COCH₃ | iPr | C≡C-3-thienyl |
| 1637 | 6-COCH₃ | Et | C≡C-cycPr |
| 1638 | 6-COCH₃ | Et | C≡C-iPr |
| 1639 | 6-COCH₃ | Et | C≡C-nPr |
| 1640 | 6-COCH₃ | Et | C≡C—Et |
| 1641 | 6-CH₃ | cycPr | C≡C-cycPr |
| 1642 | 6-CH₃ | cycPr | C≡C-nPr |
| 1643 | 6-CH₃ | cycPr | C≡C—Et |
| 1644 | 6-CH₃ | cycPr | C≡C-3-Pyridyl |
| 1645 | 6-CH₃ | cycPr | C≡C-2-furanyl |
| 1646 | 6-CH₃ | cycPr | C≡C-3-furanyl |
| 1647 | 6-CH₃ | cycPr | C≡C-2-thienyl |
| 1648 | 6-CH₃ | cycPr | C≡C-3-thienyl |
| 1649 | 6-CH₃ | iPr | C≡C-nPr |
| 1650 | 6-CH₃ | iPr | C≡C—Et |
| 1651 | 6-CH₃ | iPr | C≡C-3-Pyridyl |
| 1652 | 6-CH₃ | iPr | C≡C-2-furanyl |
| 1653 | 6-CH₃ | iPr | C≡C-3-furanyl |
| 1654 | 6-CH₃ | iPr | C≡C-2-thienyl |
| 1655 | 6-CH₃ | iPr | C≡C-3-thienyl |
| 1656 | 6-CH₃ | Et | C≡C-cycPr |
| 1657 | 6-CH₃ | Et | C≡C-nPr |
| 1658 | 6,8-diCl | cycPr | C≡C-cycPr |
| 1659 | 6,8-diCl | cycPr | C≡C-iPr |
| 1660 | 6,8-diCl | cycPr | C≡C-nPr |
| 1661 | 6,8-diCl | cycPr | C≡C—Et |
| 1662 | 6,8-diCl | cycPr | C≡C-3-Pyridyl |
| 1663 | 6,8-diCl | cycPr | C≡C-2-furanyl |
| 1664 | 6,8-diCl | cycPr | C≡C-3-furanyl |
| 1665 | 6,8-diCl | cycPr | C≡C-2-thienyl |
| 1666 | 6,8-diCl | cycPr | C≡C-3-thienyl |
| 1667 | 6,8-diCl | iPr | C≡C-cycPr |
| 1668 | 6,8-diCl | iPr | C≡C-iPr |
| 1669 | 6,8-diCl | iPr | C≡C-nPr |
| 1670 | 6,8-diCl | iPr | C≡C—Et |
| 1671 | 6,8-diCl | iPr | C≡C-3-Pyridyl |
| 1672 | 6,8-diCl | iPr | C≡C-2-furanyl |
| 1673 | 6,8-diCl | iPr | C≡C-3-furanyl |
| 1674 | 6,8-diCl | iPr | C≡C-2-thienyl |
| 1675 | 6,8-diCl | iPr | C≡C-3-thienyl |
| 1676 | 6,8-diCl | Et | C≡C-cycPr |
| 1677 | 6,8-diCl | Et | C≡C-iPr |
| 1678 | 6,8-diCl | Et | C≡C-nPr |
| 1679 | 6,8-diCl | Et | C≡C—Et |
| 1680 | 5,6,8-triF | cycPr | C≡C-cycPr |
| 1681 | 5,6,8-triF | cycPr | C≡C-iPr |
| 1682 | 5,6,8-triF | cycPr | C≡C-nPr |
| 1683 | 5,6,8-triF | cycPr | C≡C—Et |
| 1684 | 5,6,8-triF | cycPr | C≡C-3-Pyridyl |
| 1685 | 5,6,8-triF | cycPr | C≡C-2-furanyl |
| 1686 | 5,6,8-triF | cycPr | C≡C-3-furanyl |
| 1687 | 5,6,8-triF | cycPr | C≡C-2-thienyl |
| 1688 | 5,6,8-triF | cycPr | C≡C-3-thienyl |
| 1689 | 5,6,8-triF | iPr | C≡C-cycPr |
| 1690 | 5,6,8-triF | iPr | C≡C-iPr |
| 1691 | 5,6,8-triF | iPr | C≡C-nPr |
| 1692 | 5,6,8-triF | iPr | C≡C—Et |
| 1693 | 5,6,8-triF | iPr | C≡C-3-Pyridyl |
| 1694 | 5,6,8-triF | iPr | C≡C-2-furanyl |
| 1695 | 5,6,8-triF | iPr | C≡C-3-furanyl |
| 1696 | 5,6,8-triF | iPr | C≡C-2-thienyl |
| 1697 | 5,6,8-triF | iPr | C≡C-3-thienyl |
| 1698 | 5,6,8-triF | Et | C≡C-cycPr |
| 1699 | 5,6,8-triF | Et | C≡C-iPr |
| 1700 | 5,6,8-triF | Et | C≡C-nPr |
| 1701 | 5,6,8-triF | Et | C≡C—Et |
| 1702 | 5,8-diF | cycPr | C≡C-cycPr |
| 1703 | 5,8-diF | cycPr | C≡C-iPr |
| 1704 | 5,8-diF | cycPr | C≡C-nPr |
| 1705 | 5,8-diF | cycPr | C≡C—Et |
| 1706 | 5,8-diF | cycPr | C≡C-3-Pyridyl |
| 1707 | 5,8-diF | cycPr | C≡C-2-furanyl |
| 1708 | 5,8-diF | cycPr | C≡C-3-furanyl |
| 1709 | 5,8-diF | cycPr | C≡C-2-thienyl |
| 1710 | 5,8-diF | cycPr | C≡C-3-thienyl |
| 1711 | 5,8-diF | iPr | C≡C-cycPr |
| 1712 | 5,8-diF | iPr | C≡C-iPr |
| 1713 | 5,8-diF | iPr | C≡C-nPr |
| 1714 | 5,8-diF | iPr | C≡C—Et |
| 1715 | S,8-diF | iPr | C≡C-3-Pyridyl |
| 1716 | 5,8-diF | iPr | C≡C-2-furanyl |
| 1717 | 5,8-diF | iPr | C≡C-3-furanyl |
| 1718 | 5,8-diF | iPr | C≡C-2-thienyl |
| 1719 | 5,8-diF | iPr | C≡C-3-thienyl |
| 1720 | 5,8-diF | Et | C≡C-cycPr |
| 1721 | 5,8-diF | Et | C≡C-iPr |
| 1722 | 5,8-diF | Et | C≡C-nPr |
| 1723 | 5,8-diF | Et | C≡C—Et |
| 1724 | 6-iPr | cycPr | C≡C-cycPr |
| 1725 | 6-iPr | cycPr | C≡C-iPr |
| 1726 | 6-iPr | cycPr | C≡C-nPr |
| 1727 | 6-iPr | cycPr | C≡C—Et |
| 1728 | 6-iPr | cycPr | C≡C-3-Pyridyl |
| 1729 | 6-iPr | cycPr | C≡C-2-furanyl |
| 1730 | 6-iPr | cycPr | C≡C-3-furanyl |
| 1731 | 6-iPr | cycPr | C≡C-2-thienyl |
| 1732 | 6-iPr | cycPr | C≡C-3-thienyl |
| 1733 | 6-iPr | iPr | C≡C-cycPr |
| 1734 | 6-iPr | iPr | C≡C-iPr |
| 1735 | 6-iPr | iPr | C≡C-nPr |
| 1736 | 6-iPr | iPr | C≡C—Et |
| 1737 | 6-iPr | iPr | C≡C-3-Pyridyl |
| 1738 | 6-iPr | iPr | C≡C-2-furanyl |
| 1739 | 6-iPr | iPr | C≡C-3-furanyl |
| 1740 | 6-iPr | iPr | C≡C-2-thienyl |
| 1741 | 6-iPr | iPr | C≡C-3-thienyl |
| 1742 | 6-iPr | Et | C≡C-cycPr |
| 1743 | 6-iPr | Et | C≡C-iPr |
| 1744 | 6-iPr | Et | C≡C-nPr |
| 1745 | 6-iPr | Et | C≡C—Et |
| 1746 | 6-OCF₃ | cycPr | C≡C-cycPr |
| 1747 | 6-OCF₃ | cycPr | C≡C-iPr |
| 1748 | 6-OCF₃ | cycPr | C≡C-nPr |
| 1749 | 6-OCF₃ | cycPr | C≡C—Et |
| 1750 | 6-OCF₃ | cycPr | C≡C-3-Pyridyl |
| 1751 | 6-OCF₃ | cycPr | C≡C-2-furanyl |
| 1752 | 6-OCF₃ | cycPr | C≡C-3-furanyl |
| 1753 | 6-OCF₃ | cycPr | C≡C-2-thienyl |
| 1754 | 6-OCF₃ | cycPr | C≡C-3-thienyl |
| 1755 | 6-OCF₃ | iPr | C≡C-cycPr |

TABLE 3-continued

| Ex. # | G | R¹ | R² |
|---|---|---|---|
| 1756 | 6-OCF₃ | iPr | C≡C-iPr |
| 1757 | 6-OCF₃ | iPr | C≡C-nPr |
| 1758 | 6-OCF₃ | iPr | C≡C—Et |
| 1759 | 6-OCF₃ | iPr | C≡C-3-Pyridyl |
| 1760 | 6-OCF₃ | iPr | C≡C-2-furanyl |
| 1761 | 6-OCF₃ | iPr | C≡C-3-furanyl |
| 1762 | 6-OCF₃ | iPr | C≡C-2-thienyl |
| 1763 | 6-OCF₃ | iPr | C≡C-3-thienyl |
| 1764 | 6-OCF₃ | Et | C≡C-cycPr |
| 1765 | 6-OCF₃ | Et | C≡C-iPr |
| 1766 | 6-OCF₃ | Et | C≡C-nPr |
| 1767 | 6-OCF₃ | Et | C≡C—Et |
| 1768 | 6-(pyrazol-5-yl) | cycPr | C≡C-cycPr |
| 1769 | 6-(pyrazol-5-yl) | cycPr | C≡C-iPr |
| 1770 | 6-(pyrazol-5-yl) | cycPr | C≡C-nPr |
| 1771 | 6-(pyrazol-5-yl) | cycPr | C≡C—Et |
| 1772 | 6-(pyrazol-5-yl) | cycPr | C≡C-3-Pyridyl |
| 1773 | 6-(pyrazol-5-yl) | cycPr | C≡C-2-furanyl |
| 1774 | 6-(pyrazol-5-yl) | cycPr | C≡C-3-furanyl |
| 1775 | 6-(pyrazol-5-yl) | cycPr | C≡C-2-thienyl |
| 1776 | 6-(pyrazol-5-yl) | cycPr | C≡C-3-thienyl |
| 1777 | 6-(pyrazol-5-yl) | iPr | C≡C-cycPr |
| 1778 | 6-(pyrazol-5-yl) | iPr | C≡C-iPr |
| 1779 | 6-(pyrazol-5-yl) | iPr | C≡C-nPr |
| 1780 | 6-(pyrazol-5-yl) | iPr | C≡C—Et |
| 1781 | 6-(pyrazol-5-yl) | iPr | C≡C-3-Pyridyl |
| 1782 | 6-(pyrazol-5-yl) | iPr | C≡C-2-furanyl |
| 1783 | 6-(pyrazol-5-yl) | iPr | C≡C-3-furanyl |
| 1784 | 6-(pyrazol-5-yl) | iPr | C≡C-2-thienyl |
| 1785 | 6-(pyrazol-5-yl) | iPr | C≡C-3-thienyl |
| 1786 | 6-(pyrazol-5-yl) | Et | C≡C-cycPr |
| 1787 | 6-(pyrazol-5-yl) | Et | C≡C-iPr |
| 1788 | 6-(pyrazol-5-yl) | Et | C≡C-nPr |
| 1789 | 6-(pyrazol-5-yl) | Et | C≡C—Et |
| 1790 | H | cycPr | C≡C-cycPr |
| 1791 | H | cycPr | C≡C-iPr |
| 1792 | H | cycPr | C≡C-nPr |
| 1793 | H | cycPr | C≡C—Et |
| 1794 | H | cycPr | C≡C-3-Pyridyl |
| 1795 | H | cycPr | C≡C-2-furanyl |
| 1796 | H | cycPr | C≡C-3-furanyl |
| 1797 | H | cycPr | C≡C-2-thienyl |
| 1798 | H | cycPr | C≡C-3-thienyl |
| 1799 | H | iPr | C≡C-cycPr |
| 1800 | H | iPr | C≡C-iPr |
| 1801 | H | iPr | C≡C-nPr |
| 1802 | H | iPr | C≡C—Et |
| 1803 | H | iPr | C≡C-3-pyridyl |
| 1804 | H | iPr | C≡C-2-furanyl |
| 1805 | H | iPr | C≡C-3-furanyl |
| 1806 | H | iPr | C≡C-2-thienyl |
| 1807 | H | iPr | C≡C-3-thienyl |
| 1808 | H | Et | C≡C-cycPr |
| 1809 | H | Et | C≡C-iPr |
| 1810 | H | Et | C≡C-nPr |
| 1811 | H | Et | C≡C—Et |
| 1812 | 6-Ph | cycPr | C≡C-cycPr |
| 1813 | 6-Ph | cycPr | C≡C-iPr |
| 1814 | 6-Ph | cycPr | C≡C-nPr |
| 1815 | 6-Ph | cycPr | C≡C—Et |
| 1816 | 6-Ph | cycPr | C≡C-3-pyridyl |
| 1817 | 6-Ph | cycPr | C≡C-2-furanyl |
| 1818 | 6-Ph | cycPr | C≡C-3-furanyl |
| 1819 | 6-Ph | cycPr | C≡C-2-thienyl |
| 1820 | 6-Ph | cycPr | C≡C-3-thienyl |
| 1821 | 6-Ph | iPr | C≡C-cycPr |
| 1822 | 6-Ph | iPr | C≡C-iPr |
| 1823 | 6-Ph | iPr | C≡C-nPr |
| 1824 | 6-Ph | iPr | C≡C—Et |
| 1825 | 6-Ph | iPr | C≡C-3-Pyridyl |
| 1826 | 6-Ph | iPr | C≡C-2-furanyl |
| 1827 | 6-Ph | iPr | C≡C-3-furanyl |
| 1828 | 6-Ph | iPr | C≡C-2-thienyl |
| 1829 | 6-Ph | iPr | C≡C-3-thienyl |
| 1830 | 6-Ph | Et | C≡C-cycPr |
| 1831 | 6-Ph | Et | C≡C-iPr |
| 1832 | 6-Ph | Et | C≡C-nPr |
| 1833 | 6-Ph | Et | C≡C—Et |
| 1834 | 6-CN | cycPr | C≡C-cycPr |
| 1835 | 6-CN | cycPr | C≡C-iPr |
| 1836 | 6-CN | cycPr | C≡C-nPr |
| 1837 | 6-CN | cycPr | C≡C—Et |
| 1838 | 6-CN | cycPr | C≡C-3-Pyridyl |
| 1839 | 6-CN | cycPr | C≡C-2-furanyl |
| 1840 | 6-CN | cycPr | C≡C-3-furanyl |
| 1841 | 6-CN | cycPr | C≡C-2-thienyl |
| 1842 | 6-CN | cycPr | C≡C-3-thienyl |
| 1843 | 6-CN | iPr | C≡C-cycPr |
| 1844 | 6-CN | iPr | C≡C-iPr |
| 1845 | 6-CN | iPr | C≡C-nPr |
| 1846 | 6-CN | iPr | C≡C—Et |
| 1847 | 6-CN | iPr | C≡C-3-Pyridyl |
| 1848 | 6-CN | iPr | C≡C-2-furanyl |
| 1849 | 6-CN | iPr | C≡C-3-furanyl |
| 1850 | 6-CN | iPr | C≡C-2-thienyl |
| 1851 | 6-CN | iPr | C≡C-3-thienyl |
| 1852 | 6-CN | Et | C≡C-cycPr |
| 1853 | 6-CN | Et | C≡C-iPr |
| 1854 | 6-CN | Et | C≡C-nPr |
| 1855 | 6-CN | Et | C≡C—Et |
| 1856 | 6-NO₂ | cycPr | C≡C-cycPr |
| 1857 | 6-NO₂ | cycPr | C≡C-iPr |
| 1858 | 6-NO₂ | cycPr | C≡C-nPr |
| 1859 | 6-NO₂ | cycPr | C≡C—Et |
| 1860 | 6-NO₂ | cycPr | C≡C-3-Pyridyl |
| 1861 | 6-NO₂ | cycPr | C≡C-2-furanyl |
| 1862 | 6-NO₂ | cycPr | C≡C-3-furanyl |
| 1863 | 6-NO₂ | cycPr | C≡C-2-thienyl |
| 1864 | 6-NO₂ | cycPr | C≡C-3-thienyl |
| 1865 | 6-NO₂ | iPr | C≡C-cycPr |
| 1866 | 6-NO₂ | iPr | C≡C-iPr |
| 1867 | 6-NO₂ | iPr | C≡C-nPr |
| 1868 | 6-NO₂ | iPr | C≡C—Et |
| 1869 | 6-NO₂ | iPr | C≡C-3-Pyridyl |
| 1870 | 6-NO₂ | iPr | C≡C-2-furanyl |
| 1871 | 6-NO₂ | iPr | C≡C-3-furanyl |
| 1872 | 6-NO₂ | iPr | C≡C-2-thienyl |
| 1873 | 6-NO₂ | iPr | C≡C-3-thienyl |
| 1874 | 6-NO₂ | Et | C≡C-cycPr |
| 1875 | 6-NO₂ | Et | C≡C-iPr |
| 1876 | 6-NO₂ | Et | C≡C-nPr |
| 1877 | 6-NO₂ | Et | C≡C—Et |
| 1878 | 6-NHMe | cycPr | C≡C-cycPr |
| 1879 | 6-NHMe | cycPr | C≡C-iPr |
| 1880 | 6-NHMe | cycPr | C≡C-nPr |
| 1881 | 6-NHMe | cycPr | C≡C—Et |
| 1882 | 6-NHMe | cycPr | C≡C-3-Pyridyl |
| 1883 | 6-NHMe | cycPr | C≡C-2-furanyl |
| 1884 | 6-NHMe | cycPr | C≡C-3-furanyl |
| 1885 | 6-NHMe | cycPr | C≡C-2-thienyl |
| 1886 | 6-NHMe | cycPr | C≡C-3-thienyl |
| 1887 | 6-NHMe | iPr | C≡C-cycPr |
| 1888 | 6-NHMe | iPr | C≡C-iPr |
| 1889 | 6-NHMe | iPr | C≡C-nPr |
| 1890 | 6-NHMe | iPr | C≡C—Et |
| 1891 | 6-NHMe | iPr | C≡C-3-Pyridyl |

TABLE 3-continued

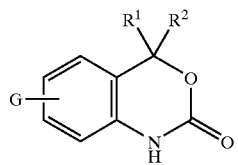

| Ex. # | G | R¹ | R² |
|---|---|---|---|
| 1892 | 6-NHMe | iPr | C≡C-2-furanyl |
| 1893 | 6-NHMe | iPr | C≡C-3-furanyl |
| 1894 | 6-NHMe | iPr | C≡C-2-thienyl |
| 1895 | 6-NHMe | iPr | C≡C-3-thienyl |
| 1896 | 6-NHMe | Et | C≡C-cycPr |
| 1897 | 6-NHMe | Et | C≡C-iPr |
| 1898 | 6-NHMe | Et | C≡C-nPr |
| 1899 | 6-NHMe | Et | C≡C—Et |
| 1900 | 6,7-diCl | cycPr | C≡C-cycPr |
| 1901 | 6,7-diCl | cycPr | C≡C-nPr |
| 1902 | 6,7-diCl | cycPr | C≡C—Et |
| 1903 | 6,7-diCl | cycPr | C≡C-3-Pyridyl |
| 1904 | 6,7-diCl | cycPr | C≡C-2-furanyl |
| 1905 | 6,7-diCl | cycPr | C≡C-3-furanyl |
| 1906 | 6,7-diCl | cycPr | C≡C-2-thienyl |
| 1907 | 6,7-diCl | cycPr | C≡C-3-thienyl |
| 1908 | 6,7-diCl | iPr | C≡C-cycPr |
| 1909 | 6,7-diCl | iPr | C≡C-nPr |
| 1910 | 6,7-diCl | iPr | C≡C—Et |
| 1911 | 6,7-diCl | iPr | C≡C-3-Pyridyl |
| 1912 | 6,7-diCl | iPr | C≡C-2-furanyl |
| 1913 | 6,7-diCl | iPr | C≡C-3-furanyl |
| 1914 | 6,7-diCl | iPr | C≡C-2-thienyl |
| 1915 | 6,7-diCl | iPr | C≡C-3-thienyl |
| 1916 | 6,7-diCl | Et | C≡C-cycPr |
| 1917 | 6,7-diCl | Et | C≡C-iPr |
| 1918 | 6,7-diCl | Et | C≡C-nPr |
| 1919 | 6,7-diCl | Et | C≡C—Et |
| 1920 | 7-Cl | cycPr | C≡C-nPr |
| 1921 | 7-Cl | cycPr | C≡C—Et |
| 1922 | 7-Cl | cycPr | C≡C-3-Pyridyl |
| 1923 | 7-Cl | cycPr | C≡C-2-furanyl |
| 1924 | 7-Cl | cycPr | C≡C-3-furanyl |
| 1925 | 7-Cl | cycPr | C≡C-2-thienyl |
| 1926 | 7-Cl | cycPr | C≡C-3-thienyl |
| 1927 | 7-Cl | iPr | C≡C-nPr |
| 1928 | 7-Cl | iPr | C≡C—Et |
| 1929 | 7-Cl | iPr | C≡C-3-Pyridyl |
| 1930 | 7-Cl | iPr | C≡C-2-furanyl |
| 1931 | 7-Cl | iPr | C≡C-3-furanyl |
| 1932 | 7-Cl | iPr | C≡C-2-thienyl |
| 1933 | 7-Cl | iPr | C≡C-3-thienyl |
| 1934 | 7-Cl | Et | C≡C-cycPr |
| 1935 | 7-Cl | Et | C≡C-iPr |
| 1936 | 7-Cl | Et | C≡C-nPr |
| 1937 | 7-Cl | Et | C≡C—Et |

*Unless otherwise noted, stereochemistry is (+/−).

TABLE 4

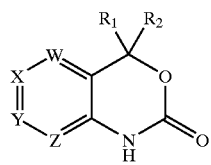

| Ex. # | W | X | Y | Z | R¹ | R² |
|---|---|---|---|---|---|---|
| 2001 | CH | CCl | CH | N | $CF_3$ | C≡C-nPr |
| 2002 | CH | CCl | CH | N | $CF_3$ | C≡C—Bu |
| 2003 | CH | CCl | CH | N | $CF_3$ | C≡C-iBu |
| 2004 | CH | CCl | CH | N | $CF_3$ | C≡C-tBu |
| 2005 | CH | CCl | CH | N | $CF_3$ | C≡C—Et |
| 2006 | CH | CCl | CH | N | $CF_3$ | C≡C—Me |
| 2007 | CH | CCl | CH | N | $CF_3$ | C≡C—Ph |
| 2008 | CH | CCl | CH | N | $CF_3$ | C≡C-2-Pyridyl |
| 2009 | CH | CCl | CH | N | $CF_3$ | C≡C-3-Pyridyl |
| 2010 | CH | CCl | CH | N | $CF_3$ | C≡C-4-Pyridyl |
| 2011 | CH | CCl | CH | N | $CF_3$ | C≡C-2-furanyl |
| 2012 | CH | CCl | CH | N | $CF_3$ | C≡C-3-furanyl |
| 2013 | CH | CCl | CH | N | $CF_3$ | C≡C-2-thienyl |
| 2014 | CH | CCl | CH | N | $CF_3$ | C≡C-3-thienyl |
| 2015 | CH | CCl | CH | N | $CF_3$ | CH=CH-cycPr |
| 2016 | CH | CCl | CH | N | $CF_3$ | CH=CH-iPr |
| 2017 | CH | CCl | CH | N | $CF_3$ | CH=CH-nPr |
| 2018 | CH | CCl | CH | N | $CF_3$ | CH=CH—Bu |
| 2019 | CH | CCl | CH | N | $CF_3$ | CH=CH-iBu |
| 2020 | CH | CCl | CH | N | $CF_3$ | CH=CH-tBu |
| 2021 | CH | CCl | CH | N | $CF_3$ | CH=CH—Et |
| 2022 | CH | CCl | CH | N | $CF_3$ | CH=CH—Me |
| 2023 | CH | CCl | CH | N | $CF_3$ | CH=CH—Ph |
| 2024 | CH | CCl | CH | N | $CF_3$ | CH=CH-2-Pyridyl |
| 2025 | CH | CCl | CH | N | $CF_3$ | CH=CH-3-Pyridyl |
| 2026 | CH | CCl | CH | N | $CF_3$ | CH=CH-4-Pyridyl |
| 2027 | CH | CCl | CH | N | $CF_3$ | CH=CH-2-furanyl |
| 2028 | CH | CCl | CH | N | $CF_3$ | CH=CH-3-furanyl |
| 2029 | CH | CCl | CH | N | $CF_3$ | CH=CH-2-thienyl |
| 2030 | CH | CCl | CH | N | $CF_3$ | CH=CH-3-thienyl |
| 2031 | CH | CCl | CH | N | $CF_3$ | $CH_2CH_2CH_2CH_2CH_3$ |
| 2032 | CH | CCl | CH | N | $CF_3$ | $CH_2CH_2CH(CH_3)_2$ |
| 2033 | CH | CCl | CH | N | $CF_3$ | $CH_2CH_2CH_2CH_3$ |
| 2034 | CH | CCl | CH | N | $CF_3$ | $CH_2CH_2CH_3$ |
| 2035 | CH | CCl | CH | N | $CF_3$ | $CH_2CH_2$-cycPr |
| 2036 | CH | CCl | CH | N | $CF_3$ | $CH_2CH_2$-tBu |
| 2037 | CH | CCl | CH | N | $CF_3$ | $CH_2CH_2$-2-Pyridyl |
| 2038 | CH | CCl | CH | N | $CF_3$ | $CH_2CH_2$-3-Pyridyl |
| 2039 | CH | CCl | CH | N | $CF_3$ | $CH_2CH_2$-4-Pyridyl |
| 2040 | CH | CCl | CH | N | $CF_3$ | $CH_2CH_2$-2-furanyl |
| 2041 | CH | CCl | CH | N | $CF_3$ | $CH_2CH_2$-3-furanyl |
| 2042 | CH | CCl | CH | N | $CF_3$ | $CH_2CH_2$-2-thienyl |
| 2043 | CH | CCl | CH | N | $CF_3$ | $CH_2CH_2$-3-thienyl |
| 2044 | CH | C(OCH₃) | CH | N | $CF_3$ | C≡C-cycPr |
| 2045 | CH | C(OCH₃) | CH | N | $CF_3$ | C≡C-iPr |
| 2046 | CH | C(OCH₃) | CH | N | $CF_3$ | C≡C-nPr |
| 2047 | CH | C(OCH₃) | CH | N | $CF_3$ | C≡C—Bu |
| 2048 | CH | C(OCH₃) | CH | N | $CF_3$ | C≡C-iBu |
| 2049 | CH | C(OCH₃) | CH | N | $CF_3$ | C≡C-tBu |
| 2050 | CH | C(OCH₃) | CH | N | $CF_3$ | C≡C—Et |
| 2051 | CH | C(OCH₃) | CH | N | $CF_3$ | C≡C—Me |
| 2052 | CH | C(OCH₃) | CH | N | $CF_3$ | C≡C—Ph |
| 2053 | CH | C(OCH₃) | CH | N | $CF_3$ | C≡C-2-Pyridyl |
| 2054 | CH | C(OCH₃) | CH | N | $CF_3$ | C≡C-3-Pyridyl |
| 2055 | CH | C(OCH₃) | CH | N | $CF_3$ | C≡C-4-Pyridyl |
| 2056 | CH | C(OCH₃) | CH | N | $CF_3$ | C≡C-2-furanyl |
| 2057 | CH | C(OCH₃) | CH | N | $CF_3$ | C≡C-3-furanyl |
| 2058 | CH | C(OCH₃) | CH | N | $CF_3$ | C≡C-2-thienyl |
| 2059 | CH | C(OCH₃) | CH | N | $CF_3$ | C≡C-3-thienyl |
| 2060 | CH | C(OCH₃) | CH | N | $CF_3$ | CH=CH-cycPr |
| 2061 | CH | C(OCH₃) | CH | N | $CF_3$ | CH=CH-iPr |
| 2062 | CH | C(OCH₃) | CH | N | $CF_3$ | CH=CH-nPr |
| 2063 | CH | C(OCH₃) | CH | N | $CF_3$ | CH=CH—Bu |
| 2064 | CH | C(OCH₃) | CH | N | $CF_3$ | CH=CH-iBu |
| 2065 | CH | C(OCH₃) | CH | N | $CF_3$ | CH=CH-tBu |
| 2066 | CH | C(OCH₃) | CH | N | $CF_3$ | CH=CH—Et |
| 2067 | CH | C(OCH₃) | CH | N | $CF_3$ | CH=CH—Me |
| 2068 | CH | C(OCH₃) | CH | N | $CF_3$ | CH=CH—Ph |
| 2069 | CH | C(OCH₃) | CH | N | $CF_3$ | CH=CH-2-Pyridyl |
| 2070 | CH | C(OCH₃) | CH | N | $CF_3$ | CH=CH-3-Pyridyl |
| 2071 | CH | C(OCH₃) | CH | N | $CF_3$ | CH=CH-4-Pyridyl |
| 2072 | CH | C(OCH₃) | CH | N | $CF_3$ | CH=CH-2-furanyl |
| 2073 | CH | C(OCH₃) | CH | N | $CF_3$ | CH=CH-3-furanyl |

TABLE 4-continued

| Ex. # | W | X | Y | Z | R¹ | R² |
|---|---|---|---|---|---|---|
| 2074 | CH | C(OCH$_3$) | CH | N | CF$_3$ | CH=CH-2-thienyl |
| 2075 | CH | C(OCH$_3$) | CH | N | CF$_3$ | CH=CH-3-thienyl |
| 2076 | CH | C(OCH$_3$) | CH | N | CF$_3$ | CH$_2$CH$_2$CH$_2$CH$_2$CH$_3$ |
| 2077 | CH | C(OCH$_3$) | CH | N | CF$_3$ | CH$_2$CH$_2$CH(CH$_3$)$_2$ |
| 2078 | CH | C(OCH$_3$) | CH | N | CF$_3$ | CH$_2$CH$_2$CH$_2$CH$_3$ |
| 2079 | CH | C(OCH$_3$) | CH | N | CF$_3$ | CH$_2$CH$_2$CH$_3$ |
| 2080 | CH | C(OCH$_3$) | CH | N | CF$_3$ | CH$_2$CH$_2$-cycPr |
| 2081 | CH | C(OCH$_3$) | CH | N | CF$_3$ | CH$_2$CH$_2$-tBu |
| 2082 | CH | C(OCH$_3$) | CH | N | CF$_3$ | CH$_2$CH$_2$—Ph |
| 2083 | CH | C(OCH$_3$) | CH | N | CF$_3$ | CH$_2$CH$_2$-2-Pyridyl |
| 2084 | CH | C(OCH$_3$) | CH | N | CF$_3$ | CH$_2$CH$_2$-3-Pyridyl |
| 2085 | CH | C(OCH$_3$) | CH | N | CF$_3$ | CH$_2$CH$_2$-4-Pyridyl |
| 2086 | CH | C(OCH$_3$) | CH | N | CF$_3$ | CH$_2$CH$_2$-2-furanyl |
| 2087 | CH | C(OCH$_3$) | CH | N | CF$_3$ | CH$_2$CH$_2$-3-furanyl |
| 2088 | CH | C(OCH$_3$) | CH | N | CF$_3$ | CH$_2$CH$_2$-2-thienyl |
| 2089 | CH | C(OCH$_3$) | CH | N | CF$_3$ | CH$_2$CH$_2$-3-thienyl |
| 2090 | CH | CH | CH | N | CF$_3$ | C≡C-cycPr |
| 2091 | CH | CH | CH | N | CF$_3$ | C≡C-iPr |
| 2092 | CH | CH | CH | N | CF$_3$ | C≡C-nPr |
| 2093 | CH | CH | CH | N | CF$_3$ | C≡C—Et |
| 2094 | CH | CH | CH | N | CF$_3$ | C≡C-3-Pyridyl |
| 2095 | CH | CH | CH | N | CF$_3$ | C≡C-2-furanyl |
| 2096 | CH | CH | CH | N | CF$_3$ | C≡C-3-furanyl |
| 2097 | CH | CH | CH | N | CF$_3$ | C≡C-2-thienyl |
| 2098 | CH | CH | CH | N | CF$_3$ | C≡C-3-thienyl |
| 2099 | CH | CCl | N | CH | CF$_3$ | C≡C-iPr |
| 2100 | CH | CCl | N | CH | CF$_3$ | C≡C-nPr |
| 2101 | CH | CCl | N | CH | CF$_3$ | C≡C—Bu |
| 2102 | CH | CCl | N | CH | CF$_3$ | C≡C-iBu |
| 2103 | CH | CCl | N | CH | CF$_3$ | C≡C-tBu |
| 2104 | CH | CCl | N | CH | CF$_3$ | C≡C—Et |
| 2105 | CH | CCl | N | CH | CF$_3$ | C≡C—Me |
| 2106 | CH | CCl | N | CH | CF$_3$ | C≡C—Ph |
| 2107 | CH | CCl | N | CH | CF$_3$ | C≡C-2-Pyridyl |
| 2108 | CH | CCl | N | CH | CF$_3$ | C≡C-3-Pyridyl |
| 2109 | CH | CCl | N | CH | CF$_3$ | C≡C-4-Pyridyl |
| 2110 | CH | CCl | N | CH | CF$_3$ | C≡C-2-furanyl |
| 2111 | CH | CCl | N | CH | CF$_3$ | C≡C-3-furanyl |
| 2112 | CH | CCl | N | CH | CF$_3$ | C≡C-2-thienyl |
| 2113 | CH | CCl | N | CH | CF$_3$ | C≡C-3-thienyl |
| 2114 | CH | CCl | N | CH | CF$_3$ | CH=CH-cycPr |
| 2115 | CH | CCl | N | CH | CF$_3$ | CH=CH-iPr |
| 2116 | CH | CCl | N | CH | CF$_3$ | CH=CH-nPr |
| 2117 | CH | CCl | N | CH | CF$_3$ | CH=CH—Bu |
| 2118 | CH | CCl | N | CH | CF$_3$ | CH=CH-iBu |
| 2119 | CH | CCl | N | CH | CF$_3$ | CH=CH-tBu |
| 2120 | CH | CCl | N | CH | CF$_3$ | CH=CH—Et |
| 2121 | CH | CCl | N | CH | CF$_3$ | CH=CH—Me |
| 2122 | CH | CCl | N | CH | CF$_3$ | CH=CH—Ph |
| 2123 | CH | CCl | N | CH | CF$_3$ | CH=CH-2-Pyridyl |
| 2124 | CH | CCl | N | CH | CF$_3$ | CH=CH-3-Pyridyl |
| 2125 | CH | CCl | N | CH | CF$_3$ | CH=CH-4-Pyridyl |
| 2126 | CH | CCl | N | CH | CF$_3$ | CH=CH-2-furanyl |
| 2127 | CH | CCl | N | CH | CF$_3$ | CH=CH-3-furanyl |
| 2128 | CH | CCl | N | CH | CF$_3$ | CH=CH-2-thienyl |
| 2129 | CH | CCl | N | CH | CF$_3$ | CH=CH-3-thienyl |
| 2130 | CH | CCl | N | CH | CF$_3$ | CH$_2$CH$_2$CH$_2$CH$_2$CH$_3$ |
| 2131 | CH | CCl | N | CH | CF$_3$ | CH$_2$CH$_2$CH(CH$_3$)$_2$ |
| 2132 | CH | CCl | N | CH | CF$_3$ | CH$_2$CH$_2$CH$_2$CH$_3$ |
| 2133 | CH | CCl | N | CH | CF$_3$ | CH$_2$CH$_2$CH$_3$ |
| 2134 | CH | CCl | N | CH | CF$_3$ | CH$_2$CH$_2$-cycPr |
| 2135 | CH | CCl | N | CH | CF$_3$ | CH$_2$CH$_2$-tBu |
| 2136 | CH | CCl | N | CH | CF$_3$ | CH$_2$CH$_2$—Ph |
| 2137 | CH | CCl | N | CH | CF$_3$ | CH$_2$CH$_2$-2-Pyridyl |
| 2138 | CH | CCl | N | CH | CF$_3$ | CH$_2$CH$_2$-3-Pyridyl |
| 2139 | CH | CCl | N | CH | CF$_3$ | CH$_2$CH$_2$-4-Pyridyl |
| 2140 | CH | CCl | N | CH | CF$_3$ | CH$_2$CH$_2$-2-furanyl |
| 2141 | CH | CCl | N | CH | CF$_3$ | CH$_2$CH$_2$-3-furanyl |
| 2142 | CH | CCl | N | CH | CF$_3$ | CH$_2$CH$_2$-2-thienyl |
| 2143 | CH | CCl | N | CH | CF$_3$ | CH$_2$CH$_2$-3-thienyl |
| 2144 | CH | C(OCH$_3$) | N | CH | CF$_3$ | C≡C-iPr |
| 2145 | CH | C(OCH$_3$) | N | CH | CF$_3$ | C≡C-nPr |
| 2146 | CH | C(OCH$_3$) | N | CH | CF$_3$ | C≡C—Bu |
| 2147 | CH | C(OCH$_3$) | N | CH | CF$_3$ | C≡C-iBu |
| 2148 | CH | C(OCH$_3$) | N | CH | CF$_3$ | C≡C-tBu |
| 2149 | CH | C(OCH$_3$) | N | CH | CF$_3$ | C≡C—Et |
| 2150 | CH | C(OCH$_3$) | N | CH | CF$_3$ | C≡C—Me |
| 2151 | CH | C(OCH$_3$) | N | CH | CF$_3$ | C≡C—Ph |
| 2152 | CH | C(OCH$_3$) | N | CH | CF$_3$ | C≡C-2-Pyridyl |
| 2153 | CH | C(OCH$_3$) | N | CH | CF$_3$ | C≡C-3-Pyridyl |
| 2154 | CH | C(OCH$_3$) | N | CH | CF$_3$ | C≡C-4-Pyridyl |
| 2155 | CH | C(OCH$_3$) | N | CH | CF$_3$ | C≡C-2-furanyl |
| 2156 | CH | C(OCH$_3$) | N | CH | CF$_3$ | C≡C-3-furanyl |
| 2157 | CH | C(OCH$_3$) | N | CH | CF$_3$ | C≡C-2-thienyl |
| 2158 | CH | C(OCH$_3$) | N | CH | CF$_3$ | C≡C-3-thienyl |
| 2159 | CH | C(OCH$_3$) | N | CH | CF$_3$ | CH=CH-cycPr |
| 2160 | CH | C(OCH$_3$) | N | CH | CF$_3$ | CH=CH-iPr |
| 2161 | CH | C(OCH$_3$) | N | CH | CF$_3$ | CH=CH-nPr |
| 2162 | CH | C(OCH$_3$) | N | CH | CF$_3$ | CH=CH—Bu |
| 2163 | CH | C(OCH$_3$) | N | CH | CF$_3$ | CH=CH-iBu |
| 2164 | CH | C(OCH$_3$) | N | CH | CF$_3$ | CH=CH-tBu |
| 2165 | CH | C(OCH$_3$) | N | CH | CF$_3$ | CH=CH—Et |
| 2166 | CH | C(OCH$_3$) | N | CH | CF$_3$ | CH=CH—Me |
| 2167 | CH | C(OCH$_3$) | N | CH | CF$_3$ | CH=CH—Ph |
| 2168 | CH | C(OCH$_3$) | N | CH | CF$_3$ | CH=CH-2-Pyridyl |
| 2169 | CH | C(OCH$_3$) | N | CH | CF$_3$ | CH=CH-3-Pyridyl |
| 2170 | CH | C(OCH$_3$) | N | CH | CF$_3$ | CH=CH-4-Pyridyl |
| 2171 | CH | C(OCH$_3$) | N | CH | CF$_3$ | CH=CH-2-furanyl |
| 2172 | CH | C(OCH$_3$) | N | CH | CF$_3$ | CH=CH-3-furanyl |
| 2173 | CH | C(OCH$_3$) | N | CH | CF$_3$ | CH=CH-2-thienyl |
| 2174 | CH | C(OCH$_3$) | N | CH | CF$_3$ | CH=CH-3-thienyl |
| 2175 | CH | C(OCH$_3$) | N | CH | CF$_3$ | CH$_2$CH$_2$CH$_2$CH$_2$CH$_3$ |
| 2176 | CH | C(OCH$_3$) | N | CH | CF$_3$ | CH$_2$CH$_2$CH(CH$_3$)$_2$ |
| 2177 | CH | C(OCH$_3$) | N | CH | CF$_3$ | CH$_2$CH$_2$CH$_2$CH$_3$ |
| 2178 | CH | C(OCH$_3$) | N | CH | CF$_3$ | CH$_2$CH$_2$CH$_3$ |
| 2179 | CH | C(OCH$_3$) | N | CH | CF$_3$ | CH$_2$CH$_2$-cycPr |
| 2180 | CH | C(OCH$_3$) | N | CH | CF$_3$ | CH$_2$CH$_2$-tBu |
| 2181 | CH | C(OCH$_3$) | N | CH | CF$_3$ | CH$_2$CH$_2$—Ph |
| 2182 | CH | C(OCH$_3$) | N | CH | CF$_3$ | CH$_2$CH$_2$-2-Pyridyl |
| 2183 | CH | C(OCH$_3$) | N | CH | CF$_3$ | CH$_2$CH$_2$-3-Pyridyl |
| 2184 | CH | C(OCH$_3$) | N | CH | CF$_3$ | CH$_2$CH$_2$-4-Pyridyl |
| 2185 | CH | C(OCH$_3$) | N | CH | CF$_3$ | CH$_2$CH$_2$-2-furanyl |
| 2186 | CH | C(OCH$_3$) | N | CH | CF$_3$ | CH$_2$CH$_2$-3-furanyl |
| 2187 | CH | C(OCH$_3$) | N | CH | CF$_3$ | CH$_2$CH$_2$-2-thienyl |
| 2188 | CH | C(OCH$_3$) | N | CH | CF$_3$ | CH$_2$CH$_2$-3-thienyl |
| 2189 | CH | CH | N | CH | CF$_3$ | C≡C-cycPr |
| 2190 | CH | CH | N | CH | CF$_3$ | C≡C-iPr |
| 2191 | CH | CH | N | CH | CF$_3$ | C≡C-nPr |
| 2192 | CH | CH | N | CH | CF$_3$ | C≡C—Et |
| 2193 | CH | CH | N | CH | CF$_3$ | C≡C-3-Pyridyl |
| 2194 | CH | CH | N | CH | CF$_3$ | C≡C-2-furanyl |
| 2195 | CH | CH | N | CH | CF$_3$ | C≡C-3-furanyl |
| 2196 | CH | CH | N | CH | CF$_3$ | C≡C-2-thienyl |
| 2197 | CH | CH | N | CH | CF$_3$ | C≡C-3-thienyl |
| 2198 | CCl | N | CH | CH | CF$_3$ | C≡C-cycPr |
| 2199 | CCl | N | CH | CH | CF$_3$ | C≡C-iPr |
| 2200 | CCl | N | CH | CH | CF$_3$ | C≡C-nPr |
| 2201 | CCl | N | CH | CH | CF$_3$ | C≡C—Bu |
| 2202 | CCl | N | CH | CH | CF$_3$ | C≡C-iBu |
| 2203 | CCl | N | CH | CH | CF$_3$ | C≡C-tBu |
| 2204 | CCl | N | CH | CH | CF$_3$ | C≡C—Et |
| 2205 | CCl | N | CH | CH | CF$_3$ | C≡C—Me |
| 2206 | CCl | N | CH | CH | CF$_3$ | C≡C—Ph |
| 2207 | CCl | N | CH | CH | CF$_3$ | C≡C-2-Pyridyl |
| 2208 | CCl | N | CH | CH | CF$_3$ | C≡C-3-Pyridyl |
| 2209 | CCl | N | CH | CH | CF$_3$ | C≡C-4-Pyridyl |

TABLE 4-continued

| Ex. # | W | X | Y | Z | R¹ | R² |
|---|---|---|---|---|---|---|
| 2210 | CCl | N | CH | CH | CF₃ | C≡C-2-furanyl |
| 2211 | CCl | N | CH | CH | CF₃ | C≡C-3-furanyl |
| 2212 | CCl | N | CH | CH | CF₃ | C≡C-2-thienyl |
| 2213 | CCl | N | CH | CH | CF₃ | C≡C-3-thienyl |
| 2214 | CCl | N | CH | CH | CF₃ | CH=CH-cycPr |
| 2215 | CCl | N | CH | CH | CF₃ | CH=CH-iPr |
| 2216 | CCl | N | CH | CH | CF₃ | CH=CH-nPr |
| 2217 | CCl | N | CH | CH | CF₃ | CH=CH—Bu |
| 2218 | CCl | N | CH | CH | CF₃ | CH=CH-iBu |
| 2219 | CCl | N | CH | CH | CF₃ | CH=CH-tBu |
| 2220 | CCl | N | CH | CH | CF₃ | CH=CH—Et |
| 2221 | CCl | N | CH | CH | CF₃ | CH=CH—Me |
| 2222 | CCl | N | CH | CH | CF₃ | CH=CH—Ph |
| 2223 | CCl | N | CH | CH | CF₃ | CH=CH-2-Pyridyl |
| 2224 | CCl | N | CH | CH | CF₃ | CH=CH-3-Pyridyl |
| 2225 | CCl | N | CH | CH | CF₃ | CH=CH-4-Pyridyl |
| 2226 | CCl | N | CH | CH | CF₃ | CH=CH-2-furanyl |
| 2227 | CCl | N | CH | CH | CF₃ | CH=CH-3-furanyl |
| 2228 | CCl | N | CH | CH | CF₃ | CH=CH-2-thienyl |
| 2229 | CCl | N | CH | CH | CF₃ | CH=CH-3-thienyl |
| 2230 | CCl | N | CH | CH | CF₃ | CH₂CH₂CH₂CH₂CH₃ |
| 2231 | CCl | N | CH | CH | CF₃ | CH₂CH₂CH(CH₃)₂ |
| 2232 | CCl | N | CH | CH | CF₃ | CH₂CH₂CH₂CH₃ |
| 2233 | CCl | N | CH | CH | CF₃ | CH₂CH₂CH₃ |
| 2234 | CCl | N | CH | CH | CF₃ | CH₂CH₂-cycPr |
| 2235 | CCl | N | CH | CH | CF₃ | CH₂CH₂-tBu |
| 2236 | CCl | N | CH | CH | CF₃ | CH₂CH₂—Ph |
| 2237 | CCl | N | CH | CH | CF₃ | CH₂CH₂-2-Pyridyl |
| 2238 | CCl | N | CH | CH | CF₃ | CH₂CH₂-3-Pyridyl |
| 2239 | CCl | N | CH | CH | CF₃ | CH₂CH₂-4-Pyridyl |
| 2240 | CCl | N | CH | CH | CF₃ | CH₂CH₂-2-furanyl |
| 2241 | CCl | N | CH | CH | CF₃ | CH₂CH₂-3-furanyl |
| 2242 | CCl | N | CH | CH | CF₃ | CH₂CH₂-2-thienyl |
| 2243 | CCl | N | CH | CH | CF₃ | CH₂CH₂-3-thienyl |
| 2244 | CH | N | CH | CH | CF₃ | C≡C-iPr |
| 2245 | CH | N | CH | CH | CF₃ | C≡C-nPr |
| 2246 | CH | N | CH | CH | CF₃ | C≡C—Et |
| 2247 | CH | N | CH | CH | CF₃ | C≡C-3-Pyridyl |
| 2248 | CH | N | CH | CH | CF₃ | C≡C-2-furanyl |
| 2249 | CH | N | CH | CH | CF₃ | C≡C-3-furanyl |
| 2250 | CH | N | CH | CH | CF₃ | C≡C-2-thienyl |
| 2251 | CH | N | CH | CH | CF₃ | C≡C-3-thienyl |
| 2252 | N | CCl | CH | CH | CF₃ | C≡C-cycPr |
| 2253 | N | CCl | CH | CH | CF₃ | C≡C-iPr |
| 2254 | N | CCl | CH | CH | CF₃ | C≡C-nPr |
| 2255 | N | CCl | CH | CH | CF₃ | C≡C—Bu |
| 2256 | N | CCl | CH | CH | CF₃ | C≡C-iBu |
| 2257 | N | CCl | CH | CH | CF₃ | C≡C-tBu |
| 2258 | N | CCl | CH | CH | CF₃ | C≡C—Et |
| 2259 | N | CCl | CH | CH | CF₃ | C≡C—Me |
| 2260 | N | CCl | CH | CH | CF₃ | C≡C—Ph |
| 2261 | N | CCl | CH | CH | CF₃ | C≡C-2-Pyridyl |
| 2262 | N | CCl | CH | CH | CF₃ | C≡C-3-Pyridyl |
| 2263 | N | CCl | CH | CH | CF₃ | C≡C-4-Pyridyl |
| 2264 | N | CCl | CH | CH | CF₃ | C≡C-2-furanyl |
| 2265 | N | CCl | CH | CH | CF₃ | C≡C-3-furanyl |
| 2266 | N | CCl | CH | CH | CF₃ | C≡C-2-thienyl |
| 2267 | N | CCl | CH | CH | CF₃ | C≡C-3-thienyl |
| 2268 | N | CCl | CH | CH | CF₃ | CH=CH-cycPr |
| 2269 | N | CCl | CH | CH | CF₃ | CH=CH-iPr |
| 2270 | N | CCl | CH | CH | CF₃ | CH=CH-nPr |
| 2271 | N | CCl | CH | CH | CF₃ | CH=CH—Bu |
| 2272 | N | CCl | CH | CH | CF₃ | CH=CH-iBu |
| 2273 | N | CCl | CH | CH | CF₃ | CH=CH-tBu |
| 2274 | N | CCl | CH | CH | CF₃ | CH=CH—Et |
| 2275 | N | CCl | CH | CH | CF₃ | CH=CH—Me |
| 2276 | N | CCl | CH | CH | CF₃ | CH=CH—Ph |
| 2277 | N | CCl | CH | CH | CF₃ | CH=CH-2-Pyridyl |
| 2278 | N | CCl | CH | CH | CF₃ | CH=CH-3-Pyridyl |
| 2279 | N | CCl | CH | CH | CF₃ | CH=CH-4-Pyridyl |
| 2280 | N | CCl | CH | CH | CF₃ | CH=CH-2-furanyl |
| 2281 | N | CCl | CH | CH | CF₃ | CH=CH-3-furanyl |
| 2282 | N | CCl | CH | CH | CF₃ | CH=CH-2-thienyl |
| 2283 | N | CCl | CH | CH | CF₃ | CH=CH-3-thienyl |
| 2284 | N | CCl | CH | CH | CF₃ | CH₂CH₂CH₂CH₂CH₃ |
| 2285 | N | CCl | CH | CH | CF₃ | CH₂CH₂CH(CH₃)₂ |
| 2286 | N | CCl | CH | CH | CF₃ | CH₂CH₂CH₂CH₃ |
| 2287 | N | CCl | CH | CH | CF₃ | CH₂CH₂CH₃ |
| 2288 | N | CCl | CH | CH | CF₃ | CH₂CH₂-cycPr |
| 2289 | N | CCl | CH | CH | CF₃ | CH₂CH₂-tBu |
| 2290 | N | CCl | CH | CH | CF₃ | CH₂CH₂—Ph |
| 2291 | N | CCl | CH | CH | CF₃ | CH₂CH₂-2-Pyridyl |
| 2292 | N | CCl | CH | CH | CF₃ | CH₂CH₂-3-Pyridyl |
| 2293 | N | CCl | CH | CH | CF₃ | CH₂CH₂-4-Pyridyl |
| 2294 | N | CCl | CH | CH | CF₃ | CH₂CH₂-2-furanyl |
| 2295 | N | CCl | CH | CH | CF₃ | CH₂CH₂-3-furanyl |
| 2296 | N | CCl | CH | CH | CF₃ | CH₂CH₂-2-thienyl |
| 2297 | N | CCl | CH | CH | CF₃ | CH₂CH₂-3-thienyl |
| 2298 | N | C(OCH₃) | CH | CH | CF₃ | C≡C-cycPr |
| 2299 | N | C(OCH₃) | CH | CH | CF₃ | C≡C-iPr |
| 2300 | N | C(OCH₃) | CH | CH | CF₃ | C≡C-nPr |
| 2301 | N | C(OCH₃) | CH | CH | CF₃ | C≡C—Bu |
| 2302 | N | C(OCH₃) | CH | CH | CF₃ | C≡C-iBu |
| 2303 | N | C(OCH₃) | CH | CH | CF₃ | C≡C-tBu |
| 2304 | N | C(OCH₃) | CH | CH | CF₃ | C≡C—Et |
| 2305 | N | C(OCH₃) | CH | CH | CF₃ | C≡C—Me |
| 2306 | N | C(OCH₃) | CH | CH | CF₃ | C≡C—Ph |
| 2307 | N | C(OCH₃) | CH | CH | CF₃ | C≡C-2-Pyridyl |
| 2308 | N | C(OCH₃) | CH | CH | CF₃ | C≡C-3-Pyridyl |
| 2309 | N | C(OCH₃) | CH | CH | CF₃ | C≡C-4-Pyridyl |
| 2310 | N | C(OCH₃) | CH | CH | CF₃ | C≡C-2-furanyl |
| 2311 | N | C(OCH₃) | CH | CH | CF₃ | C≡C-3-furanyl |
| 2312 | N | C(OCH₃) | CH | CH | CF₃ | C≡C-2-thienyl |
| 2313 | N | C(OCH₃) | CH | CH | CF₃ | C≡C-3-thienyl |
| 2314 | N | C(OCH₃) | CH | CH | CF₃ | CH=CH-cycPr |
| 2315 | N | C(OCH₃) | CH | CH | CF₃ | CH=CH-iPr |
| 2316 | N | C(OCH₃) | CH | CH | CF₃ | CH=CH-nPr |
| 2317 | N | C(OCH₃) | CH | CH | CF₃ | CH=CH—Bu |
| 2318 | N | C(OCH₃) | CH | CH | CF₃ | CH=CH-iBu |
| 2319 | N | C(OCH₃) | CH | CH | CF₃ | CH=CH-tBu |
| 2320 | N | C(OCH₃) | CH | CH | CF₃ | CH=CH—Et |
| 2321 | N | C(OCH₃) | CH | CH | CF₃ | CH=CH—Me |
| 2322 | N | C(OCH₃) | CH | CH | CF₃ | CH=CH—Ph |
| 2323 | N | C(OCH₃) | CH | CH | CF₃ | CH=CH-2-Pyridyl |
| 2324 | N | C(OCH₃) | CH | CH | CF₃ | CH=CH-3-Pyridyl |
| 2325 | N | C(OCH₃) | CH | CH | CF₃ | CH=CH-4-Pyridyl |
| 2326 | N | C(OCH₃) | CH | CH | CF₃ | CH=CH-2-furanyl |
| 2327 | N | C(OCH₃) | CH | CH | CF₃ | CH=CH-3-furanyl |
| 2328 | N | C(OCH₃) | CH | CH | CF₃ | CH=CH-2-thienyl |
| 2329 | N | C(OCH₃) | CH | CH | CF₃ | CH=CH-3-thienyl |
| 2330 | N | C(OCH₃) | CH | CH | CF₃ | CH₂CH₂CH₂CH₂CH₃ |
| 2331 | N | C(OCH₃) | CH | CH | CF₃ | CH₂CH₂CH(CH₃)₂ |
| 2332 | N | C(OCH₃) | CH | CH | CF₃ | CH₂CH₂CH₂CH₃ |
| 2333 | N | C(OCH₃) | CH | CH | CF₃ | CH₂CH₂CH₃ |
| 2334 | N | C(OCH₃) | CH | CH | CF₃ | CH₂CH₂-cycPr |
| 2335 | N | C(OCH₃) | CH | CH | CF₃ | CH₂CH₂-tBu |
| 2336 | N | C(OCH₃) | CH | CH | CF₃ | CH₂CH₂—Ph |
| 2337 | N | C(OCH₃) | CH | CH | CF₃ | CH₂CH₂-2-Pyridyl |
| 2338 | N | C(OCH₃) | CH | CH | CF₃ | CH₂CH₂-3-Pyridyl |
| 2339 | N | C(OCH₃) | CH | CH | CF₃ | CH₂CH₂-4-Pyridyl |
| 2340 | N | C(OCH₃) | CH | CH | CF₃ | CH₂CH₂-2-furanyl |
| 2341 | N | C(OCH₃) | CH | CH | CF₃ | CH₂CH₂-3-furanyl |
| 2342 | N | C(OCH₃) | CH | CH | CF₃ | CH₂CH₂-2-thienyl |
| 2343 | N | C(OCH₃) | CH | CH | CF₃ | CH₂CH₂-3-thienyl |
| 2344 | N | CH | CH | CH | CF₃ | C≡C-cycPr |

TABLE 4-continued

| Ex. # | W | X | Y | Z | R¹ | R² |
|---|---|---|---|---|---|---|
| 2345 | N | CH | CH | CH | CF₃ | C≡C-iPr |
| 2346 | N | CH | CH | CH | CF₃ | C≡C-nPr |
| 2347 | N | CH | CH | CH | CF₃ | C≡C—Et |
| 2348 | N | CH | CH | CH | CF₃ | C≡C-3-Pyridyl |
| 2349 | N | CH | CH | CH | CF₃ | C≡C-2-furanyl |
| 2350 | N | CH | CH | CH | CF₃ | C≡C-3-furanyl |
| 2351 | N | CH | CH | CH | CF₃ | C≡C-2-thienyl |
| 2352 | N | CH | CH | CH | CF₃ | C≡C-3-thienyl |

*Unless otherwise noted, stereochemistry is (+/−).

TABLE 5

| Ex. # | G | R¹ | R² | m.p. (° C.) | Mass Spec |
|---|---|---|---|---|---|
| 2401 | 6-Cl | cycPr | C≡C—Et | 137–138.5 | |
| 2402 | 6-Cl | CF₃ | C≡C—Et | 178 | |
| 2403 | 6-Cl | Et | C≡C—Et | 175–176 | |
| 2404 | 6-Cl | CH₃ | CH₃ | 202 | 212.0440 |
| 2405 | 6-Cl | CH₃ | C≡C-cycPr | 184 | |
| 2406 | 6-Cl | CH₃ | CH₃ | 221–222 | 228.0262 |
| 2407 | 6-Cl | CH₃ | C≡C-iPr | 168 | 264.0790 |
| 2408 | 6-Cl | CF₃ | CH=CH-cycPr (cis) | | |
| 2409 | 6-Cl | CF₃ | C≡C-iPr | 167–168 | |
| 2410 | 6-Cl | CF₃ | CH=CH-iPr (cis) | 146–147 | |
| 2411 | 6-Cl | CF₃ | CH₂CH₂-iPr | 129–131 | |
| 2412 | 6-Cl | CF₃ | C≡C-iPr | 116–118 | |
| 2413 | 6-Cl | CF₃ | CH=CH-iPr (trans) | 127–129 | |
| 2414 | 6-Cl | OMe | CH₂CH₂—Ph | | 318.0897 |
| 2415 | 6-Cl | OEt | Ph | | 304 (MH⁺) |
| 2416 | 6-Cl | CF₃ | C≡C—1-d-cycPr | 180–181 | 317.0406 |
| 2417 | 6-Cl | CF₃ | C≡C—1-d-cycPr | 133–134 | 317.0417 |
| 2418 | 6-Cl | CF₃ | C≡C—1-Me-cycPr | 158–159 | 347.0785 |
| 2419 | 6-Cl | CF₃ | Butyl | 135–136 | |
| 2420 | 6-Cl | CF₃ | C≡C-cycBu | 183–185 | 330.0495 |
| 2421 | 6-Cl | CF₃ | C(Me)₂CC≡CH | | |
| 2422 | 6-Cl | CF₃ | CF₃ | 148–149 | |
| 2423 | 6-Cl | CF₃ | C≡C—CF₃ | 155–156 | |
| 2424 | 6-Cl | CF₃ | Pentyl | | |
| 2425 | 6-Cl | CF₃ | C≡C—Ph | | 352.0353 |
| 2426 | 6-Cl | CF₃ | C≡C-3-py | | |
| 2427 | 6-Cl | CF₃ | C≡C—2-thiazole | | |
| 2428 | 6-Cl | CF₃ | NH-iBu | 182–183 | |
| 2429 | 6-Cl | CF₃ | C≡C-4-py | | |
| 2430 | 6-Cl | CH₃ | C≡C—Ph | 181–182 | 298.0620 |
| 2431 | 6-Cl | iPr | C≡C-iPr | oil | 292.1106 |
| 2432 | 6-Cl | iPr | C≡C-iBu | oil | 306.1268 |
| 2433 | 6-Cl | iPr | C≡C-cycPr | amorphous | 290.0938 |
| 2434 | 6-Cl | iPr | C≡C—Ph | 177–178 | 326.0955 |
| 2435 | 6-Cl | Et | C≡C-cycPr | 183–184 | 276.0792 |
| 2436 | 6-Cl | Et | C≡C-iPr | 143–144 | 278.0958 |
| 2437 | 6-Cl | Et | C≡C—Ph | 165–166 | 312.0790 |
| 2438 | 6-Cl | Et | C≡C-iBu | 136–137 | 292.1100 |
| 2439 | 6-Cl | cycPr | C≡C-cycPr | 142–143 | 288.0789 |
| 2440 | 6-Cl | cycPr | C≡C-iPr | 152–153 | 290.0950 |
| 2441 | 6-Cl | cycPr | C≡C—Ph | 156–157 | 324.0778 |
| 2442 | 6-Cl | cycPr | C≡C-iBu | 142–143 | 304.1102 |
| 2443 | 6-Cl | iPr | CH₂CH₂-iPr | oil | 296.1417 |
| 2444 | 6-Cl | cycPr | CH₂CH₂CH=CH₂ | oil | 278.0946 |
| 2445 | 6-Cl | C≡C-cycPr | C≡C-cycPr | 129–131 | 312.0786 |

TABLE 5-continued

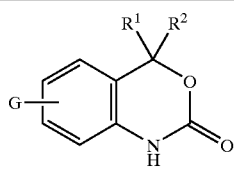

| Ex. # | G | R¹ | R² | m.p. (° C.) | Mass Spec |
|---|---|---|---|---|---|
| 2446 | 6-Cl | $CF_3$ | C≡C-iBu | 176–177 | 332.0664 |
| 2447 | 6-Cl | C≡C-iPr | C≡C-iPr | 139 | 316.1104 |
| 2448 | 6-Cl | iPr | $CH_2CH_2CH=CH_2$ | oil | 280.1109 |
| 2449 | 6-Cl | C≡CH | C≡C-iPr | 161–162 | 274.0638 |
| 2450 | 6-Cl | $CF_3$ | $C(Me)_2CH=CH_2$ | 113–114 | 320.0662 |
| 2451 | 6-Cl | $CF_3$ | C≡C—2-Py | | |
| 2452 | 6-Cl | $CF_3$ | C≡C-nPr | 193–194 | 318.0500 (MH⁺) |
| 2453 | 6-Cl | $CF_3$ | C≡C—1-OH-cycPr | | |
| 2454 | 6-Cl | C≡CH | C≡C—Et | 157–159 | 260.0483 |
| 2455 | 6-Cl | $CF_3$ | $CH_2$-iPr | 177–178 | 308.0659 |
| 2456 | 6-Cl | iPr | $CH_2$-iPr | 132–133 | 282.1261 |
| 2457 | 6-Cl | cycPr | $CH_2$-iPr | 136–137 | 280.1104 |
| 2458 | 6-Cl | iPr | C≡C—Et | amorphous | |
| 2459 | 6-Cl | $CF_3$ | C≡C—Et | 142–146 | |
| 2460 | 6-Cl | $CF_3$ | C≡C—Et | 143–147 | |
| 2461 | 6-Cl | $CF_3$ | $CH_2CH_2$-iPr | amorphous | |
| 2462 | 6-Cl | $CF_3$ | $CH_2CH_2$-iPr | amorphous | |
| 2463 | 6-Cl | iPr | C≡C-cycPr | amorphous | |
| 2464 | 6-Cl | iPr | C≡C-cycPr | amorphous | |
| 2465 | 6-Cl | $CF_3$ | $CH_2$—C≡C—Me | 196–199 | |
| 2466 | 6-Cl | $CF_3$ | $CH_2$—C≡C—Et | 140–145 | |
| 2467 | 6-Cl | $CF_3$ | $NHCH_2CH_2CH_3$ | 184–185 | 309.0628 |
| 2468 | 6-Cl | $CF_3$ | C≡C-2-furanyl | 170–171 | |
| 2469 | 6-Cl | $CF_3$ | C≡C-3-thienyl | 176.7–178 | |
| 2470 | 6-Cl | $CF_3$ | C≡C-3-furanyl | 155–156 | |
| 2471 | 6-Cl | $CF_3$ | OBu | 132–133 | |
| 2472 | 6-Cl | $CF_3$ | C≡C-5-thiazolyl | 196–196.5 | |
| 2473 | 6-Cl | $CF_3$ | CH=CH-3-Py (t) | 188–189 | |
| 2474 | 6-Cl | $CF_3$ | C≡C-3-py | 183.5 | |
| 2475 | 6-Cl | $CF_3$ | C≡C-3-py | | |
| 2476 | 6-Cl | $CF_3$ | CH=CH-iPr (t) | | |
| 2477 | 6-Cl | $CF_3$ | CH=CH-iPr (t) | | |
| 2478 | 6-Cl | $CF_3$ | $OCH_2CH_2$-iPr | | 338.0766 |
| 2479 | 6-Cl | $CF_3$ | $OCH_2CH_2$—OMe | 127–128 | 326.0391 |
| 2480 | 6-Cl | $CF_3$ | CH=CH-cycPr (t) | 136–137 | |
| 2481 | 6-Cl | $CF_3$ | CH=CH-cycPr (t) | amorphous | |
| 2482 | 6-Cl | $CF_3$ | CH=CH-cycPr (t) | amorphous | |
| 2483 | 6-Cl | $CF_3$ | CH=CH-nPr (t) | 127–128 | |
| 2484 | 6-Cl | $CF_3$ | CH=CH—Et (t) | 146–147 | |
| 2485 | 6-Cl | $CF_3$ | C≡C—Me | 243–244 | |
| 2486 | 6-Cl | $CF_3$ | C≡C-iPr | 116–118 | |
| 2487 | 6-F | iPr | C≡C-iPr | | 276.1400 |
| 2488 | 6-F | iPr | C≡C-cycPr | | 274.1243 |
| 2489 | 6-F | $CF_3$ | C≡C-iPr | | 302.0797 |
| 2490 | 6-F | $CF_3$ | $CH_2CH_2$-iPr | | 306.1111 |
| 2491 | 6-F | $CF_3$ | C≡C-cycPr | | 300.0638 |
| 2492 | 6-F | $CF_3$ | C≡C—Ph | | 336.0648 |
| 2493 | 6-F | $CF_3$ | Pentyl | | 306.1106 |
| 2494 | 6-F | $CF_3$ | C≡C-iPr | | |
| 2495 | 6-F | $CF_3$ | C≡C-iPr | | 302.0792 |
| 2496 | 6-F | $CF_3$ | C≡C—Et | | 288.0650 (MH⁺) |
| 2497 | 6-F | $CF_3$ | C≡C-nPr | | 302.0796 |
| 2498 | 6-F | $CF_3$ | Butyl | | 292.0947 |

*Unless otherwise noted, stereochemistry is (+/−).

Utility

The compounds of this invention possess reverse transcriptase inhibitory activity, in particular, HIV inhibitory efficacy. The compounds of formula (I) possess HIV reverse transcriptase inhibitory activity and are therefore useful as antiviral agents for the treatment of HIV infection and associated diseases. The compounds of formula (I) possess HIV reverse transcriptase inhibitory activity and are effective as inhibitors of HIV growth. The ability of the compounds of the present invention to inhibit viral growth or infectivity is demonstrated in standard assay of viral growth or infectivity, for example, using the assay described below.

The compounds of formula (I) of the present invention are also useful for the inhibition of HIV in an ex vivo sample containing HIV or expected to be exposed to HIV. Thus, the compounds of the present invention may be used to inhibit HIV present in a body fluid sample (for example, a serum or semen sample) which contains or is suspected to contain or be exposed to HIV.

The compounds provided by this invention are also useful as standard or reference compounds for use in tests or assays for determining the ability of an agent to inhibit viral clone replication and/or HIV reverse transcriptase, for example in a pharmaceutical research program. Thus, the compounds of the present invention may be used as a control or reference compound in such assays and as a quality control standard. The compounds of the present invention may be provided in a commercial kit or container for use as such standard or reference compound.

Since the compounds of the present invention exhibit specificity for HIV reverse transcriptase, the compounds of the present invention may also be useful as diagnostic reagents in diagnostic assays for the detection of HIV reverse transcriptase. Thus, inhibition of the reverse transcriptase activity in an assay (such as the assays described herein) by a compound of the present invention would be indicative of the presence of HIV reverse transcriptase and HIV virus.

As used herein "$\mu$g" denotes microgram, "mg" denotes milligram, "g" denotes gram, "$\mu$L" denotes microliter, "mL" denotes milliliter, "L" denotes liter, "nM" denotes nanomolar, "$\mu$M" denotes micromolar, "mM" denotes millimolar, "M" denotes molar and "nm" denotes nanometer. "Sigma" stands for the Sigma-Aldrich Corp. of St. Louis, Mo.

HIV RNA Assay

DNA Plasmids and in vitro RNA Transcripts

Plasmid pDAB 72 containing both gag and pol sequences of BH10 (bp 113–1816) cloned into PTZ 19R was prepared according to Erickson-Viitanen et al. *AIDS Research and Human Retroviruses* 1989, 5, 577. The plasmid was linearized with Bam HI prior to the generation of in vitro RNA transcripts using the Riboprobe Gemini system II kit (Promega) with T7 RNA polymerase. Synthesized RNA was purified by treatment with RNase free DNAse (Promega), phenol-chloroform extraction, and ethanol precipitation. RNA transcripts were dissolved in water, and stored at −70° C. The concentration of RNA was determined from the $A_{260}$.

Probes

Biotinylated capture probes were purified by HPLC after synthesis on an Applied Biosystems (Foster City, Calif.) DNA synthesizer by addition of biotin to the 5' terminal end of the oligonucleotide, using the biotin-phosphoramidite reagent of Cocuzza, *Tet. Lett.* 1989, 30, 6287. The gag biotinylated capture probe (5-biotin-CTAGCTCCCTGCTTGCCCATACTA 3') was complementary to nucleotides 889–912 of HXB2 and the pol biotinylated capture probe (5'-biotin -CCCTATCATTTT TGGTTTCCAT 3') was complementary to nucleotides 2374–2395 of HXB2. Alkaline phosphatase conjugated oligonucleotides used as reporter probes were prepared by Syngene (San Diego, Calif.). The pol reporter probe (5' CTGTCTTACTTTGATAAAACCTC 3') was complementary to nucleotides 2403–2425 of HXB2. The gag reporter probe (5' CCCAGTATTTGTCTACAGCCTTCT 3') was complementary to nucleotides 950–973 of HXB2. All nucleotide positions are those of the GenBank Genetic Sequence Data Bank as accessed through the Genetics Computer Group Sequence Analysis Software Package (Devereau *Nucleic Acids Research* 1984, 12,387). The reporter probes were prepared as 0.5 $\mu$M stocks in 2×SSC (0.3 M NaCl, 0.03 M sodium citrate), 0.05 M Tris pH 8.8, 1 mg/mL BSA. The biotinylated capture probes were prepared as 100 $\mu$M stocks in water.

Streptavidin Coated Plates

Streptavidin coated plates were obtained from Du Pont Biotechnology Systems (Boston, Mass.).

Cells and Virus Stocks

MT-2 and MT-4 cells were maintained in RPMI 1640 supplemented with 5% fetal calf serum (FCS) for MT-2 cells or 10% FCS for MT-4 cells, 2 mM L-glutamine and 50 $\mu$g/mL gentamycin, all from Gibco. HIV-1 RF was propagated in MT-4 cells in the same medium. Virus stocks were prepared approximately 10 days after acute infection of MT-4 cells and stored as aliquots at −70° C. Infectious titers of HIV-1 (RF) stocks were 1–3×$10^7$ PFU (plaque forming units)/mL as measured by plaque assay on MT-2 cells (see below). Each aliquot of virus stock used for infection was thawed only once.

For evaluation of antiviral efficacy, cells to be infected were subcultured one day prior to infection. On the day of infection, cells were resuspended at 5×$10^5$ cells/mL in RPMI 1640, 5% FCS for bulk infections or at 2×$10^6$/mL in Dulbecco's modified Eagles medium with 5% FCS for infection in microtiter plates. Virus was added and culture continued for 3 days at 37° C.

HIV FNA Assay

Cell lysates or purified RNA in 3 M or 5 M GED were mixed with 5 M GED and capture probe to a final guanidinium isothiocyanate concentration of 3 M and a final biotin oligonucleotide concentration of 30 nM. Hybridization was carried out in sealed U bottom 96 well tissue culture plates (Nunc or Costar) for 16–20 hours at 37° C. RNA hybridization reactions were diluted three-fold with deionized water to a final guanidinium isothiocyanate concentration of 1 M and aliquots (150 $\mu$L) were transferred to streptavidin coated microtiter plates wells. Binding of capture probe and capture probe-RNA hybrid to the immobilized streptavidin was allowed to proceed for 2 hours at room temperature, after which the plates were washed 6 times with DuPont ELISA plate wash buffer (phosphate buffered saline(PBS), 0.05% Tween 20.) A second hybridization of reporter probe to the immobilized complex of capture probe and hybridized target RNA was carried out in the washed streptavidin coated well by addition of 120 $\mu$l of a hybridization cocktail containing 4×SSC, 0.66% Triton X 100, 6.66% deionized formamide, 1 mg/mL BSA and 5 nM reporter probe. After hybridization for one hour at 37° C., the plate was again washed 6 times. Immobilized alkaline phosphatase activity was detected by addition of 100 $\mu$L of 0.2 mM 4-methylumbelliferyl phosphate (MUBP, JBL Scientific) in buffer $\delta$(2.5 M diethanolamine pH 8.9 (JBL Scientific), 10 mM MgCl$_2$, 5 mM zinc acetate dihydrate and 5 mM N-hydroxyethyl-ethylene-diamine-triacetic acid). The plates were incubated at 37° C. Fluorescence at 450 nM was measured using a microplate fluorometer (Dynateck) exciting at 365 nM.

Microplate Based Compound Evaluation in HIV-1 Infected MT-2 Cells

Compounds to be evaluated were dissolved in DMSO and diluted in culture medium to twice the highest concentration to be tested and a maximum DMSO concentration of 2%. Further three-fold serial dilutions of the compound in culture medium were performed directly in U bottom microtiter plates (Nunc). After compound dilution, MT-2 cells (50 $\mu$L) were added to a final concentration of 5×$10^5$ per mL (1×$10^5$ per well). Cells were incubated with compounds for 30 minutes at 37° C. in a CO$_2$ incubator. For evaluation of antiviral potency, an appropriate dilution of HIV-1 (RF) virus stock (50 $\mu$L) was added to culture wells containing cells and dilutions of the test compounds. The final volume in each well was 200 μL. Eight wells per plate were left uninfected with 50 μL of medium added in place of virus, while eight wells were infected in the absence of any antiviral compound. For evaluation of compound toxicity, parallel plates were cultured without virus infection.

After 3 days of culture at 37° C. in a humidified chamber inside a $CO_2$ incubator, all but 25 μL of medium/well was removed from the HIV infected plates. Thirty seven μL of 5 M GED containing biotinylated capture probe was added to the settled cells and remaining medium in each well to a final concentration of 3 M GED and 30 nM capture probe. Hybridization of the capture probe to HIV RNA in the cell lysate was carried out in the same microplate well used for virus culture by sealing the plate with a plate sealer (Costar), and incubating for 16–20 hrs in a 37° C. incubator. Distilled water was then added to each well to dilute the hybridization reaction three-fold and 150 μL of this diluted mixture was transferred to a streptavidin coated microtiter plate. HIV RNA was quantitated as described above. A standard curve, prepared by adding known amounts of PDAB 72 in vitro RNA transcript to wells containing lysed uninfected cells, was run on each microtiter plate in order to determine the amount of viral RNA made during the infection.

In order to standardize the virus inoculum used in the evaluation of compounds for antiviral activity, dilutions of virus were selected which resulted in an $IC_{90}$ value (concentration of compound required to reduce the HIV RNA level by 90%) for dideoxycytidine (ddC) of 0.2 μg/mL. $IC_{90}$ values of other antiviral compounds, both more and less potent than ddC, were reproducible using several stocks of HIV-1 (RF) when this procedure was followed. This concentration of virus corresponded to ~3×10$^5$ PFU (measured by plaque assay on MT-2 cells) per assay well and typically produced approximately 75% of the maximum viral RNA level achievable at any virus inoculum. For the HIV RNA assay, $IC_{90}$ values were determined from the percent reduction of net signal (signal from infected cell samples minus signal from uninfected cell samples) in the RNA assay relative to the net signal from infected, untreated cells on the same culture plate (average of eight wells). Valid performance of individual infection and RNA assay tests was judged according to three criteria. It was required that the virus infection should result in an RNA assay signal equal to or greater than the signal generated from 2 ng of PDAB 72 in vitro RNA transcript. The $IC_{90}$ for ddC, determined in each assay run, should be between 0.1 and 0.3 μg/mL. Finally, the plateau level of viral RNA produced by an effective reverse transcriptase inhibitor should be less than 10% of the level achieved in an uninhibited infection. A compound was considered active if its $IC_{90}$ was found to be less than 20 μM.

For antiviral potency tests, all manipulations in microtiter plates, following the initial addition of 2× concentrated compound solution to a single row of wells, were performed using a Perkin Elmer/Cetus ProPette.

HIV-1 RT Assay Materials and Methods

This assay measures HIV-1 RT RNA dependent DNA polymerase activity by the incorporation of 3H dTMP onto the template primer Poly (rA) oligo (dT)12–18. The template primer containing the incorporated radioactivity was separated from unincorporated label by one of two methods:

Method 1. The template primer was precipitated with TCA, collected on glass fiber filters and counted for radioactivity with a scintillation counter.

Method 2. The currently used method is more rapid and convenient. The template primer is captured on an diethyl amino ethyl (DEAE) ion exchange membrane which is then counted for radioactivity after washing off the free nucleotide.

Materials and Reagents

The template primer Poly (rA) oligo (dT)12–18 and dTTP were purchased from Pharmacia Biotech. The template primer and nucleotide were dissolved in diethyl pyrocarbonate water to a concentration of 1 mg/ml and 5.8 mM respectively. The substrates were aliquoted (template primer at 20 μl/aliquot, dTTP at 9 μl/aliquot) and frozen at −20 C.

The 3H dTTP (2.5 mCi/ml in 10 mM Tricine at pH 7.6; specific activity of 90–120 Ci/mmol) and the recombinant HIV-1 Reverse Transcriptase (HxB2 background; 100 U/10 μl in 100 mM potassium phosphate at pH 7.1, 1 mM dithiothreitol and 50% glycerol) were purchased from DuPont NEN. 1 Unit of enzyme is defined by DuPont NEN as the amount required to incorporate 1 nmol of labelled dTTP into acid-insoluble material in 10 minutes at 37 C. The 3H dTTP was aliquoted at 23.2 μl/microfuge tube (58 μCi) and frozen at −20 C. The HIV-1 Reverse Transcriptase (RT) was diluted 10 fold with RT buffer (80 mM KCl, 50 mM Tris HCl, 12 mM MgCl2, 1 mM DTT, 50 μM EGTA, 5 mg/ml BSA, 0.01% Triton-X 100, pH 8.2) and aliquoted at 10 μl/microfuge tube (10 Units/10 μl). One aliquot (enough for 8 assays) was diluted further to 10 Units/100 μl and aliquoted into 8 tubes (1.25 Units/12.5 μl). All aliquots were frozen at −70 C.

The Millipore Multiscreen DE 96 well filter plates, multiscreen plate adaptors, and microplate press-on adhesive sealing film were purchased from Millipore. The filter plate containing 0.65 μm pore size diethyl amino ethyl cellulose (DEAE) paper disks was pretreated with 0.3 M ammonium formate and 10 mM sodium pyrophosphate (2 times 200 μl/well) at pH 8.0 prior to use. A Skatron 96 well cell harvester and glass fiber filter mats were purchased from Skatron Instruments. Microscint 20 scintillation cocktail was purchased from Packard. Beckman Ready Flow III scintillation cocktail was purchased from Beckman.

HIV-1 RT Assay

The enzyme and substrate mixture were freshly prepared from the above stock solutions. 1.25 Units of enzyme was diluted with RT buffer (containing 5 mg/ml BSA) to a concentration of 0.05 Units/10 μl or 0.7 nM. Final enzyme and BSA concentrations in the assay were 0.01 Units or 0.14 nM and 1 mg/ml respectively. The inhibitor and substrate mixture were diluted with RT buffer containing no BSA. All inhibitors were dissolved in dimethyl sulfoxide (DMSO) at a stock concentration of 3 mM and stored at −20 C. after use. A Biomek robot was used to dilute the inhibitors in a 96 well plate. Inhibitors were initially diluted 96 fold from stock and then serially diluted two times (10 fold/dilution) from 31.25 μM to 3125 nM and 312.5 nM. Depending on the potency of the inhibitor, one of the three dilutions was further diluted. Typically the highest concentration (31.25 μM) was serially diluted three times at 5 fold/dilution to 6.25, 1.25, and 0.25 μM. Final inhibitor concentrations in the assay were 12.5, 2.5, 0.5, and 0.1 μM. For potent inhibitors of HIV-1 RT, the final inhibitor concentrations used were 0.1 or 0.01 that stated above. The substrate mixture contained 6.25 μg/ml of Poly (rA) oligo (dT)12–18 and 12.5 μM of dTTP (58 μCi 3H dTTP). The final substrate concentrations were 2.5 μg/ml and 5 μM respectively.

Using the Beckman Instruments Biomek robot, 10 μl of HIV-1 RT was combined with 20 μl of inhibitor in a 96 well U bottom plate. The enzyme and inhibitor were preincubated at ambient temperature for 6 minutes. 20 μl of the substrate mixture was added to each well to initiate the reaction (total volume was 50 µl). The reactions were incubated at 37 C. and terminated after 45 minutes.

For method 1, 200 µl of an ice-cold solution of 13% trichloroacetic acid (TCA) and 10 mM sodium pyrophosphate was added to each of the 96 wells. The 96 well plate was then placed in an ice-water bath for 30 minutes. Using A Skatron 96 well cell harvester, the acid precipitable material was collected on a glass fiber filter mat that had been presoaked in 13% TCA and 10 mM sodium pyrophosphate. The filter disks were washed 3 times (2.0 ml/wash) with 1 N HCl and 10 mM sodium pyrophosphate. The filter disks were punched out into scintillation vials, 2.0 ml of Beckman Ready Flow III scintillant was added, and the vials were counted for radioactivity for 1 minute.

For method 2, the assay was terminated with the addition of 175 µl/well of 50 mM EDTA at pH 8.0. Then 180 µl of the mixture was transferred to a pretreated Millipore DE 96 well filter plate. Vacuum was applied to the filter plate to aspirate away the liquid and immobilize the template primer on the DEAE filter disks. Each well was washed 3 times with 200 µl of 0.3 M ammonium formate and 10 mM sodium pyrophosphate at pH 8.0. 50 µl of microscint 20 scintillation cocktail was added to each well and the plate was counted for radioactivity on a Packard Topcount at 1 minute/well.

The $IC_{50}$ values are calculated with the equation:

$$IC_{50}=[Inh]/(1/\text{fractional activity}-1)$$

where the fractional activity=RT activity (dpms) in the presence of inhibitor/RT activity (dpms) in the absence of inhibitor. For a given inhibitor, the $IC_{50}$ values were calculated for the inhibitor concentrations that range between 0.1–0.8 fractional activity. The $IC_{50}$ values in this range (generally 2 values) were averaged. A compound was considered active if its $IC_{50}$ was found to be less than 12 µM.

Protein Binding and Mutant Resistance

In order to characterize NNRTI analogs for their clinical efficacy potential the effect of plasma proteins on antiviral potency and measurements of antiviral potency against wild type and mutant variants of HIV which carry amino acid changes in the known binding site for NNRTIs were examined. The rationale for this testing strategy is two fold:

1. Many drugs are extensively bound to plasma proteins. Although the binding affinity for most drugs for the major components of human plasma, namely, human serum albumin (HSA) or alpha-1-acid glycoprotein (AAG), is low, these major components are present in high concentration in the blood. Only free or unbound drug is available to cross the infected cell membrane for interaction with the target site (i.e., HIV-1 reverse transcriptase, HIV-1 RT). Therefore, the effect of added HSA+AAG on the antiviral potency in tissue culture more closely reflects the potency of a given compound in the clinical setting. The concentration of compound required for 90% inhibition of virus replication as measured in a sensitive viral RNA-based detection method is designated the IC90. The fold increase in apparent IC90 for test compounds in the presence or added levels of HSA and AAG that reflect in vivo concentrations (45 mg/ml HSA, 1 mg/ml AAG) was then calculated. The lower the fold increase, the more compound will be available to interact with the target site.

2. The combination of the high rate of virus replication in the infected individual and the poor fidelity of the viral RT results in the production of a quasi-species or mixtures of HIV species in the infected individual. These species will include a majority wild type species, but also mutant variants of HIV and the proportion of a given mutant will reflect its relative fitness and replication rate. Because mutant variants including mutants with changes in the amino acid sequence of the viral RT likely pre-exist in the infected individual's quasi-species, the overall potency observed in the clinical setting will reflect the ability of a drug to inhibit not only wild type HIV-1, but mutant variants as well. We thus have constructed, in a known genetic background, mutant variants of HIV-1 which carry amino acid substitutions at positions thought to be involved in NNRTI binding, and measured the ability of test compounds to inhibit replication of these mutant viruses. The concentration of compound required for 90% inhibition of virus replication as measured in a sensitive viral RNA-based detection method is designated the IC90. It is desirable to have a compound which has high activity against a variety of mutants.

Dosage and Formulation

The antiviral compounds of this invention can be administered as treatment for viral infections by any means that produces contact of the active agent with the agent's site of action, i.e., the viral reverse transcriptase, in the body of a mammal. They can be administered by any conventional means available for use in conjunction with pharmaceuticals, either as individual therapeutic agents or in a combination of therapeutic agents. They can be administered alone, but preferably are administered with a pharmaceutical carrier selected on the basis of the chosen route of administration and standard pharmaceutical practice.

The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. A daily dosage of active ingredient can be expected to be about 0.001 to about 1000 milligrams per kilogram of body weight, with the preferred dose being about 0.1 to about 30 mg/kg.

Dosage forms of compositions suitable for administration contain from about 1 mg to about 100 mg of active ingredient per unit. In these pharmaceutical compositions the active ingredient will ordinarily be present in an amount of about 0.5–95% by weight based on the total weight of the composition. The active ingredient can be administered orally in solid dosage forms, such as capsules, tablets and powders, or in liquid dosage forms, such as elixirs, syrups and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts, and sodium EDTA. In addition, parenteral solutions can contain preservatives, such as benzalkonium chloride, methyl- or propyl-paraben and chlorobutanol. Suitable pharmaceutical carriers are described in *Remington's Pharmaceutical Sciences,* supra, a standard reference text in this field.

Useful pharmaceutical dosage-forms for administration of the compounds of this invention can be illustrated as follows:

Capsules

A large number of unit capsules can be prepared by filling standard two-piece hard gelatin capsules each with 100 mg of powdered active ingredient, 150 mg of lactose, 50 mg of cellulose, and 6 mg magnesium stearic.

Soft Gelatin Capsules

A mixture of active ingredient in a digestible oil such as soybean oil, cottonseed oil or olive oil can be prepared and injected by means of a positive displacement pump into gelatin to form soft gelatin capsules containing 100 mg of the active ingredient. The capsules should then be washed and dried.

Tablets

A large number of tablets can be prepared by conventional procedures so that the dosage unit is 100 mg of active ingredient, 0.2 mg of colloidal silicon dioxide, 5 milligrams of magnesium stearate, 275 mg of microcrystalline cellulose, 11 mg of starch and 98.8 mg of lactose. Appropriate coatings may be applied to increase palatability or delay absorption.

Suspension

An aqueous suspension can be prepared for oral administration so that each 5 mL contain 25 mg of finely divided active ingredient, 200 mg of sodium carboxymethyl cellulose, 5 mg of sodium benzoate, 1.0 g of sorbitol solution, U.S.P., and 0.025 mg of vanillin.

Injectable

A parenteral composition suitable for administration by injection can be prepared by stirring 1.5% by weight of active ingredient in 10% by volume propylene glycol and water. The solution is sterilized by commonly used techniques.

Combination of Components (a) and (b)

Each therapeutic agent component of this invention can independently be in any dosage form, such as those described above, and can also be administered in various ways, as described above. In the following description component (b) is to be understood to represent one or more agents as described previously. Thus, if components (a) and (b) are to be treated the same or independently, each agent of component (b) may also be treated the same or independently.

Components (a) and (b) of the present invention may be formulated together, in a single dosage unit (that is, combined together in one capsule, tablet, powder, or liquid, etc.) as a combination product. When component (a) and (b) are not formulated together in a single dosage unit, the component (a) may be administered at the same time as component (b) or in any order; for example component (a) of this invention may be administered first, followed by administration of component (b), or they may be administered in the revserse order. If component (b) contains more that one agent, e.g., one RT inhibitor and one protease inhibitor, these agents may be administered together or in any order. When not administered at the same time, preferably the administration of component (a) and (b) occurs less than about one hour apart. Preferably, the route of administration of component (a) and (b) is oral. The terms oral agent, oral inhibitor, oral compound, or the like, as used herein, denote compounds which may be orally administered. Although it is preferable that component (a) and component (b) both be administered by the same route (that is, for example, both orally) or dosage form, if desired, they may each be administered by different routes (that is, for example, one component of the combination product may be administered orally, and another component may be administered intravenously) or dosage forms.

As is appreciated by a medical practitioner skilled in the art, the dosage of the combination therapy of the invention may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired, as described above.

The proper dosage of components (a) and (b) of the present invention will be readily ascertainable by a medical practitioner skilled in the art, based upon the present disclosure. By way of general guidance, typically a daily dosage may be about 100 milligrams to about 1.5 grams of each component. If component (b) represents more than one compound, then typically a daily dosage may be about 100 milligrams to about 1.5 grams of each agent of component (b). By way of general guidance, when the compounds of component (a) and component (b) are administered in combination, the dosage amount of each component may be reduced by about 70–80% relative to the usual dosage of the component when it is administered alone as a single agent for the treatment of HIV infection, in view of the synergistic effect of the combination.

The combination products of this invention may be formulated such that, although the active ingredients are combined in a single dosage unit, the physical contact between the active ingredients is minimized. In order to minimize contact, for example, where the product is orally administered, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. Another embodiment of this invention where oral administration is desired provides for a combination product wherein one of the active ingredients is coated with a sustained-release material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a lowviscosity grade of hydroxypropyl methylcellulose or other appropriate materials as known in the art, in order to further separate the active components. The polymer coating serves to form an additional barrier to interaction with the other component. In each formulation wherein contact is prevented between components (a) and (b) via a coating or some other material, contact may also be prevented between the individual agents of component (b).

Dosage forms of the combination products of the present invention wherein one active ingredient is enteric coated can be in the form of tablets such that the enteric coated component and the other active ingredient are blended together and then compressed into a tablet or such that the enteric coated component is compressed into one tablet layer and the other active ingredient is compressed into an additional layer. Optionally, in order to further separate the two layers, one or more placebo layers may be present such that the placebo layer is between the layers of active ingredients. In addition, dosage forms of the present invention can be in the form of capsules wherein one active ingredient is compressed into a tablet or in the form of a plurality of microtablets, particles, granules or non-perils, which are then enteric coated. These enteric coated microtablets, particles, granules or non-perils are then placed into a capsule or compressed into a capsule along with a granulation of the other active ingredient.

These as well as other ways of minimizing contact between the components of combination products of the present invention, whether administered in a single dosage form or administered in separate forms but at the same time or concurrently by the same manner, will be readily apparent to those skilled in the art, based on the present disclosure.

Pharmaceutical kits useful for the treatment of HIV infection, which comprise a therapeutically effective amount of a pharmaceutical composition comprising a compound of component (a) and one or more compounds of component (b), in one or more sterile containers, are also within the ambit of the present invention. Sterilization of the container may be carried out using conventional sterilization methodology well known to those skilled in the art. Component (a) and component (b) may be in the same sterile container or in separate sterile containers. The sterile containers of materials may comprise separate containers, or one or more multi-part containers, as desired. Component (a) and component (b), may be separate, or physically combined into a single dosage form or unit as described above. Such kits may further include, if desired, one or more of various conventional pharmaceutical kit components, such as for example, one or more pharmaceutically acceptable carriers, additional vials for mixing the components, etc., as will be readily apparent to those skilled in the art. Instructions, either as inserts or as labels, indicating quantities of the components to be administered, guidelines for administration, and/or guidelines for mixing the components, may also be included in the kit.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letter Patent of United States is:

1. A process of making a compound of formula IIIb:

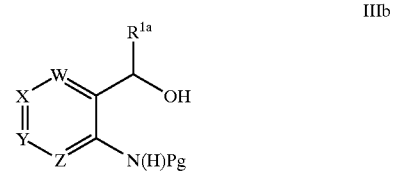

or stereoisomer or salt form thereof, comprising:

(a) contacting a compound of formula IIIa:

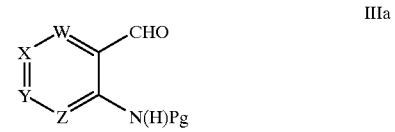

with $R^{1a}$-TMS and an anion, wherein:
the anion is a fluoride or oxyanion and is selected from tetrabutylammonium fluoride, sodium fluoride, potassium fluoride, lithium fluoride, cesium fluoride, potassium tert-butoxide, sodium methoxide, sodium ethoxide and sodium trimethylsilanolate;
Pg is an amine protecting group;
W is N or $CR^3$;
X is N or $CR^4$;
Y is N or $CR^5$;
Z is N or $CR^6$;
provided that if two of W, X, Y, and Z are N, then the remaining are other than N;
$R^{1a}$ is selected from $CF_3$, $CF_3CF_2$, and $CF_3CF_2CF_2$;
$R^3$ is selected from H, F, Cl, Br, I, $C_{1-3}$ alkoxy, and $C_{1-3}$ alkyl;
$R^4$ is selected from H, F, Cl, Br, I, $C_{1-3}$ alkyl substituted with 0–3 $R^{11}$, $C_{2-3}$ alkenyl, $C_{2-3}$ alkynyl, $C_{1-3}$ alkoxy, $OCF_3$, —CN, $NO_2$, CHO, $C(O)CH_3$, $C(O)CF_3$, $C(O)NH_2$, $C(O)NHCH_3$, $NR^7R^{7a}$, $NR^7C(O)OR^{7a}$, $C(O)OR^7$, $S(O)_pR^7$, $SO_2NHR^7$, $NR^7SO_2R^{7b}$, phenyl substituted with 0–2 $R^{10}$, and 5–6 membered aromatic heterocycle system containing from 1–4 heteroatoms selected from the group consisting of N, O, and S substituted with 0–2 $R^{10}$;
alternatively, $R^3$ and $R^4$ together form —$OCH_2O$—;
$R^5$ is selected from H, F, Cl, Br, and I;
alternatively, $R^4$ and $R^5$ together form —$OCH_2O$— or a fused benzo ring;
$R^6$ is selected from H, OH, $C_{1-3}$ alkoxy, —CN, F, Cl, Br, I, $NO_2$, $CF_3$, CHO, $C_{1-3}$ alkyl, and $C(O)NH_2$;
$R^7$ is selected from H and $C_{1-3}$ alkyl;
$R^{7a}$ is selected from H and $C_{1-3}$ alkyl;
$R^{7b}$ is $C_{1-3}$ alkyl;
$R^{10}$ is selected from OH, $C_{1-3}$ alkyl, $C_{1-3}$ alkoxy, F, Cl, Br, I, CN, $NR^7R^{7a}$, and $C(O)CH_3$;
$R^{11}$ is selected from $OR^7$, CN, F, Cl, Br, I, $NO_2$, $NR^7R^{7a}$, CHO, $C(O)CH_3$, $C(O)NH_2$;
p is selected from 0, 1, and 2.

2. The process according to claim 1, wherein:
the $R^{1a}$-TMS is trifluoromethyl trimethylsilane;
the anion is tetrabutylammonium fluoride;

Pg is trityl;

$R^{1a}$ is $CF_3$;

$R^3$ is selected from H, F, Cl, Br, I;

$R^4$ is selected from H, F, Cl, Br, I, $C_{1-3}$ alkyl substituted with 0–3 $R^{11}$, $CH=CH_2$, $C\equiv CH$, $OCH_3$, $OCF_3$, —CN, $NO_2$, CHO, $C(O)CH_3$, $C(O)CF_3$, $C(O)NH_2$, $C(O)NHCH_3$, $NR^7R^{7a}$, $C(O)OR^7$, $NR^7SO_2R^{7b}$, and 5–6 membered aromatic heterocycle system containing from 1–4 heteroatoms selected from the group consisting of N, O, and S;

alternatively, $R^3$ and $R^4$ together form —$OCH_2O$—; and, $R^5$ is selected from H, F;

$R^6$ is selected from H, OH, $OCH_3$, —CN, F, $CF_3$, $CH_3$, and $C(O)NH_2$;

$R^7$ is selected from H and $CH_3$;

$R^{7a}$ is selected from H and $CH_3$;

$R^{7b}$ is $CH_3$;

$R^{10}$ is selected from OH, $CH_3$, $OCH_3$, F, Cl, Br, I, CN, $NR^7R^{7a}$, and $C(O)CH_3$;

$R^{11}$ is selected from OH, $OCH_3$, CN, F, Cl, $NR^7R^{7a}$, $C(O)CH_3$, and $C(O)NH_2$; and, p is selected from 1 and 2.

3. The process according to claim 2, wherein the process further comprises:

(b) contacting a compound of formula IIIb with an oxidizing agent to form compound of formula IIIc:

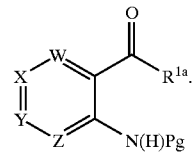

IIIc

4. The process according to claim 3, wherein the oxidizing agent is $MnO_2$.

* * * * *